US012495717B2

(12) United States Patent
Kim et al.

(10) Patent No.: US 12,495,717 B2
(45) Date of Patent: Dec. 9, 2025

(54) AMINE COMPOUND AND ORGANIC LIGHT EMITTING DIODE COMPRISING SAME

(71) Applicant: LG CHEM, LTD., Seoul (KR)

(72) Inventors: Minjun Kim, Daejeon (KR); Kongkyeom Kim, Daejeon (KR); Hyoung Seok Kim, Daejeon (KR); Min Woo Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1101 days.

(21) Appl. No.: 17/042,696

(22) PCT Filed: Apr. 5, 2019

(86) PCT No.: PCT/KR2019/004031
§ 371 (c)(1),
(2) Date: Sep. 28, 2020

(87) PCT Pub. No.: WO2019/194617
PCT Pub. Date: Oct. 10, 2019

(65) Prior Publication Data

US 2021/0057650 A1 Feb. 25, 2021

(30) Foreign Application Priority Data

Apr. 5, 2018 (KR) ........................ 10-2018-0039620

(51) Int. Cl.
*H10K 85/60* (2023.01)
*C07D 209/80* (2006.01)
(Continued)

(52) U.S. Cl.
CPC ......... *H10K 85/636* (2023.02); *C07D 209/80* (2013.01); *C07D 405/14* (2013.01);
(Continued)

(58) Field of Classification Search
CPC .. C07D 209/56; C07D 209/80; C07D 405/14; C07D 409/14; C07D 487/06;
(Continued)

(56) References Cited

U.S. PATENT DOCUMENTS

2004/0251816 A1 12/2004 Leo et al.
2014/0175402 A1 6/2014 Jeong
(Continued)

FOREIGN PATENT DOCUMENTS

CN 104672126 6/2015
CN 113444072 A * 9/2021
(Continued)

OTHER PUBLICATIONS

KR-2012116881-A, machine translation (Year: 2012).*
(Continued)

*Primary Examiner* — Elizabeth M. Dahlburg
(74) *Attorney, Agent, or Firm* — Bryan Cave Leighton Paisner LLP

(57) ABSTRACT

Provided is a compound of Chemical Formula 1:

Chemical Formula 1

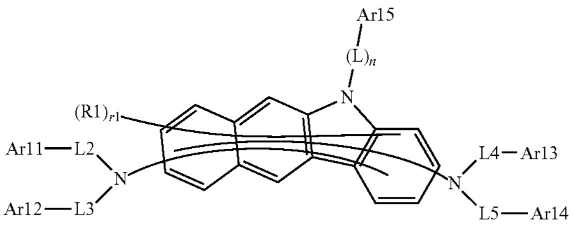

wherein:

Ar11 to Ar15 are each independently a substituted or unsubstituted aryl or heteroaryl group, or are bonded to an adjacent substituent to form a substituted or unsubstituted ring, (Continued)

L and L2 to L5 are each independently a direct bond or a substituted or unsubstituted arylene group, R1 is hydrogen, deuterium, a halogen group, a nitrile group, or a substituted or unsubstituted aryl or heteroaryl group, and is bonded to an adjacent substituent to form a substituted or unsubstituted ring, r1 is 0 to 8, and when r1 is 2 or more, the R1s are the same as or different from each other, and n is an integer from 1 to 3, and when n is 2 or 3, the Ls are the same as or different from each other, and an organic light emitting diode comprising the same.

14 Claims, 3 Drawing Sheets

(51) Int. Cl.

| | |
|---|---|
| ***C07D 405/14*** | (2006.01) |
| ***C07D 409/14*** | (2006.01) |
| ***C07D 487/06*** | (2006.01) |
| ***C09K 11/06*** | (2006.01) |
| ***H10K 50/11*** | (2023.01) |

(52) U.S. Cl.
CPC ......... *C07D 409/14* (2013.01); *C07D 487/06* (2013.01); *C09K 11/06* (2013.01); *C09K 2211/1007* (2013.01); *C09K 2211/1018* (2013.01); *H10K 50/11* (2023.02); *H10K 85/6572* (2023.02); *H10K 85/6574* (2023.02); *H10K 85/6576* (2023.02)

(58) Field of Classification Search
CPC ............ C09K 11/06; C09K 2211/1007; C09K 2211/1018; H10K 50/11; H10K 85/615; H10K 85/631; H10K 85/633; H10K 85/636; H10K 85/6572; H10K 85/6574; H10K 85/6576; H01L 51/0052; H01L 52/0059; H01L 51/006; H01L 51/0061; H01L 51/0072; H01L 51/0073; H01L 51/0074; H01L 51/5012
See application file for complete search history.

(56) References Cited

U.S. PATENT DOCUMENTS

| | | | |
|---|---|---|---|
| 2014/0316136 | A1 | 10/2014 | Yang et al. |
| 2015/0053934 | A1 | 2/2015 | Lee et al. |
| 2016/0365517 | A1 | 12/2016 | Mun et al. |
| 2017/0213985 | A1 | 7/2017 | Lee et al. |
| 2017/0324045 | A1 | 11/2017 | Takahashi et al. |
| 2018/0148641 | A1 | 5/2018 | Cha et al. |
| 2019/0106390 | A1 | 4/2019 | Lee et al. |

FOREIGN PATENT DOCUMENTS

| | | |
|---|---|---|
| JP | 2014-073965 | 4/2014 |
| KR | 10-2012-0116881 | 10/2012 |
| KR | 10-2012-0135501 | 12/2012 |
| KR | 10-2014-0083412 | 7/2014 |
| KR | 10-2015-0101933 | 9/2015 |
| KR | 10-2016-0029721 | 3/2016 |
| KR | 10-2017-0112039 | 10/2017 |
| KR | 10-2017-0125046 | 11/2017 |

OTHER PUBLICATIONS

JP-2014073965-A, machine translation (Year: 2014).*
CN-104672126-A, machine translation 1 (Year: 2015).*
CN-104672126-A, machine translation 2 (Year: 2015).*

* cited by examiner

[Figure 1]
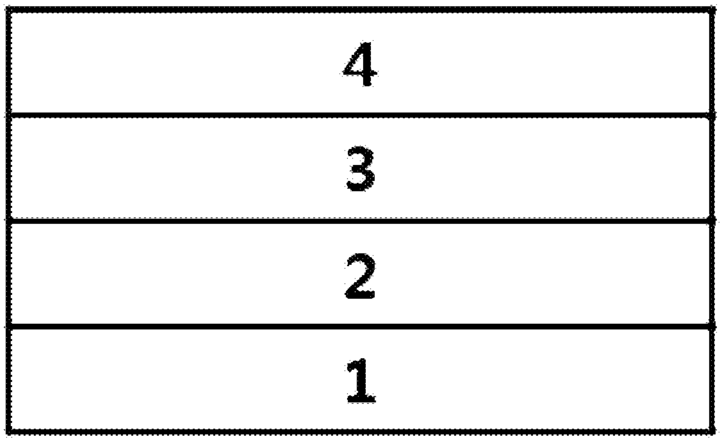
[Figure 2]
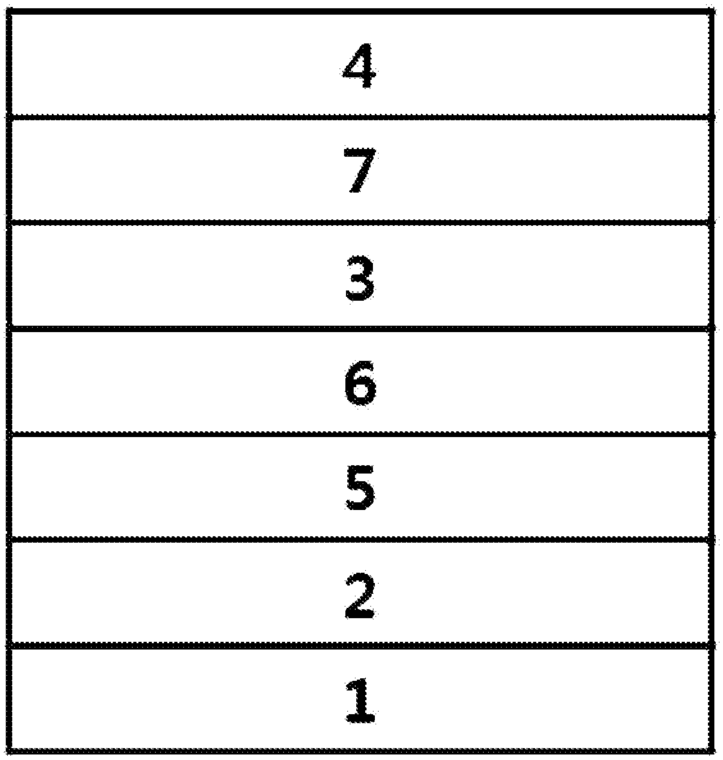

[Figure 3]
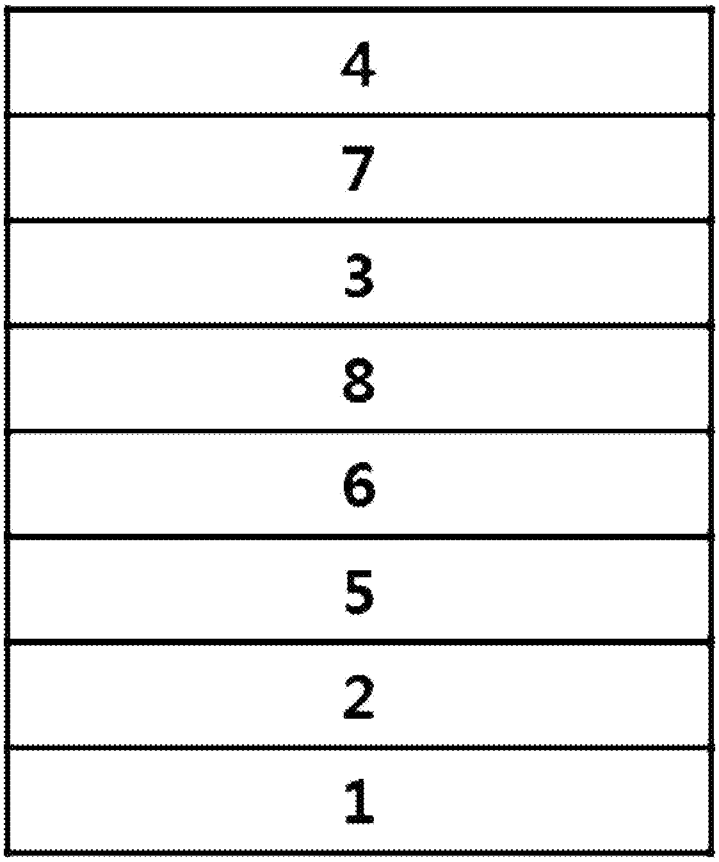

[Figure 4]
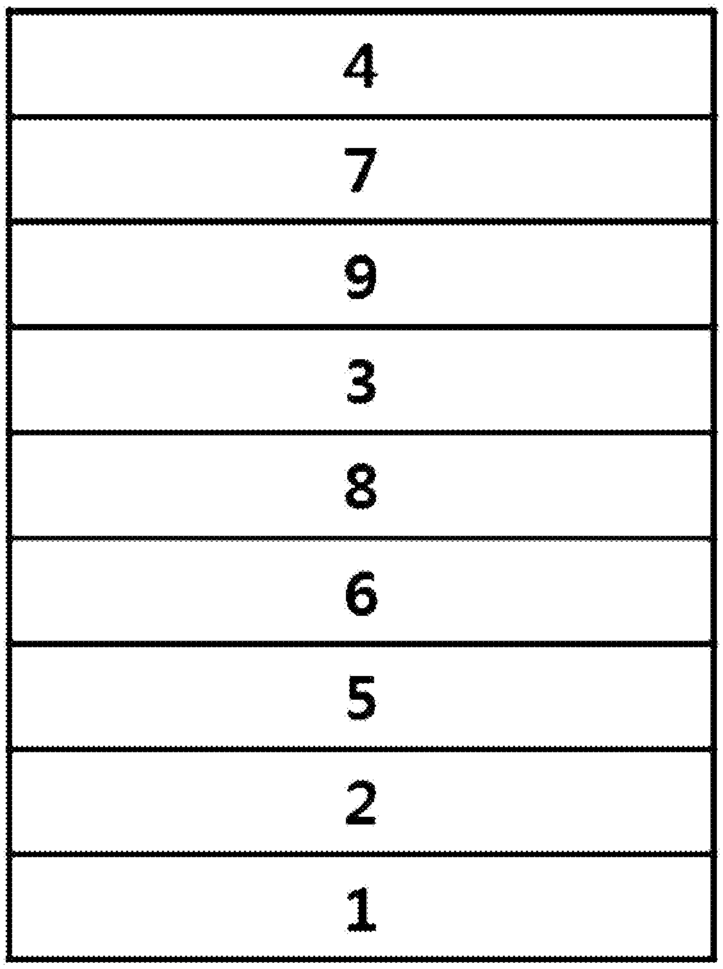

AMINE COMPOUND AND ORGANIC LIGHT EMITTING DIODE COMPRISING SAME

CROSS-REFERENCE TO RELATED APPLICATION(S)

This application is a National Stage Application of International Application No. PCT/KR2019/004031 filed on Apr. 5, 2019, which claims priority to and the benefit of Korean Patent Application No. 10-2018-0039620 filed in the Korean Intellectual Property Office on Apr. 5, 2018, the entire contents of which are incorporated herein by reference.

TECHNICAL FIELD

The present specification relates to an amine compound and an organic light emitting device including the same.

BACKGROUND

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer has in many cases a multi-layered structure composed of different materials in order to improve the efficiency and stability of the organic light emitting device, and for example, can be composed of a hole injection layer, a hole transport layer, a light emitting layer, an electron transport layer, an electron injection layer, and the like. In the structure of the organic light emitting device, if a voltage is applied between the two electrodes, holes are injected from the positive electrode into the organic material layer and electrons are injected from the negative electrode into the organic material layer, and when the injected holes and electrons meet each other, an exciton is formed, and light is emitted when the exciton falls down again to a ground state.

There is a continuous need for developing a new material for the aforementioned organic light emitting device.

BRIEF DESCRIPTION

Technical Problem

The present specification provides an amine compound and an organic light emitting device including the same.

Technical Solution

An exemplary embodiment of the present specification provides a compound of Chemical Formula 1:

Chemical Formula 1

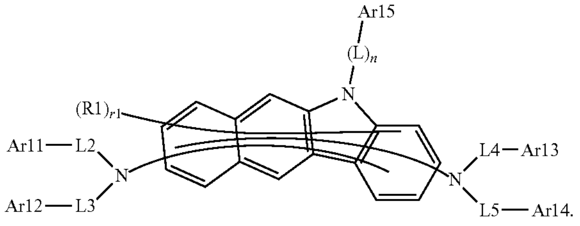

In Chemical Formula 1:

Ar11 to Ar15 are the same as or different from each other, and are each independently a substituted or unsubstituted aryl group or a substituted or unsubstituted heteroaryl group, or are bonded to an adjacent substituent to form a substituted or unsubstituted ring;

L and L2 to L5 are the same as or different from each other, and are each independently a direct bond or a substituted or unsubstituted arylene group;

R1 is hydrogen, deuterium, a halogen group, a nitrile group, a substituted or unsubstituted aryl group, or a substituted or unsubstituted heteroaryl group, and is bonded to an adjacent substituent to form a substituted or unsubstituted ring;

r1 is an integer from 0 to 8, and when r1 is 2 or more, the R1s are the same as or different from each other; and n is an integer from 1 to 3, and when n is 2 or 3, the Ls are the same as or different from each other.

Further, an exemplary embodiment of the present specification provides an organic light emitting device including: a first electrode; a second electrode provided to face the first electrode; and an organic material layer having one or more layers provided between the first electrode and the second electrode, in which one or more layers of the organic material layer include the compound of Chemical Formula 1.

Advantageous Effects

A compound according to an exemplary embodiment of the present specification can be used as a material for an organic material layer of an organic light emitting device, and it is possible to improve efficiency, achieve a low driving voltage, and/or improve service life characteristics, in the organic light emitting device by using the same.

BRIEF DESCRIPTION OF DRAWINGS

FIGS. 1 to 4 illustrate an organic light emitting device according to exemplary embodiments of the present specification.

EXPLANATION OF REFERENCE NUMERALS AND SYMBOLS

1: Substrate
2: Positive electrode
3: Light emitting layer
4: Negative electrode
5: Hole injection layer
6: Hole transport layer
7: Electron injection and transport layer
8: Electron blocking layer
9: Hole blocking layer

DETAILED DESCRIPTION

Hereinafter, the present specification will be described in more detail.

An exemplary embodiment of the present specification provides the compound of Chemical Formula 1.

The compound of Chemical Formula 1 has a structure in which two arylamine groups or arylheteroarylamine groups are linked to a core structure of benzocarbazole. When the compound of Chemical Formula 1 is used as a dopant of a blue light emitting layer, the color purity of a device is improved, and long service life, high efficiency, and low voltage characteristics are exhibited.

When one part "includes" one constituent element in the present specification, unless otherwise specifically described, this does not mean that another constituent element is excluded, but means that another constituent element can be further included.

When one member is disposed "on" another member in the present specification, this includes not only a case where the one member is brought into contact with another member, but also a case where still another member is present between the two members.

In the present specification,

or * means a moiety to be linked.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more are substituted, the two or more substituents can be the same as or different from each other.

In the present specification, the term "substituted or unsubstituted" means being substituted with one or two or more substituents selected from the group consisting of hydrogen, deuterium, a halogen group, a nitrile group, a silyl group, an alkyl group, a cycloalkyl group, a haloalkyl group, an alkoxy group, a haloalkoxy group, an aryloxy group, an aryl group, and a heterocyclic group, being substituted with a substituent to which two or more substituents among the exemplified substituents are linked, or having no substituent. For example, "the substituent to which two or more substituents are linked" can be an aryl group substituted with an aryl group, an aryl group substituted with a heteroaryl group, a heterocyclic group substituted with an aryl group, an aryl group substituted with an alkyl group, and the like.

In the present specification, the case where two or more substituents are linked means that hydrogen of any one substituent is linked to another substituent. For example, an isopropyl group can be linked to a phenyl group to become a substituent of

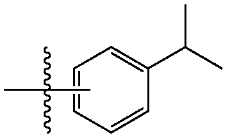

or

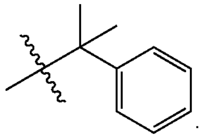

.

In the present specification, the case where three substituents are linked includes not only a case where (Substituent 1)-(Substituent 2)-(Substituent 3) are consecutively linked to one another, but also a case where (Substituent 2) and (Substituent 3) are linked to (Substituent 1). For example, two phenyl groups can be linked to an isopropyl group to become a substituent of

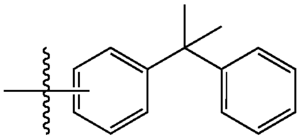

or

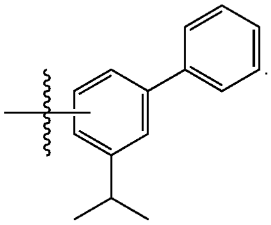

.

The same also applies to the case where four or more substituents are linked.

In the present specification, a halogen group can be F, Cl, I, and the like, and is preferably F.

In the present specification, a silyl group can be an alkyl silyl group or an aryl silyl group. The silyl group can be SiRaRbRc, and Ra to Rc can be hydrogen, an alkyl group, or an aryl group.

In the present specification, an alkyl group can be straight-chained or branched, and the number of carbon atoms thereof is not particularly limited, but is preferably 1 to 30; 1 to 10; or 1 to 5. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but has preferably 3 to 30 carbon atoms; or 3 to 13 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, a haloalkyl group can be straight-chained or branched, and refers to a group in which hydrogen of the above-described alkyl group is substituted with one or two or more halogen groups. The number of carbon atoms thereof is not particularly limited, but is preferably 1 to 30; 1 to 20; 1 to 10; or 1 to 5. The description on the above-described alkyl group can be applied to the alkyl group. Specific examples of the haloalkyl group include a fluoromethyl group, a difluoro-methyl group, a trifluoromethyl group, a chloromethyl group, a dichloromethyl group, a trichloromethyl group, a bromomethyl group, a dibromomethyl group, a tribromomethyl group, and the like, but are not limited thereto.

In the present specification, an alkoxy group can be straight-chained, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethyl-butyloxy, 2-ethylbutyloxy, n-octyloxy, n-nonyloxy, n-decyloxy, benzyloxy, p-methylbenzyloxy, and the like, but are not limited thereto.

In the present specification, a haloalkoxy group is a group in which a haloalkyl group is linked to an oxygen atom, and the description on the above-described haloalkyl group can be applied to the haloalkyl group. The number of carbon atoms thereof is not particularly limited, but is preferably 1 to 30; 1 to 20; 1 to 10; or 1 to 5.

In the present specification, an aryl group is not particularly limited, but has preferably 6 to 30 carbon atoms, and the aryl group can be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenalenyl group, a perylenyl group, a chrysenyl group, a fluorenyl group, and the like, but are not limited thereto.

In the present specification, the fluorenyl group can be substituted, and adjacent substituents can be bonded to each other to form a ring.

When the fluorenyl group is substituted, the substituent can be

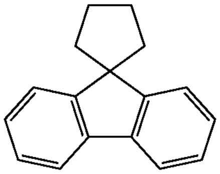,
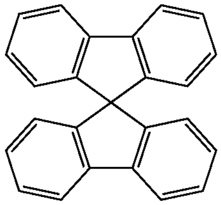,
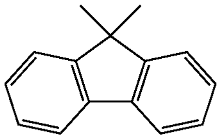,
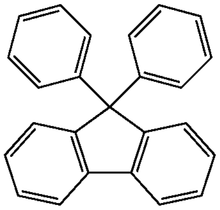,
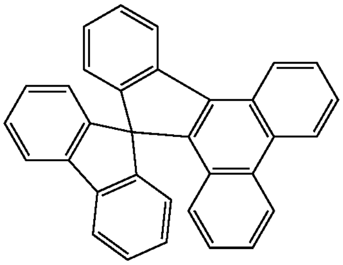,

-continued

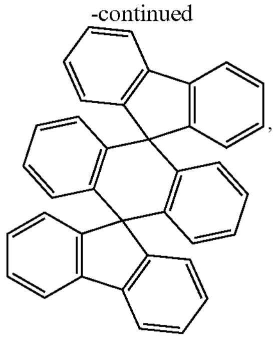, and the like. However, the substituent is not limited thereto.

In the present specification, the aryl group in the aryloxy group, the N-arylalkylamine group, and the N-arylheteroarylamine group is the same as the above-described examples of the aryl group. Specific examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like.

In the present specification, a heteroaryl group includes one or more atoms other than carbon, that is, one or more heteroatoms, and specifically, the heteroatom can include one or more atoms selected from the group consisting of O, N, Se, S, and the like. The number of carbon atoms thereof is not particularly limited, but is preferably 2 to 30, and the heteroaryl group can be monocyclic or polycyclic. Examples of a heterocyclic group include a thiophene group, a furan group, a pyrrole group, an imidazole group, a triazole group, an oxazole group, an oxadiazole group, a pyridyl group, a bipyridyl group, a pyrimidyl group, a triazinyl group, a triazole group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazole group, a benzoxazole group, a benzoimidazole group, a benzothiazole group, a benzocarbazole group, a dibenzopyrrole group, an indole group, a benzothiophene group, a dibenzothiophene group, a benzofuran group, a benzoquinolyl group, a benzonaphthothiophene group, a benzonaphthofuran group, a phenanthrolinyl group (phenanthroline), a thiazole group, an isoxazole group, an oxadiazole group, a thiadiazole group, a benzothiazole group, a phenoxazine group, a phenothiazine group, a dibenzofuran group, and the like, but are not limited thereto.

In the present specification, the above-described examples of the aryl group can be applied to an arylene group except for a divalent arylene group.

In the present specification, the above-described examples of the heteroaryl group can be applied to a heteroarylene group except for a divalent heteroarylene group.

According to an exemplary embodiment of the present specification, L and L2 to L5 are the same as or different from each other, and are each independently selected from a direct bond, phenylene, biphenylene, terphenylene, quaterphenylene, naphthylene, anthracenylene, fluorenylene which is unsubstituted or substituted with alkyl or aryl, phenanthrenylene, pyrenylene, and triphenylylene.

According to an exemplary embodiment of the present specification, L and L2 to L5 are the same as or different from each other, and can be each independently selected from a direct bond or the following structural formulae:

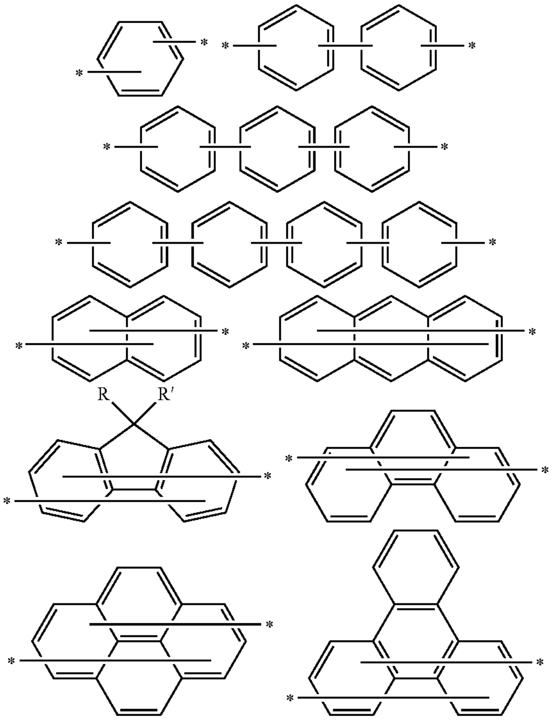

R and R' are an alkyl group or an aryl group. For example, R and R' are a methyl group or a phenyl group.

According to an exemplary embodiment of the present specification, L and L2 to L5 are the same as or different from each other, and can be each independently selected from a direct bond or the following structural formulae:

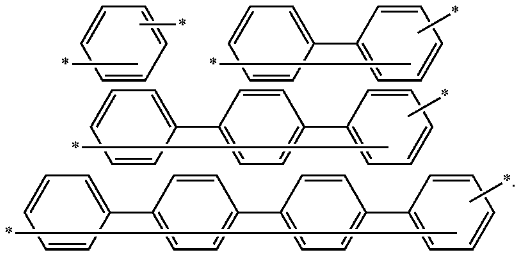

According to an exemplary embodiment of the present specification, L and L2 to L5 are the same as or different from each other, and are each independently a direct bond, phenylene, or a biphenylene group.

According to an exemplary embodiment of the present specification, L and L2 to L5 are the same as or different from each other, and are each independently a direct bond, or phenylene.

According to an exemplary embodiment of the present specification, L and L2 to L5 are the same as or different from each other, and are each independently a direct bond, p-phenylene, or m-phenylene.

According to an exemplary embodiment of the present specification, L and L2 to L5 are a direct bond.

According to an exemplary embodiment of the present specification, L is a direct bond.

According to an exemplary embodiment of the present specification, L2 to L5 are the same as or different from each other, and are each independently a direct bond, or phenylene.

According to an exemplary embodiment of the present specification, Ar11 to Ar14 are the same as or different from each other, and are each independently a substituted or unsubstituted aryl group; or a substituted or unsubstituted heteroaryl group.

According to an exemplary embodiment of the present specification, Ar11 to Ar14 are the same as or different from each other, and are each independently a substituted or unsubstituted aryl group having 6 to 30 carbon atoms; or a substituted or unsubstituted heteroaryl group having 2 to 30 carbon atoms.

According to an exemplary embodiment of the present specification, Ar11 to Ar14 are the same as or different from each other, and are each independently an aryl group which is unsubstituted or substituted with one substituent selected from the group consisting of deuterium, a halogen group, a nitrile group, an alkyl group, a haloalkyl group, an alkoxy group, a haloalkoxy group, a silyl group, and a cycloalkyl group, or a substituent to which two or more substituents selected from the group are linked; or a heteroaryl group which is unsubstituted or substituted with one substituent selected from the group consisting of deuterium, a halogen group, a nitrile group, an alkyl group, a haloalkyl group, an alkoxy group, a haloalkoxy group, a silyl group, and a cycloalkyl group, or a substituent to which two or more substituents selected from the group are linked.

In an exemplary embodiment of the present specification, when any one of Ar11 to Ar14 is an aryl group, the aryl group is a phenyl group, a naphthyl group, a biphenyl group, a fluorenyl group, or a benzofluorenyl group.

In an exemplary embodiment of the present specification, when any one of Ar11 to Ar14 is a heteroaryl group, the heteroaryl group is a dibenzofuran group, a naphthobenzofuran group, a dibenzothiophene group, or a naphthobenzothiophene group.

In an exemplary embodiment of the present specification, when any one of Ar11 to Ar14 is a substituted aryl group, the substituent of the aryl group is deuterium, a halogen group, a nitrile group, an alkyl group having 1 to 5 carbon atoms, which is unsubstituted or substituted with deuterium, a haloalkyl group having 1 to 5 carbon atoms, an alkoxy group having 1 to 5 carbon atoms, a haloalkoxy group having 1 to 5 carbon atoms, a silyl group having 3 to 20 carbon atoms, or a cycloalkyl group having 3 to 20 carbon atoms.

In an exemplary embodiment of the present specification, when any one of Ar11 to Ar14 is a substituted aryl group, the substituent of the aryl group is deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, or a cyclohexyl group.

In an exemplary embodiment of the present specification, when any one of Ar11 to Ar14 is a substituted heteroaryl group, the substituent of the heteroaryl group is deuterium, a halogen group, a nitrile group, an alkyl group having 1 to 5 carbon atoms, which is unsubstituted or substituted with deuterium, a haloalkyl group having 1 to 5 carbon atoms, an alkoxy group having 1 to 5 carbon atoms, a haloalkoxy group having 1 to 5 carbon atoms, a silyl group having 3 to 20 carbon atoms, a cycloalkyl group having 3 to 20 carbon atoms, or an aryl group having 6 to 20 carbon atoms, which is unsubstituted or substituted with deuterium.

In an exemplary embodiment of the present specification, when any one of Ar11 to Ar14 is a substituted heteroaryl group, the substituent of the heteroaryl group is deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, a phenyl group, a biphenyl group, a naphthyl group, a terphenyl group, a phenyl group which is substituted with deuterium, a biphenyl group which is substituted with deuterium, a naphthyl group which is substituted with deuterium, or a terphenyl group which is substituted with deuterium.

In an exemplary embodiment of the present specification, Ar11 to Ar14 are the same as or different from each other, and are each independently a phenyl group which is unsubstituted or substituted with deuterium, a halogen group, a nitrile group, a methyl group, an ethyl group, a propyl group, an isopropyl group, a t-butyl group, $CD_3$, a trifluoromethyl group, $OCF_3$, a methoxy group, an ethoxy group, a trimethylsilyl group, a triphenylsilyl group, or a cyclohexyl group; a biphenyl group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, or a cyclohexyl group; a naphthyl group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, or a cyclohexyl group; a fluorenyl group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, or a cyclohexyl group; a benzofluorenyl group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, or a cyclohexyl group; a dibenzofuran group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, a phenyl group, a biphenyl group, a naphthyl group, or a phenyl group which is substituted with deuterium; a naphthobenzofuran group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, or a cyclohexyl group; a dibenzothiophene group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, a phenyl group, a biphenyl group, a naphthyl group, or a phenyl group which is substituted with deuterium; or a naphthobenzothiophene group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, $OCF_3$, a trimethylsilyl group, a triphenylsilyl group, or a cyclohexyl group.

In an exemplary embodiment of the present specification, Ar11 to Ar14 are the same as or different from each other, and are each independently a phenyl group which is unsubstituted or substituted with deuterium, a halogen group, a nitrile group, a methyl group, an isopropyl group, a t-butyl group, $CD_3$, a trifluoromethyl group, $OCF_3$, a methoxy group, or a trimethylsilyl group; a biphenyl group; a naphthyl group; a dimethylfluorenyl group; a dimethylbenzofluorenyl group; a dibenzofuran group which is unsubstituted or substituted with deuterium, a methyl group, an isopropyl group, a t-butyl group, $CD_3$, a trimethylsilyl group, a phenyl group, or a phenyl group which is substituted with deuterium; a naphthobenzofuran group; a dibenzothiophene group which is unsubstituted or substituted with deuterium, a methyl group, an isopropyl group, a t-butyl group, $CD_3$, a trimethylsilyl group, a phenyl group, or a phenyl group which is substituted with deuterium; or a naphthobenzothiophene group.

According to an exemplary embodiment of the present specification, —N(-L2-Ar11) (-L3-Ar12) and —N(-L4-Ar13) (-L5-Ar14) of Chemical Formula 1 are the same as each other.

According to an exemplary embodiment of the present specification, -(L)n-Ar15 in Chemical Formula 1 is a phenyl group which is unsubstituted or substituted with deuterium, a halogen group, a nitrile group, an alkyl group which is unsubstituted or substituted with deuterium, an alkoxy group, or a silyl group; or a biphenyl group which is unsubstituted or substituted with deuterium, a halogen group, a nitrile group, an alkyl group which is unsubstituted or substituted with deuterium, an alkoxy group, or a silyl group.

In an exemplary embodiment of the present specification, Ar15 is a substituted or unsubstituted aryl group, or a substituted or unsubstituted heteroaryl group, or is bonded to an adjacent group to form a substituted or unsubstituted ring.

In an exemplary embodiment of the present specification, Ar15 is boned to adjacent R1 to form a substituted or unsubstituted aromatic hydrocarbon ring.

In an exemplary embodiment of the present specification, Ar15 is bonded to adjacent R1 to form a substituted or unsubstituted benzene ring or a substituted or unsubstituted naphthalene ring.

In an exemplary embodiment of the present specification, Ar15 is bonded to adjacent R1 to form a benzene ring which is unsubstituted or substituted with one substituent selected from the group consisting of deuterium, a halogen group, a nitrile group, an alkyl group, a haloalkyl group, an alkoxy group, a silyl group, and a cycloalkyl group, or a substituent to which two or more substituents selected from the group are linked; or a naphthalene ring which is unsubstituted or substituted with one substituent selected from the group consisting of deuterium, a halogen group, a nitrile group, an alkyl group, a haloalkyl group, an alkoxy group, a silyl group, and a cycloalkyl group, or a substituent to which two or more substituents selected from the group are linked.

In an exemplary embodiment of the present specification, Ar15 is bonded to adjacent R1 to form a benzene ring which is unsubstituted or substituted with deuterium, a halogen group, a nitrile group, a methyl group, an isopropyl group, a t-butyl group, a methoxy group, CD3, a phenyl group, a phenyl group which is substituted with deuterium, a phenyl group which is substituted with a halogen group, a phenyl group which is substituted with a nitrile group, or a phenyl group which is substituted with a methyl group; or a naphthalene ring.

In an exemplary embodiment of the present specification, Ar15 is a substituted or unsubstituted aryl group; or a substituted or unsubstituted heteroaryl group.

According to an exemplary embodiment of the present specification, Ar15 is a substituted or unsubstituted aryl group having 6 to 30 carbon atoms.

In an exemplary embodiment of the present specification, Ar15 is a substituted or unsubstituted phenyl group, a substituted or unsubstituted biphenyl group, or a substituted or unsubstituted naphthyl group.

According to an exemplary embodiment of the present specification, Ar15 is an aryl group which is unsubstituted or substituted with one substituent selected from the group consisting of deuterium, a halogen group, a nitrile group, an alkyl group, a haloalkyl group, an alkoxy group, a silyl group, and a cycloalkyl group, or a substituent to which two or more substituents selected from the group are linked.

In an exemplary embodiment of the present specification, Ar15 is a phenyl group which is unsubstituted or substituted with deuterium, a halogen group, a nitrile group, a methyl group, an ethyl group, a propyl group, an isopropyl group, a t-butyl group, $CD_3$, a trifluoromethyl group, a methoxy group, an ethoxy group, a trimethylsilyl group, a triphenylsilyl group, or a cyclohexyl group; a biphenyl group; or a naphthyl group.

In an exemplary embodiment of the present specification, R1 is hydrogen or deuterium, or is bonded to adjacent Ar15 to form a substituted or unsubstituted ring.

In an exemplary embodiment of the present specification, R1 is hydrogen or deuterium, or is bonded to adjacent Ar15 to form a substituted or unsubstituted benzene ring or a substituted or unsubstituted naphthalene ring.

In an exemplary embodiment of the present specification, r1 is 0.

In an exemplary embodiment of the present specification, r1 is 1.

In an exemplary embodiment of the present specification, Chemical Formula 1 is Chemical Formula 2:

Chemical Formula 2

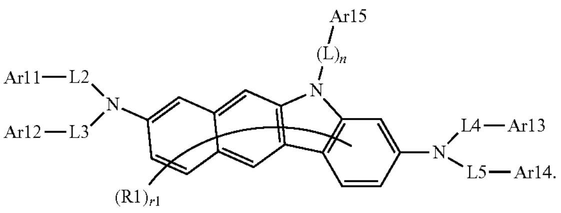

In Chemical Formula 2, the definitions of Ar11 to Ar15, L, L2 to L5, R1, r1, and n are the same as those defined in Chemical Formula 1.

In an exemplary embodiment of the present specification, Chemical Formula 1 is any one of the following Chemical Formulae 301 to 303:

Chemical Formula 301

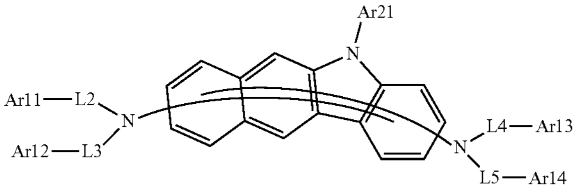

Chemical Formula 302

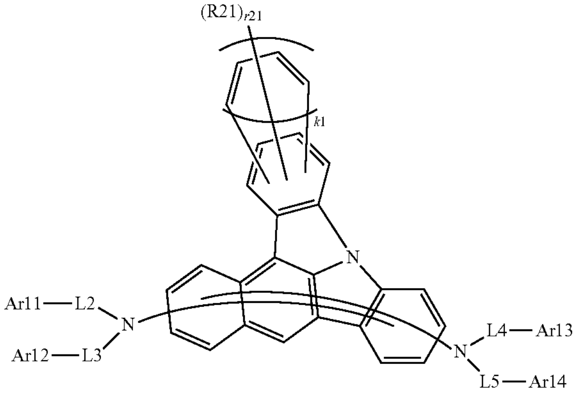

Chemical Formula 303

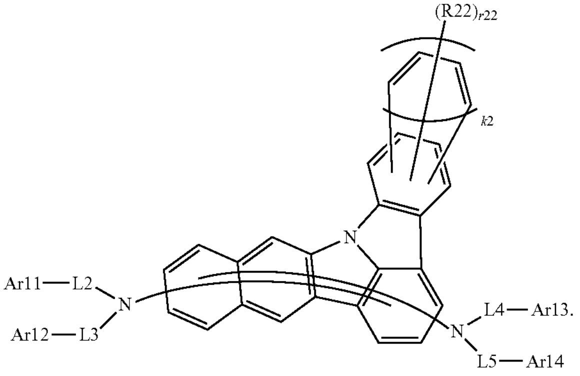

In Chemical Formulae 301 to 303:

the definitions of L2 to L5 and Ar11 to Ar14 are the same as those defined in Chemical Formula 1;

Ar21 is a substituted or unsubstituted aryl group or a substituted or unsubstituted heteroaryl group;

R21 and R22 are the same as or different from each other, and are each independently hydrogen, deuterium, a halogen group, a nitrile group, a substituted or unsubstituted alkyl group, a substituted or unsubstituted haloalkyl group, a substituted or unsubstituted silyl group, a substituted or unsubstituted alkoxy group, a substituted or unsubstituted cycloalkyl group, a substituted or unsubstituted aryl group, or a substituted or unsubstituted heteroaryl group;

k1 and k2 are 0 or 1;

r21 and r22 are an integer from 0 to 6;

when r21 is 2 or more, the R21s are the same as or different from each other; and when r22 is 2 or more, the R22s are the same as or different from each other.

In an exemplary embodiment of the present specification, when k1 or k2 is 1, a naphthalene ring is fused to benzocarbazole.

In an exemplary embodiment of the present specification, R21 and R22 are the same as or different from each other, and are each independently one substituent selected from the group consisting of deuterium, a halogen group, a nitrile group, an alkyl group, a haloalkyl group, an alkoxy group, a silyl group, and a cycloalkyl group, or a substituent to which two or more substituents selected from the group are linked.

In an exemplary embodiment of the present specification, R21 and R22 are the same as or different from each other, and are each independently deuterium, a halogen group, a nitrile group, a methyl group, an isopropyl group, a t-butyl group, a methoxy group, $CD_3$, a phenyl group, a phenyl group which is substituted with deuterium, a phenyl group which is substituted with a halogen group, a phenyl group which is substituted with a nitrile group, or a phenyl group which is substituted with a methyl group.

In an exemplary embodiment of the present specification, Chemical Formula 301 is Chemical Formula 401:

Chemical Formula 401

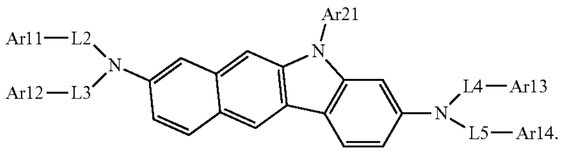

In Chemical Formula 401, definitions of Ar21, L2 to L5, and Ar11 to Ar14 are the same as those defined in Chemical Formula 301.

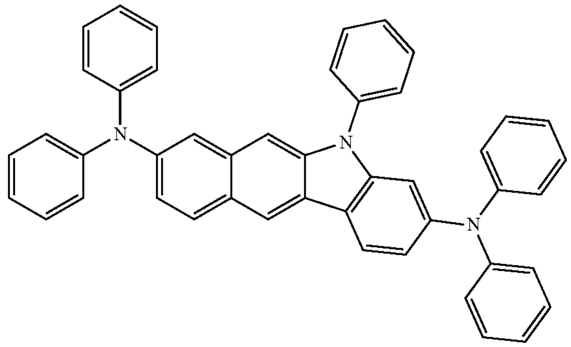

In an exemplary embodiment of the present specification, Chemical Formula 302 is Chemical Formula 402:

Chemical Formula 402

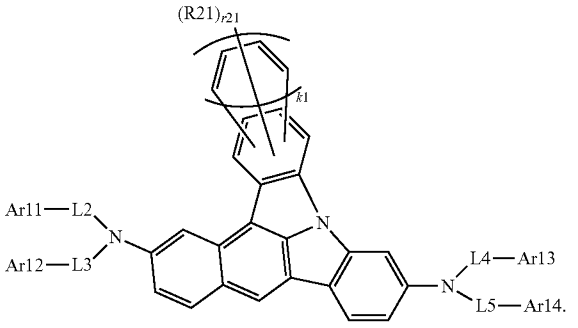

In Chemical Formula 402, the definitions of R21, r21, k1, L2 to L5, and Ar11 to Ar14 are the same as those defined in Chemical Formula 302.

In an exemplary embodiment of the present specification, Chemical Formula 303 is Chemical Formula 403:

Chemical Formula 403

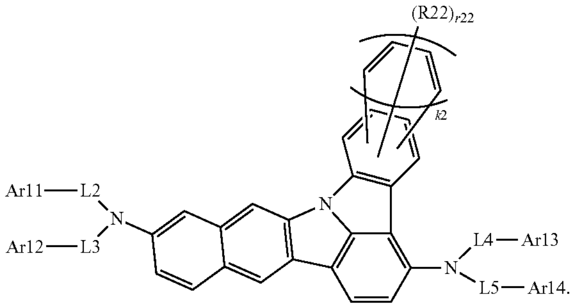

In Chemical Formula 403, definitions of R22, r22, k2, L2 to L5, and Ar11 to Ar14 are the same as those defined in Chemical Formula 303.

According to an exemplary embodiment of the present specification, Chemical Formula 1 can be any one compound selected from among the following compounds:

-continued
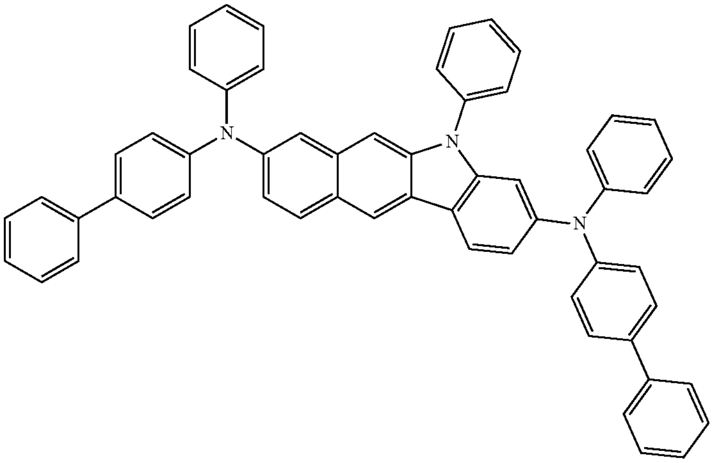
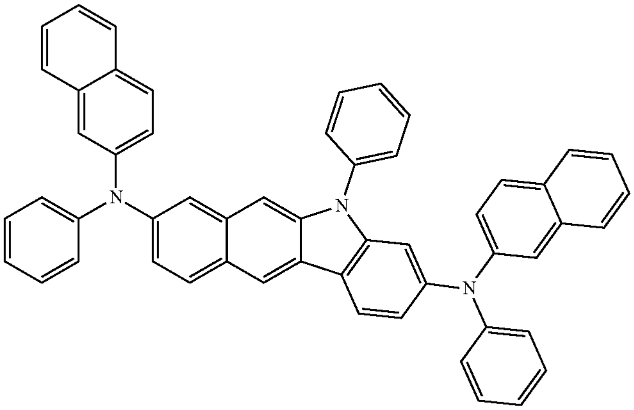
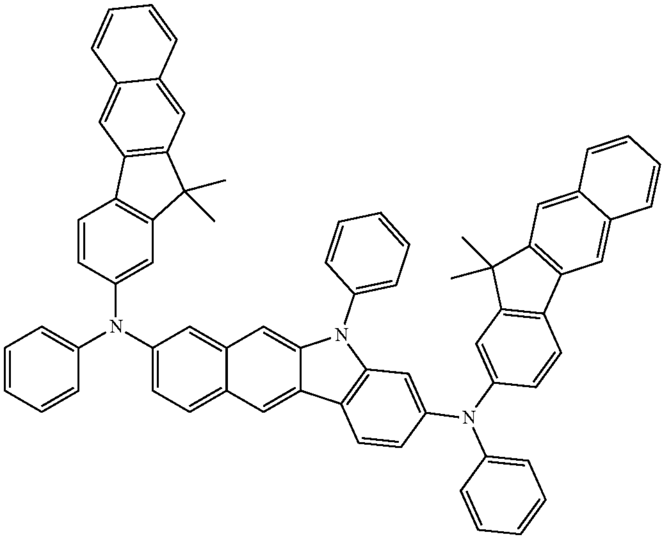

-continued
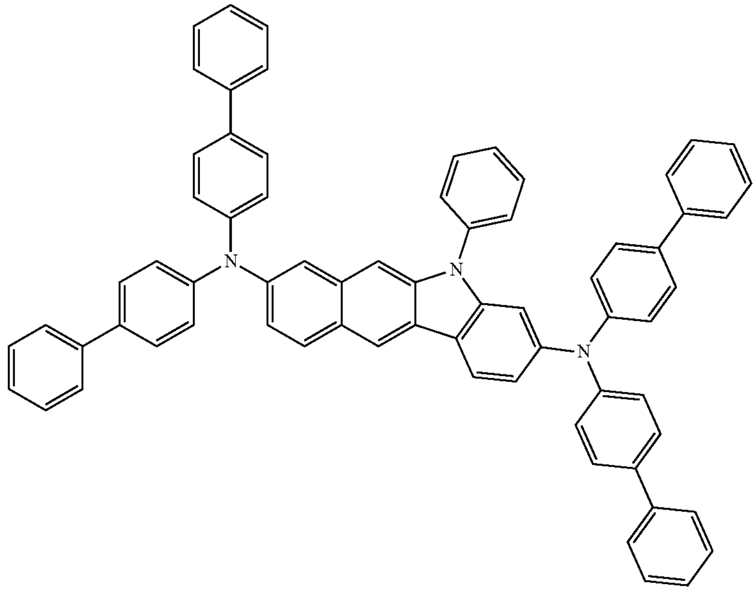
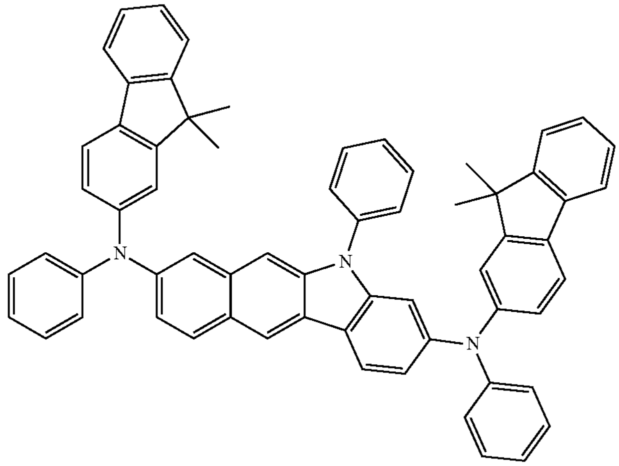
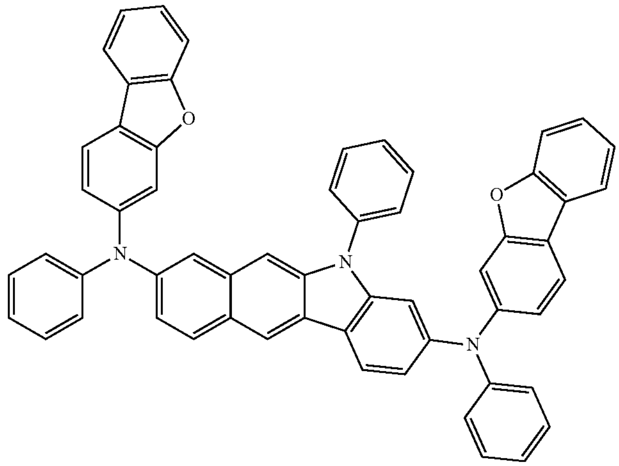

-continued
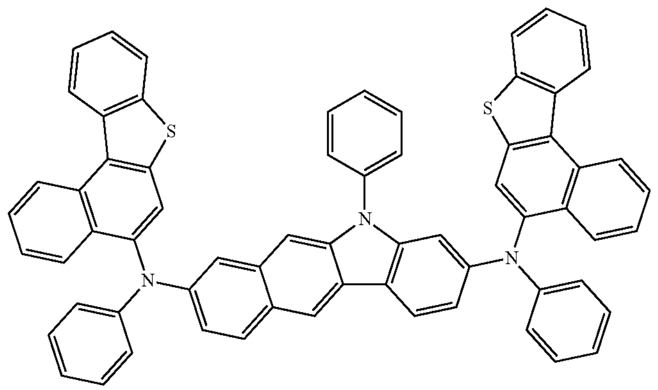
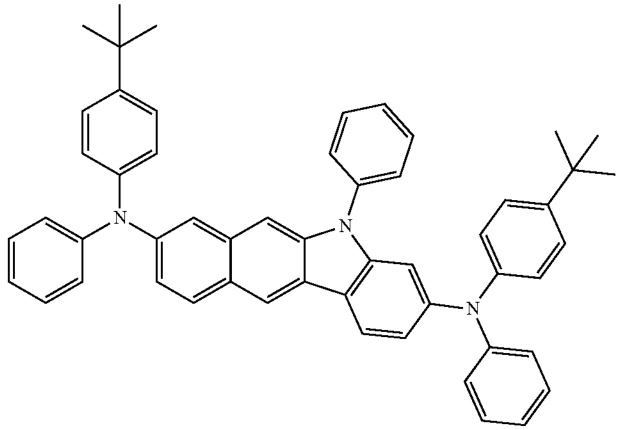
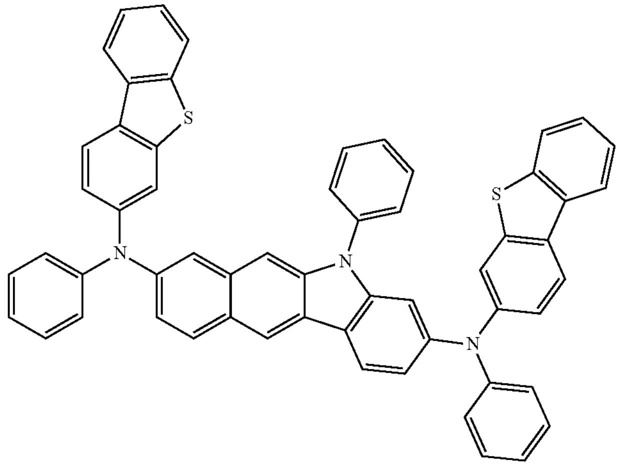
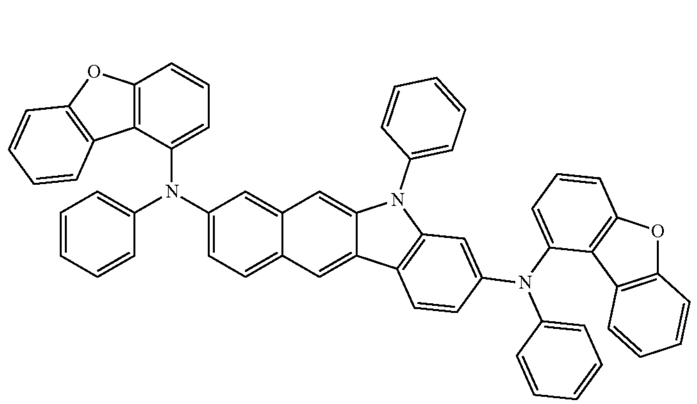

-continued
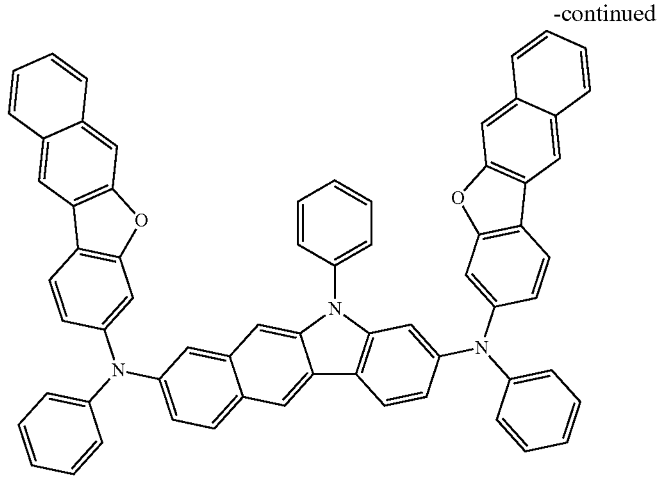
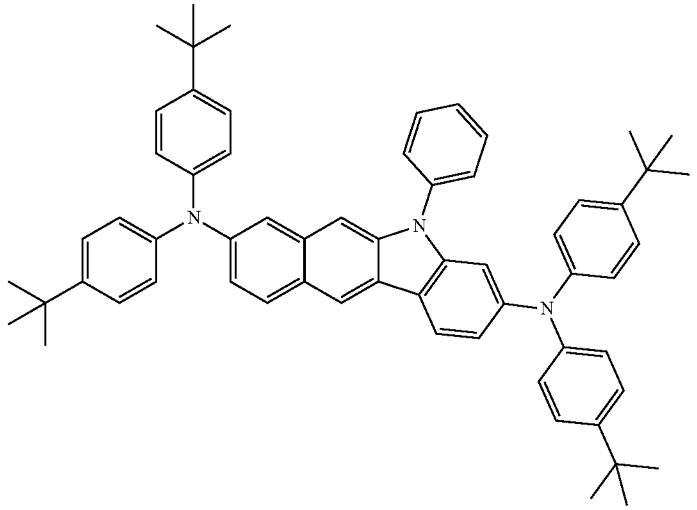
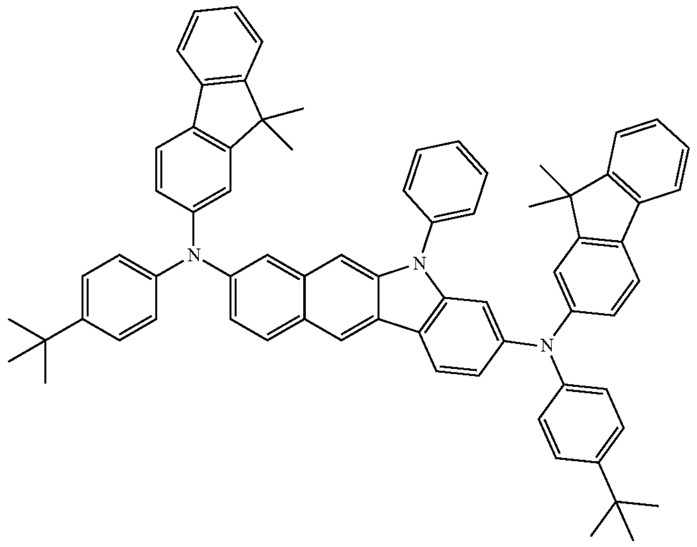

-continued
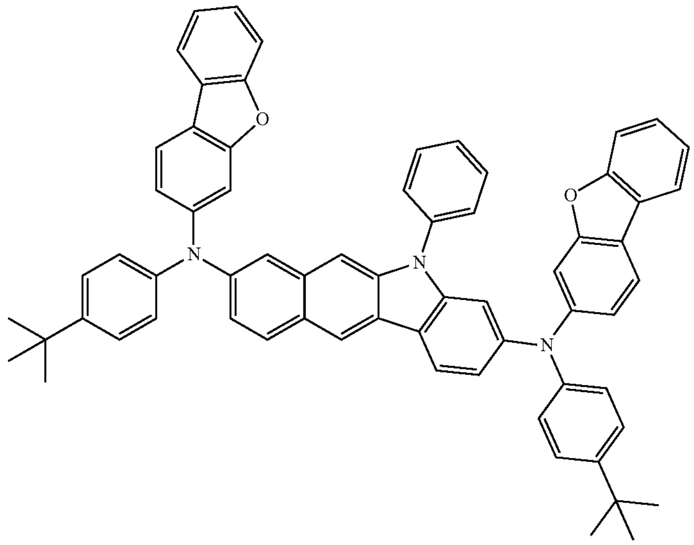
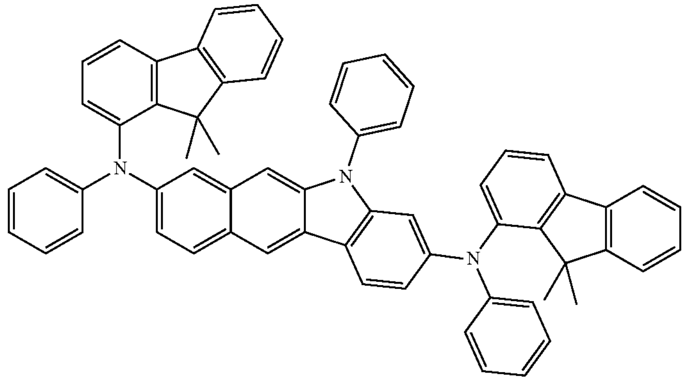
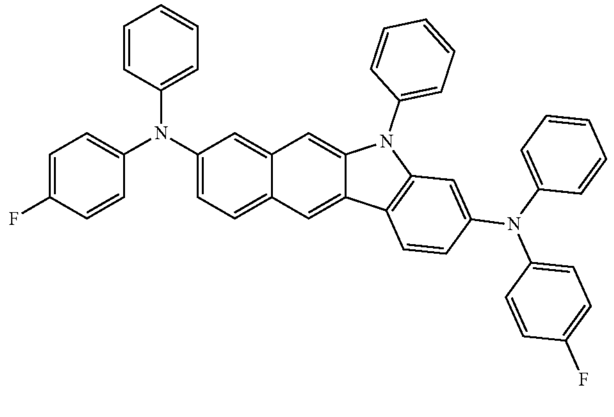

-continued
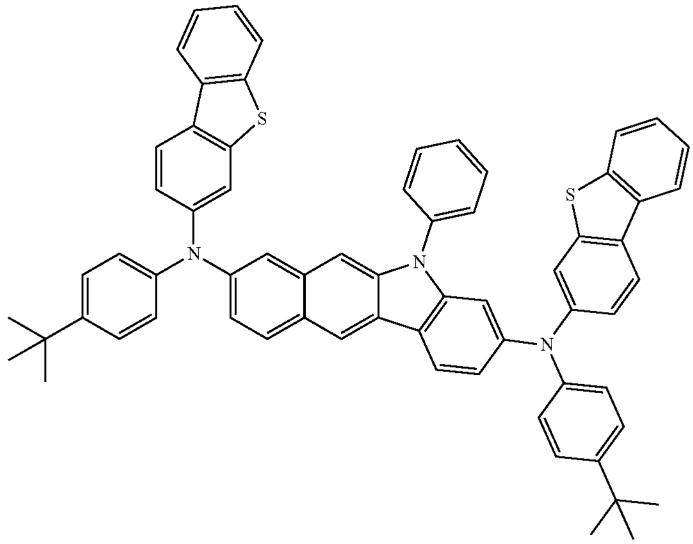
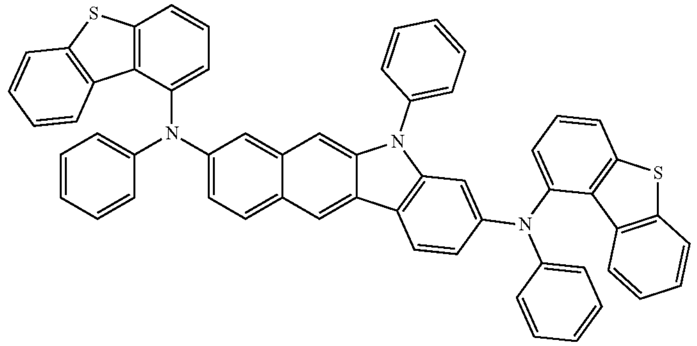
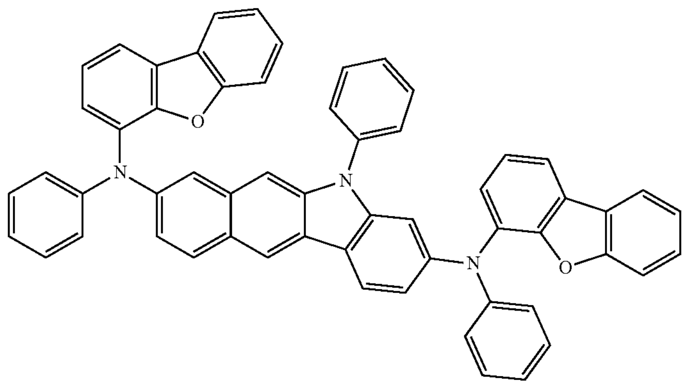

-continued
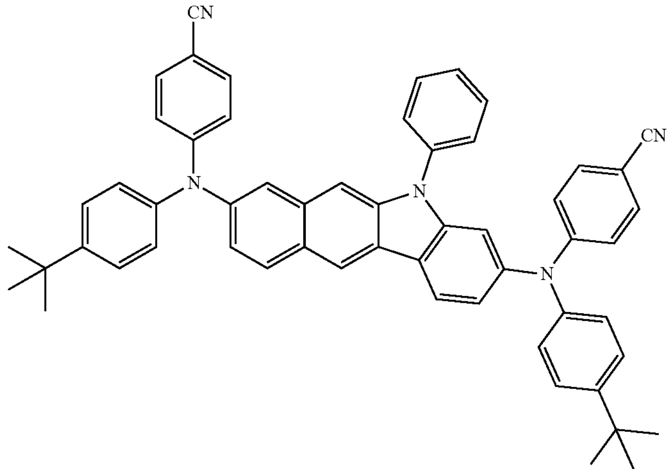
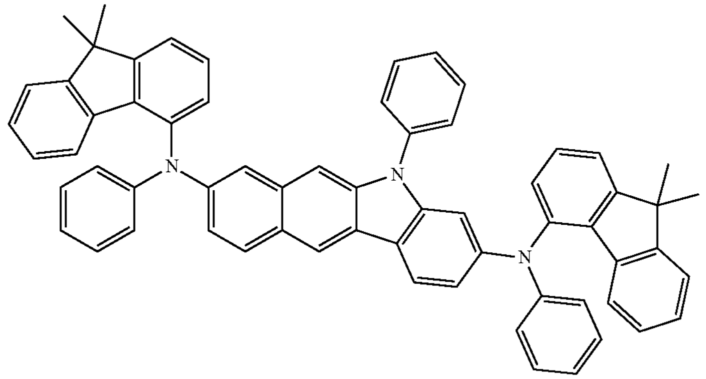
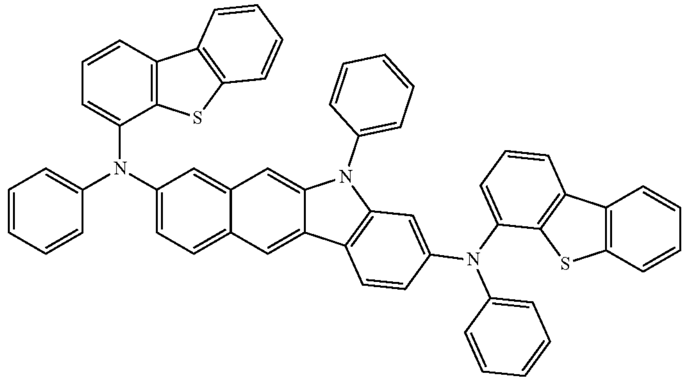
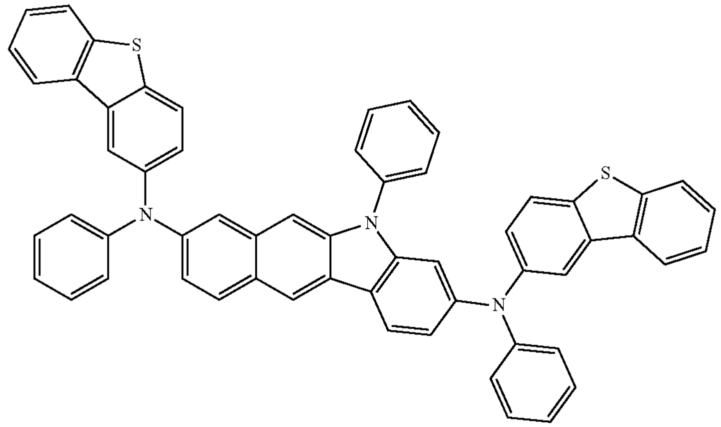

-continued
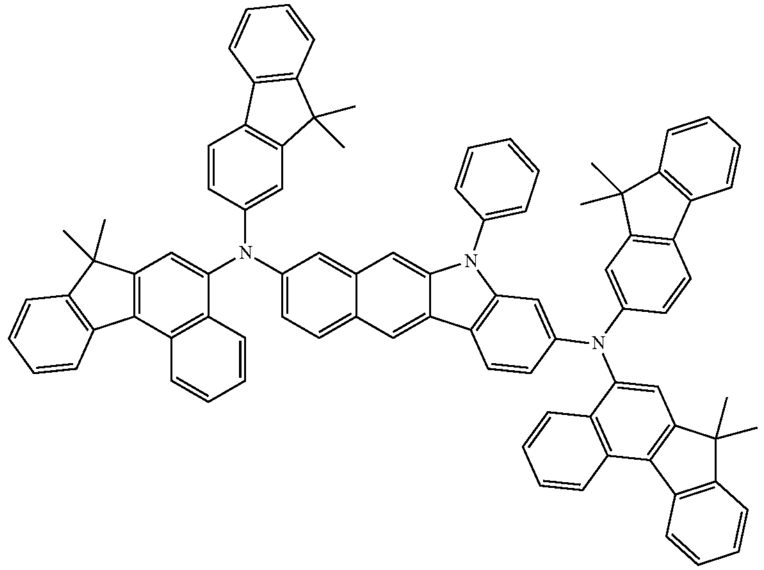
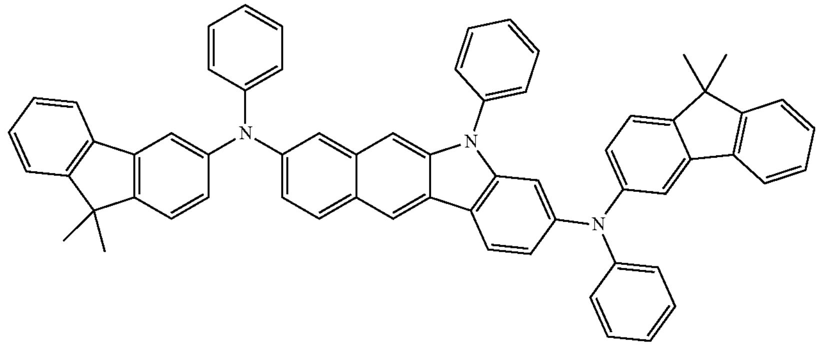
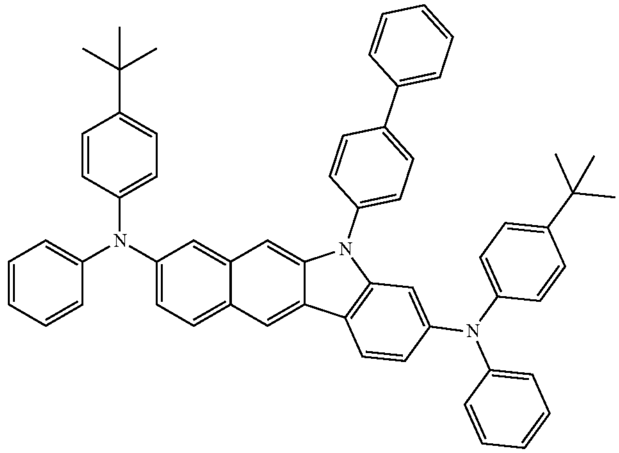
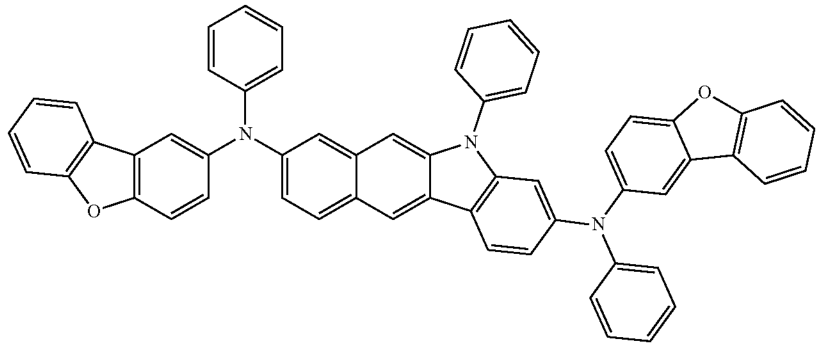

-continued
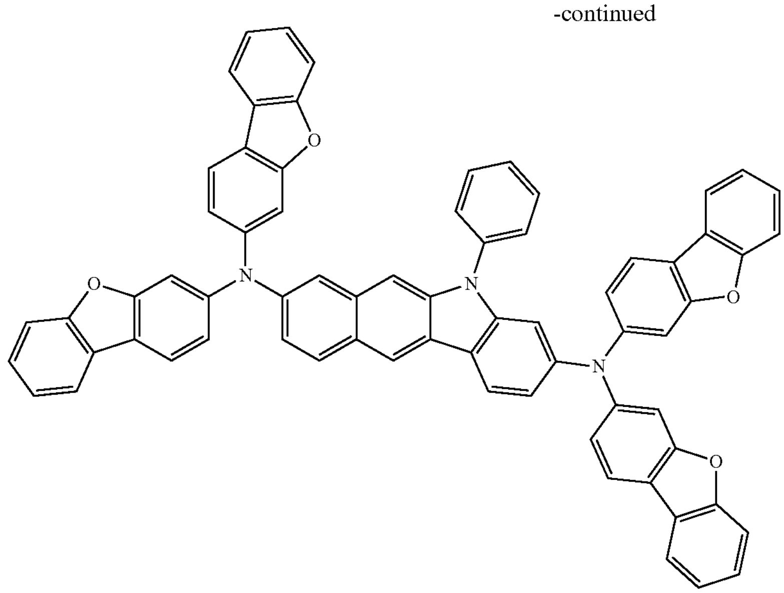
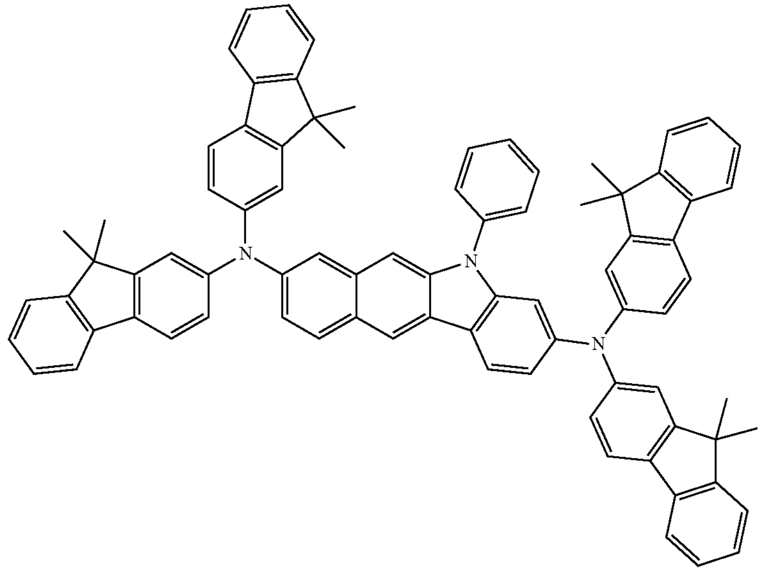
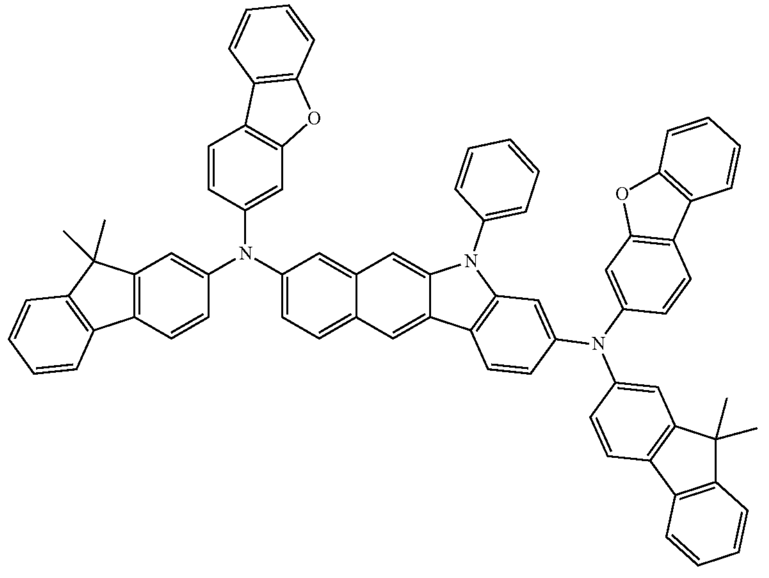

-continued
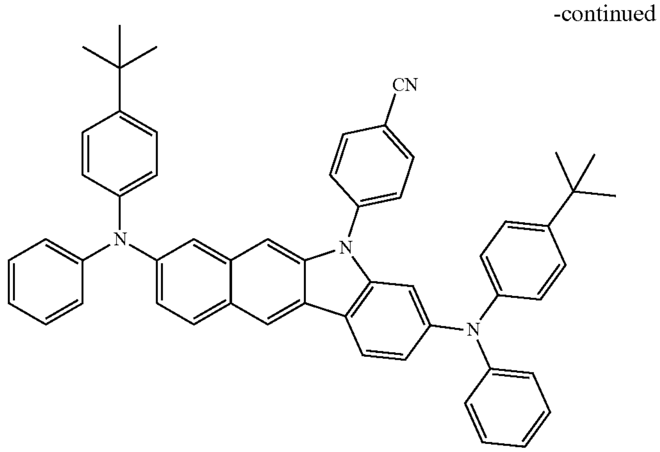
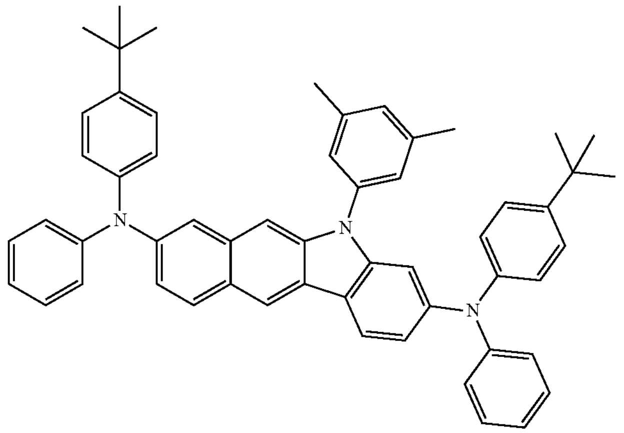
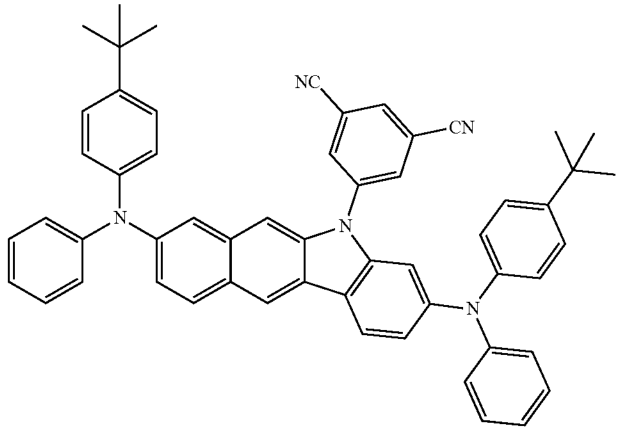
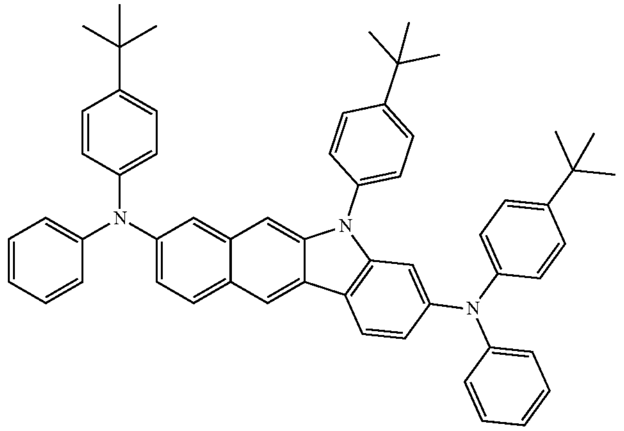

-continued
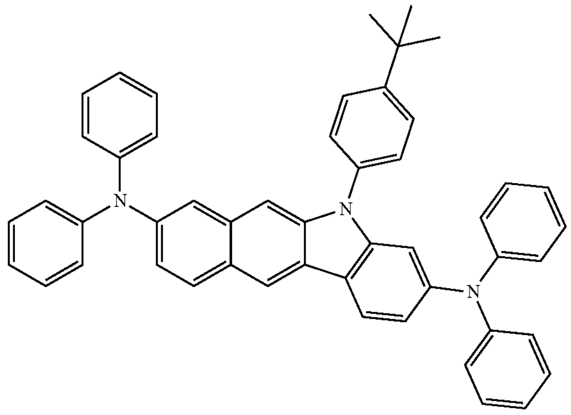
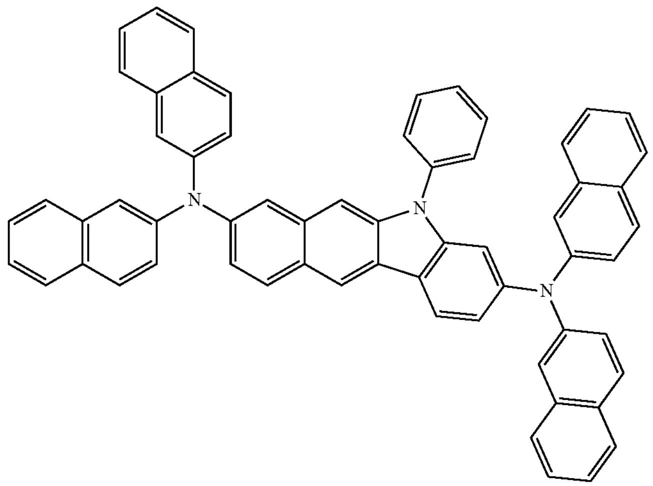
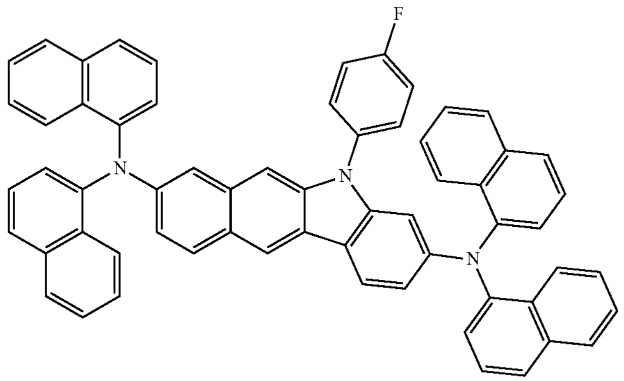

-continued
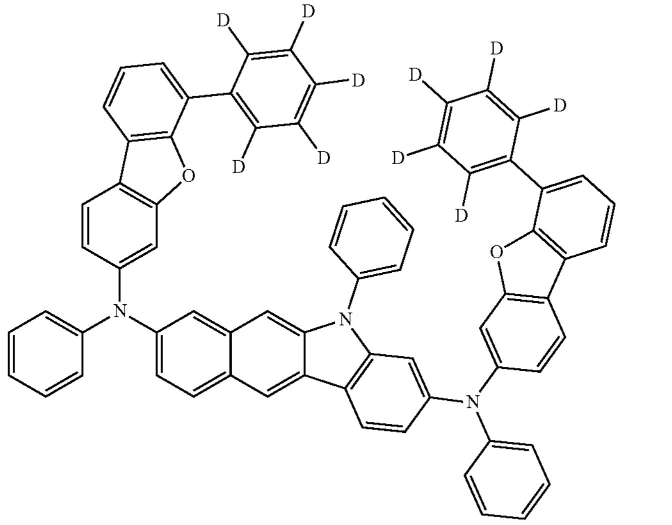
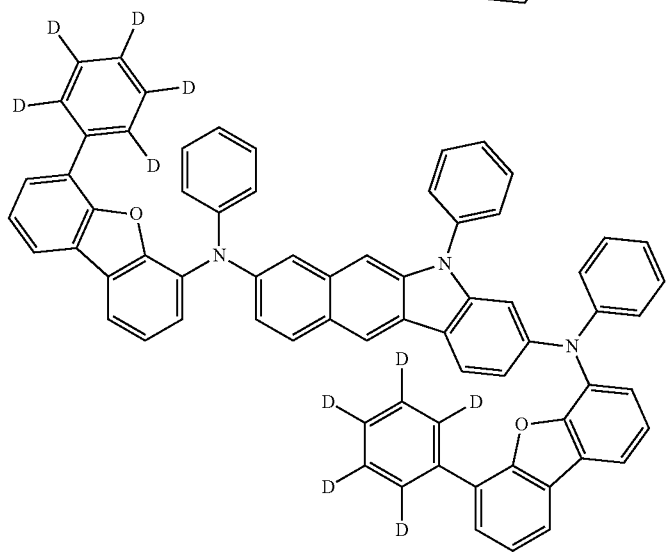
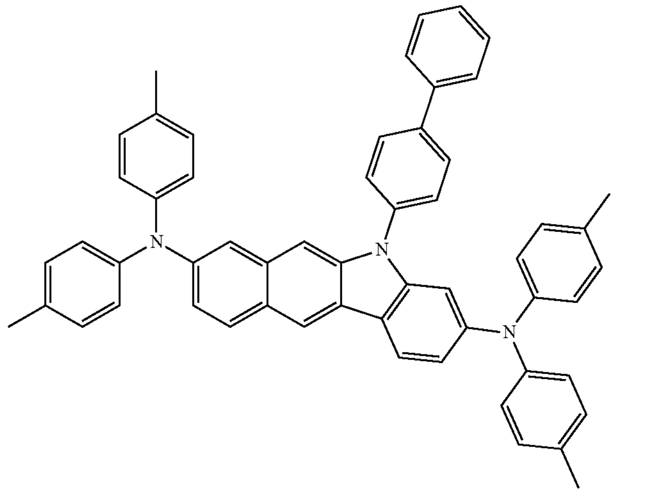

-continued
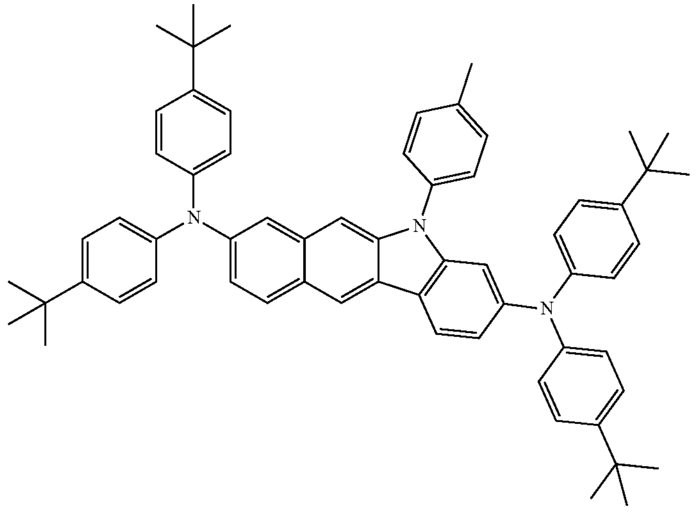
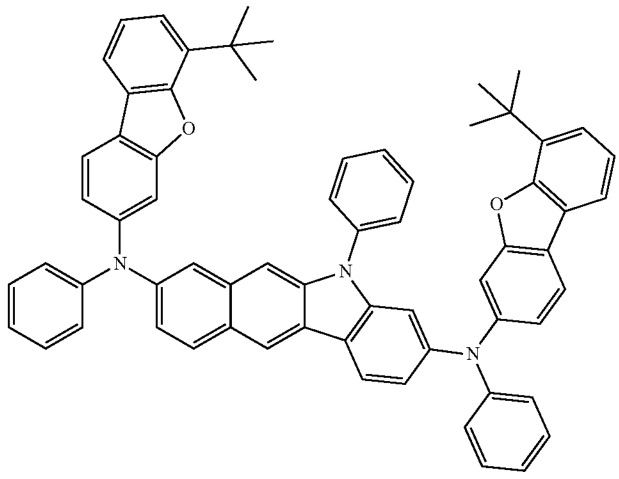
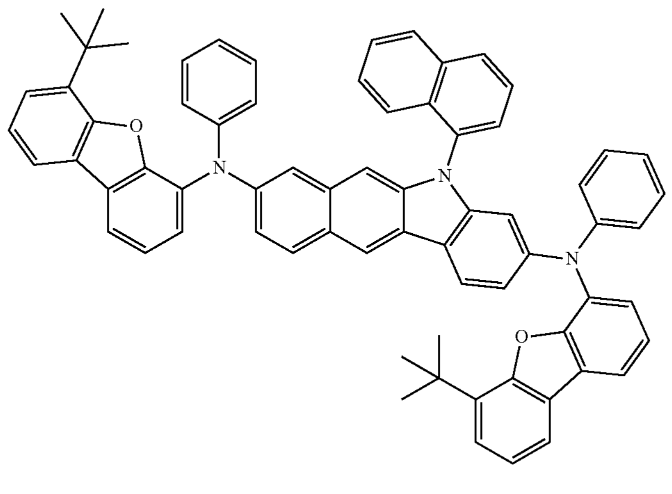

-continued
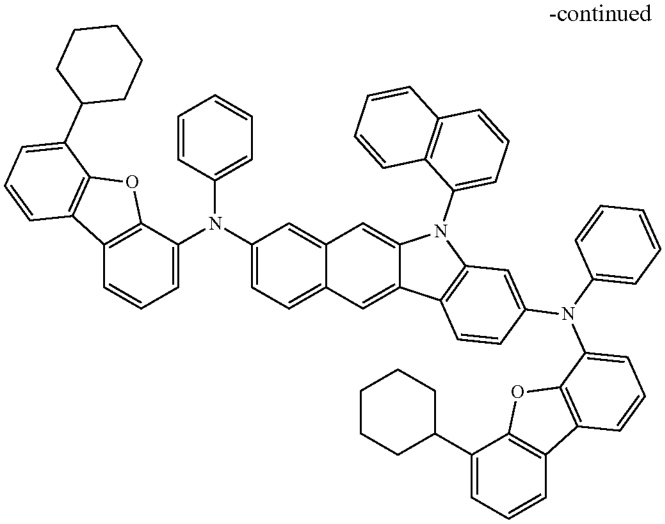
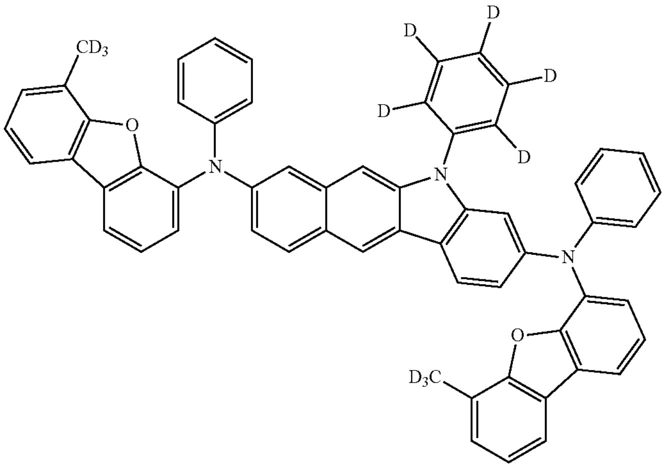
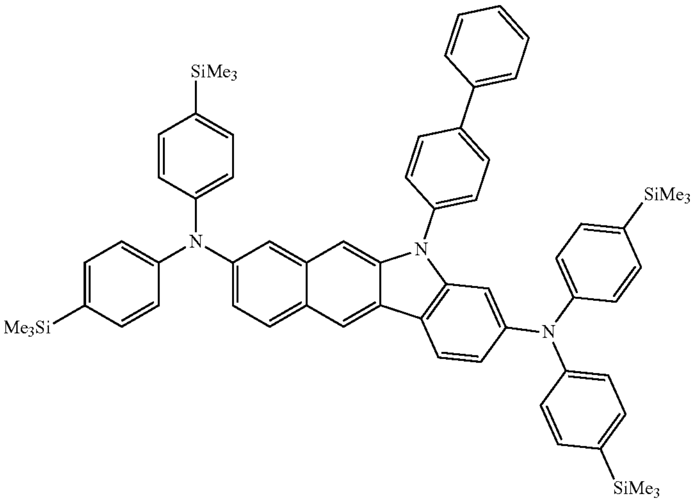

-continued
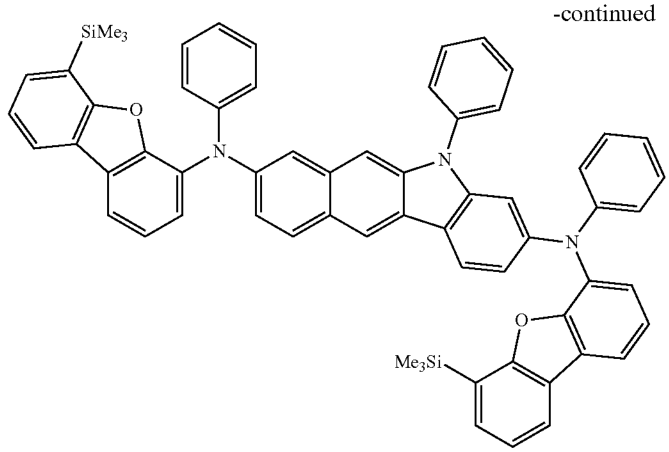
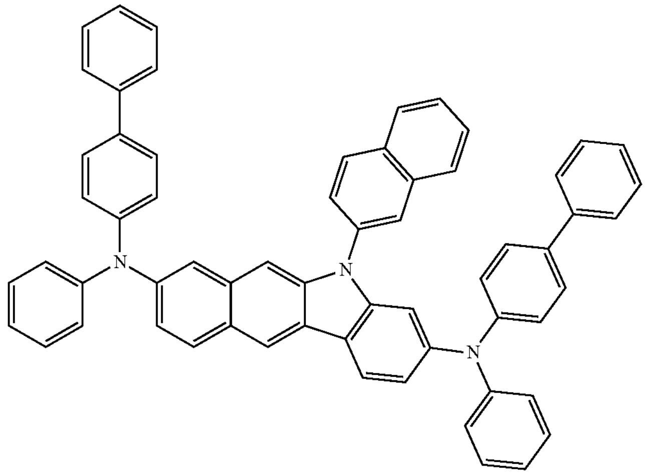
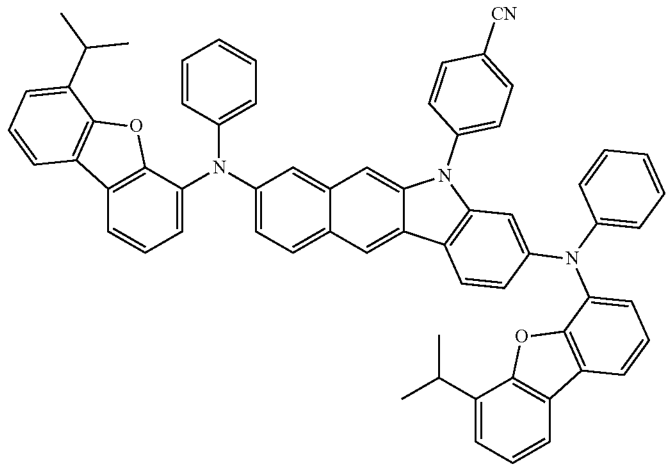

-continued
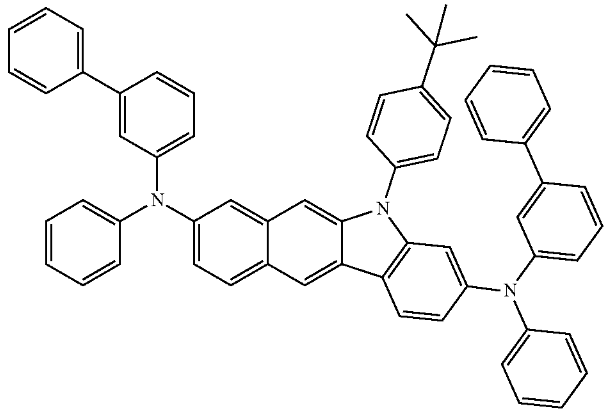
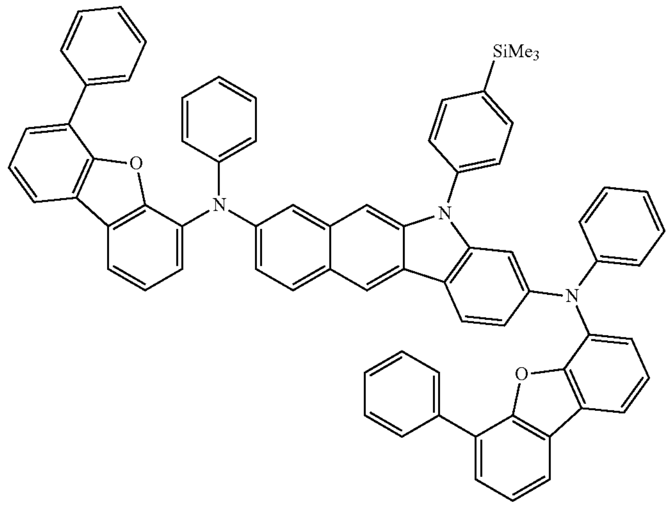
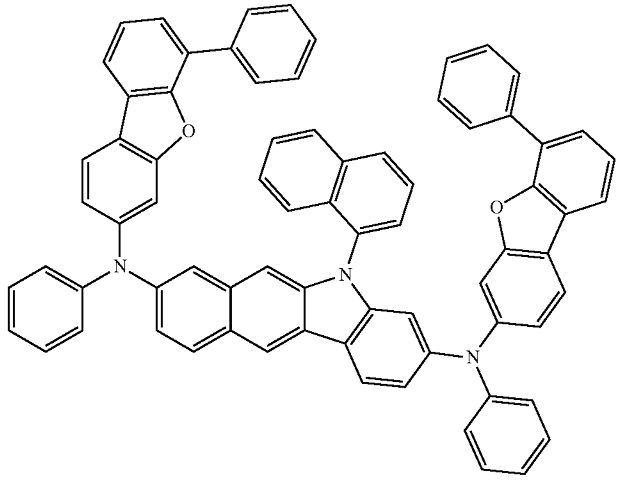

-continued
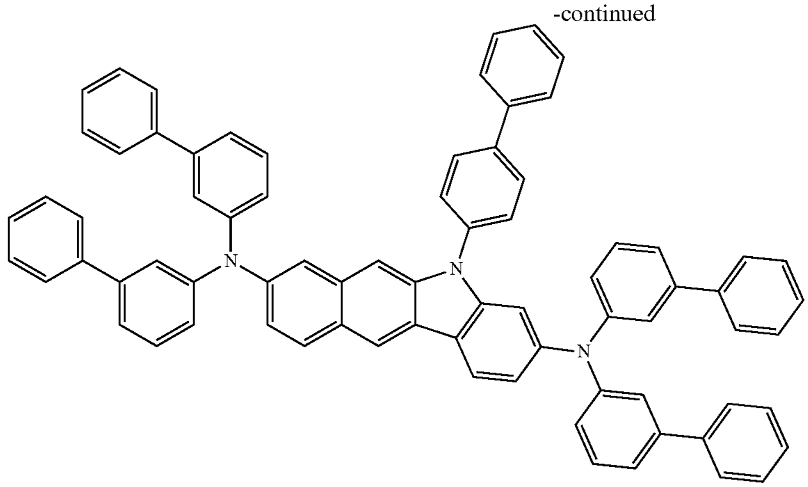
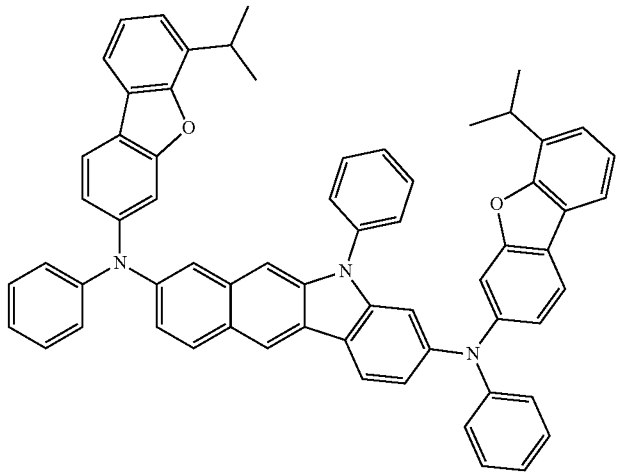
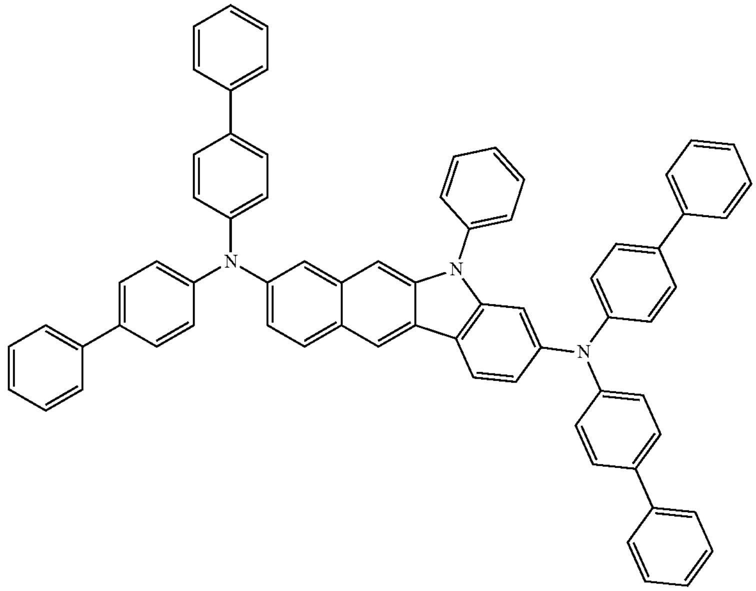

-continued
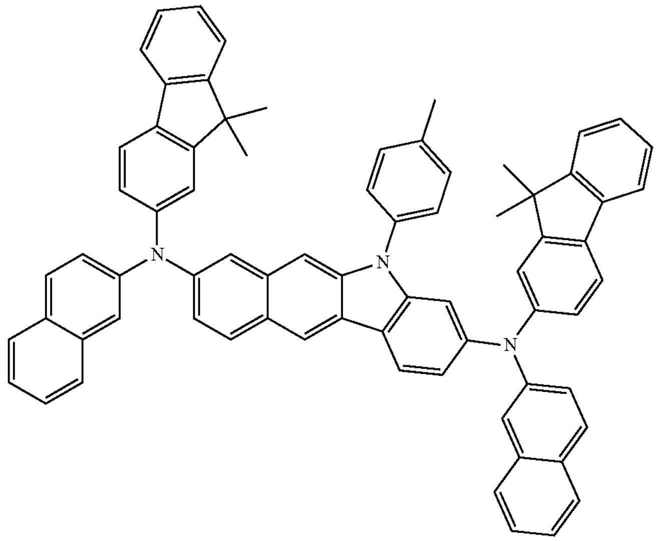
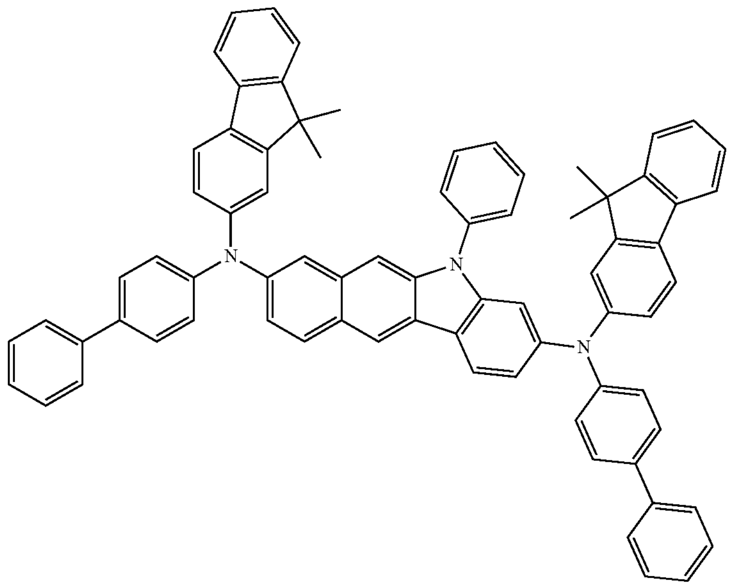
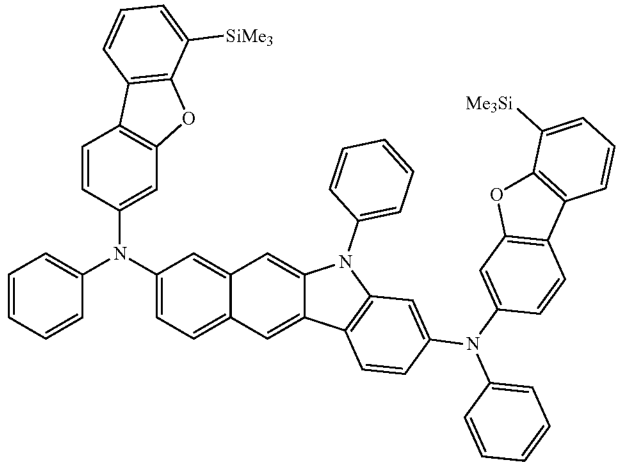

-continued
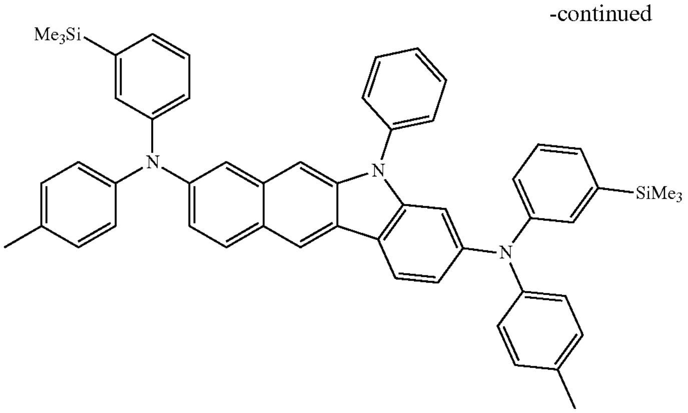
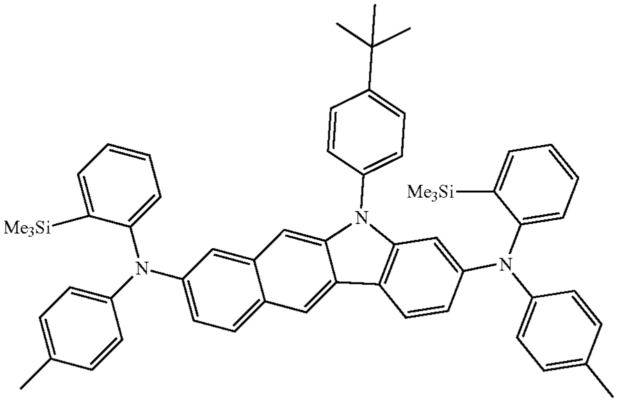
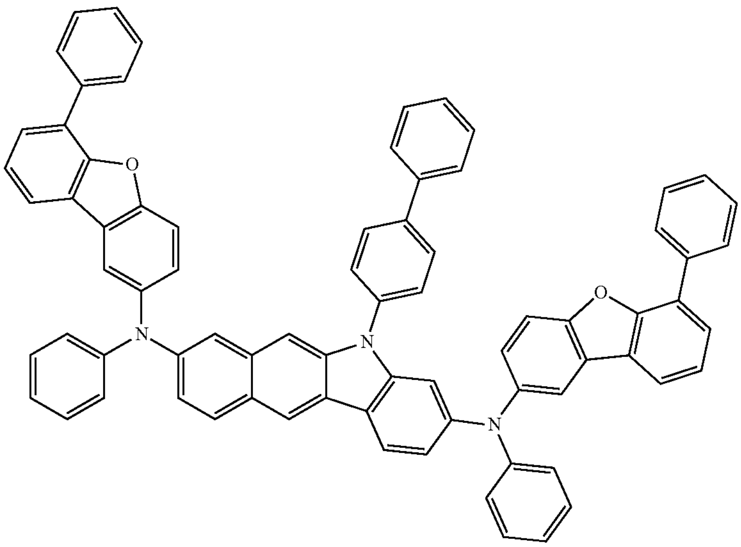

-continued
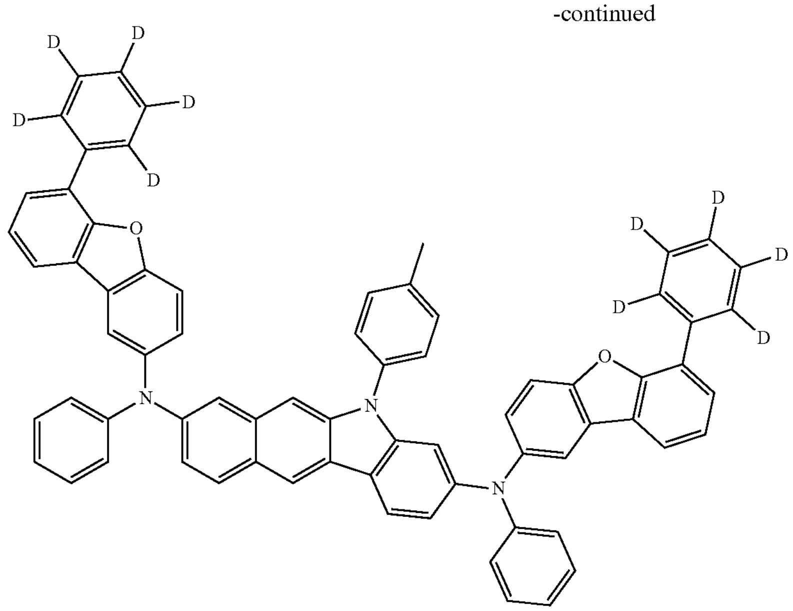
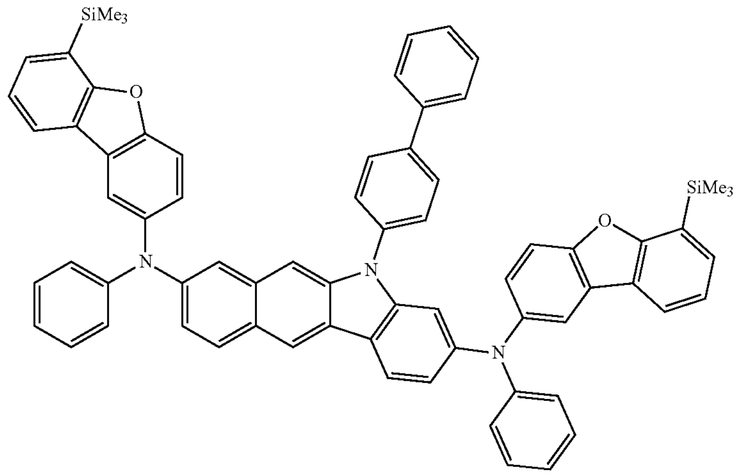
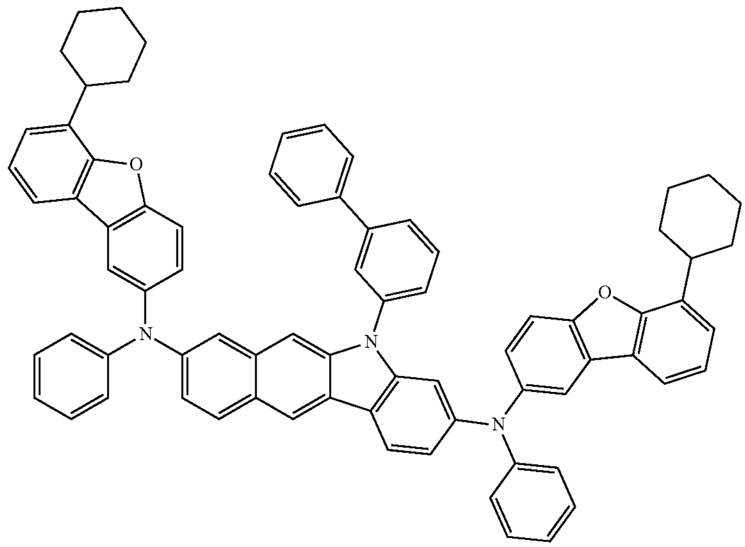

-continued
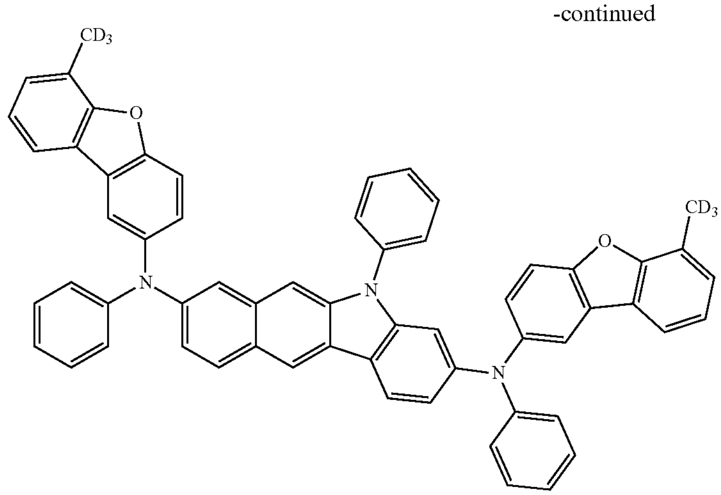
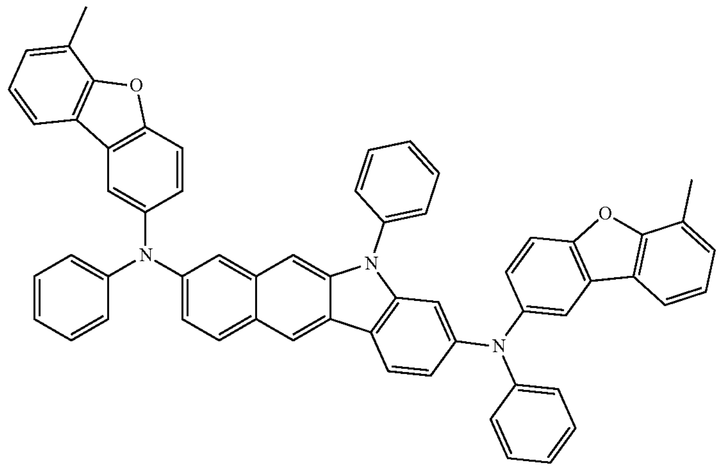
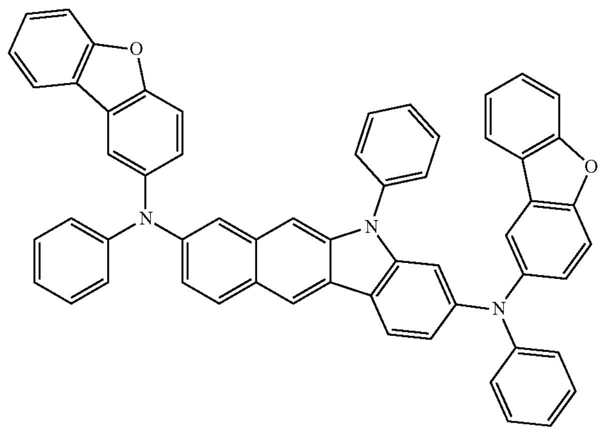

-continued
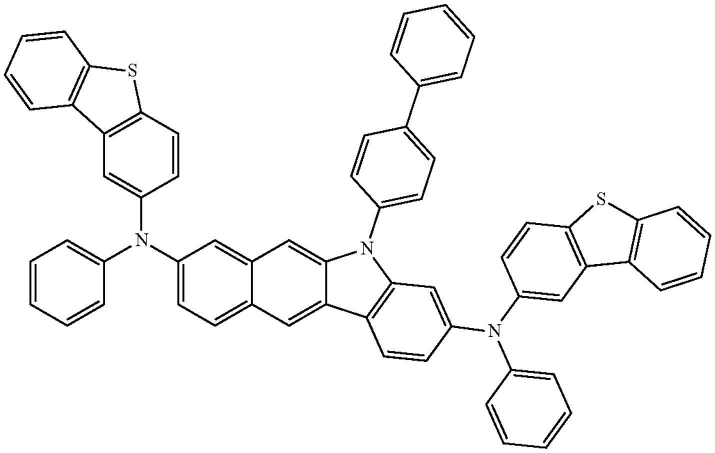
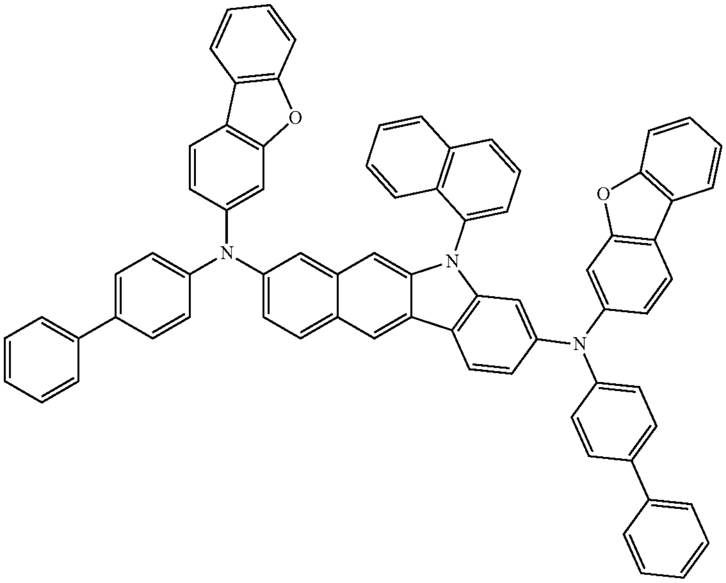
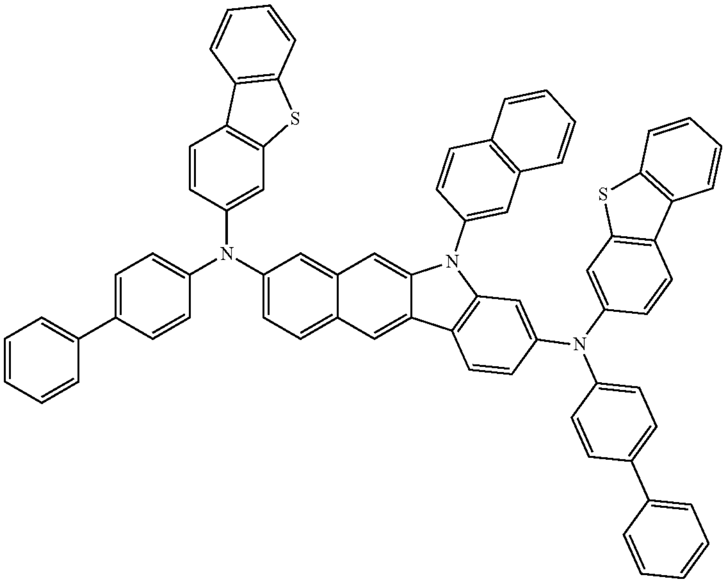

-continued
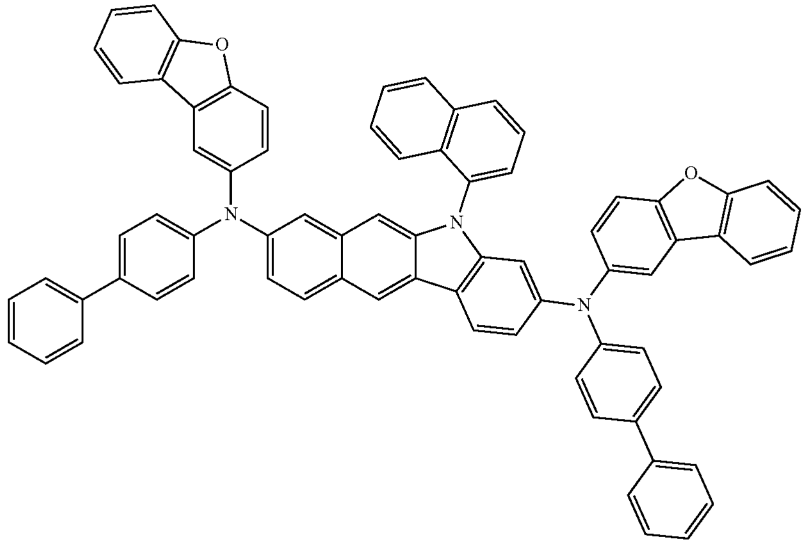
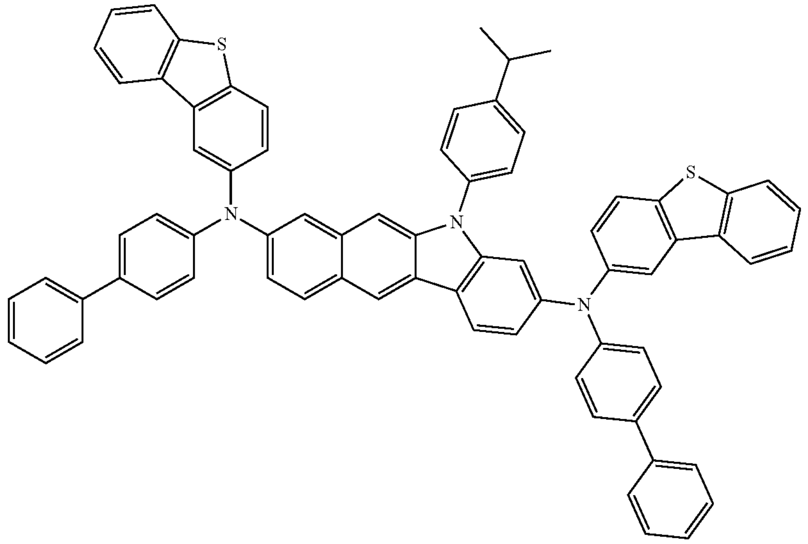
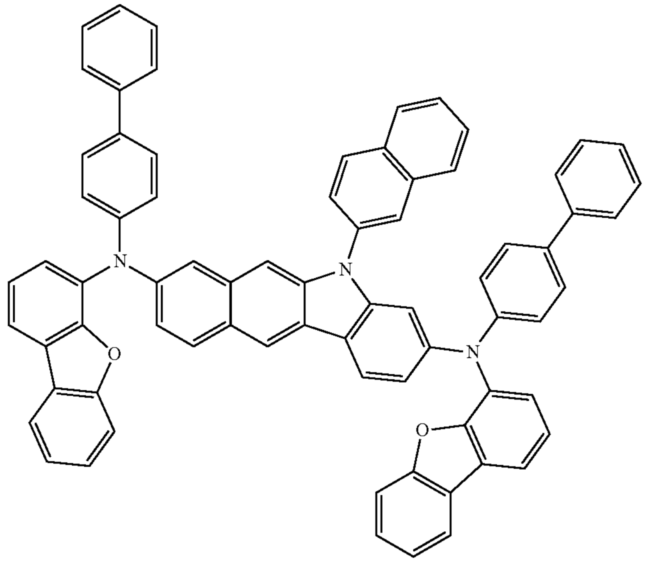

-continued
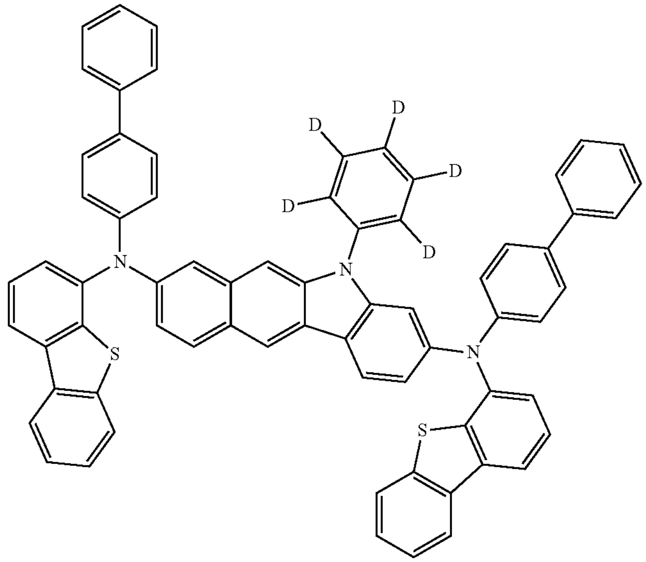
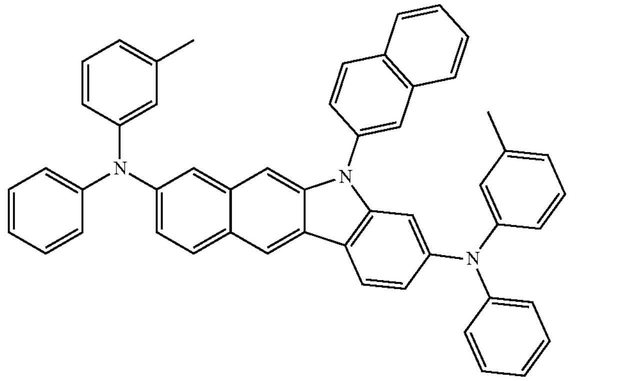
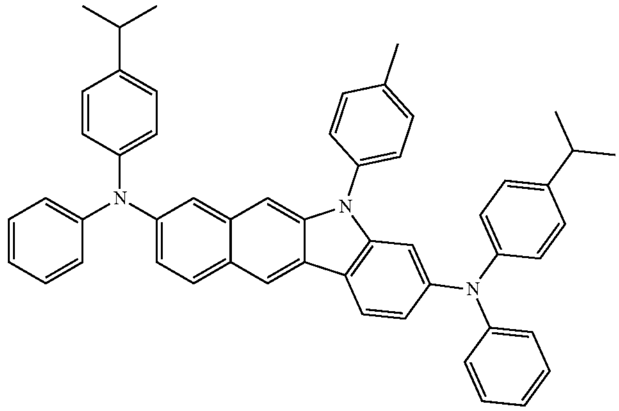

-continued
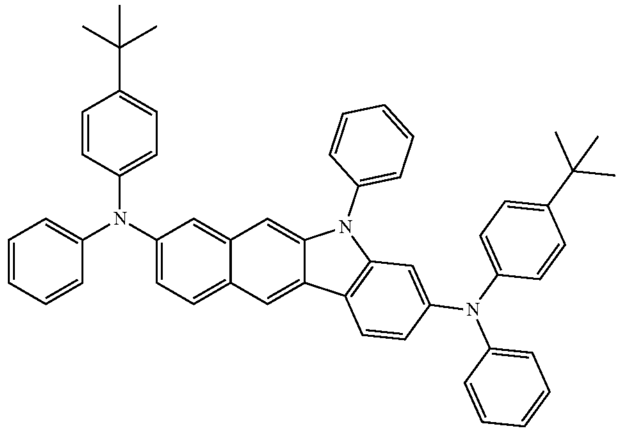
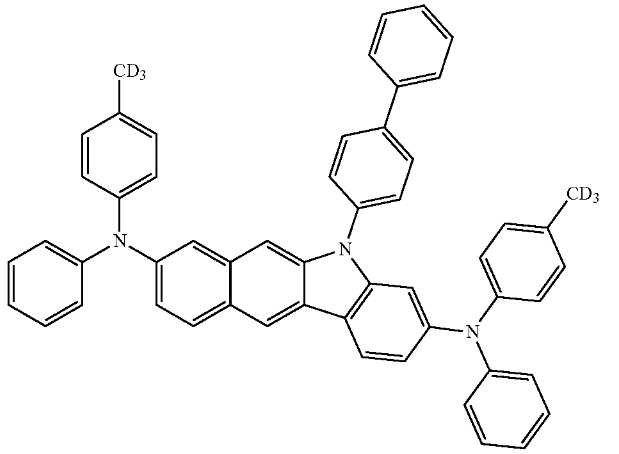
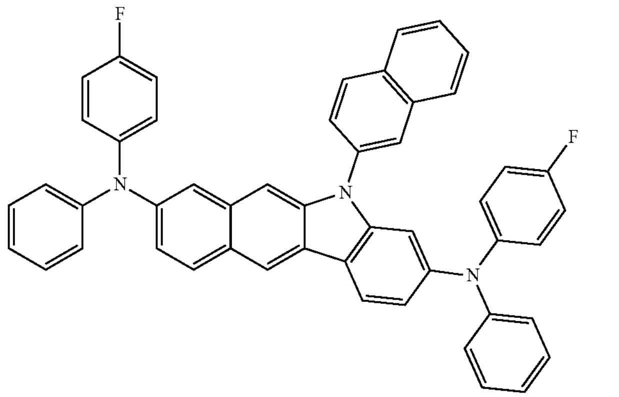
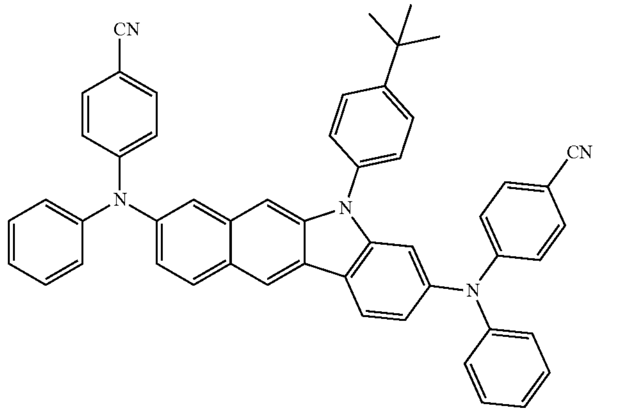

-continued
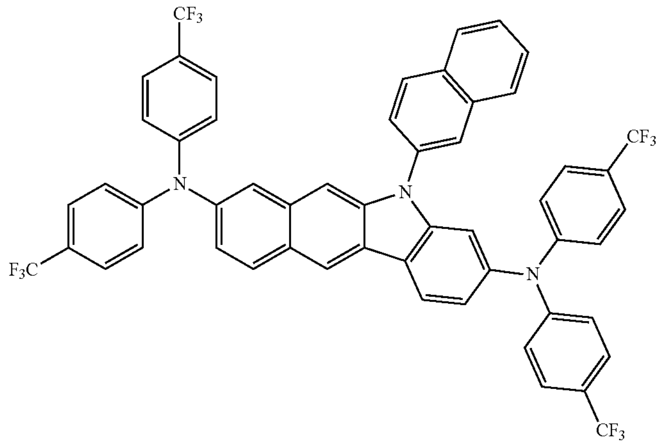
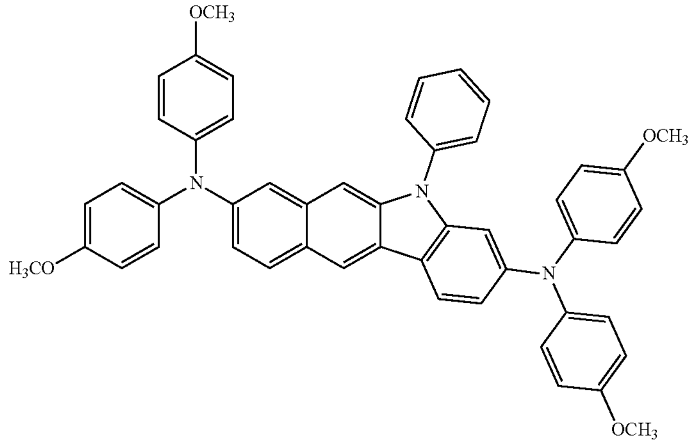
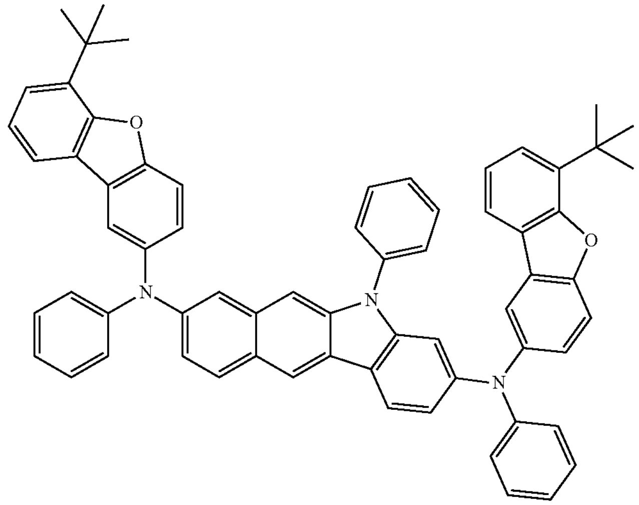

-continued
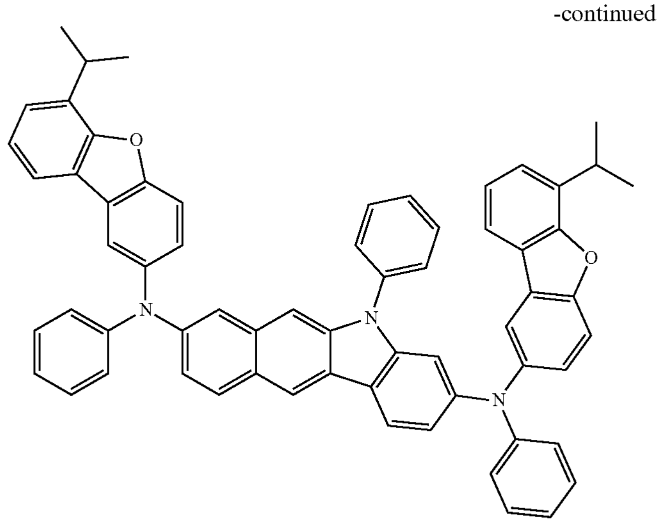
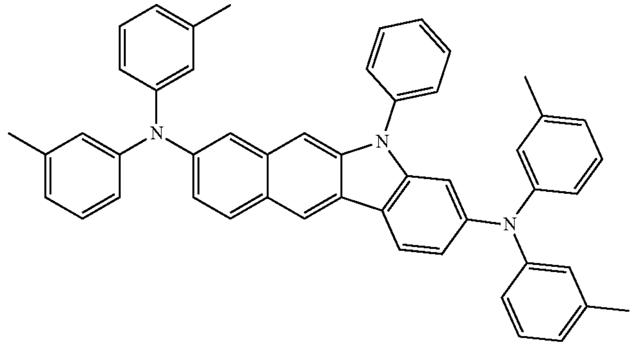
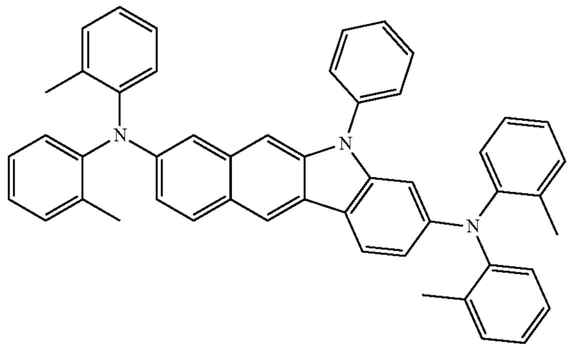
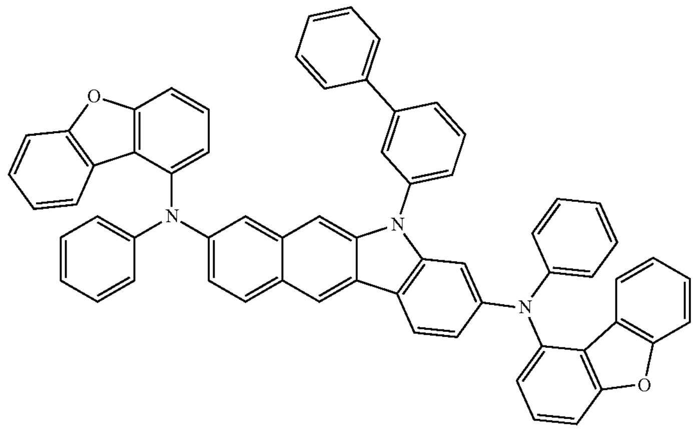

-continued
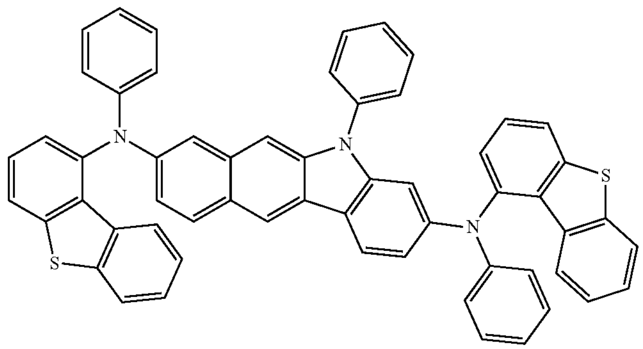
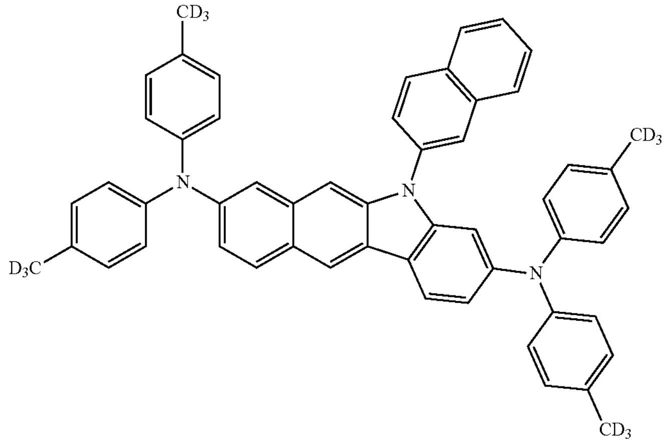
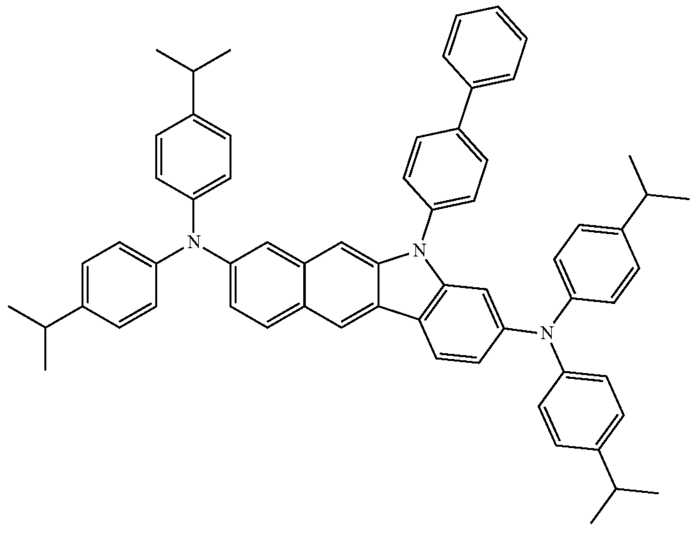

-continued
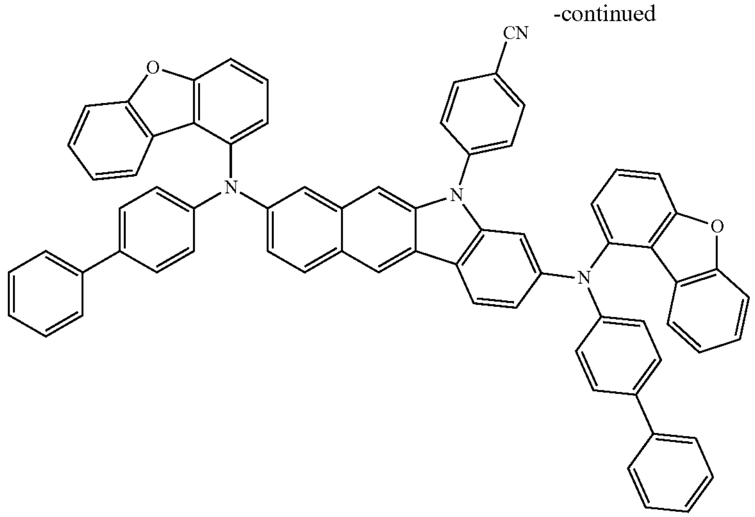
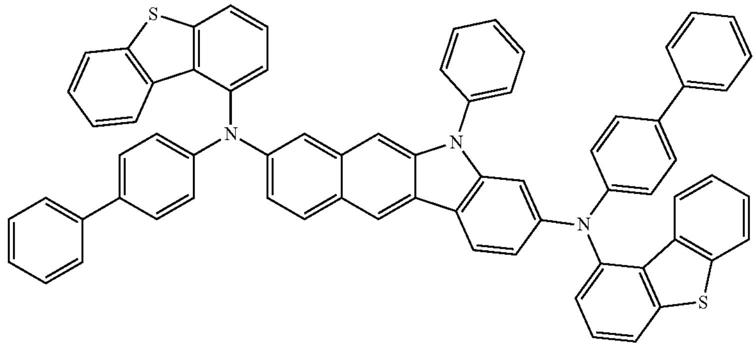
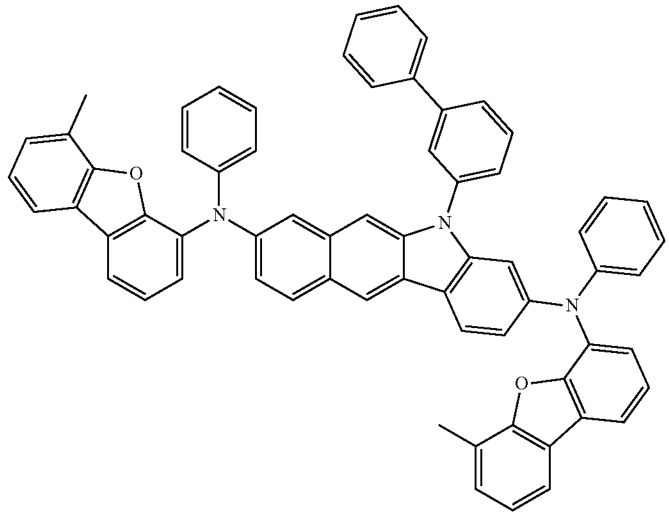

-continued
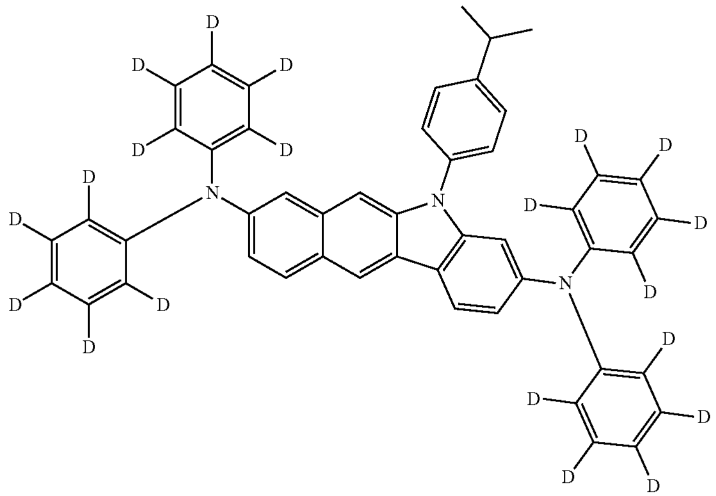
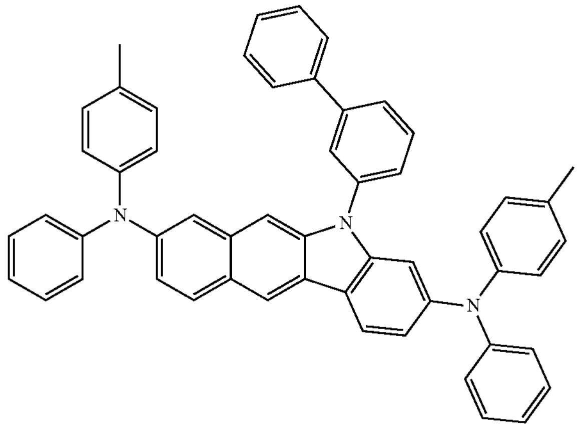
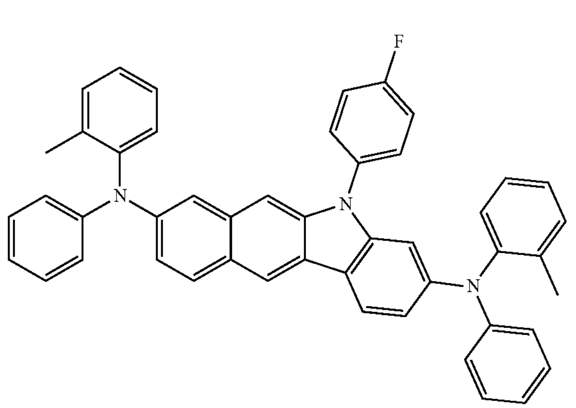

-continued
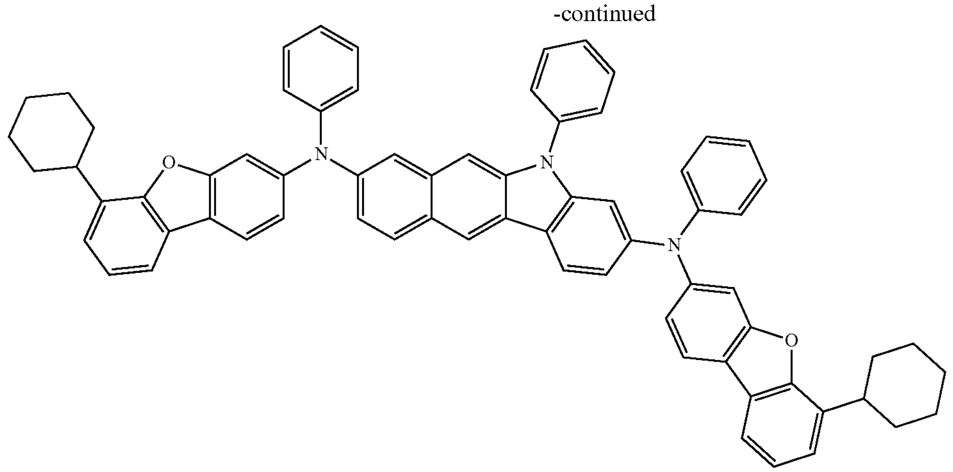
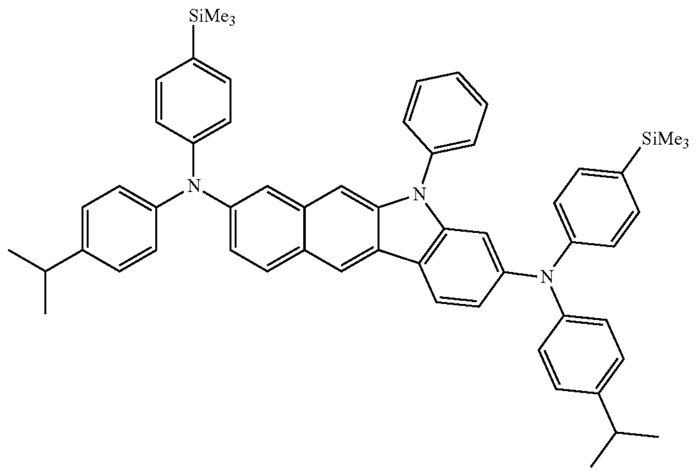
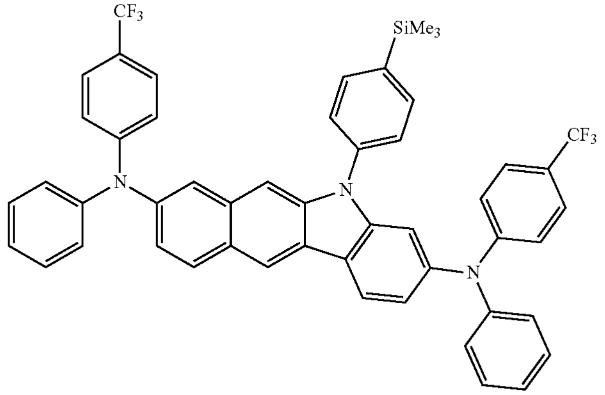

-continued
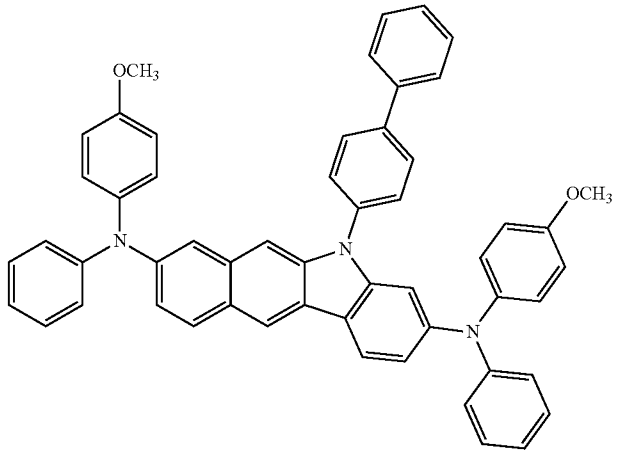
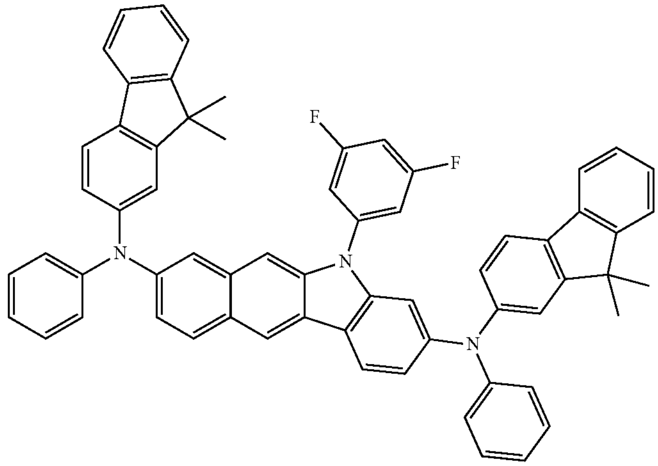
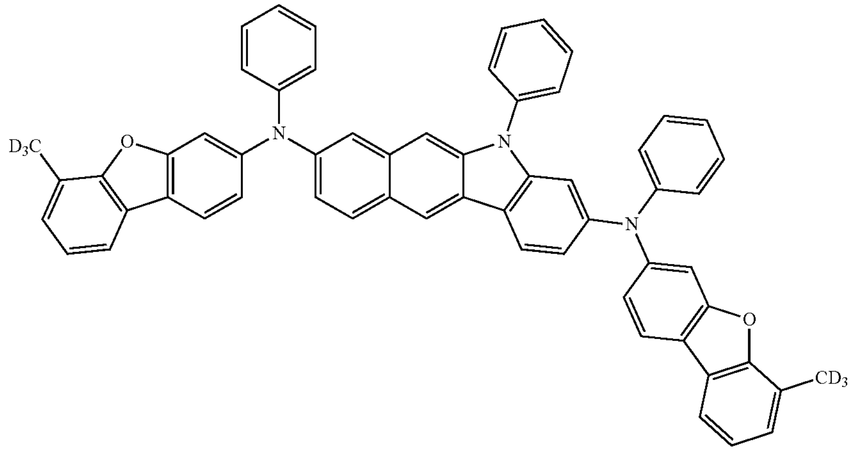

-continued
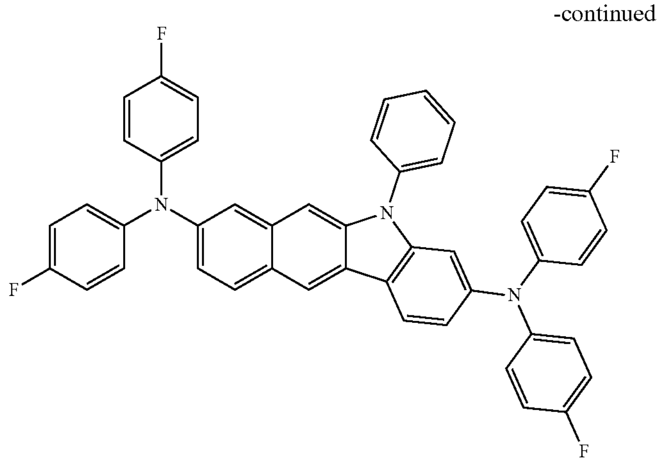
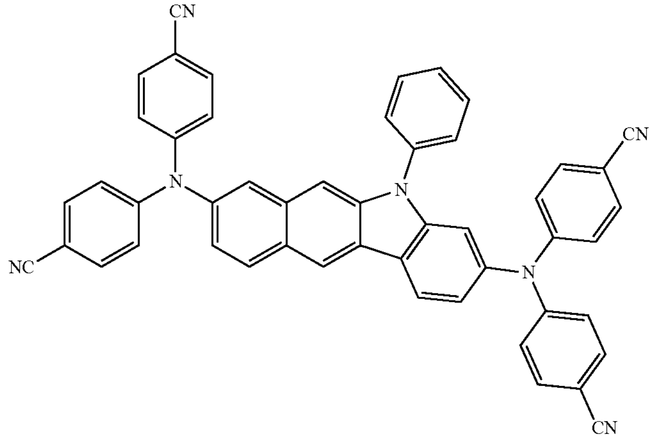
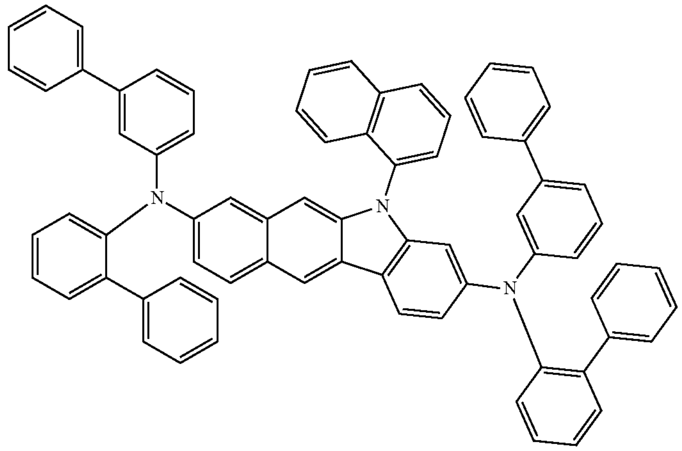

-continued
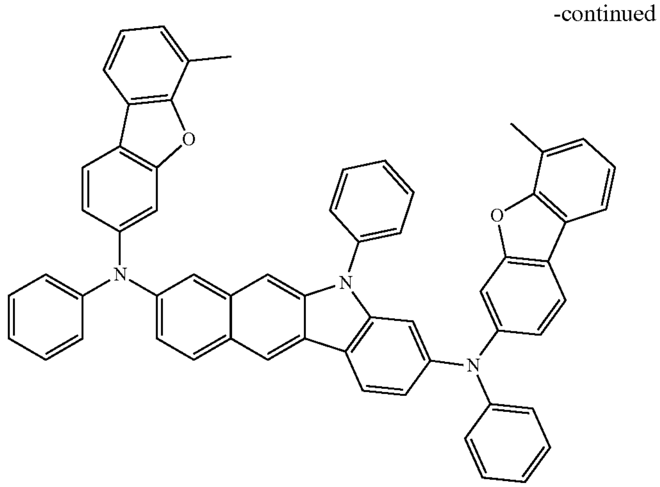
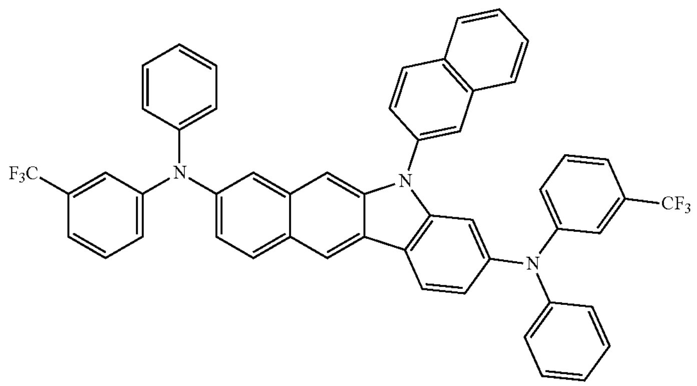
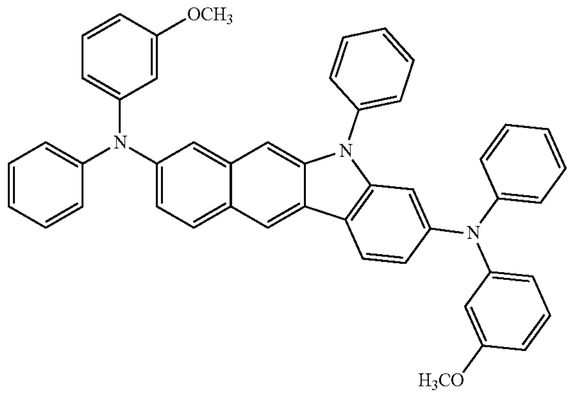
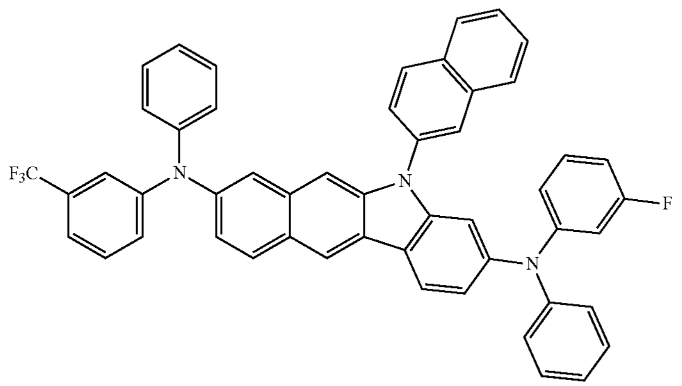

-continued
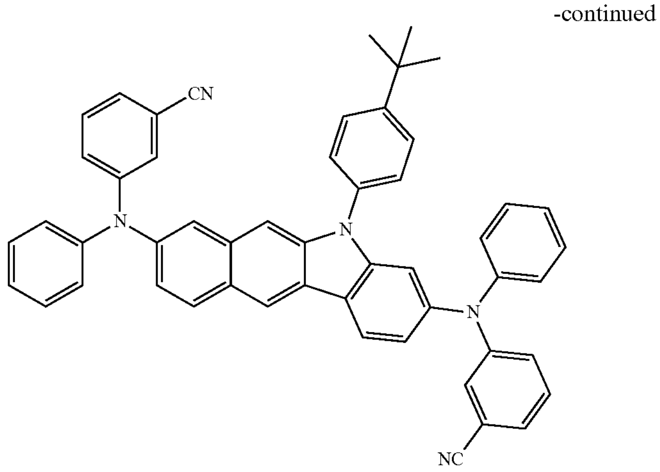
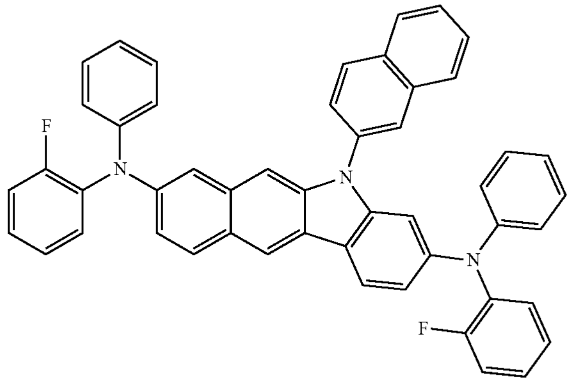
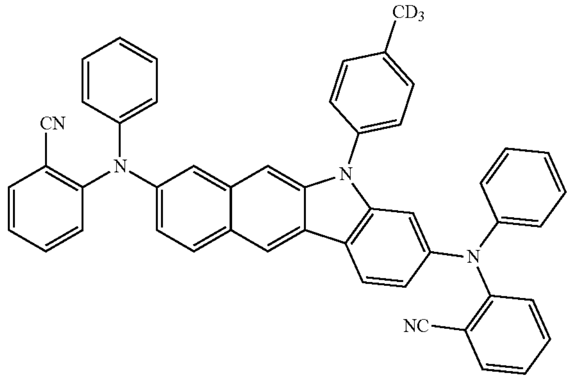
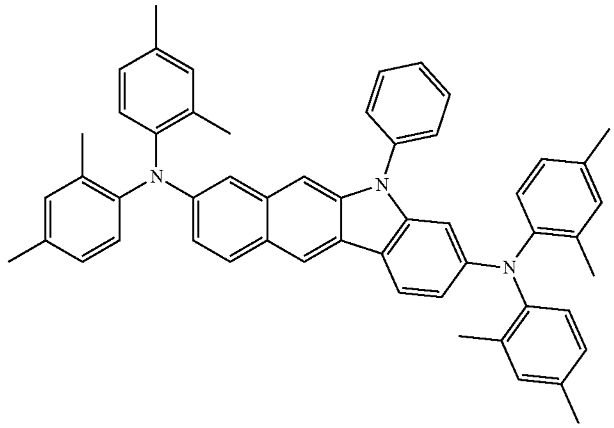

-continued
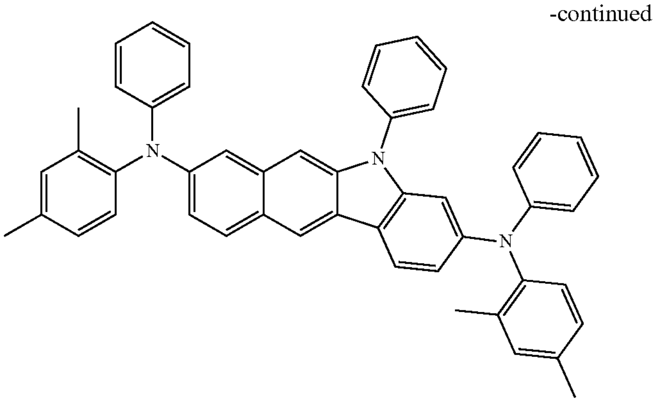
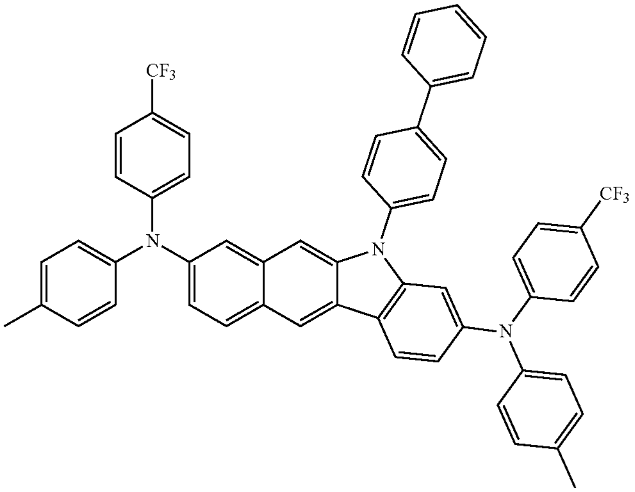
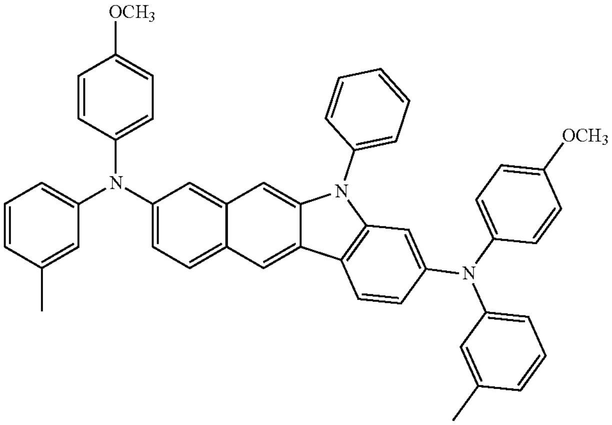
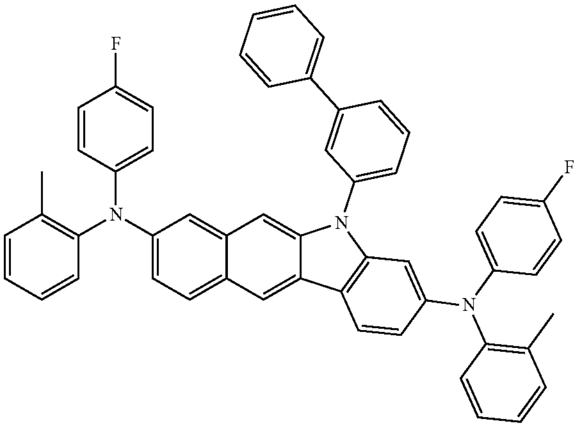

-continued
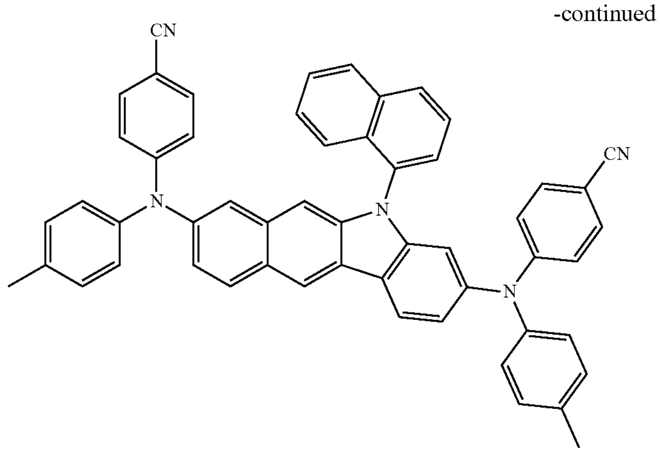
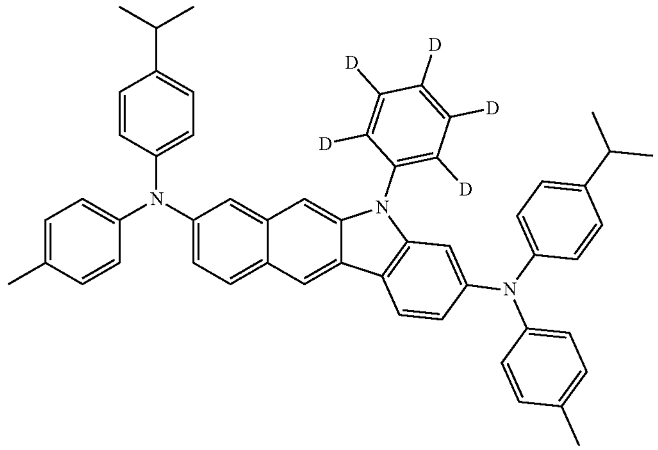
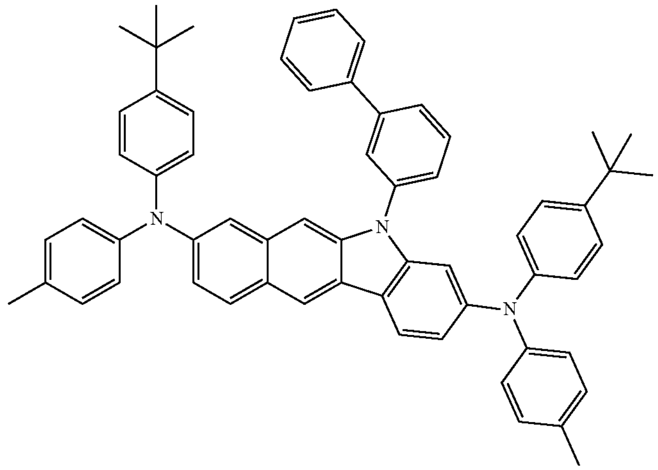

-continued
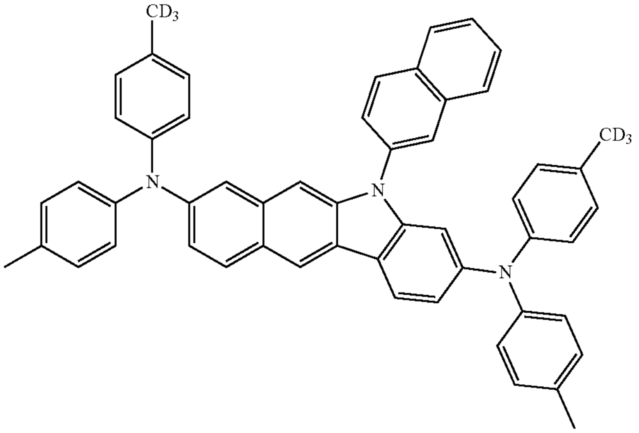
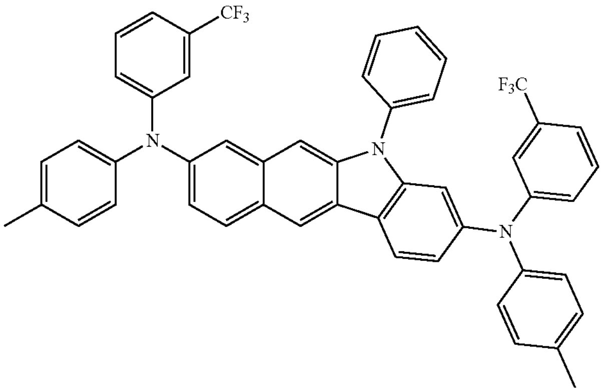
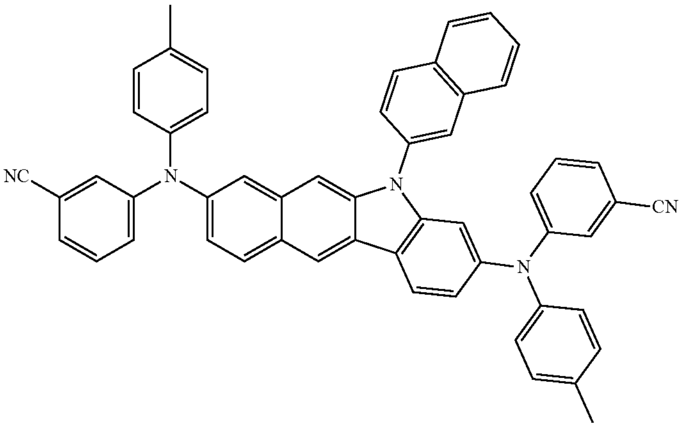
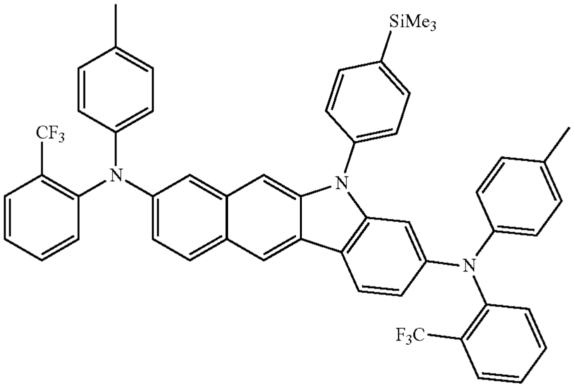

-continued
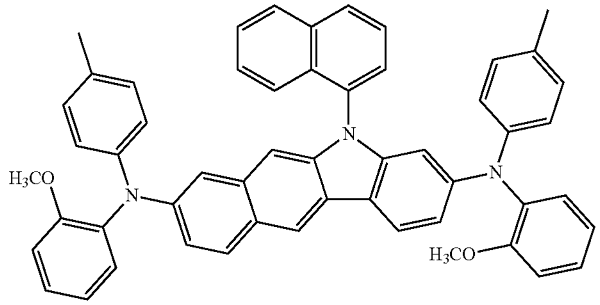
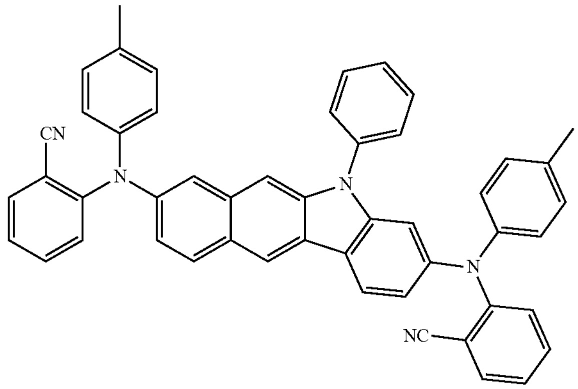
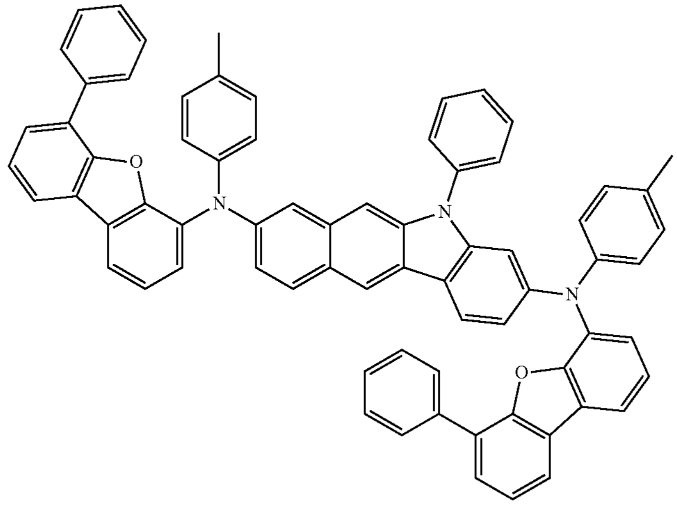
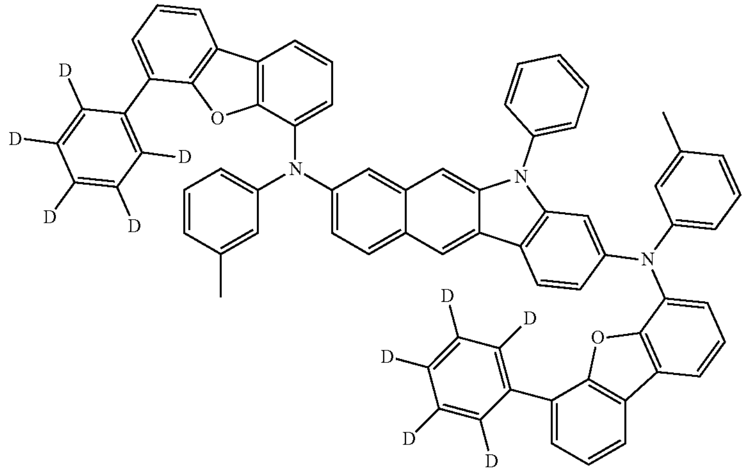

-continued
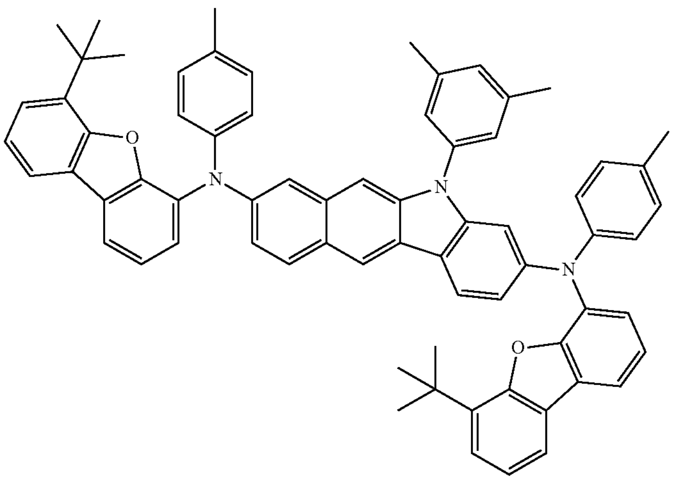
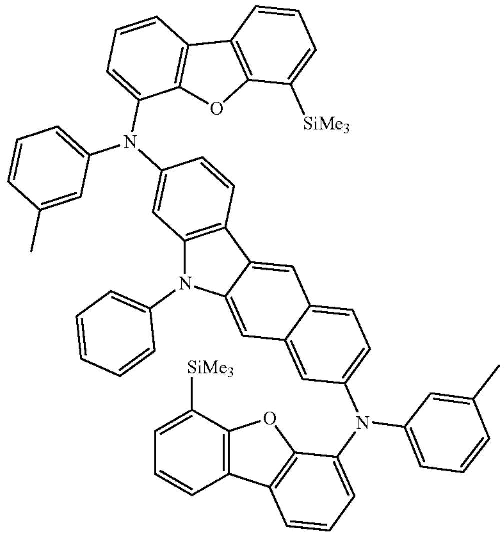
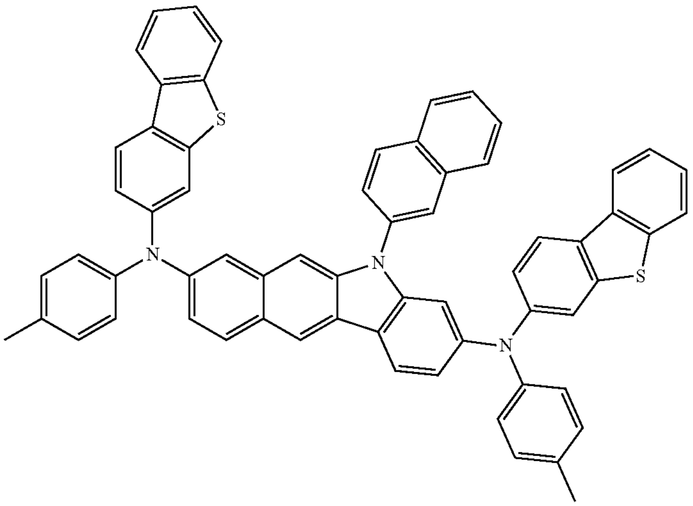
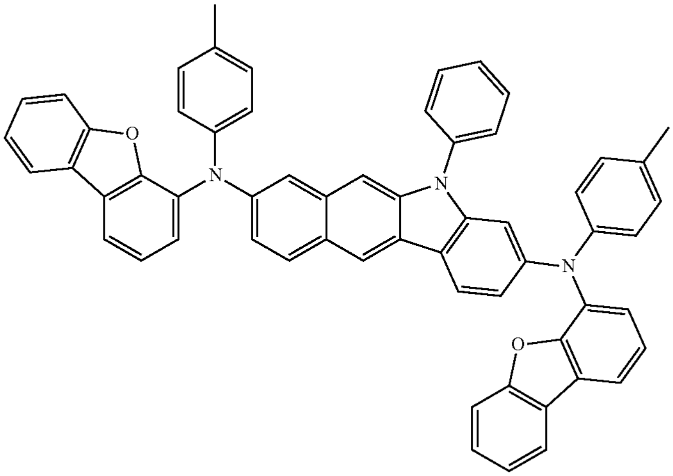

-continued
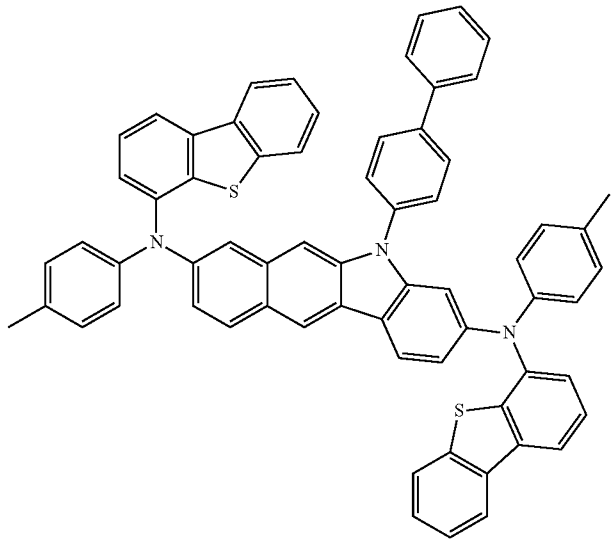
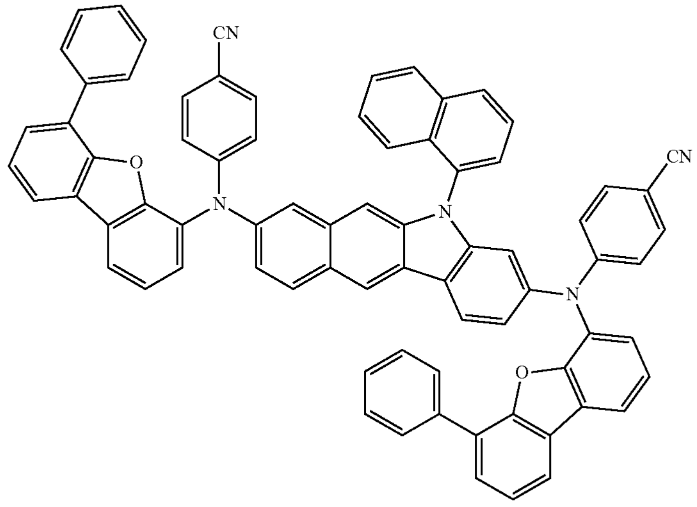
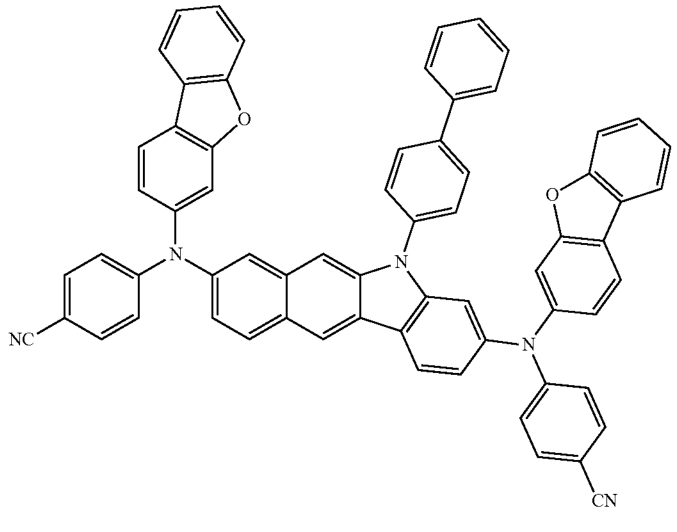

-continued
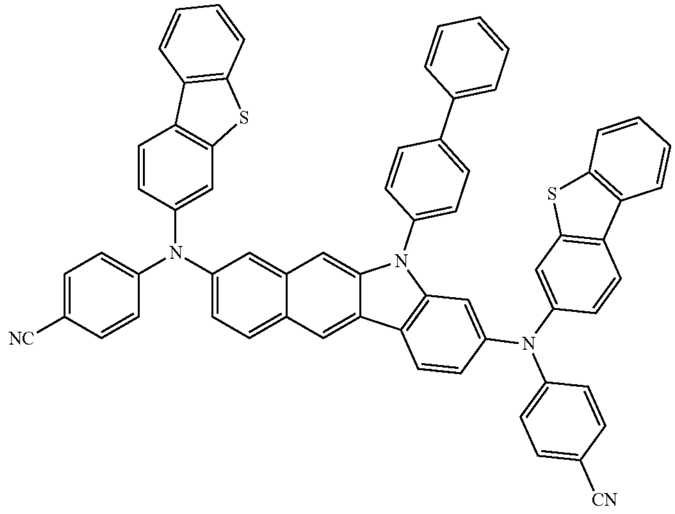
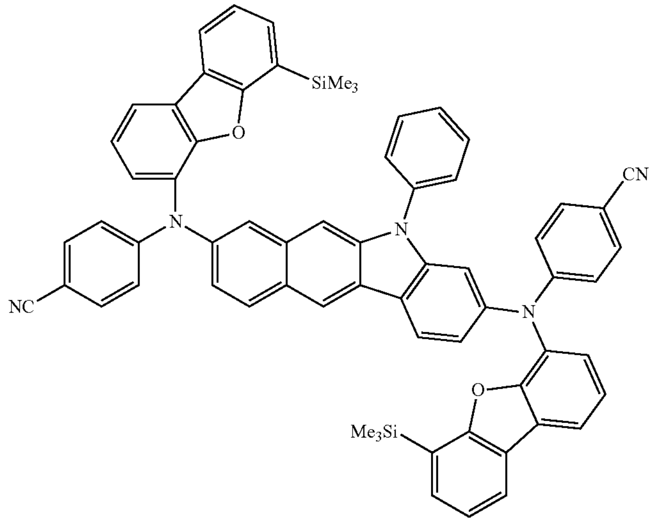
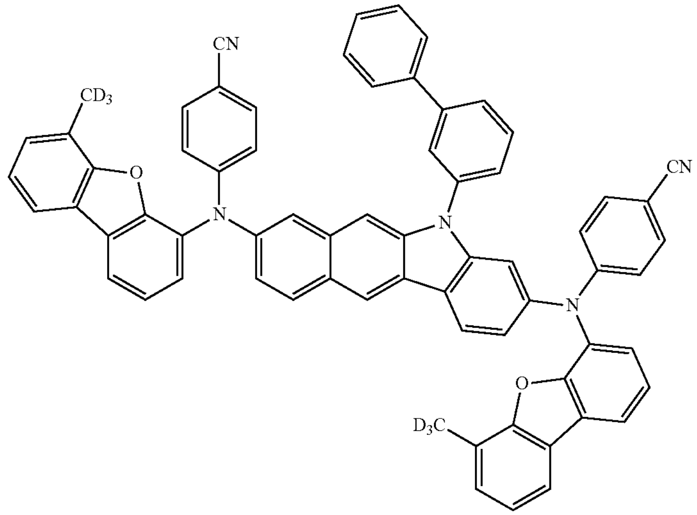

-continued
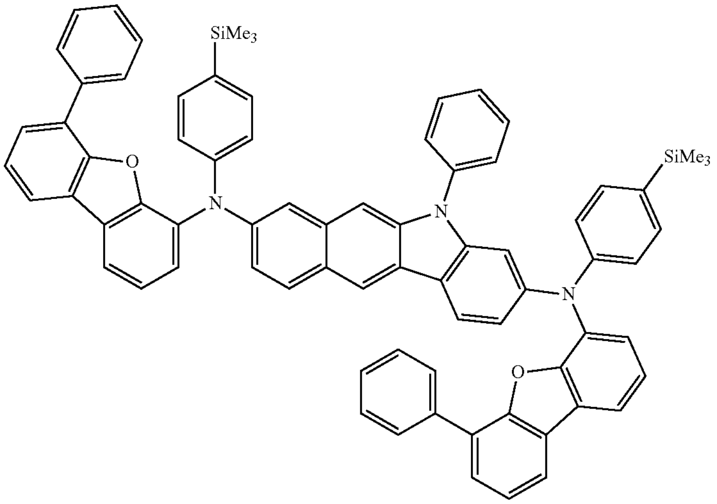
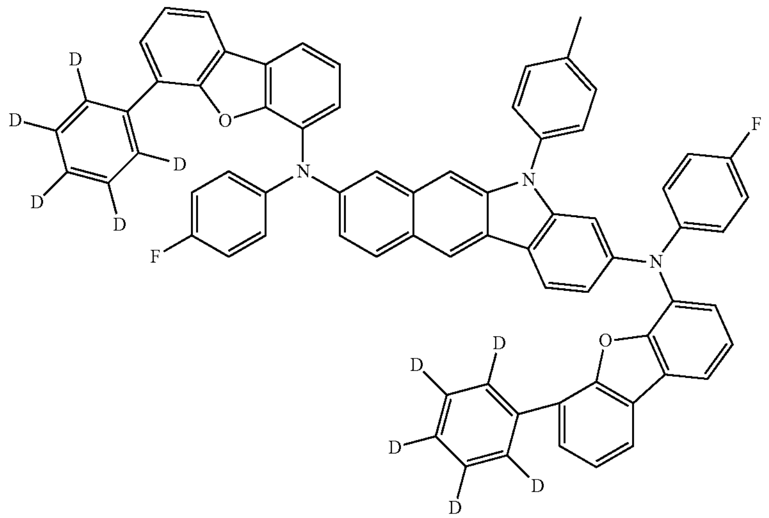
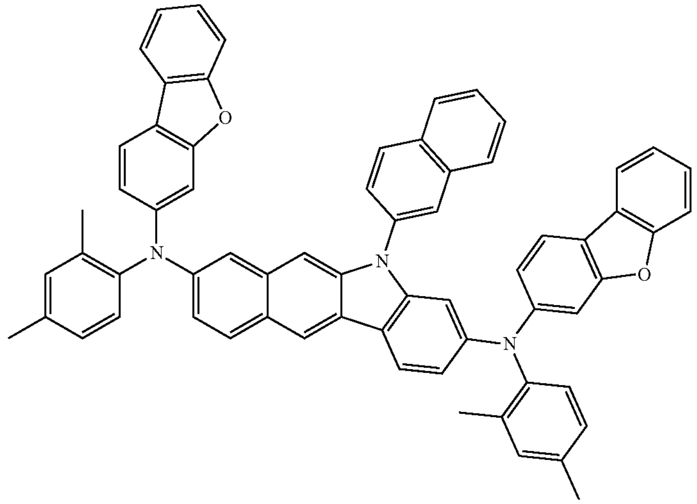

-continued
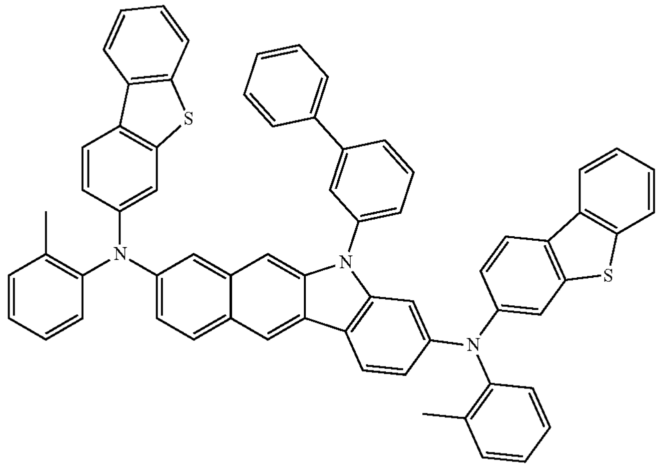
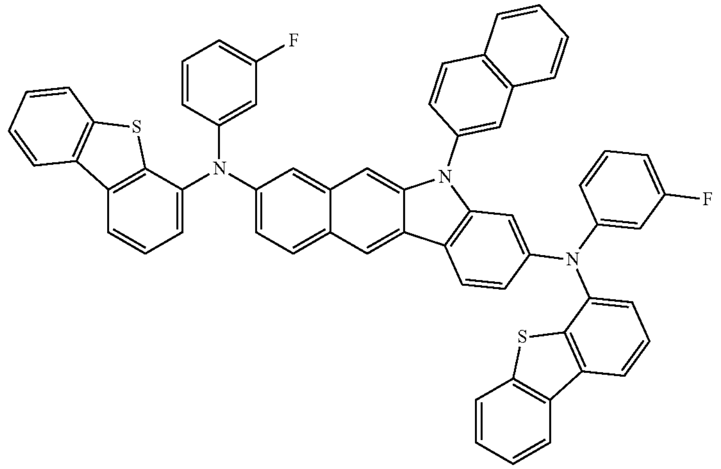
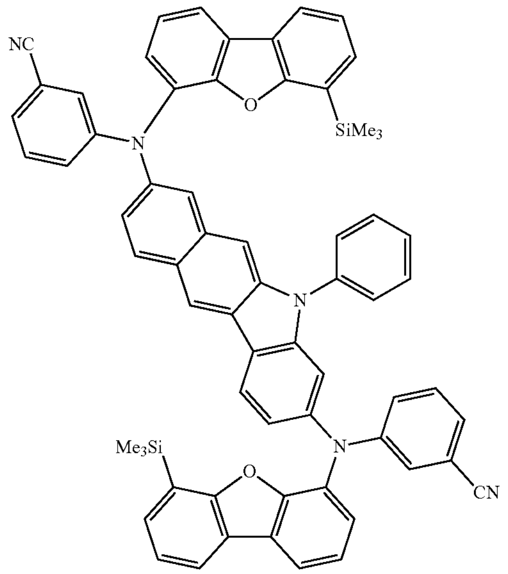
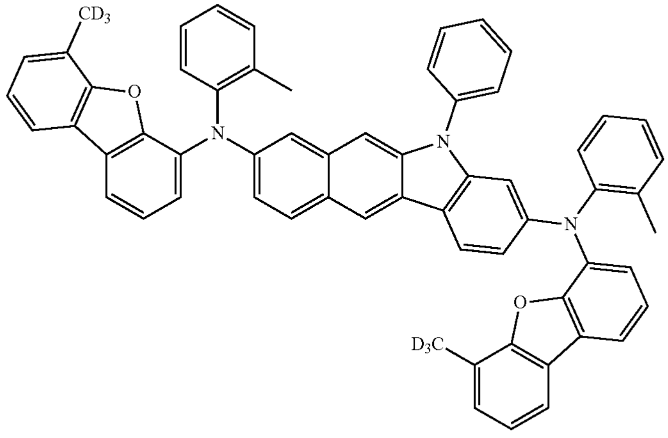

-continued
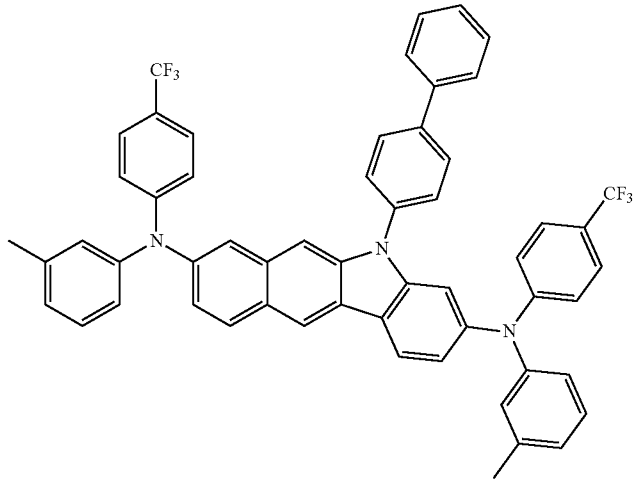
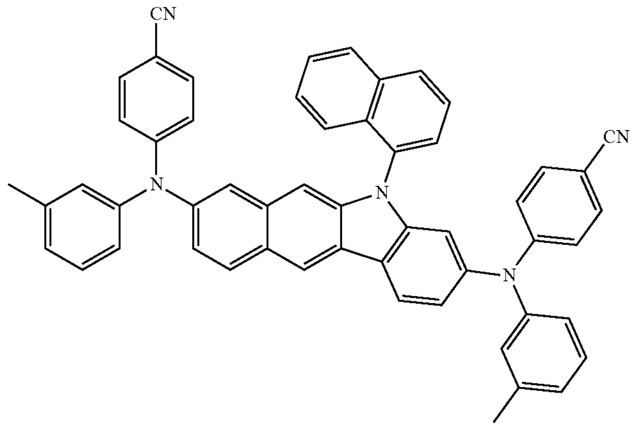
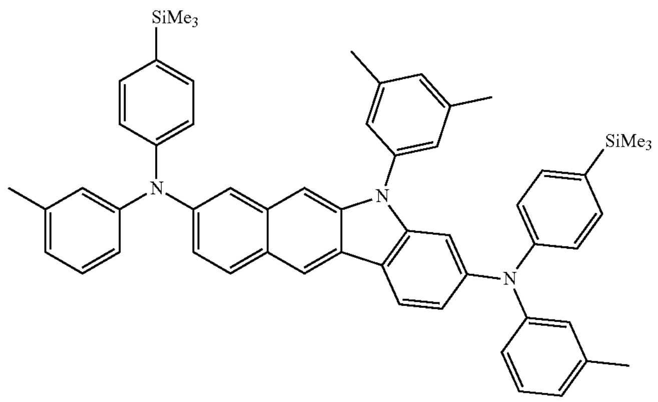

-continued
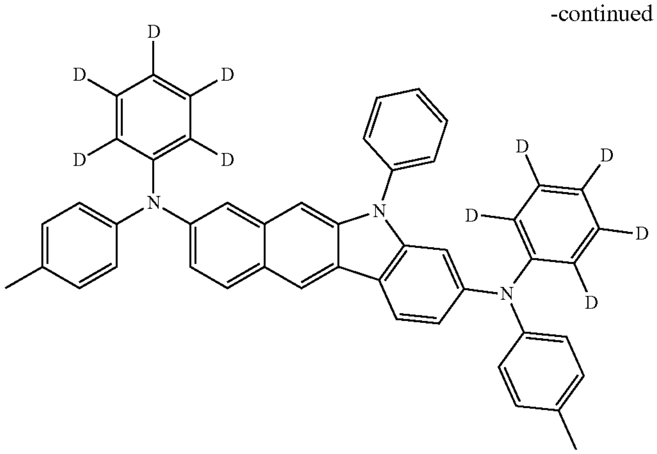
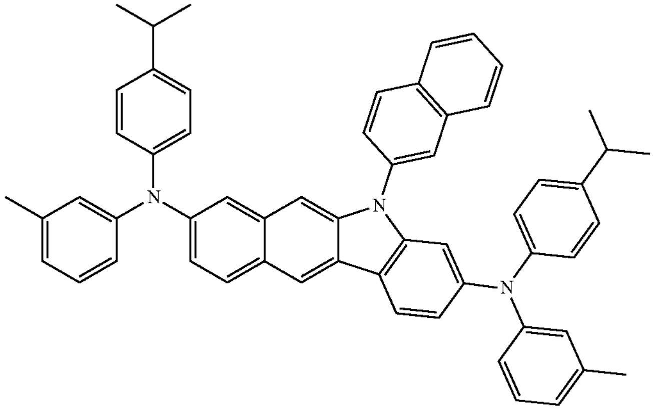
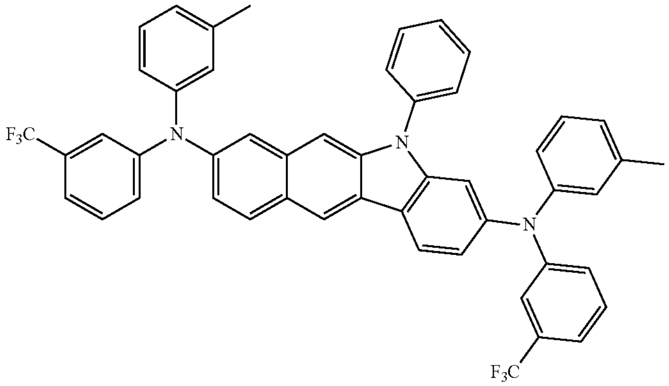
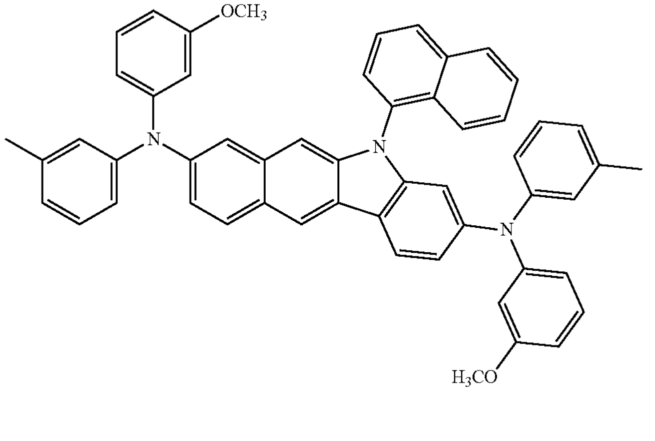

-continued
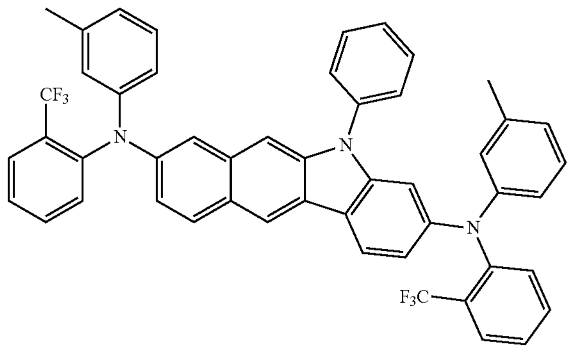
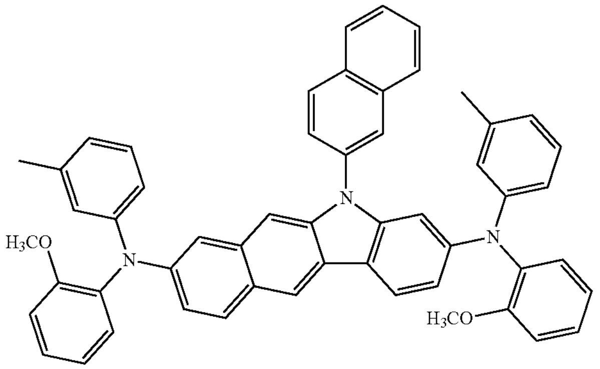
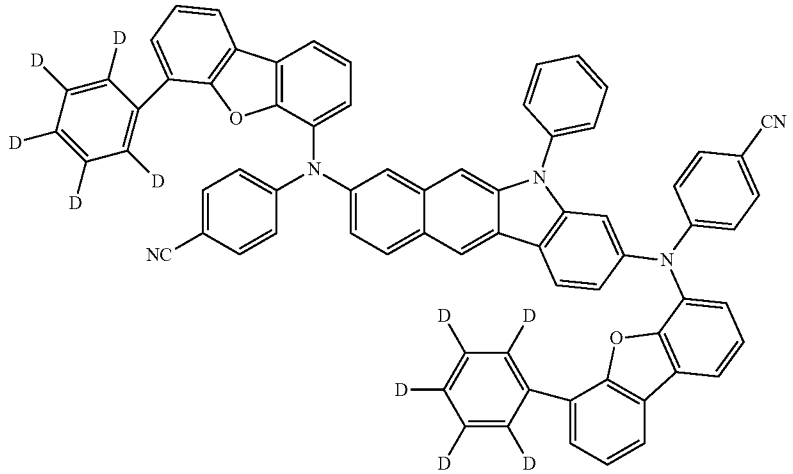
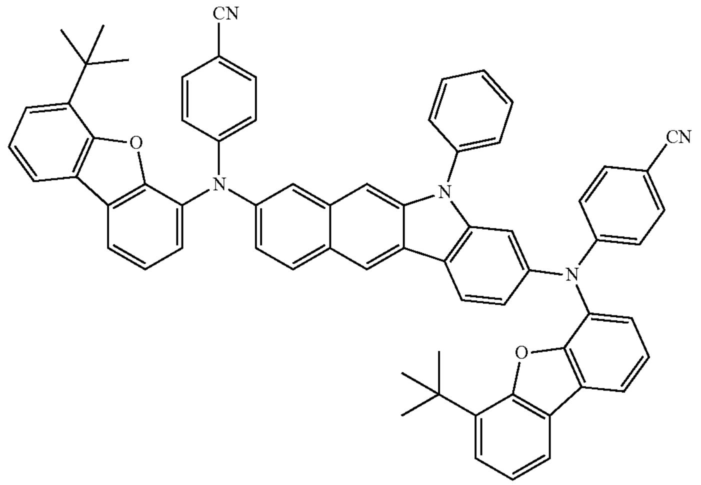

-continued
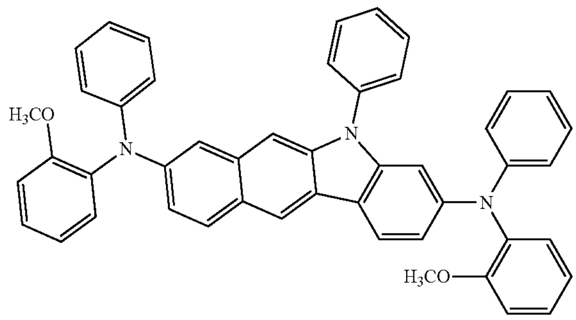
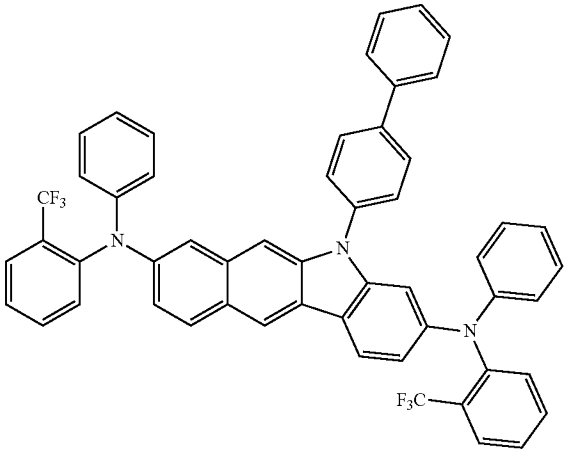
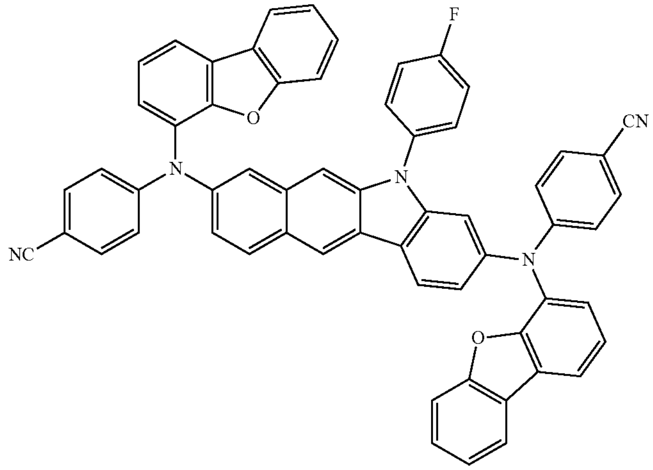
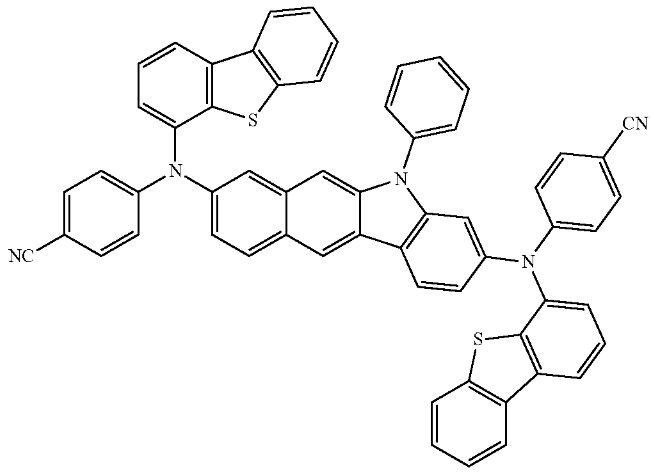

-continued
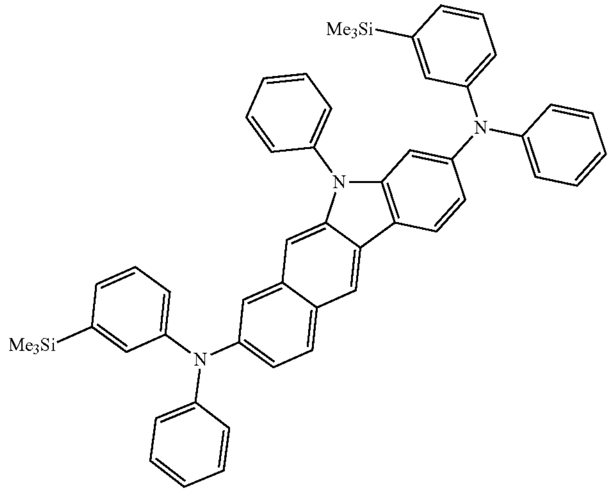
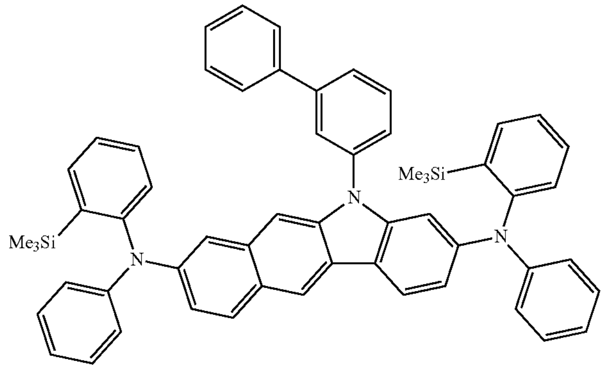
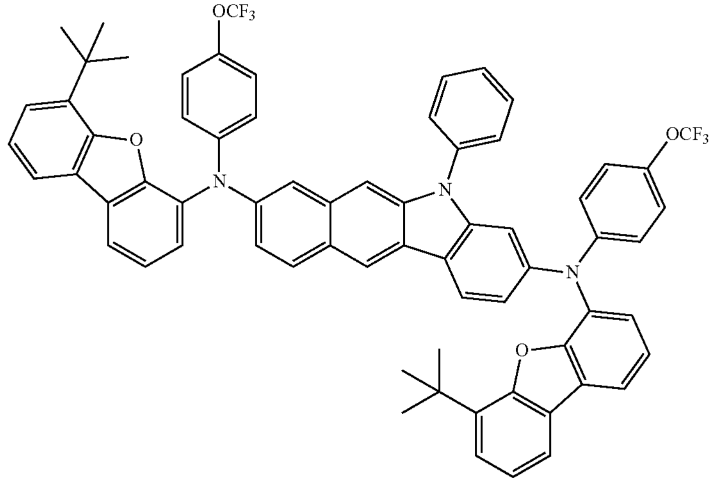

-continued
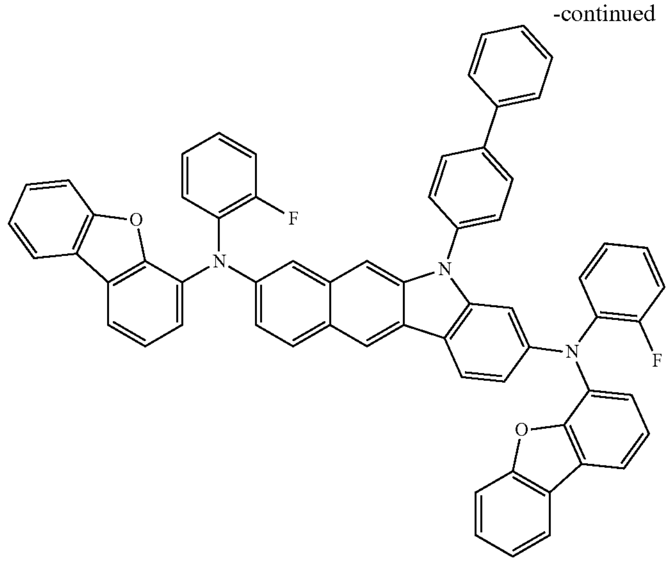
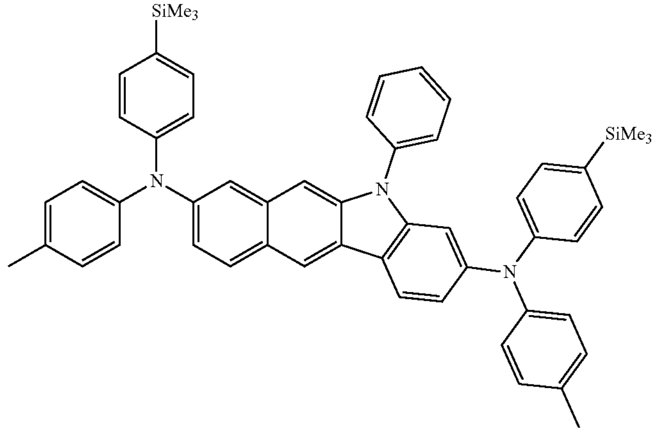
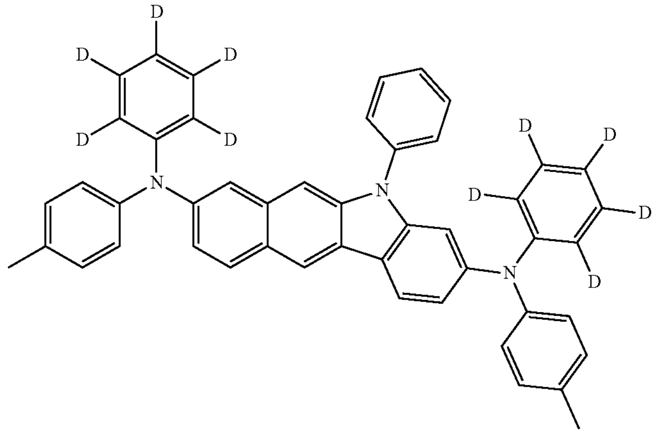

-continued
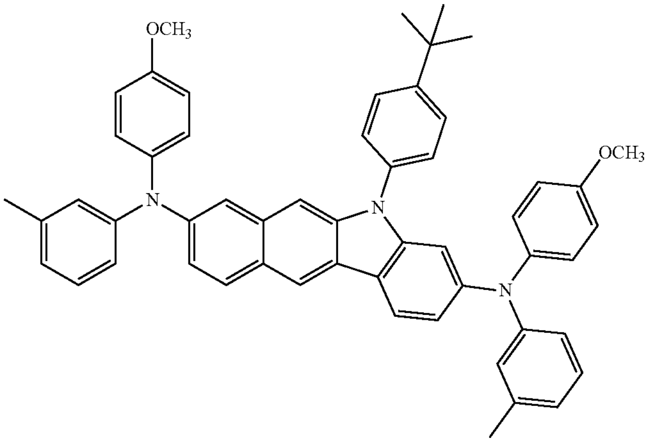
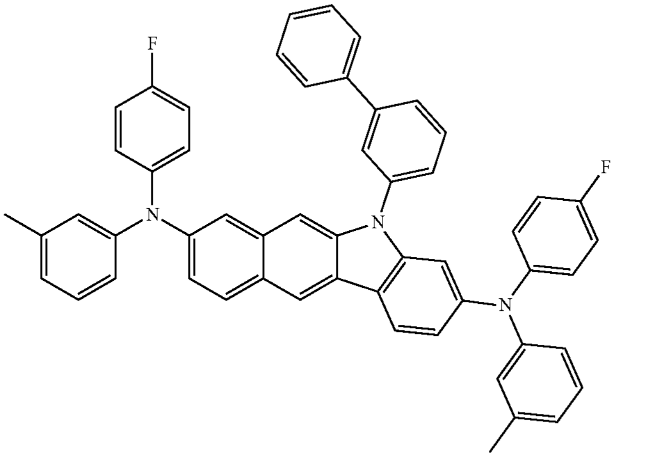
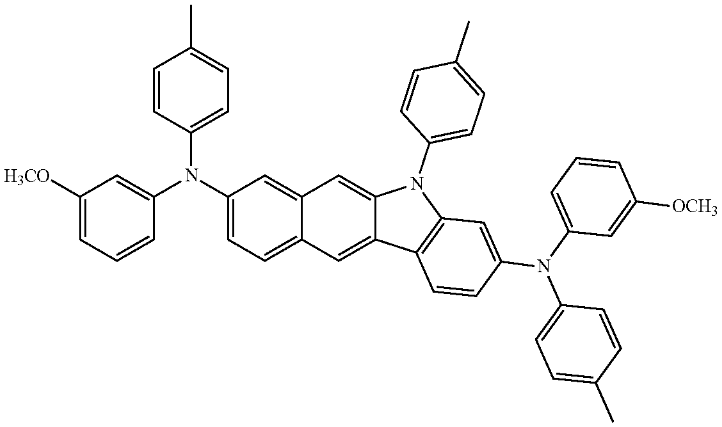
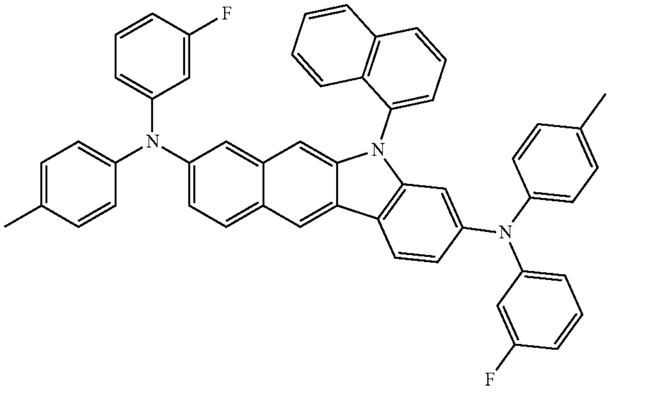

-continued
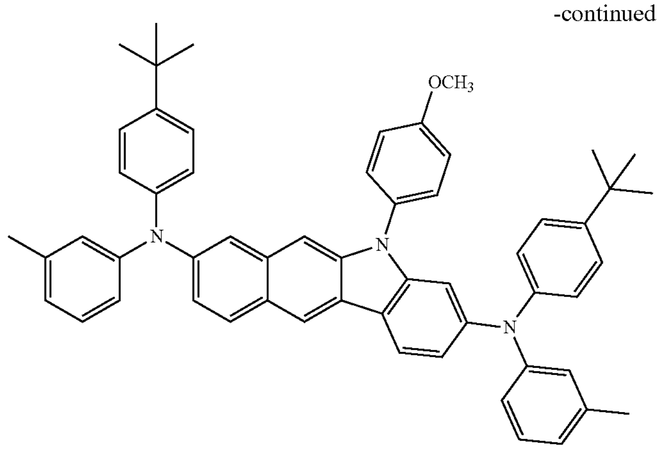
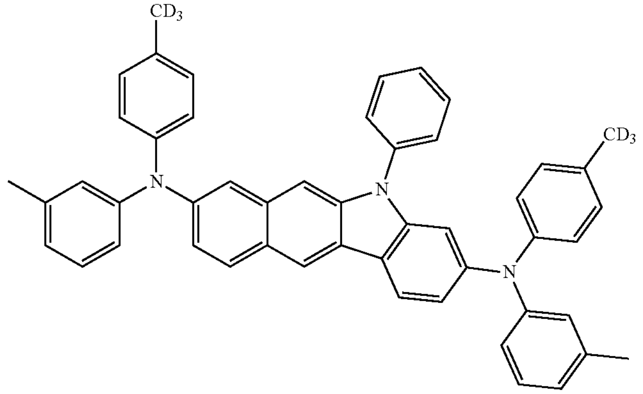
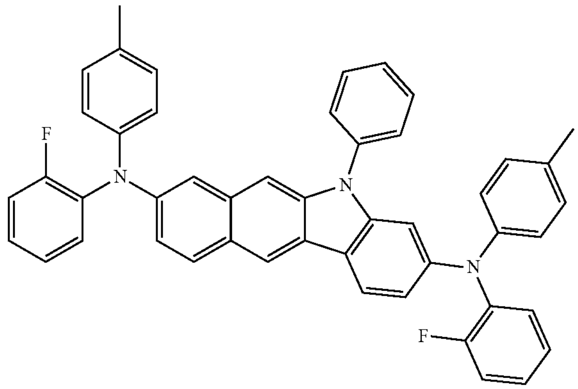
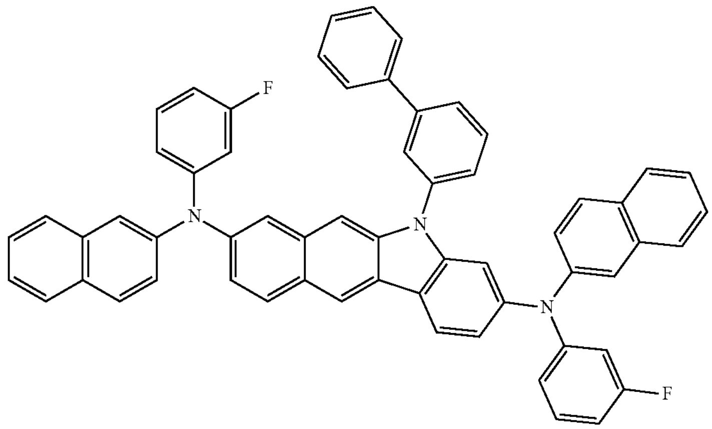

-continued
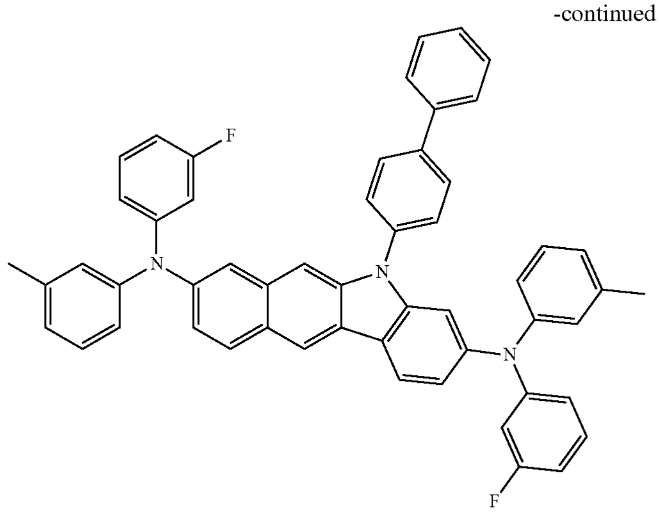
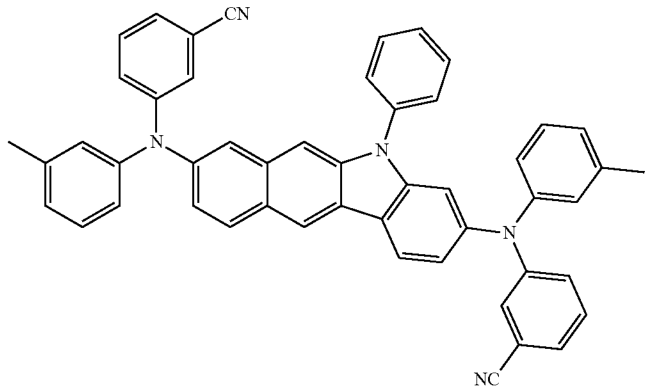
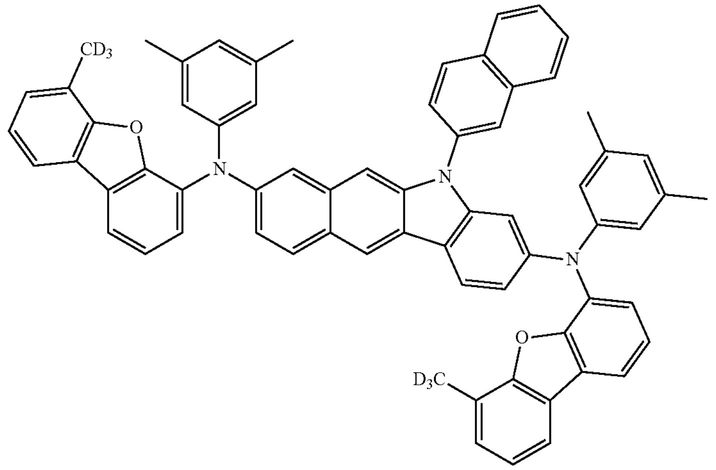

-continued
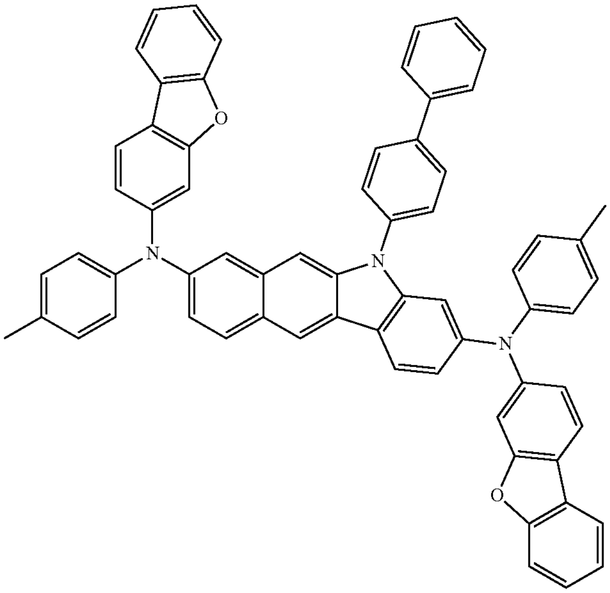
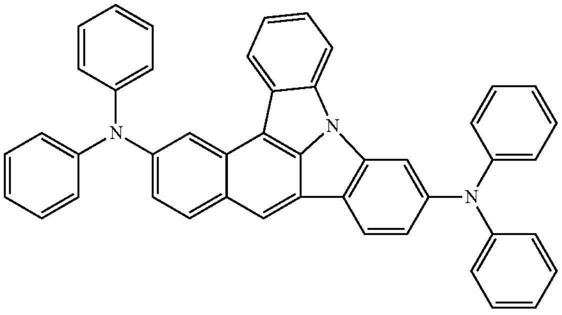
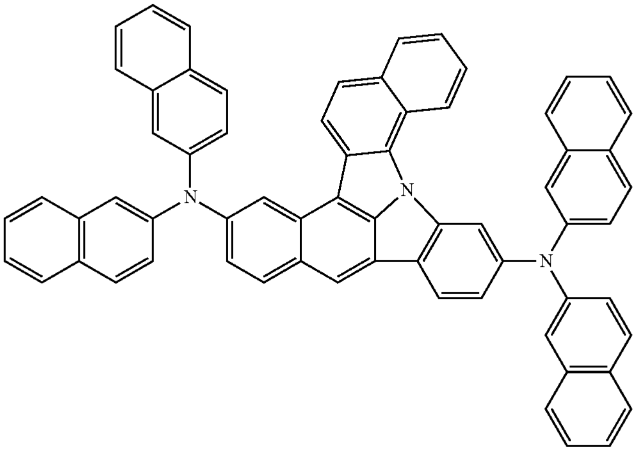
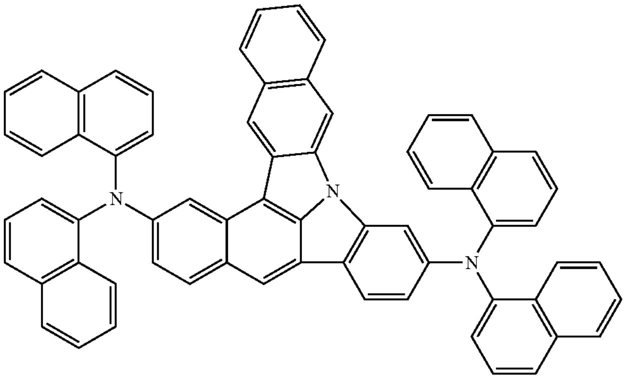

-continued
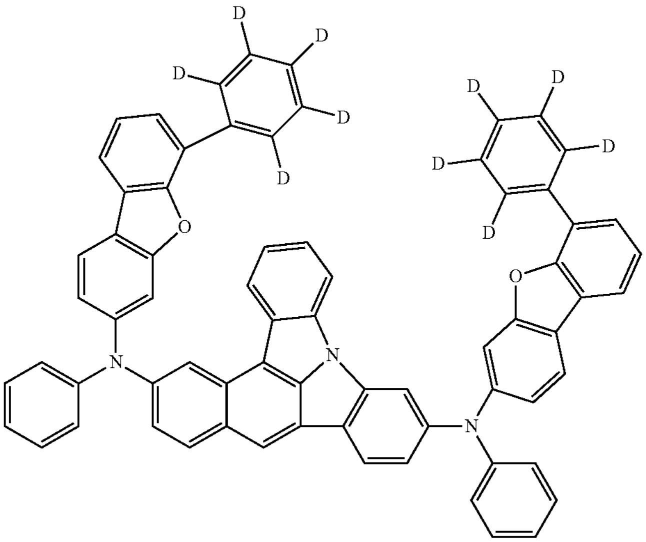
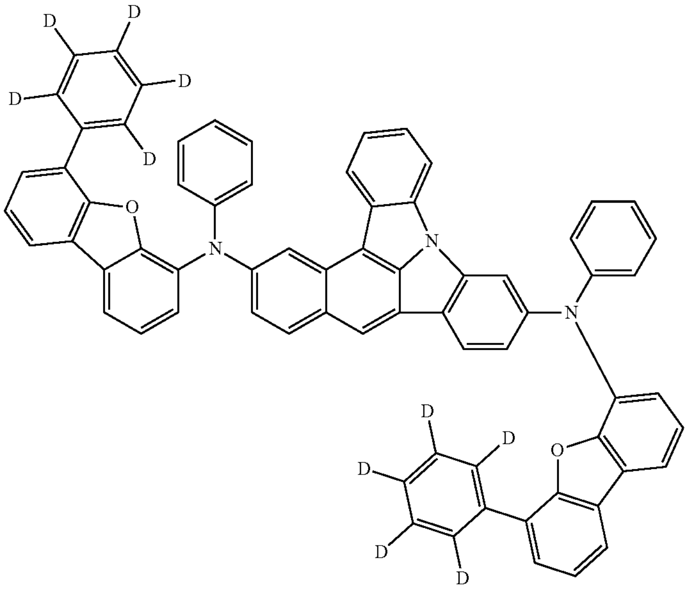
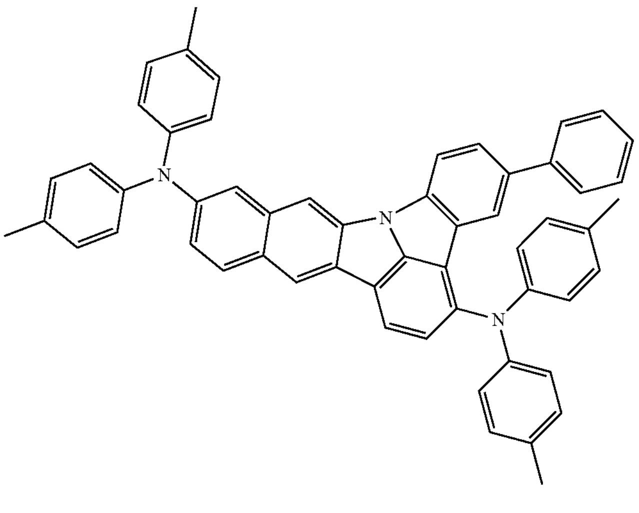

-continued
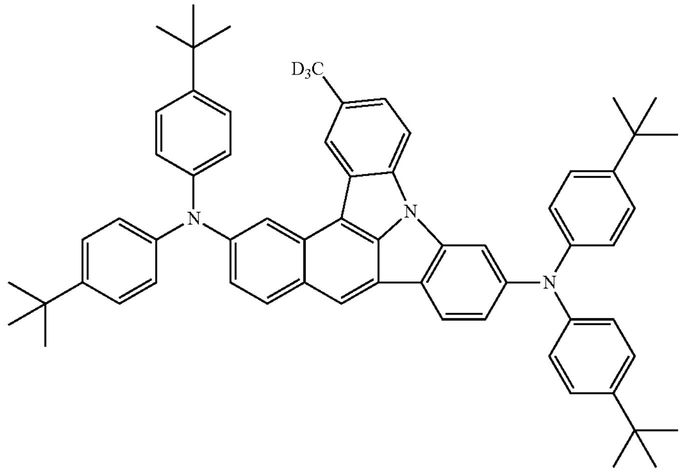
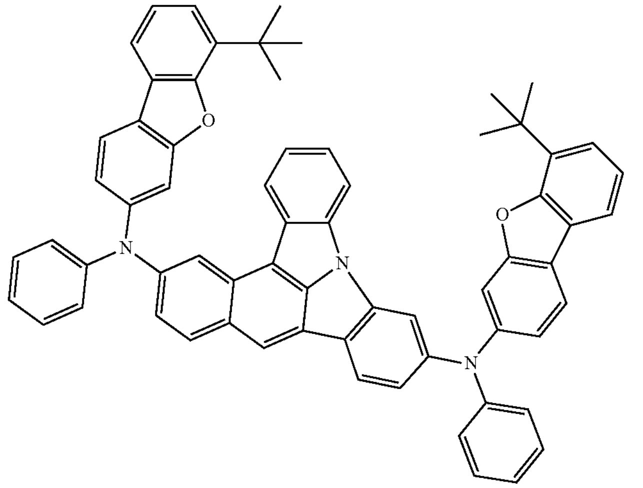
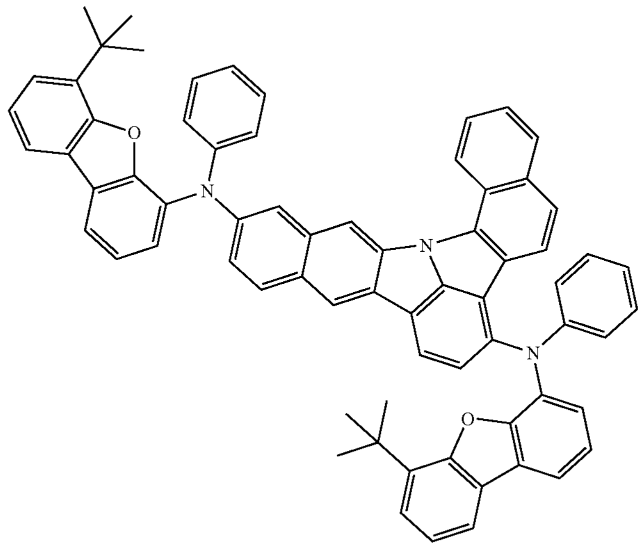

-continued
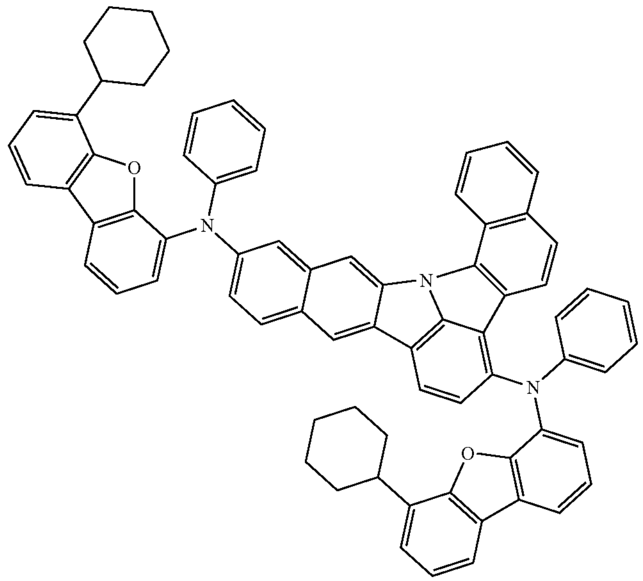
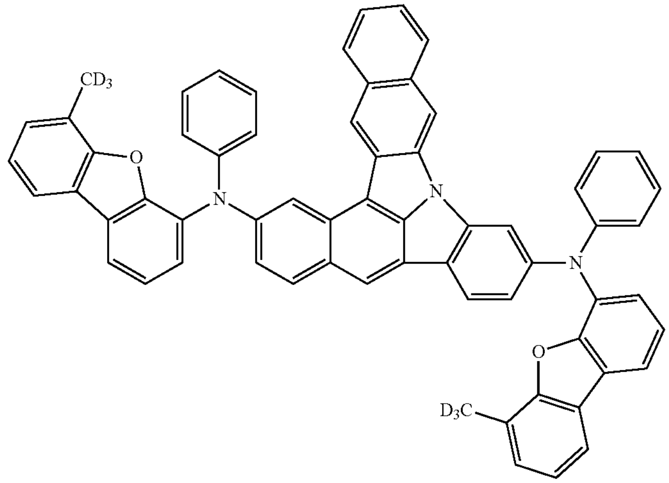
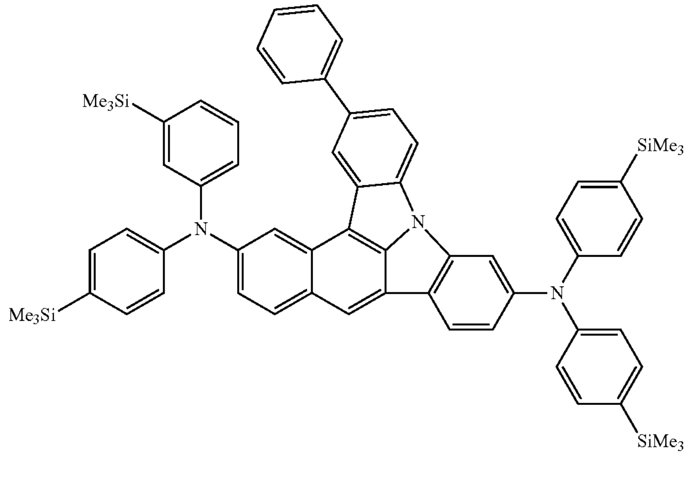

-continued
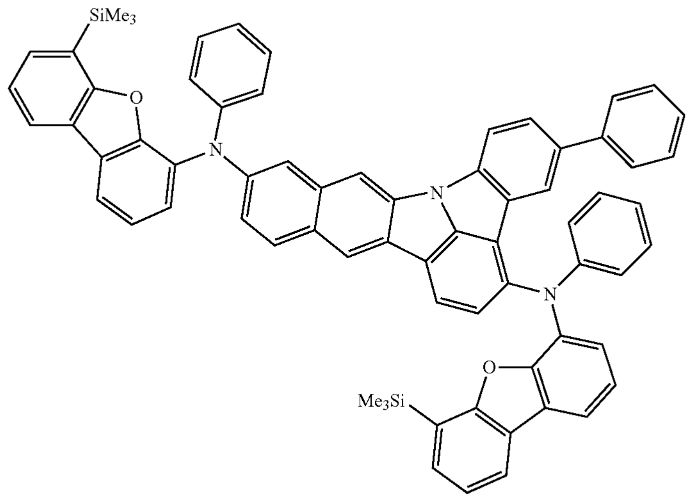
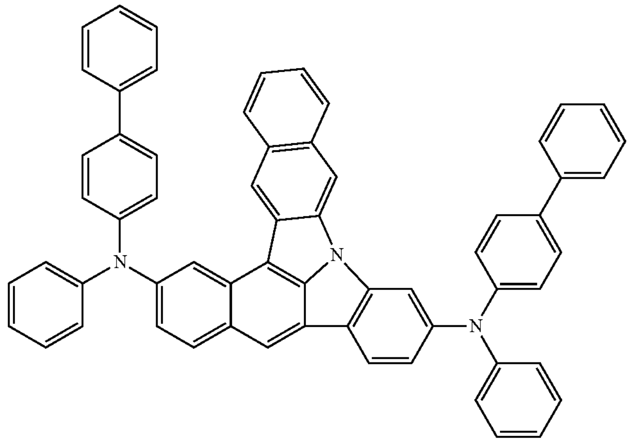
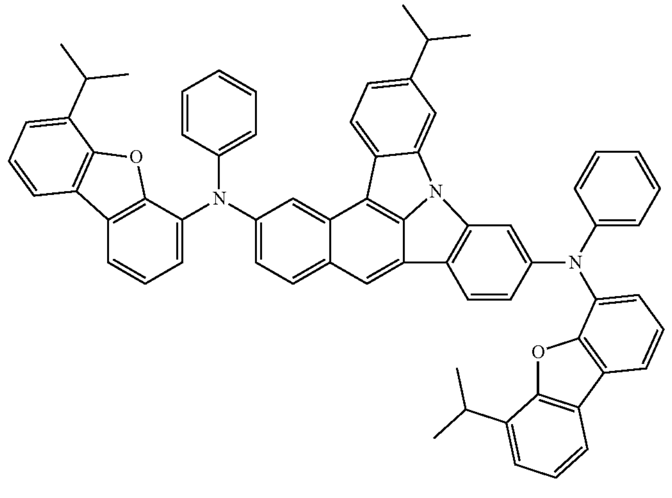

-continued
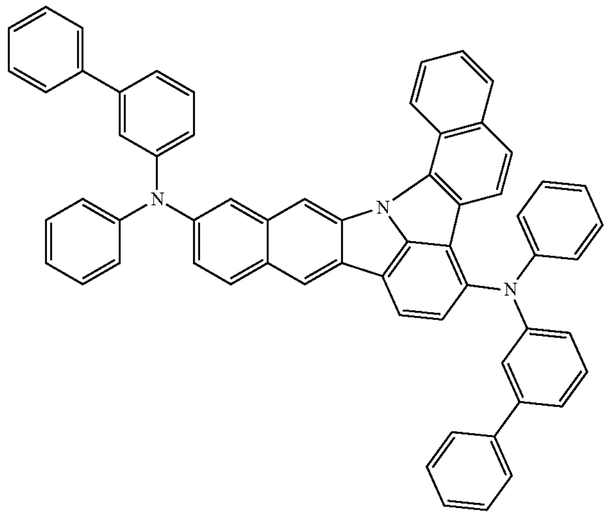
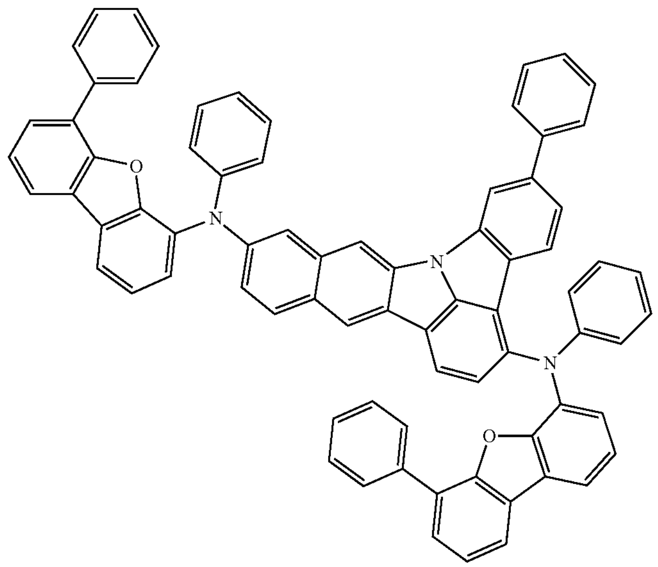
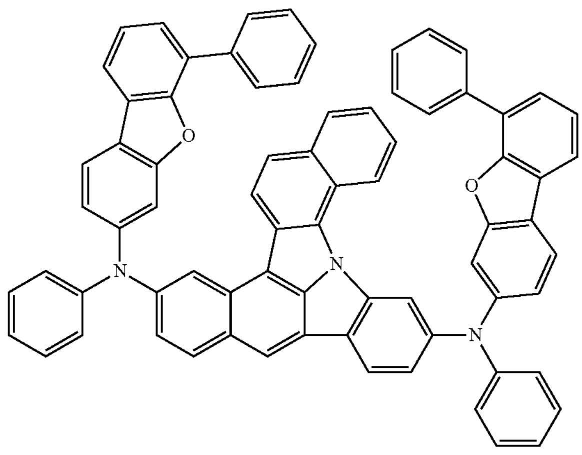

-continued
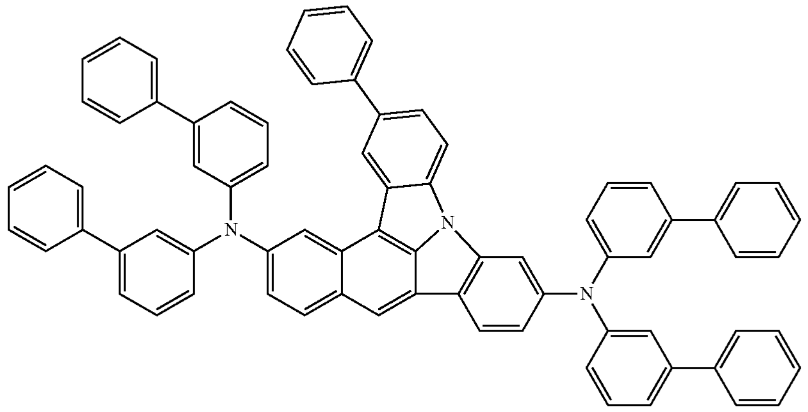
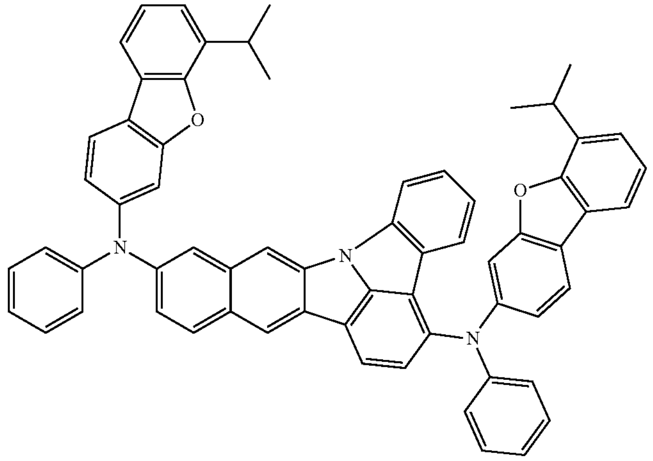
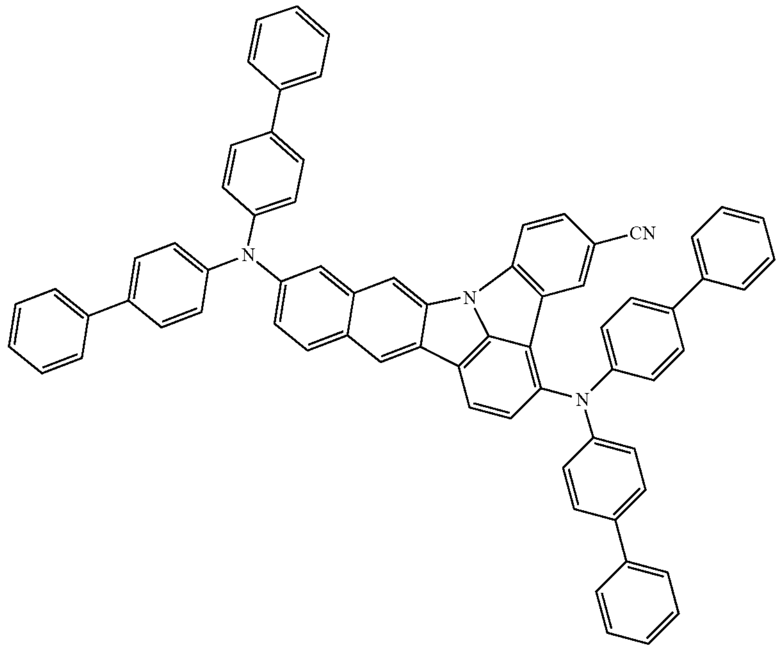

-continued
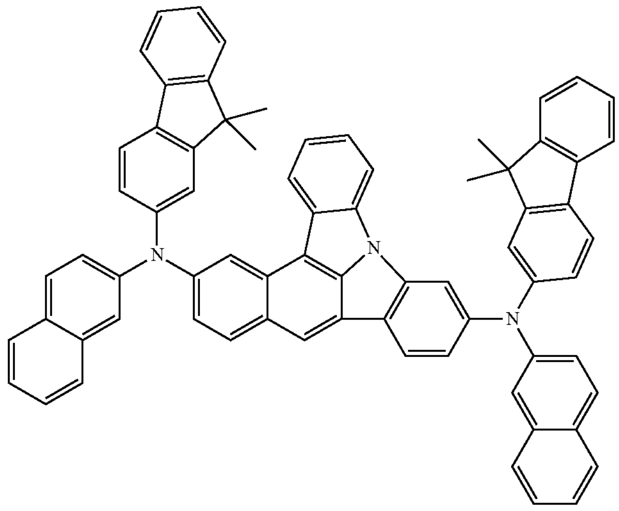
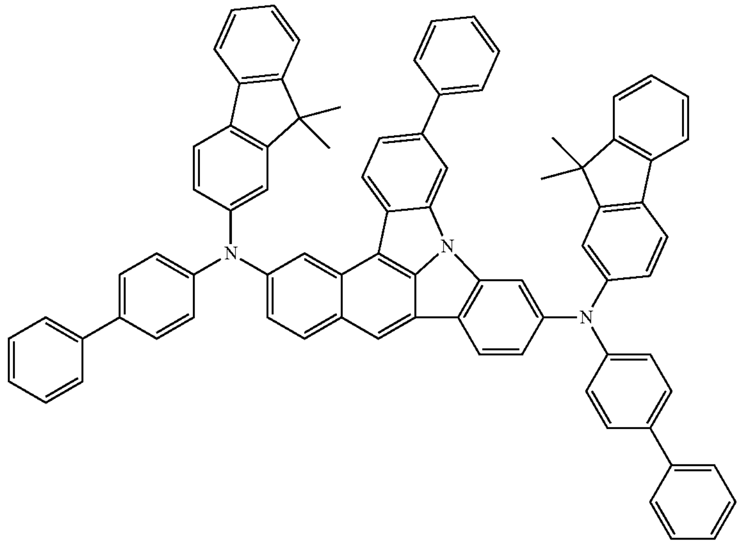
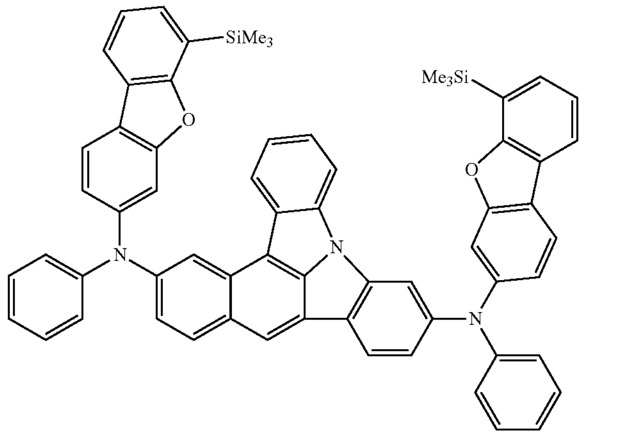

-continued
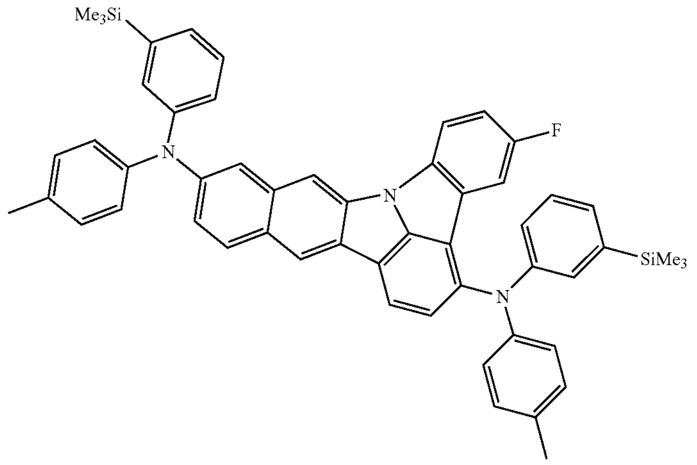
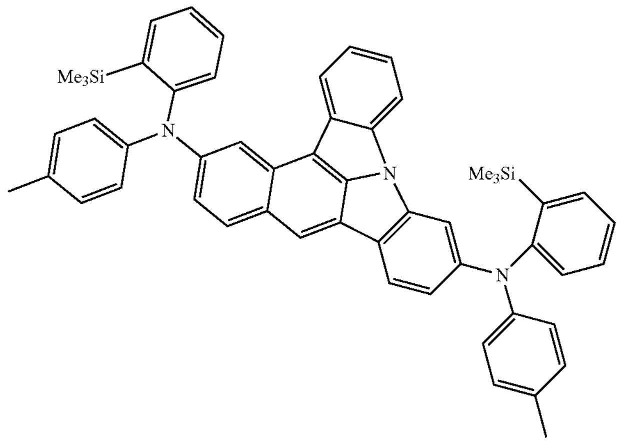
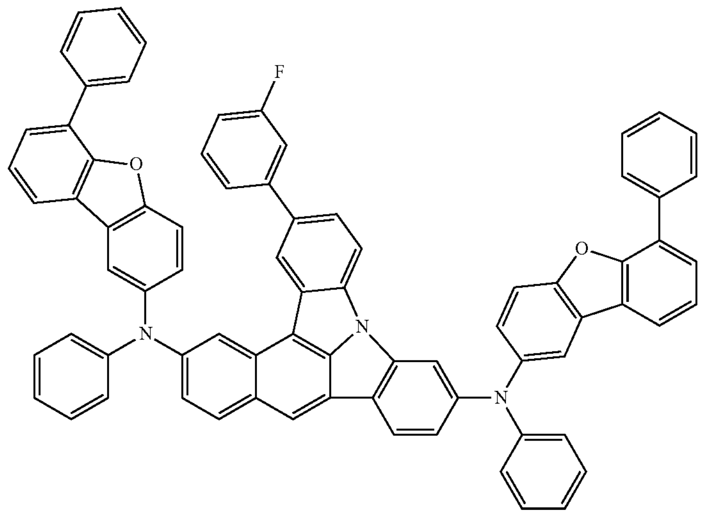

-continued
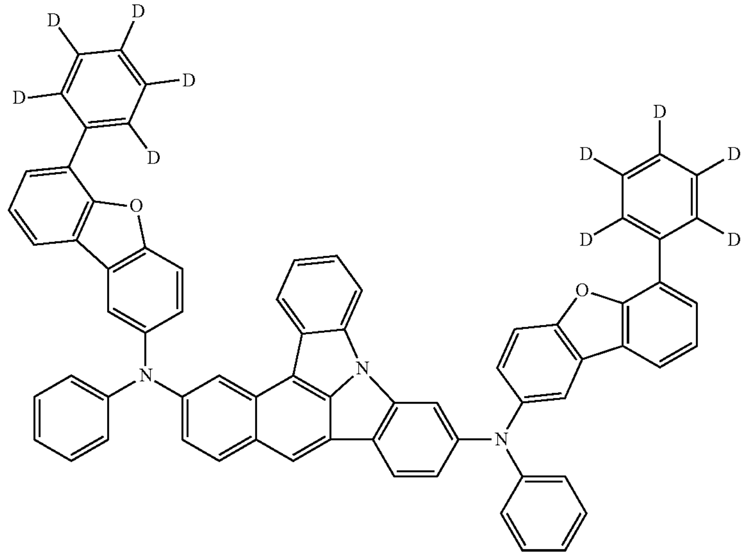
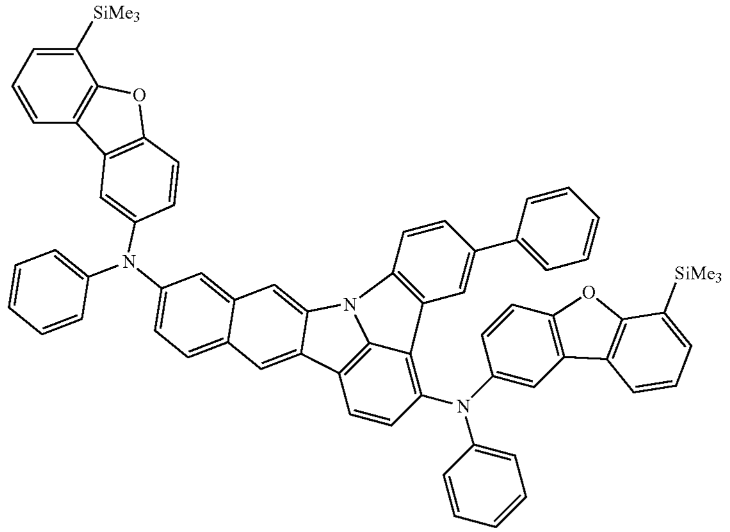
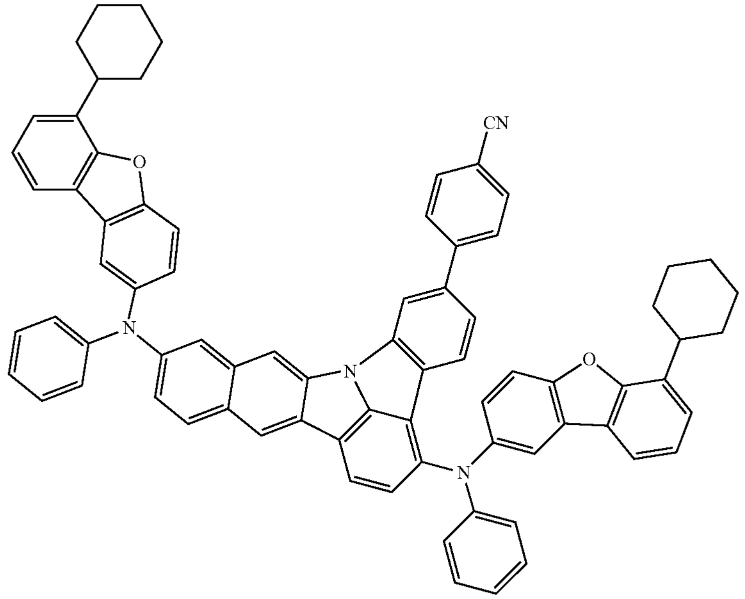

-continued
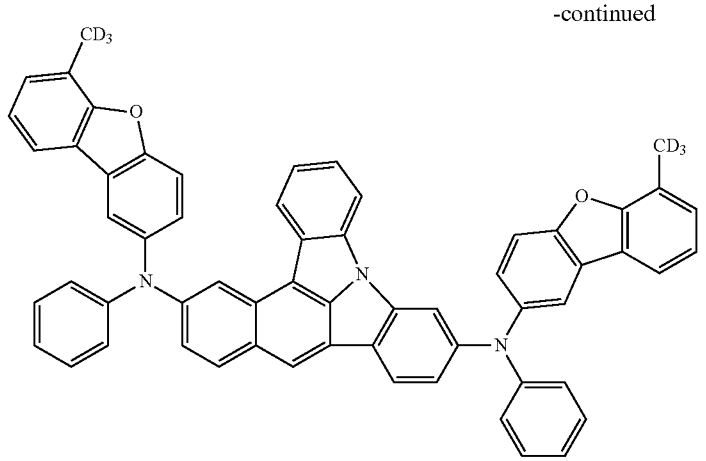
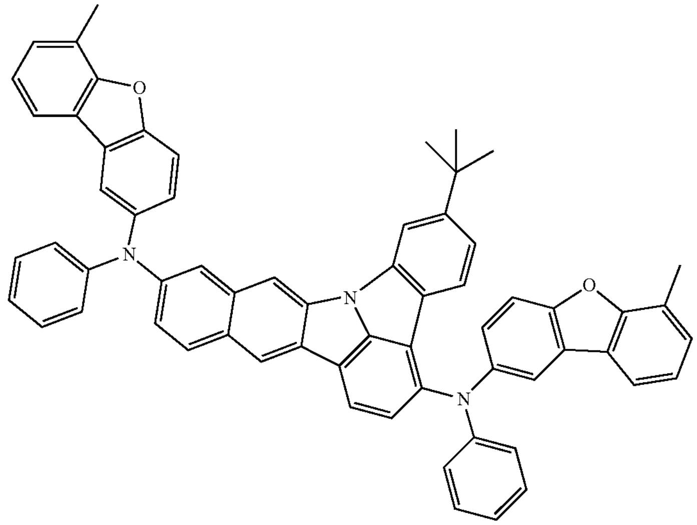
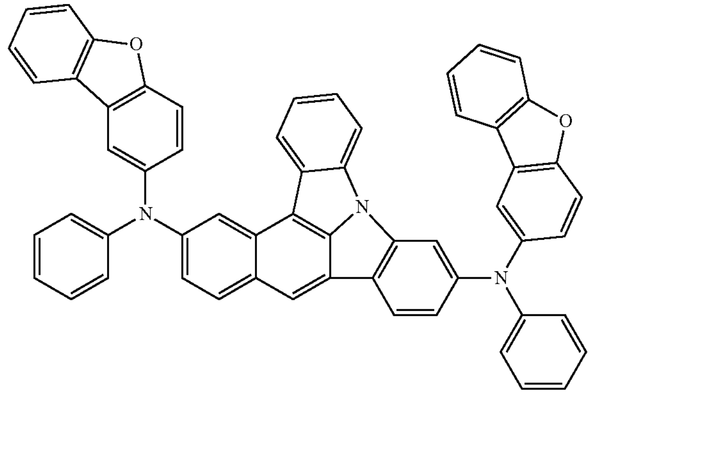

-continued
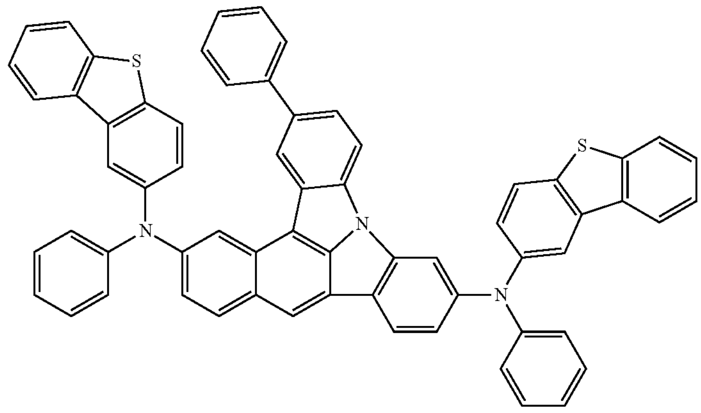
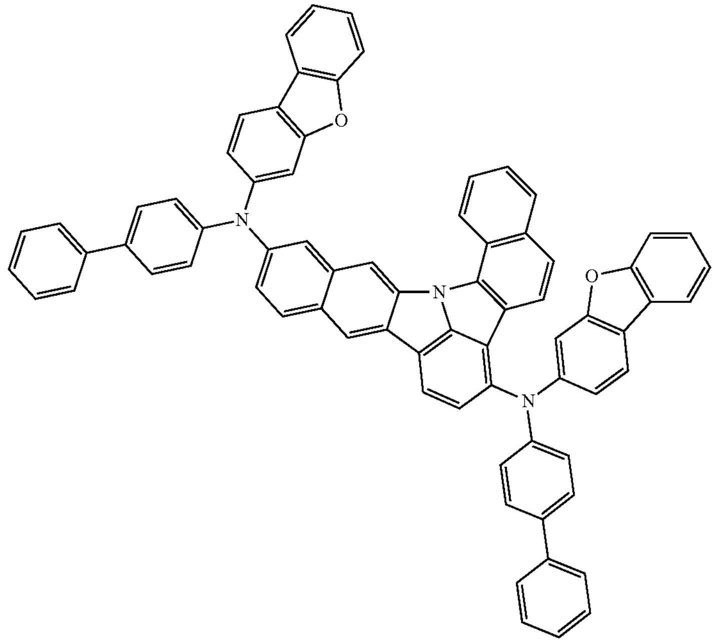
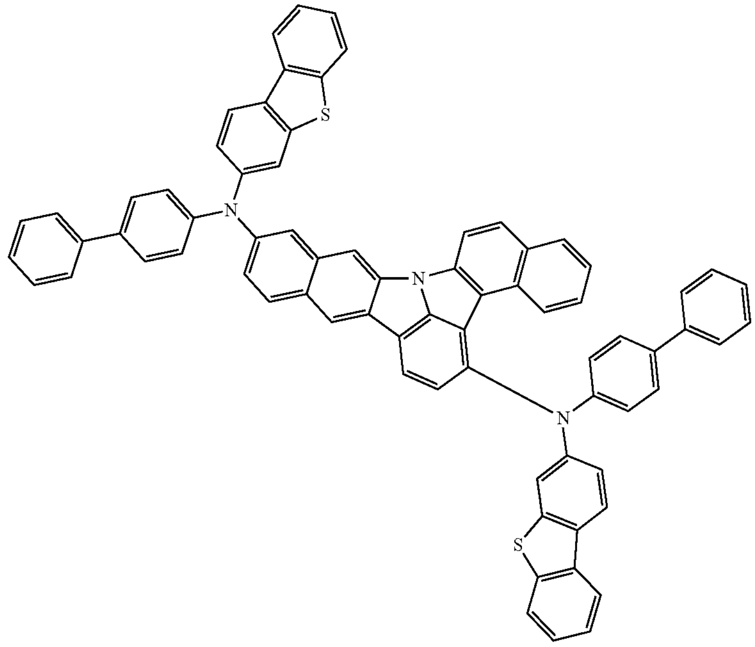

-continued
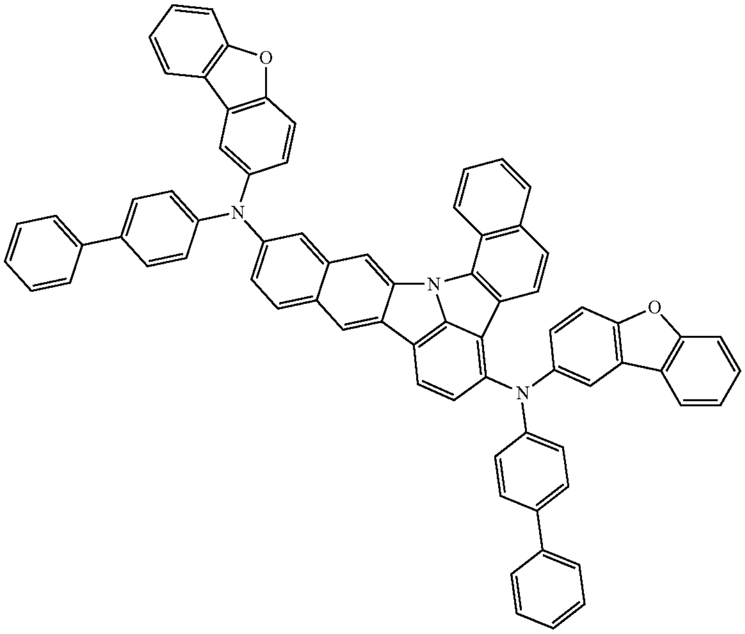
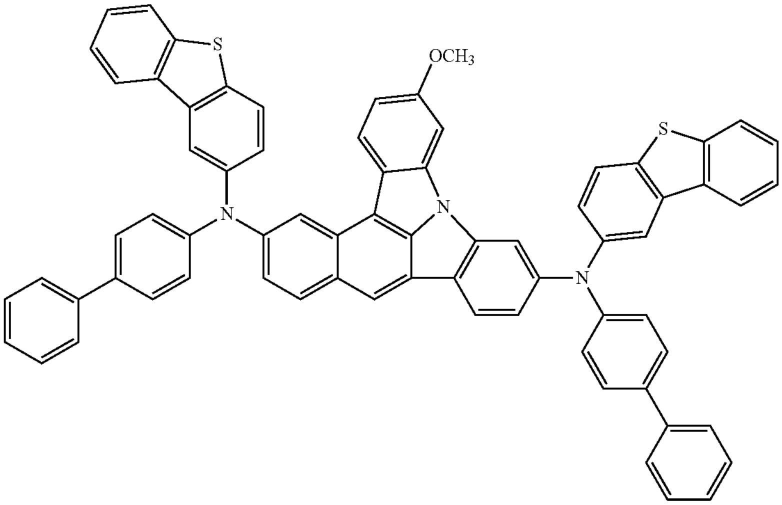

-continued
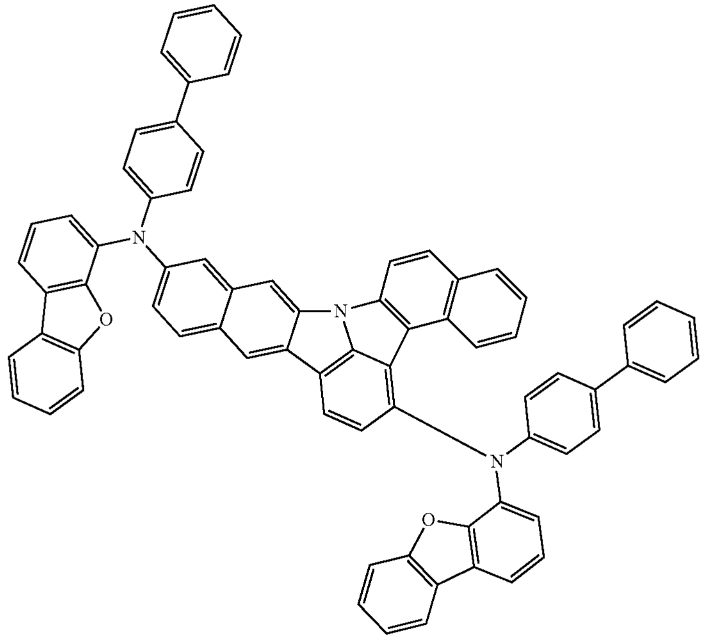
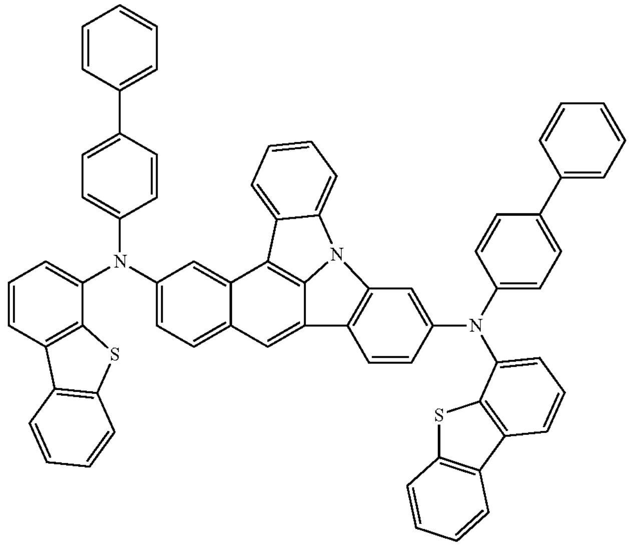
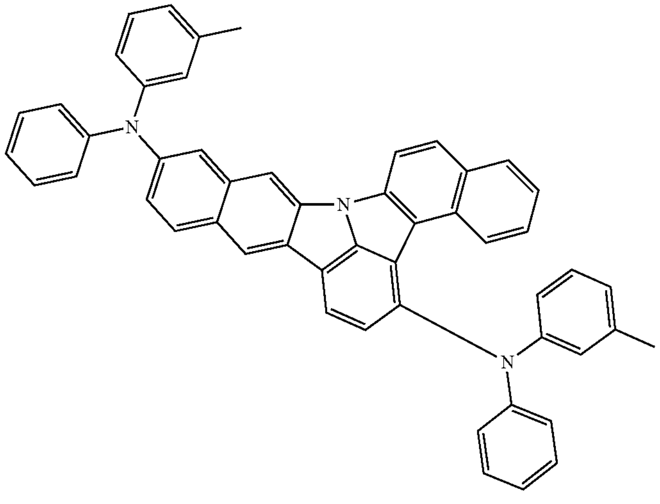

-continued
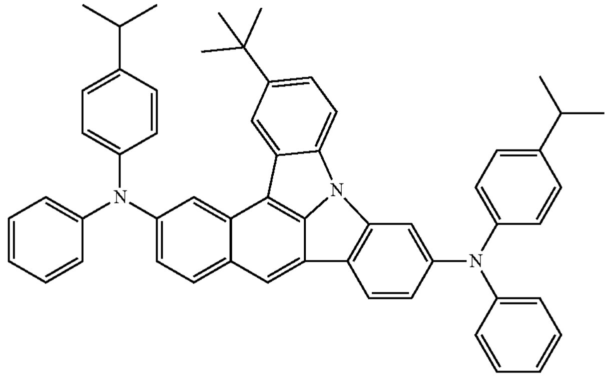
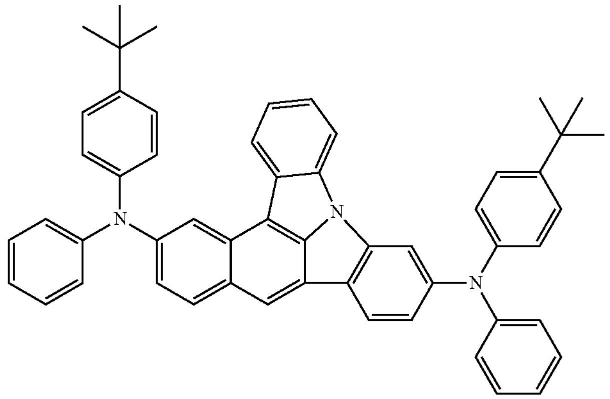
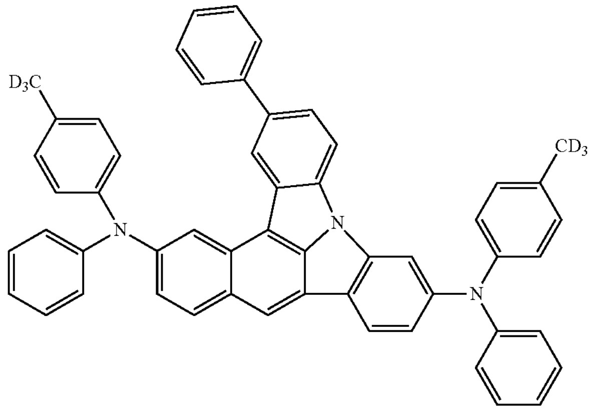
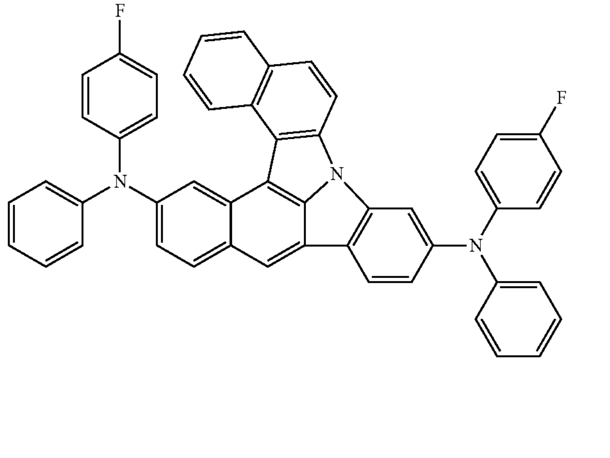

-continued
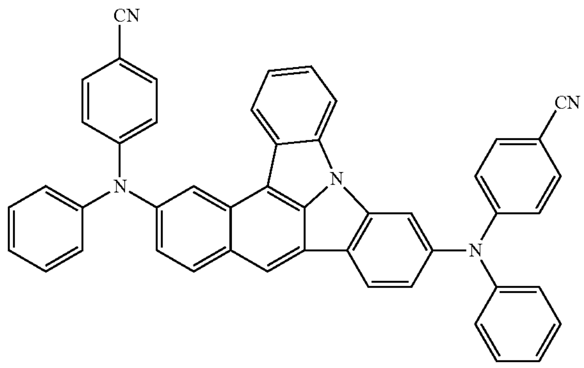
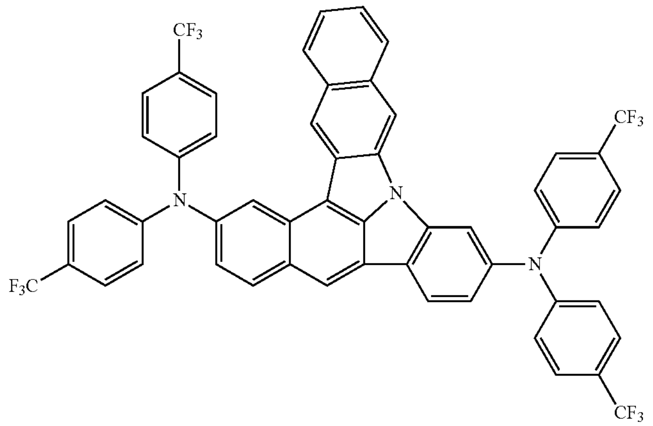
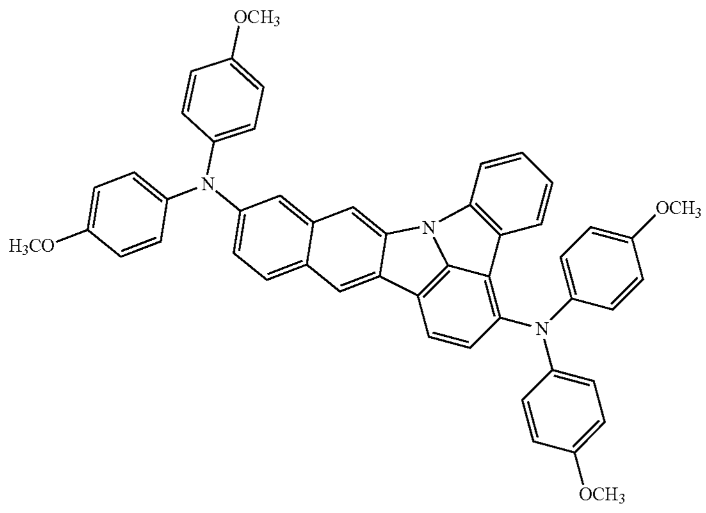

-continued
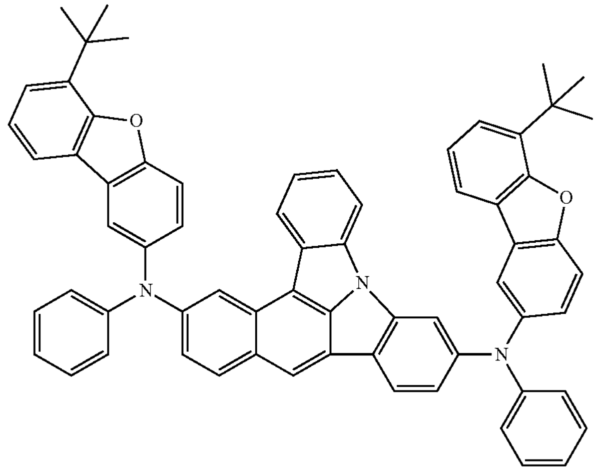
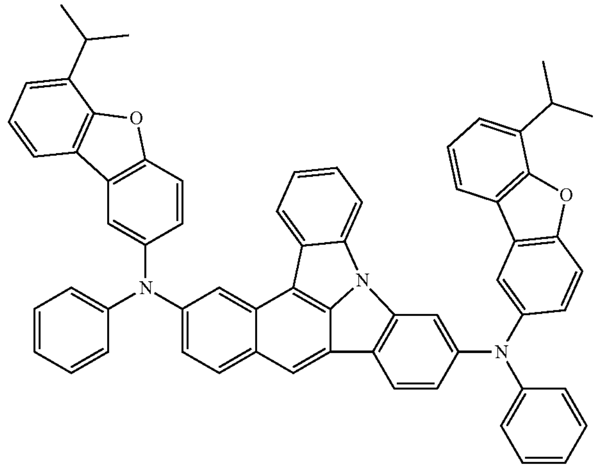
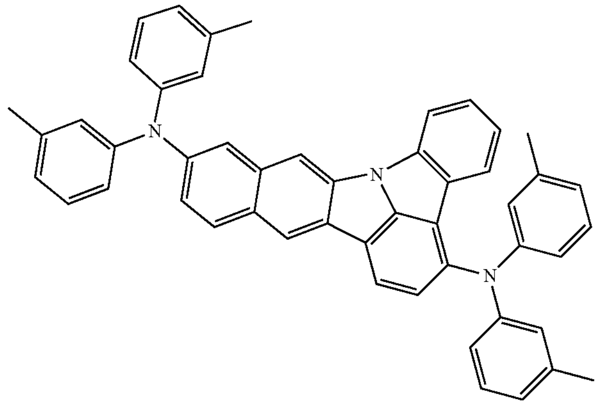
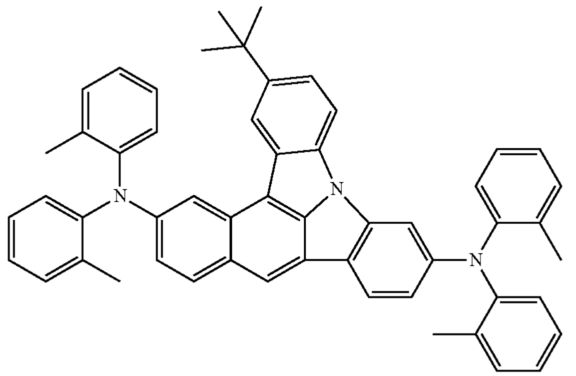

-continued
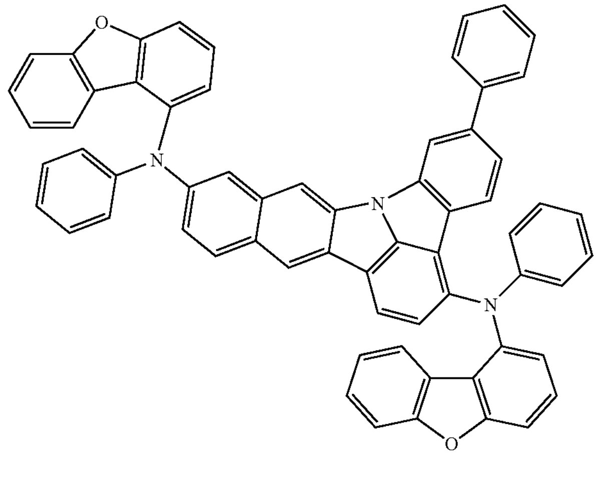
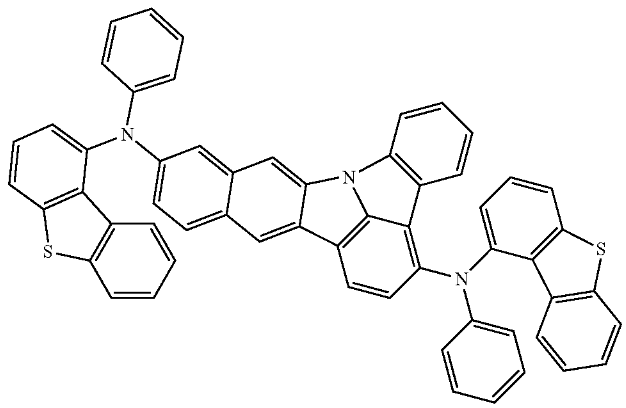
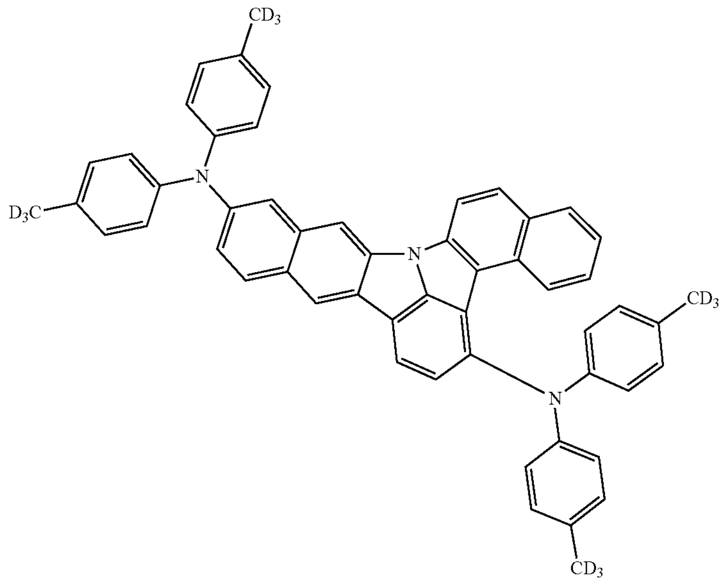

-continued
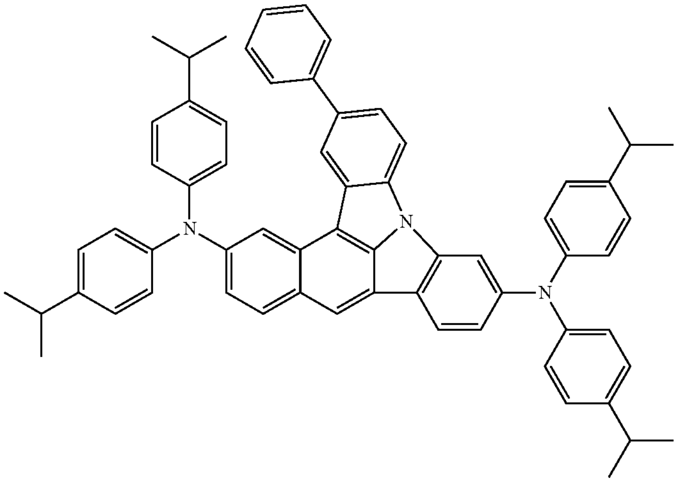
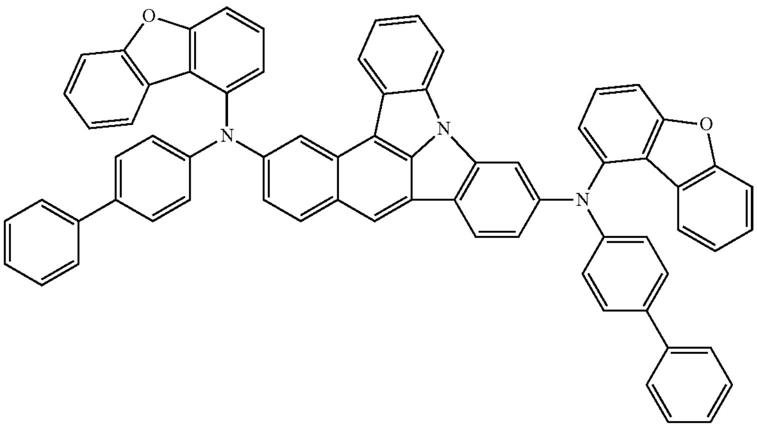
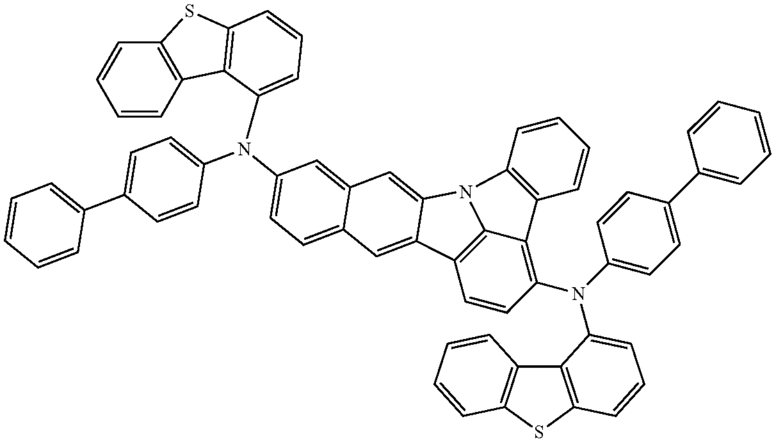

-continued
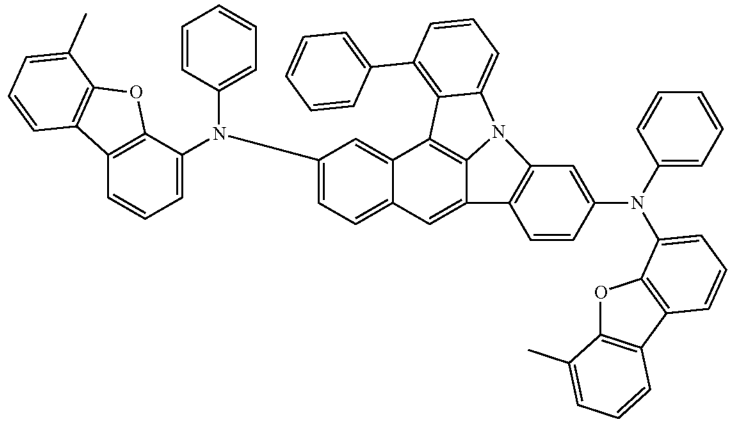
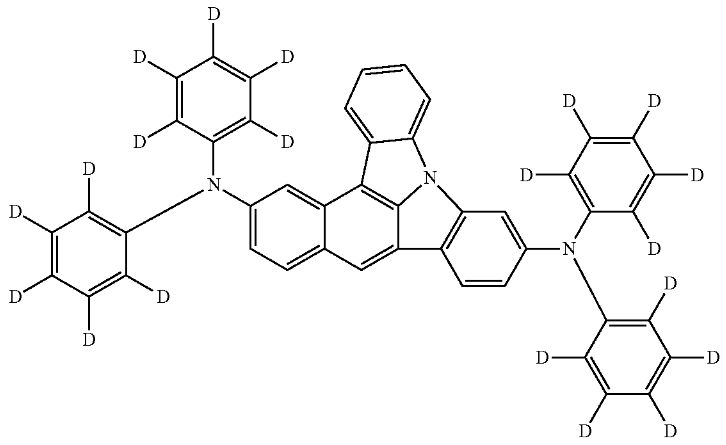
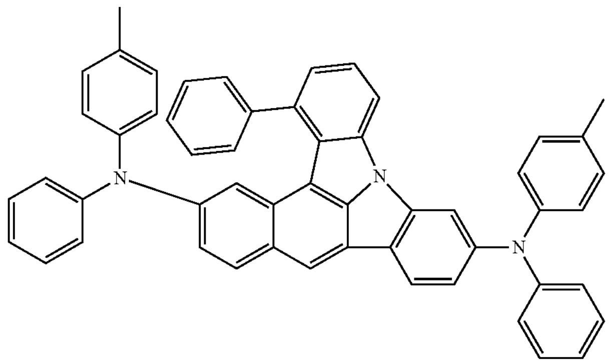
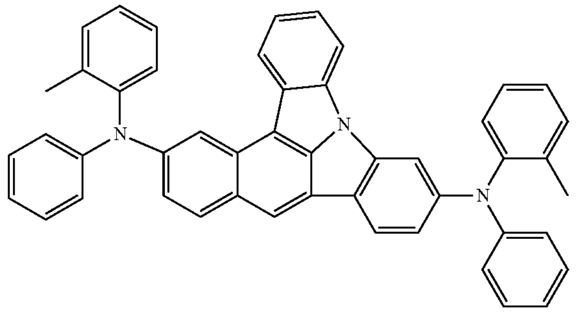

-continued
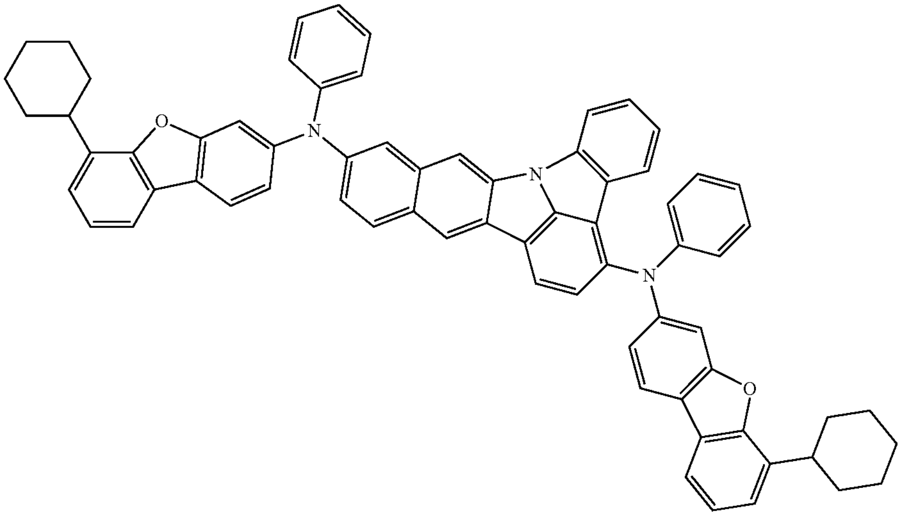
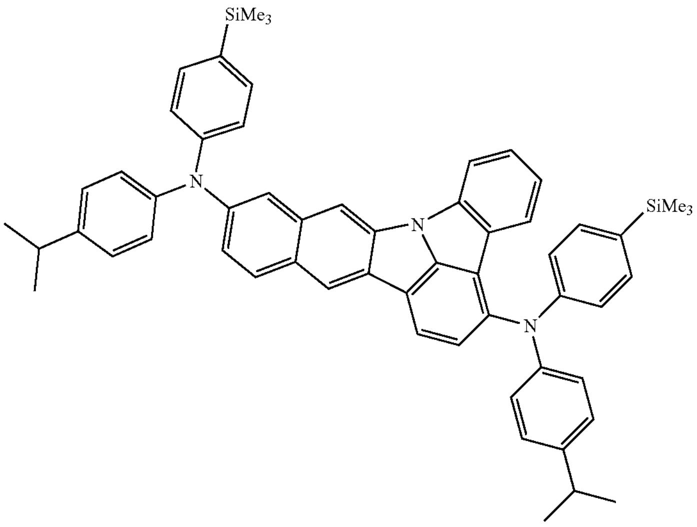
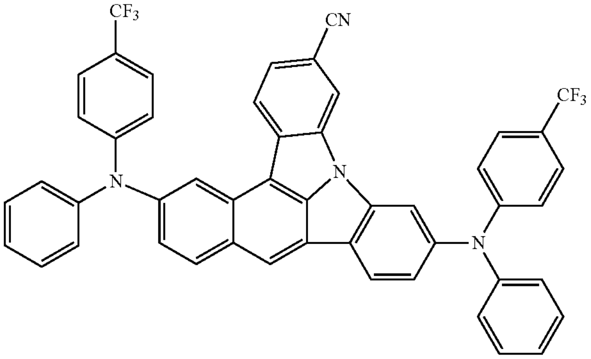

-continued
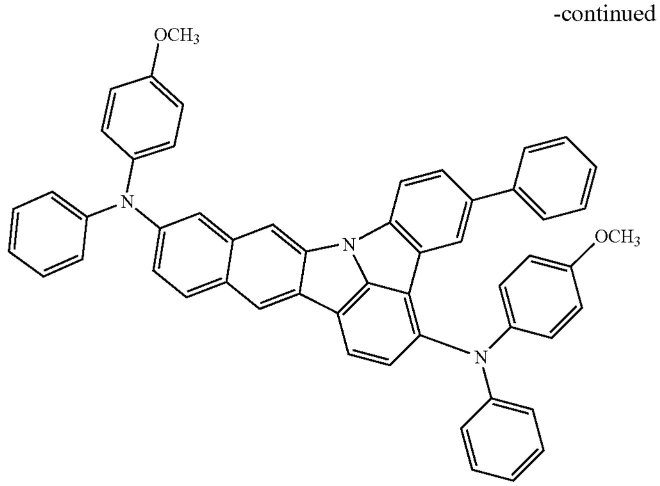
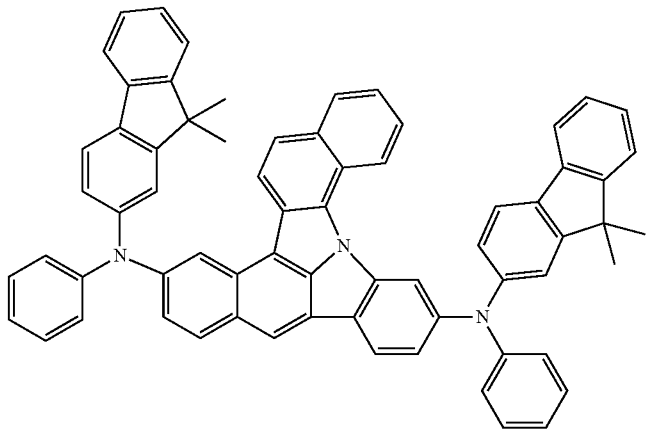
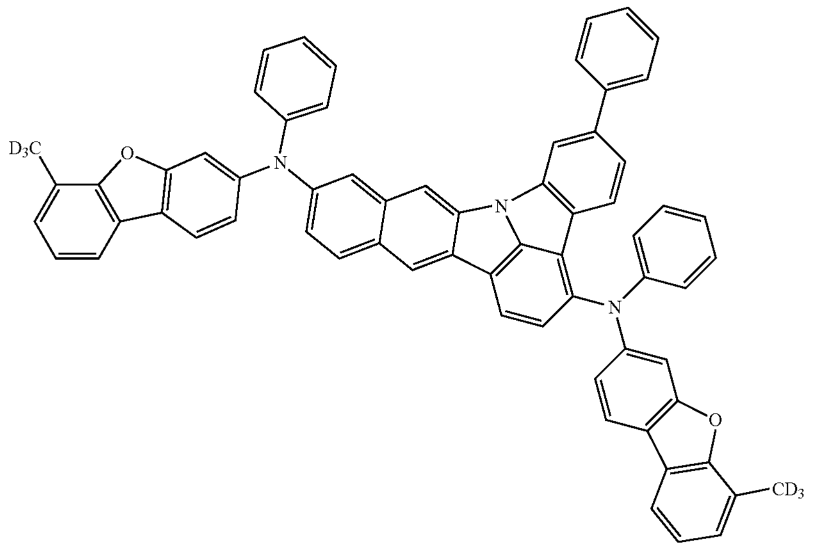

-continued
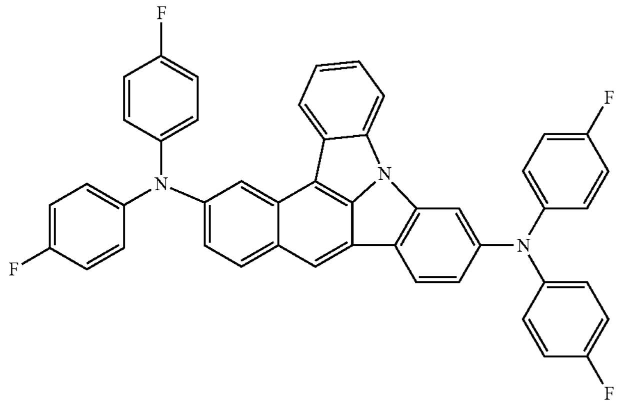
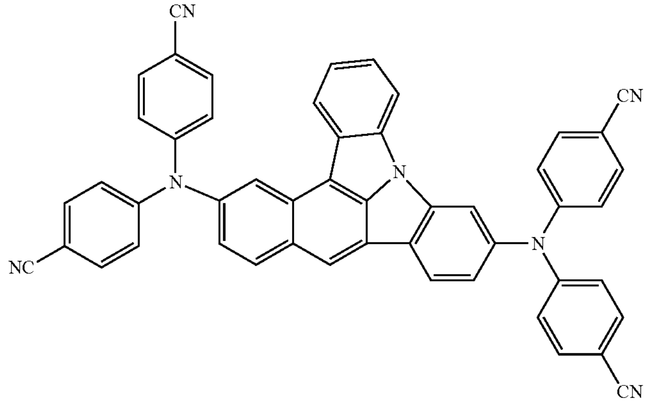
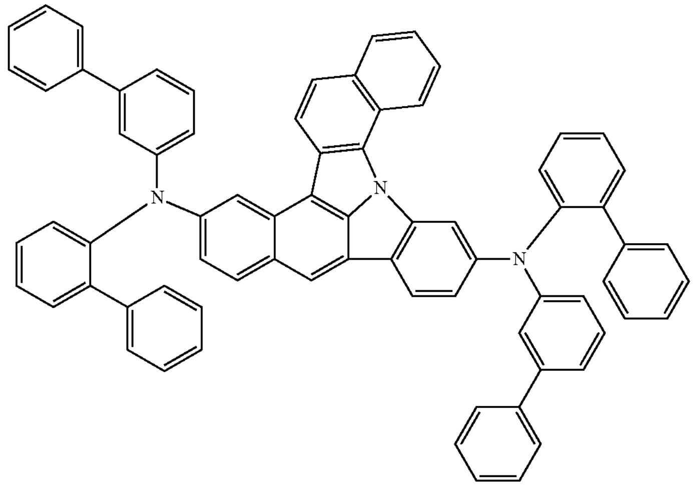

-continued
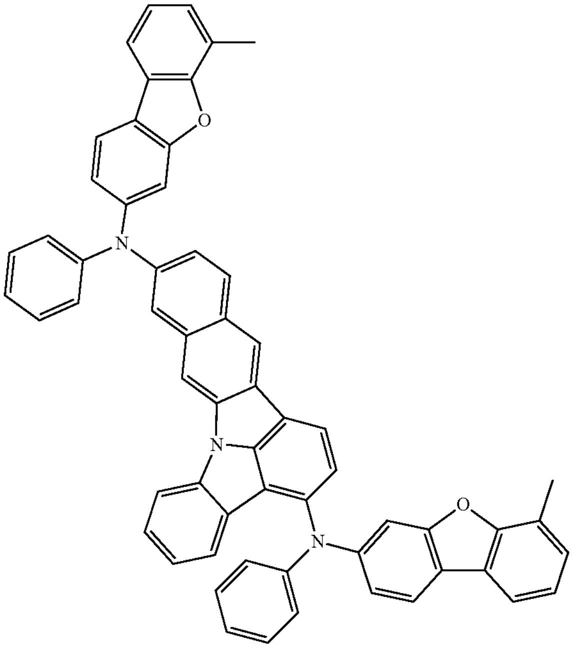
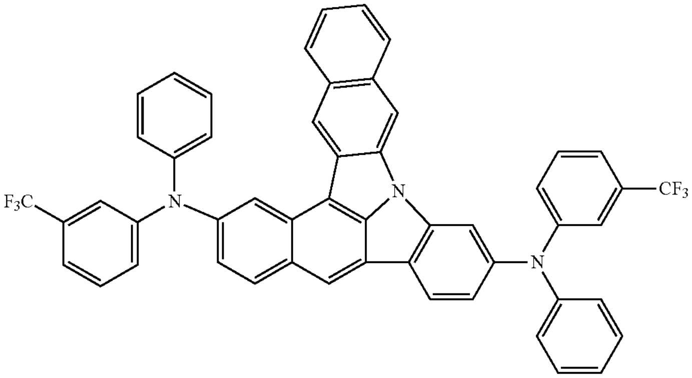
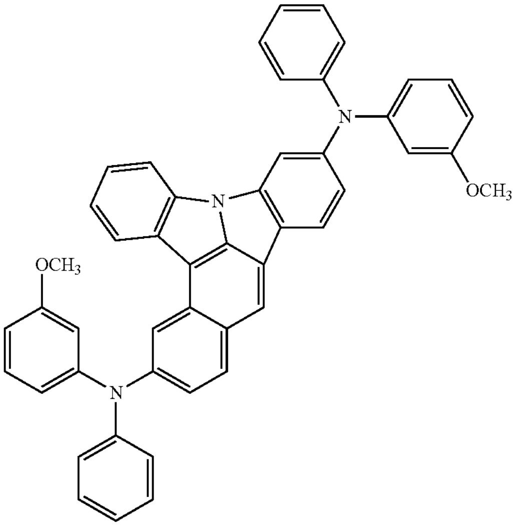
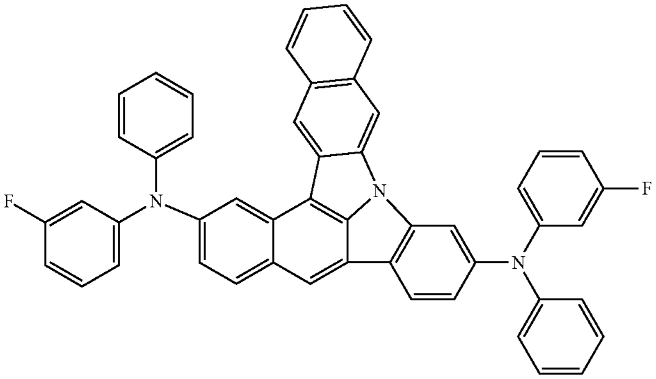

-continued
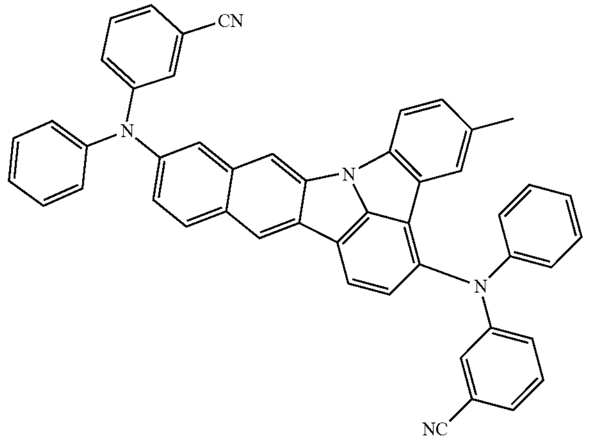
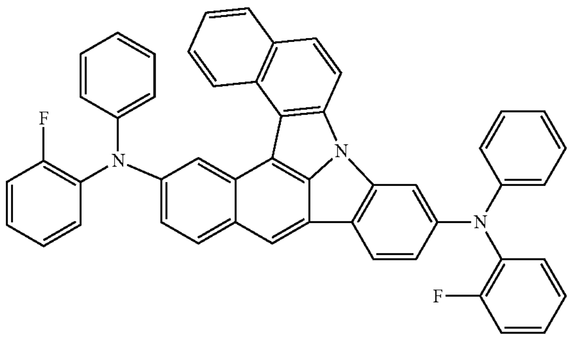
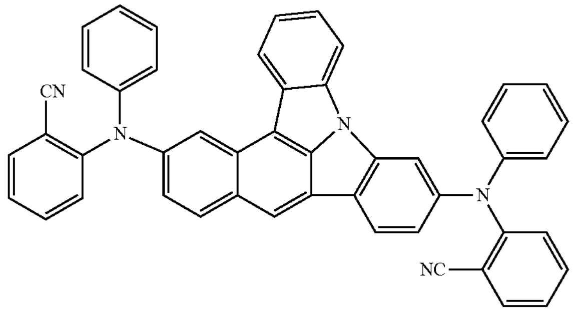
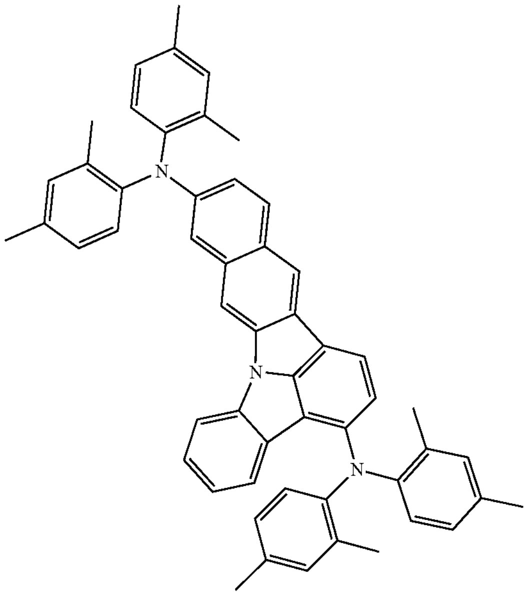
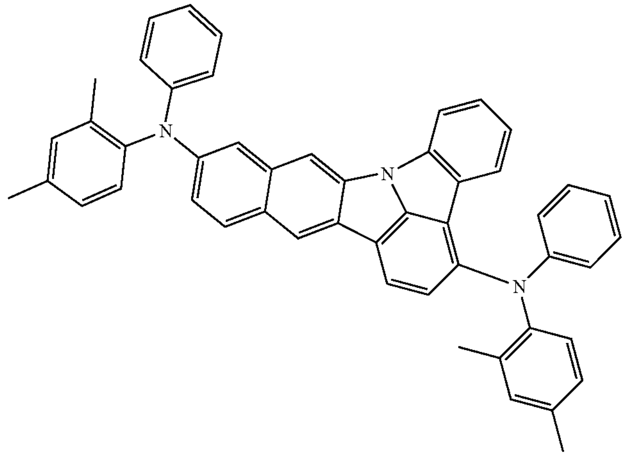

-continued
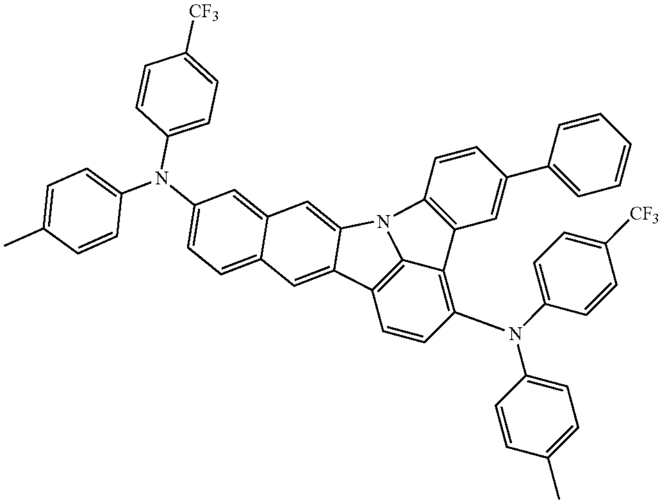
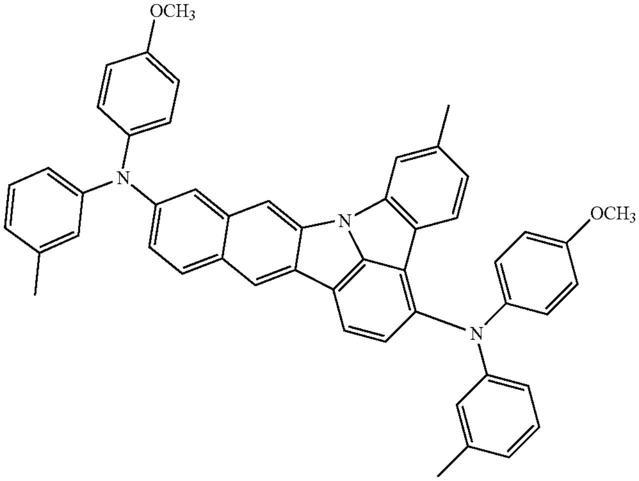
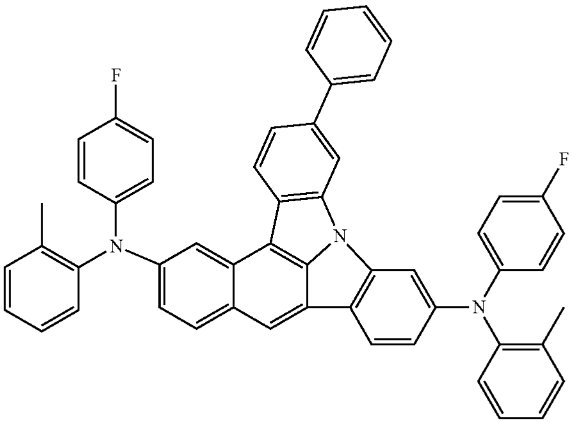

-continued
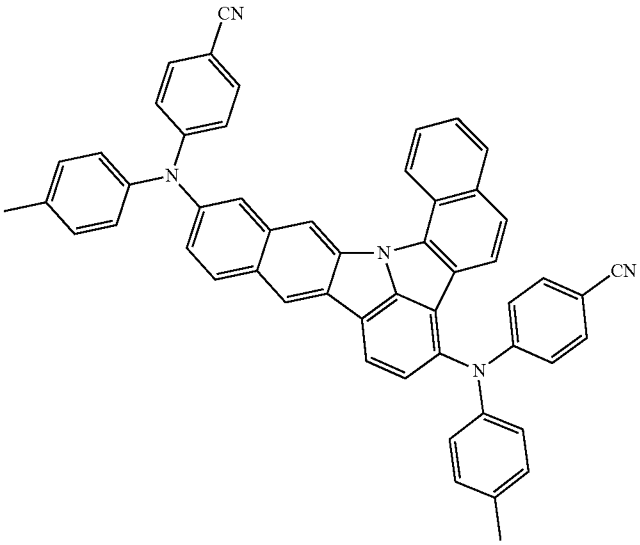
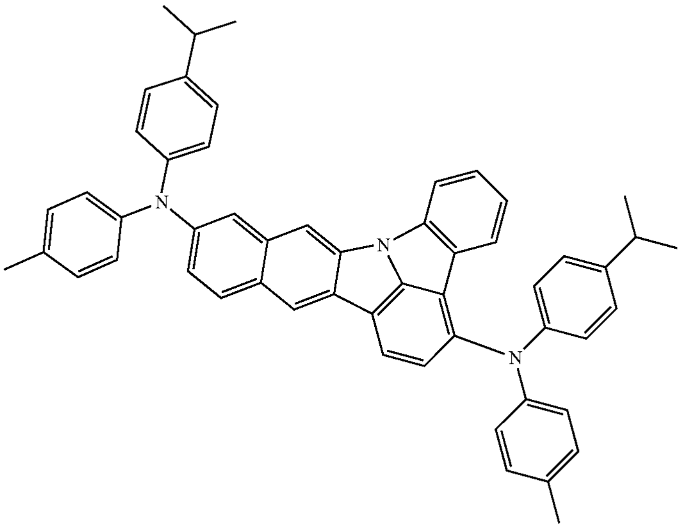
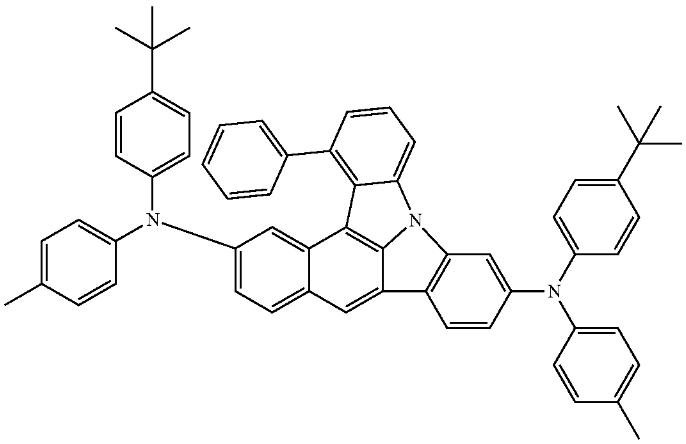

-continued
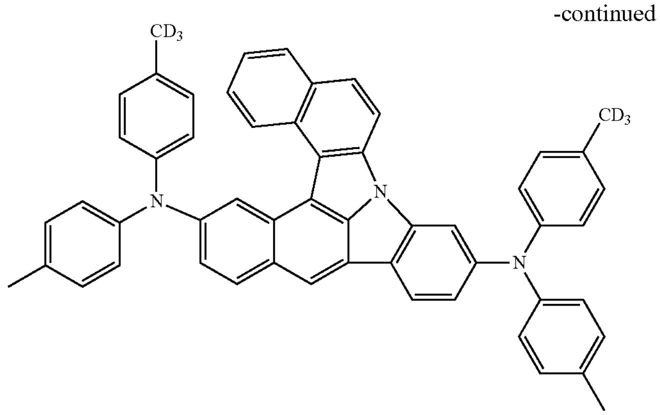
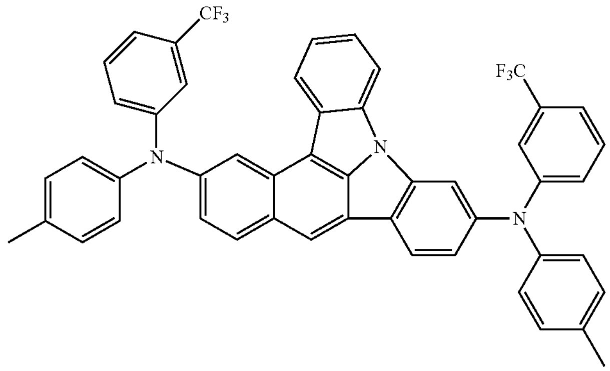
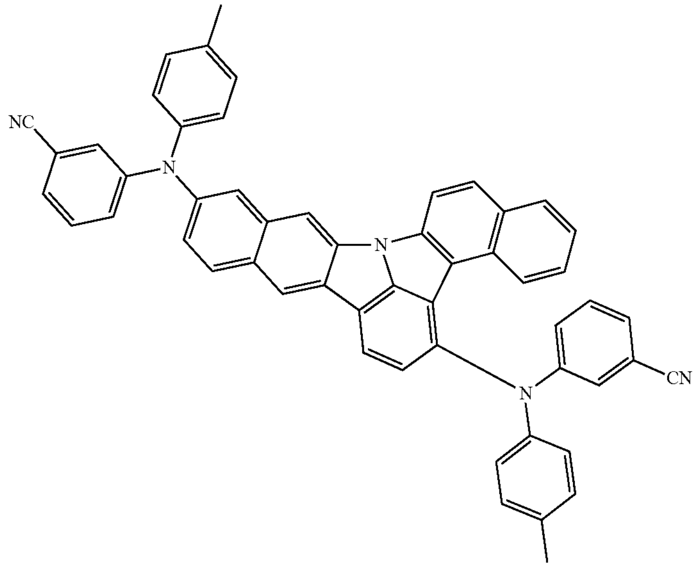
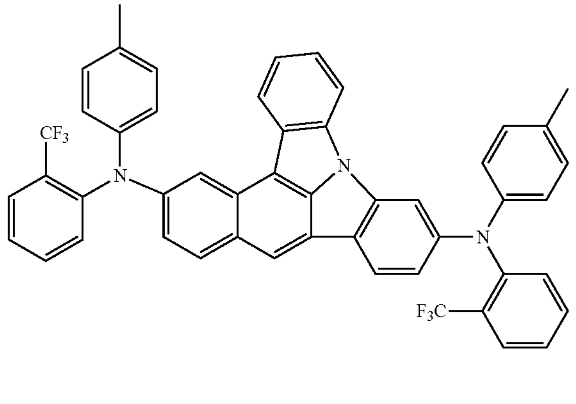

-continued
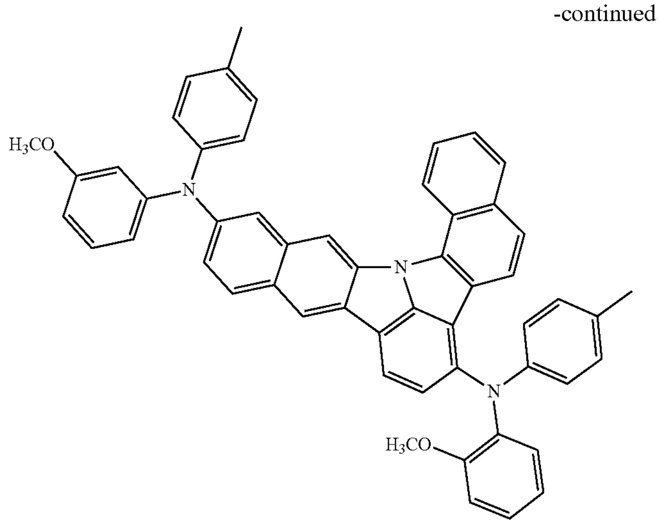
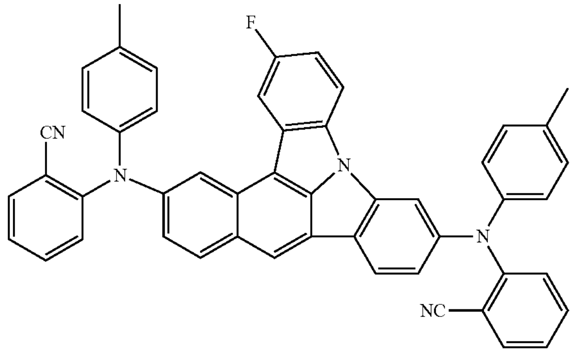
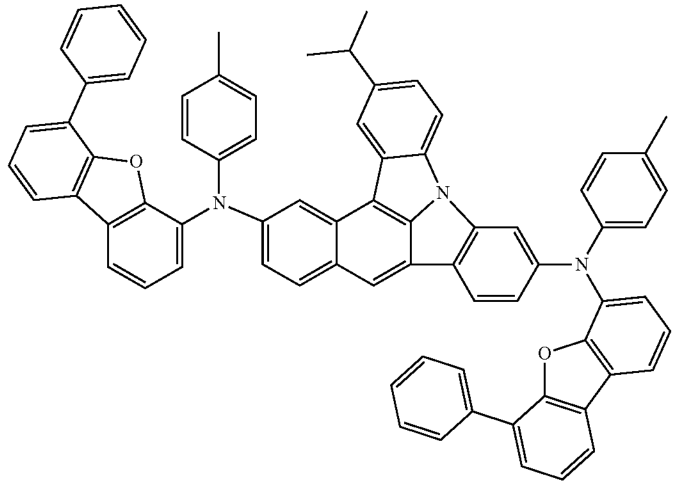

-continued
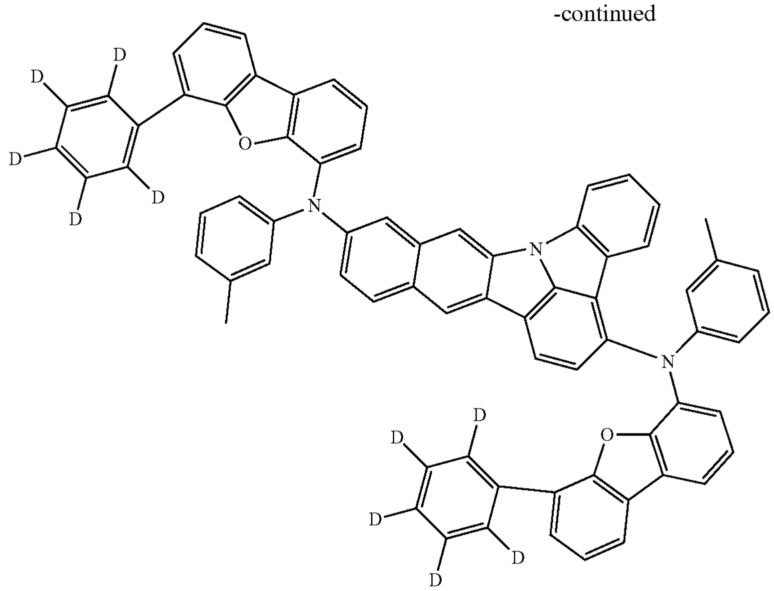
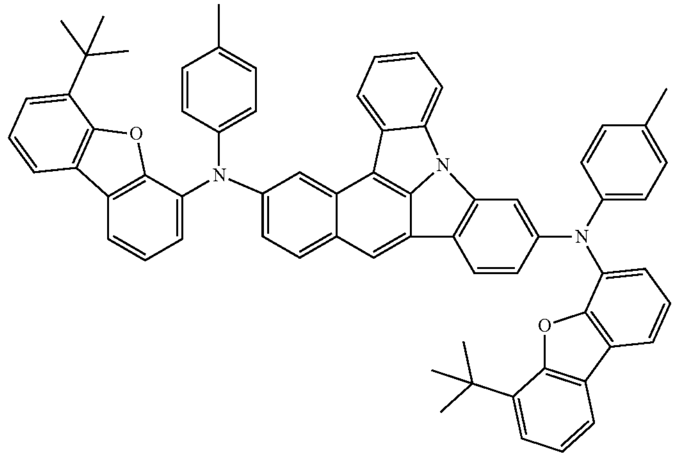
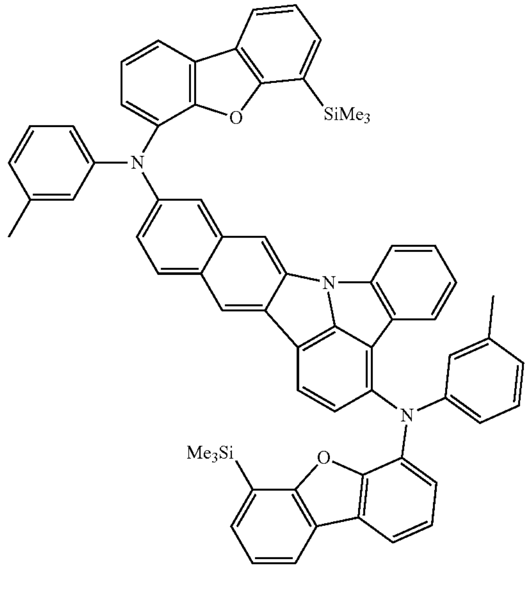

-continued
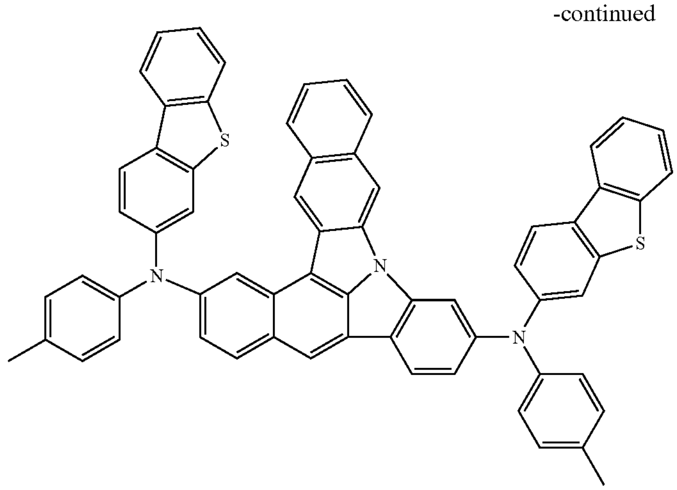
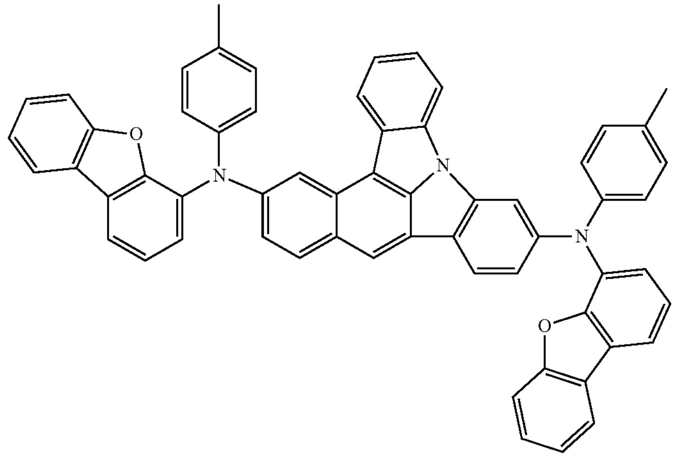
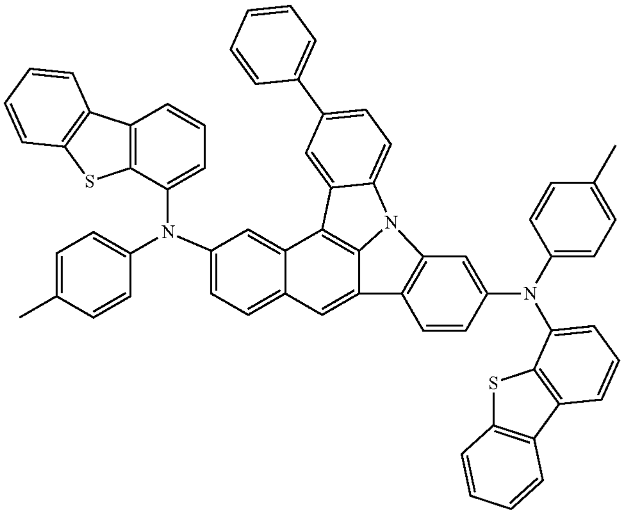

-continued
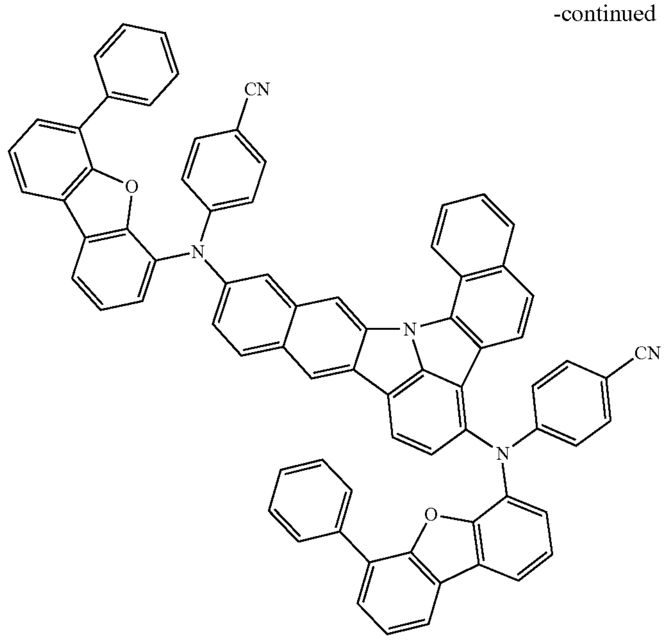
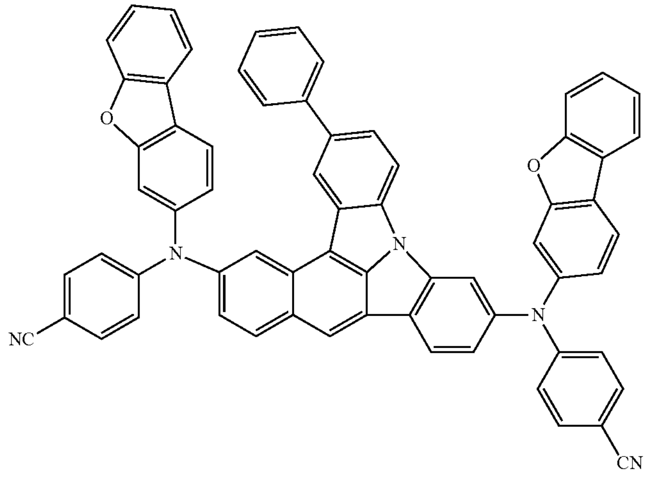
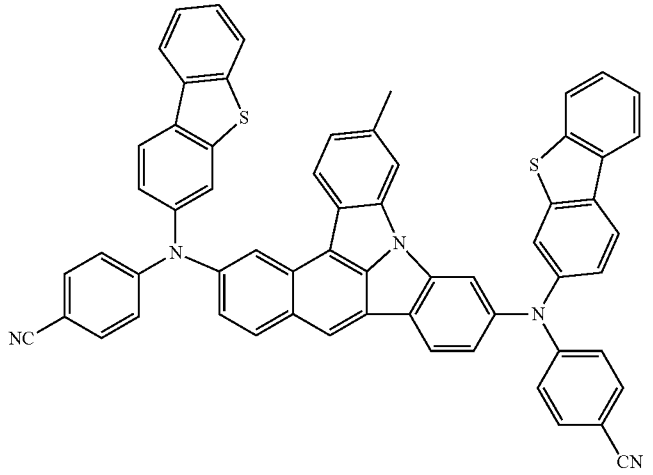

-continued
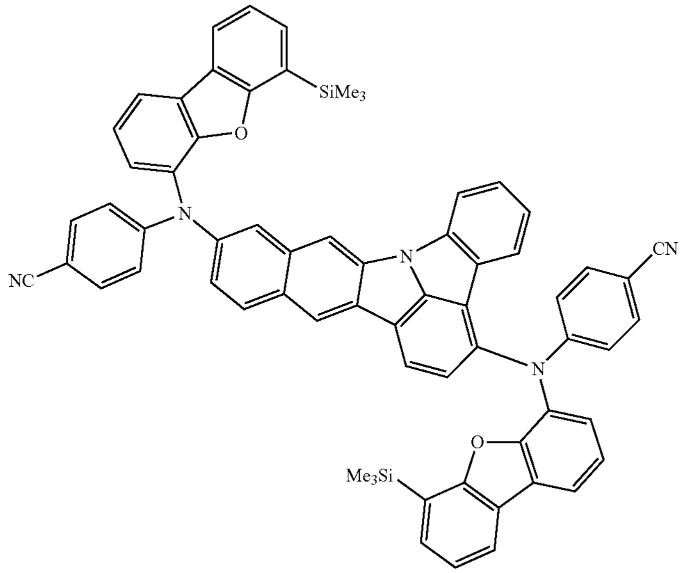
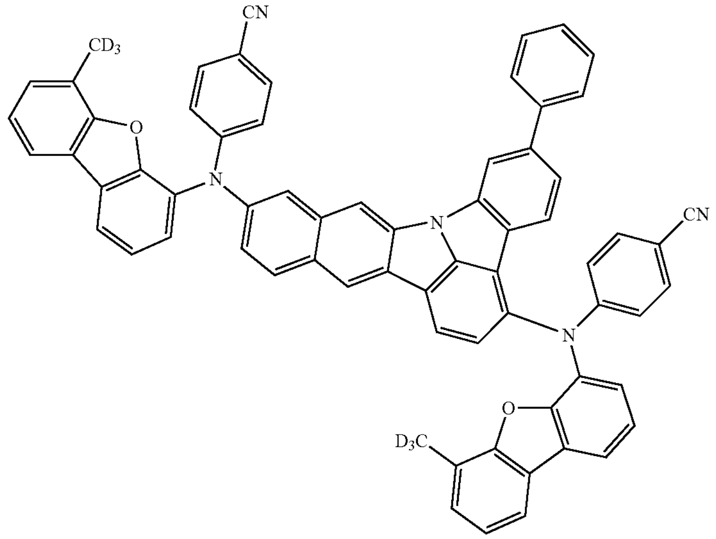
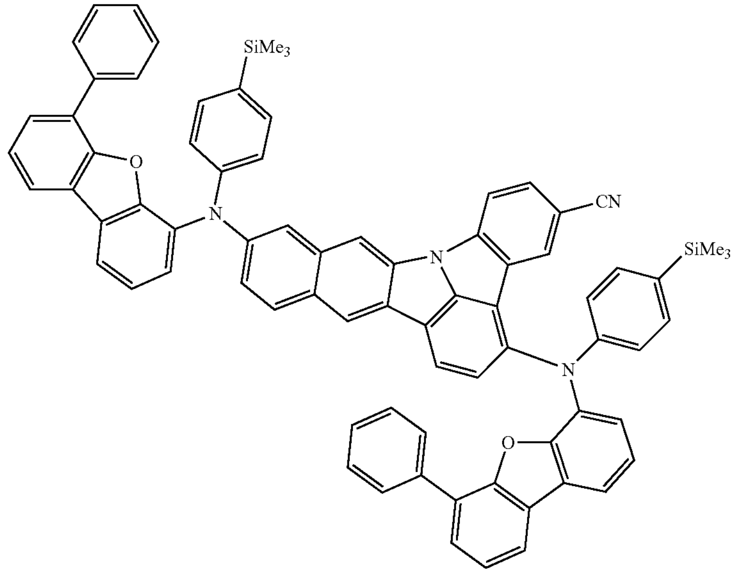

-continued
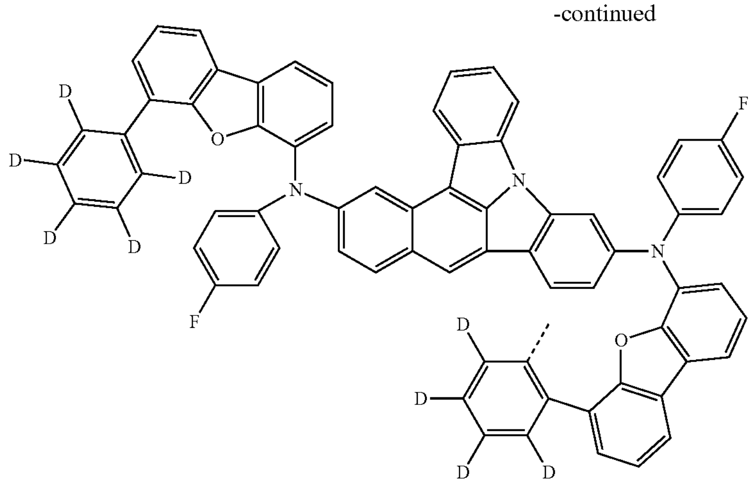
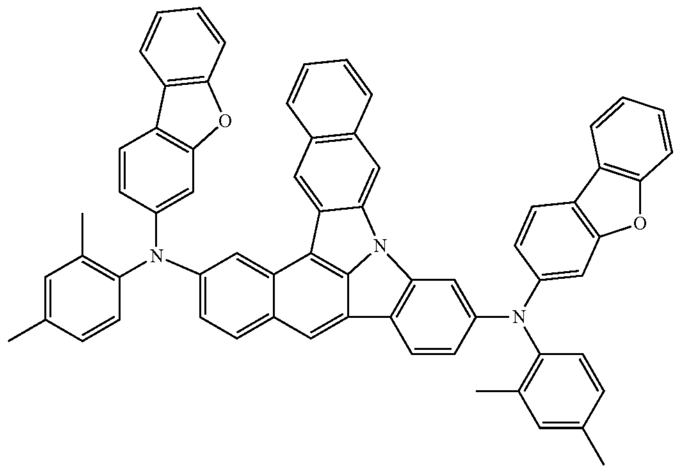
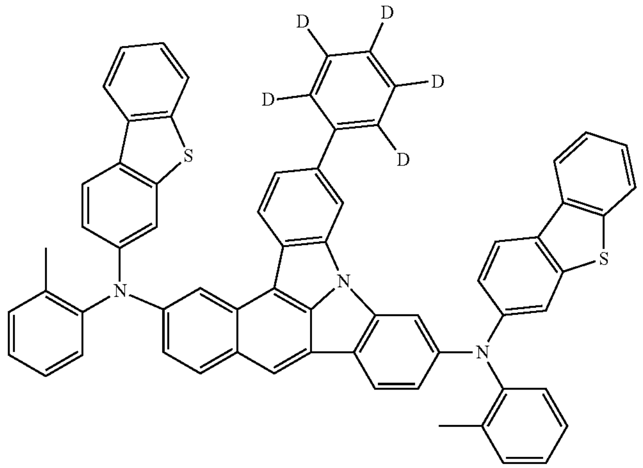

-continued
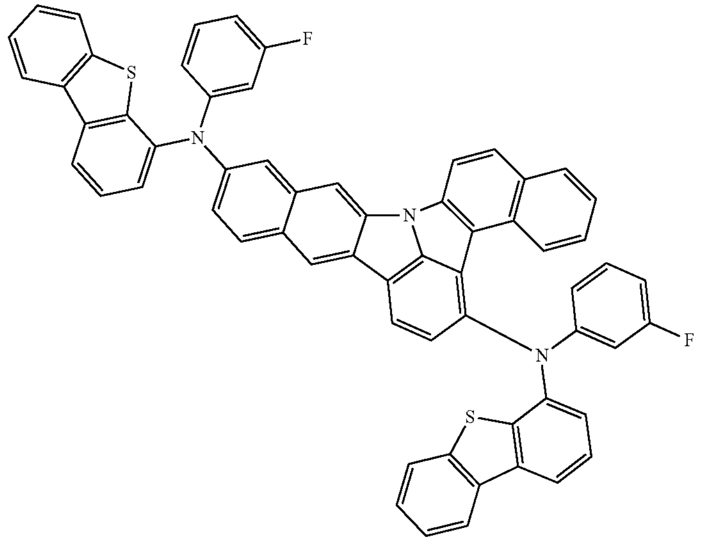
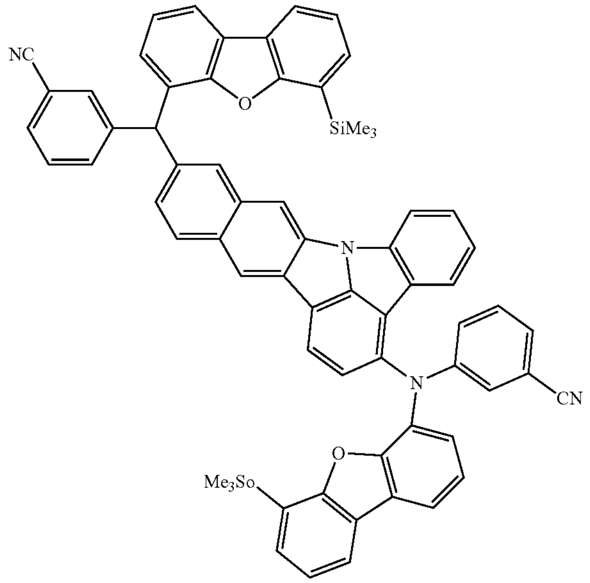
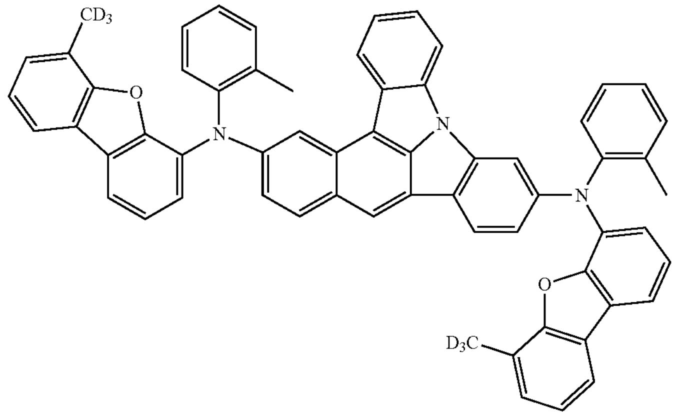

-continued
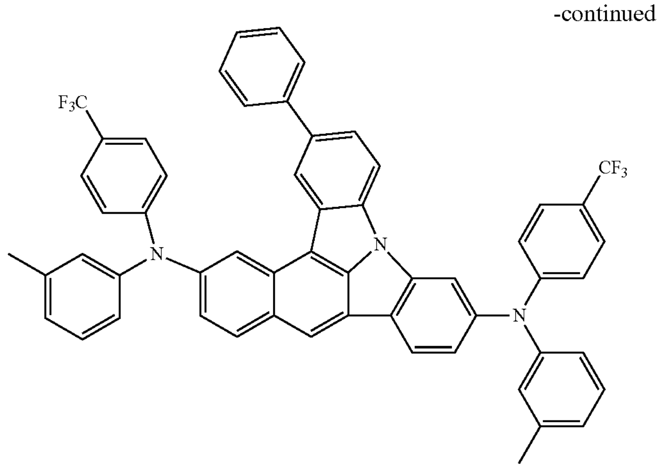
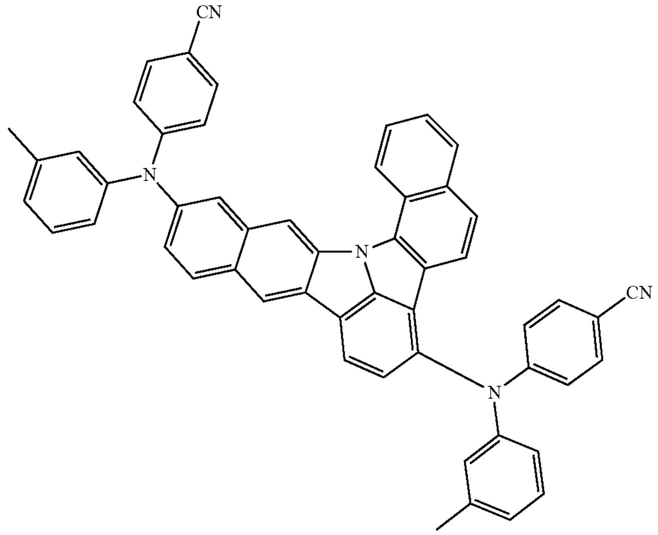
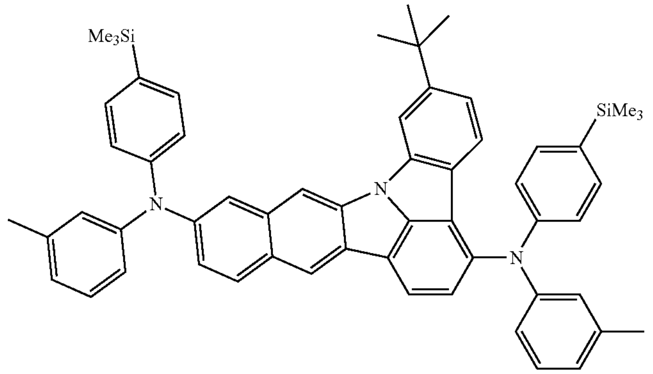

-continued
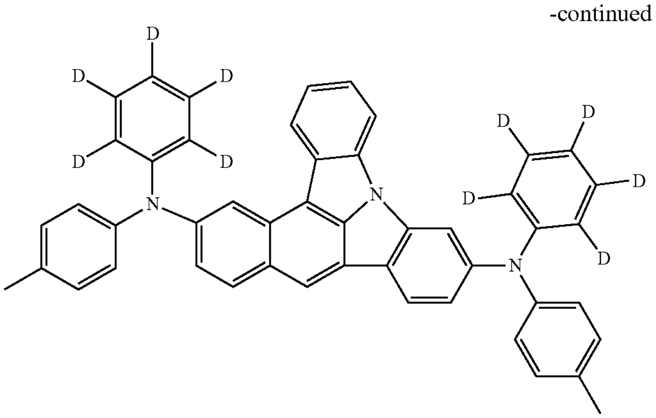
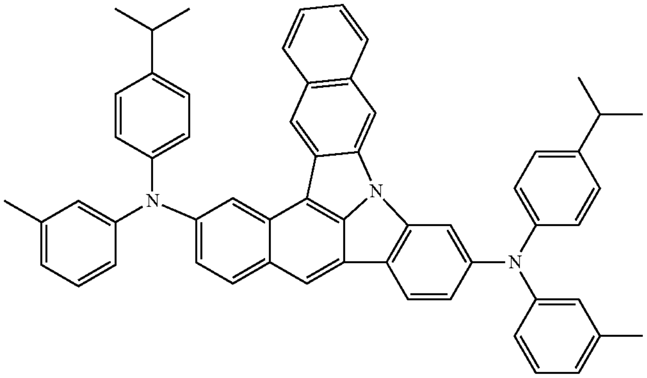
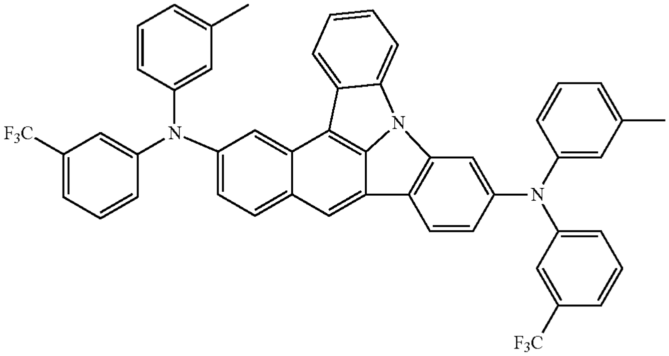
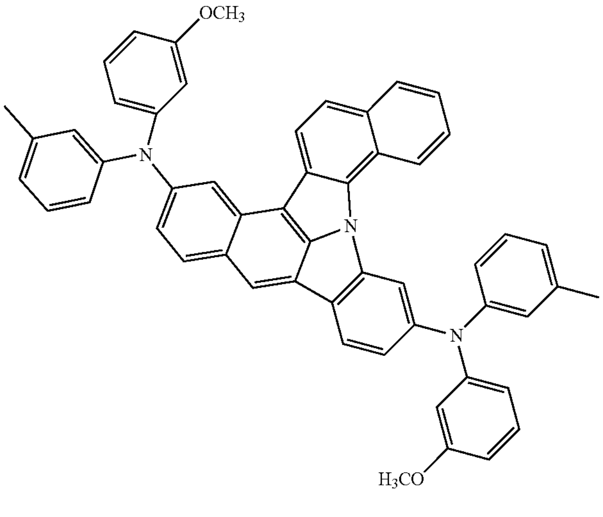

-continued
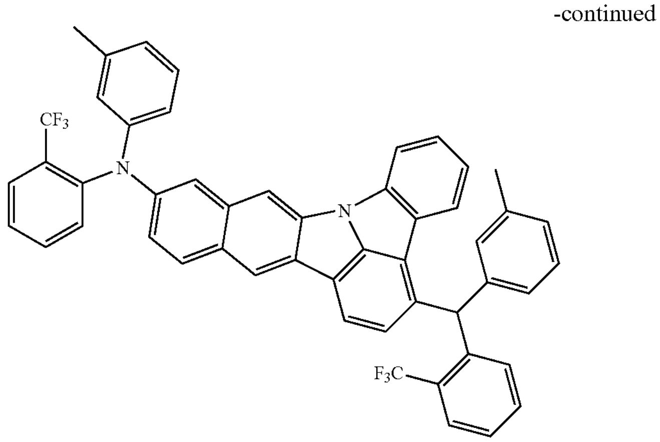
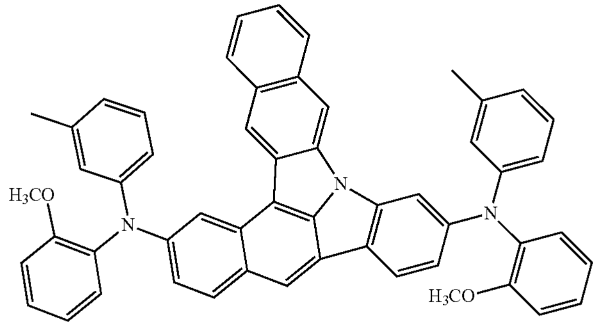
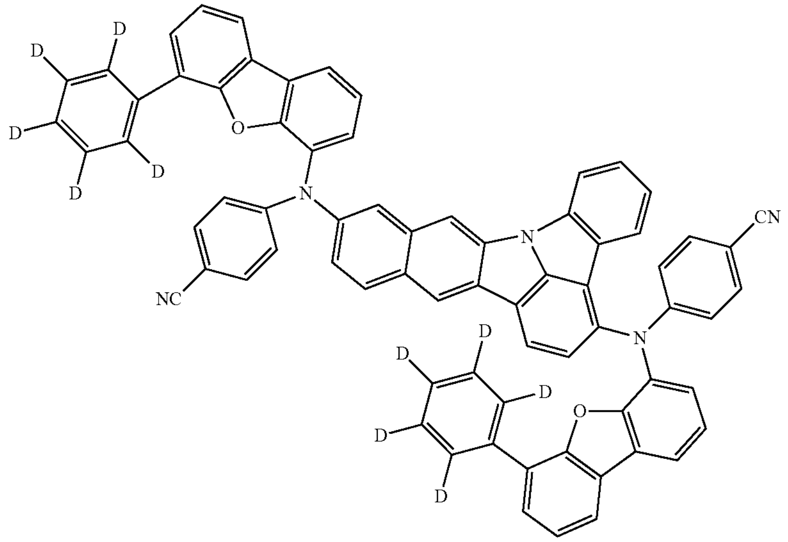

-continued
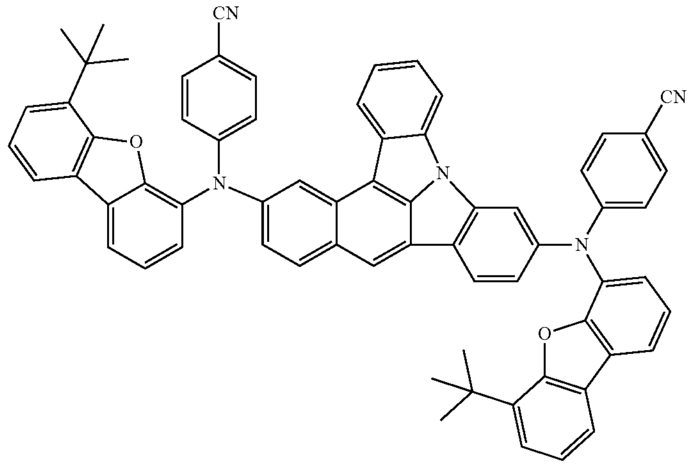
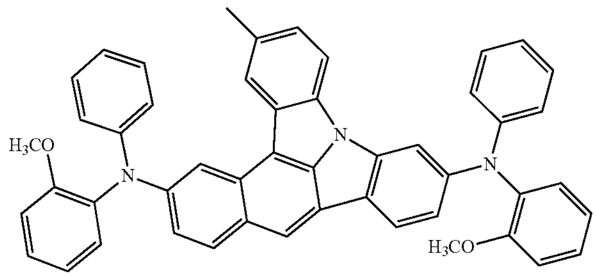
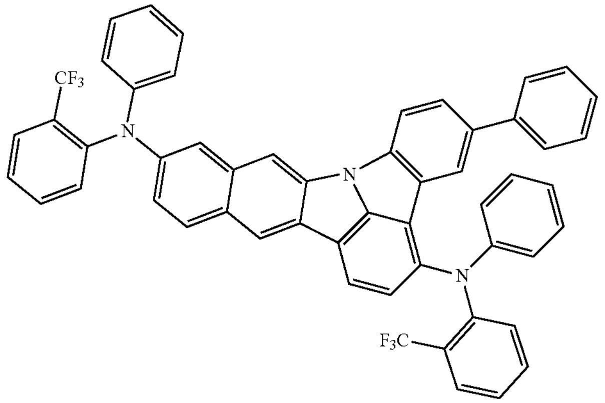
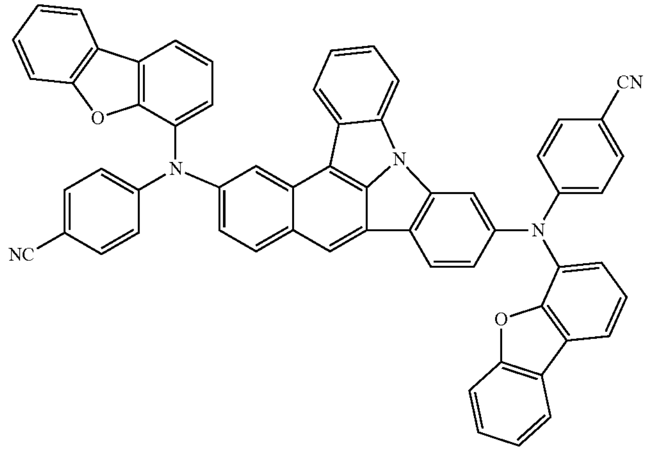

-continued
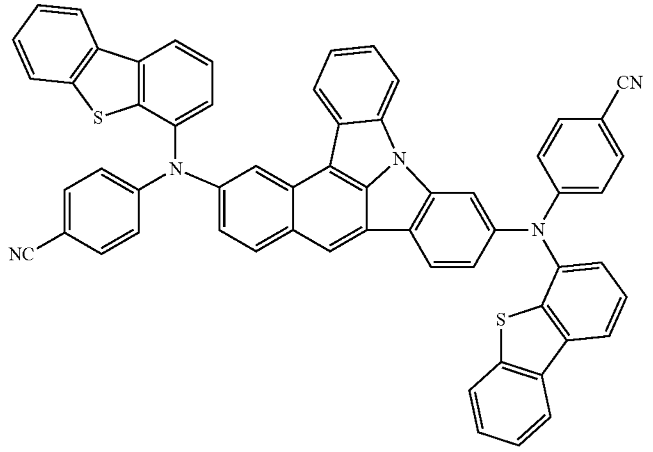
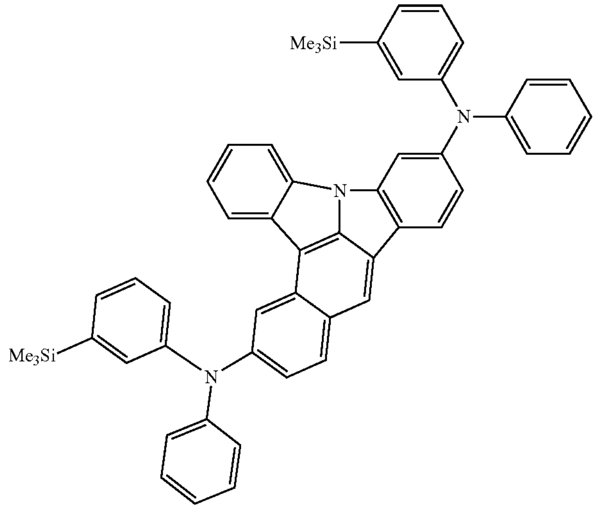
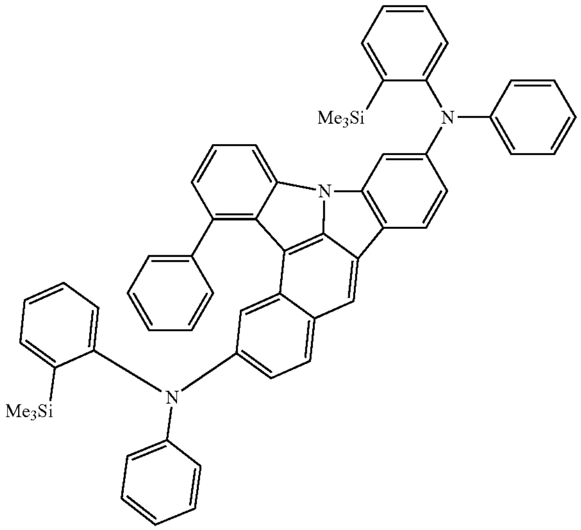
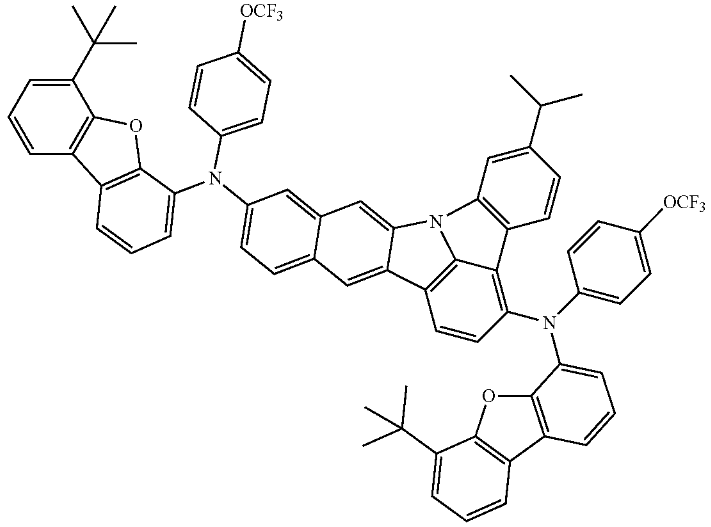

-continued
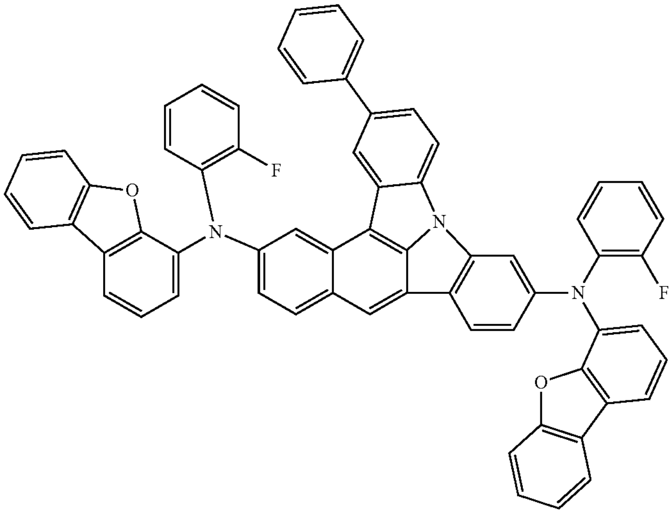
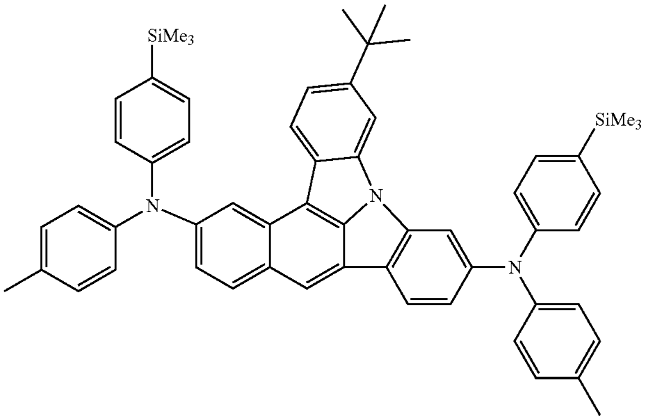
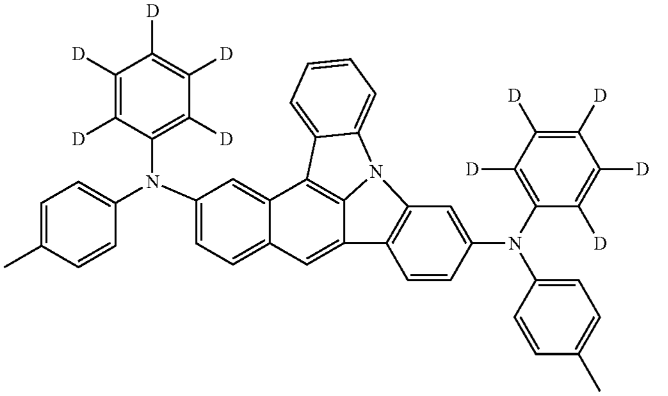
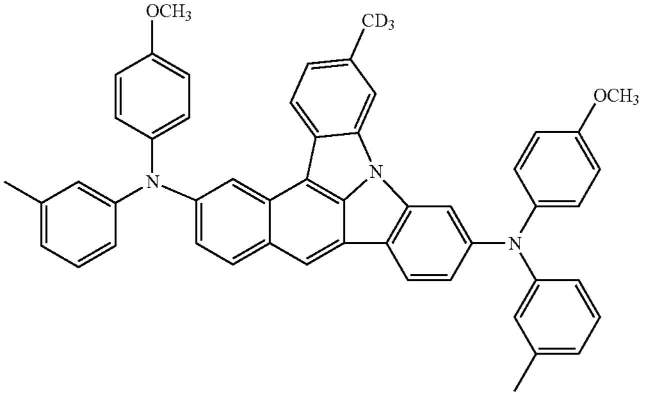

-continued
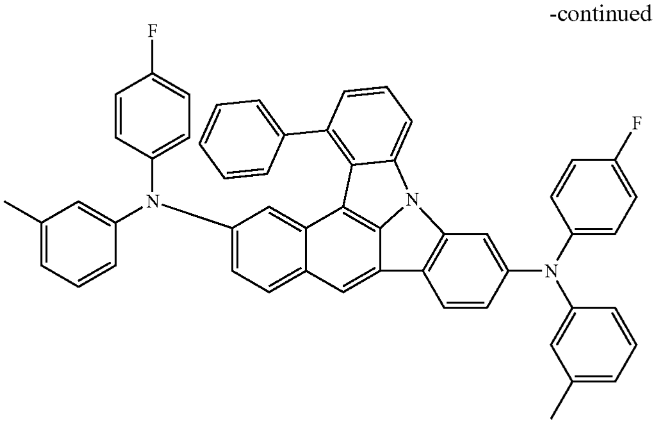
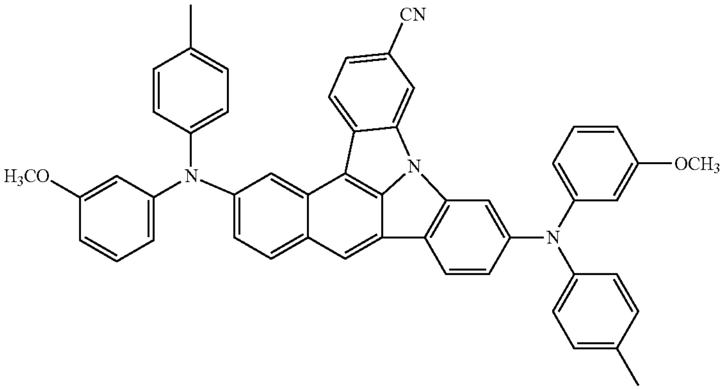
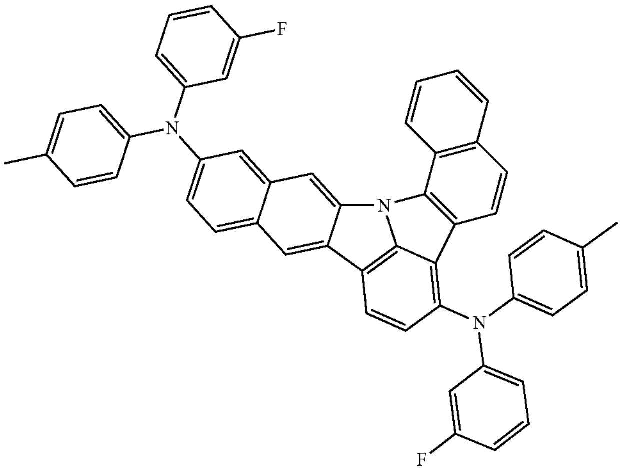
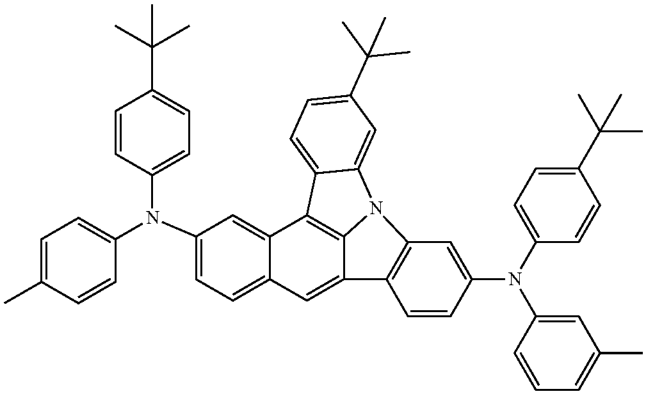

-continued
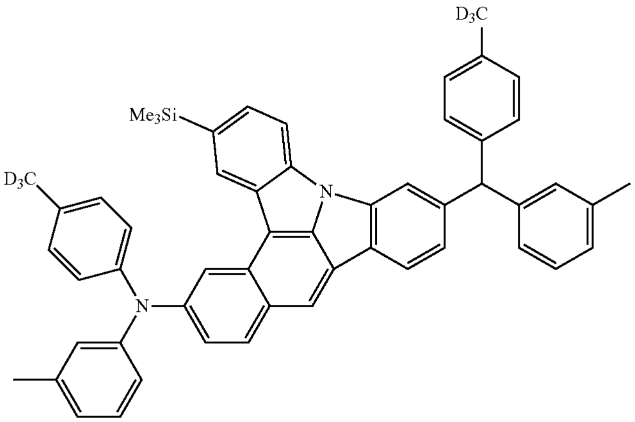
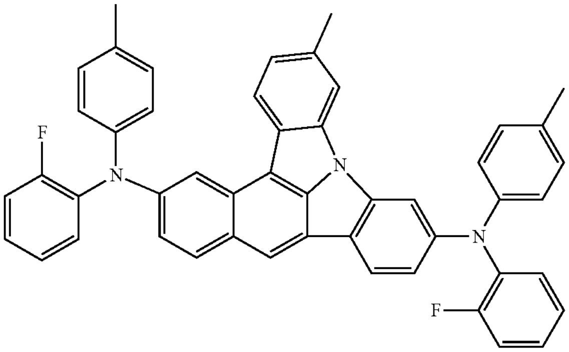
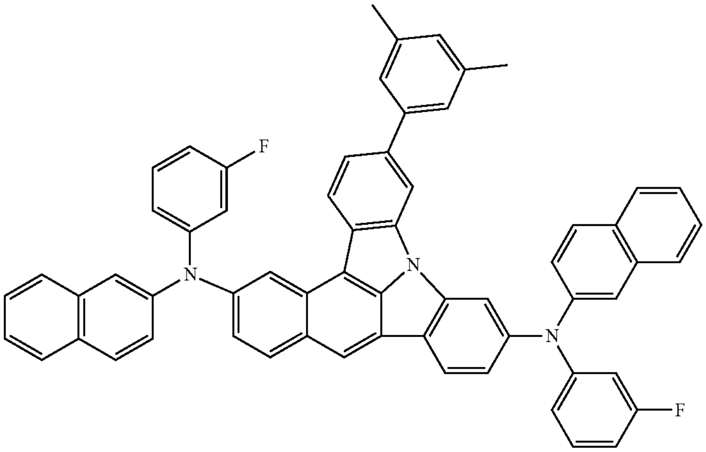
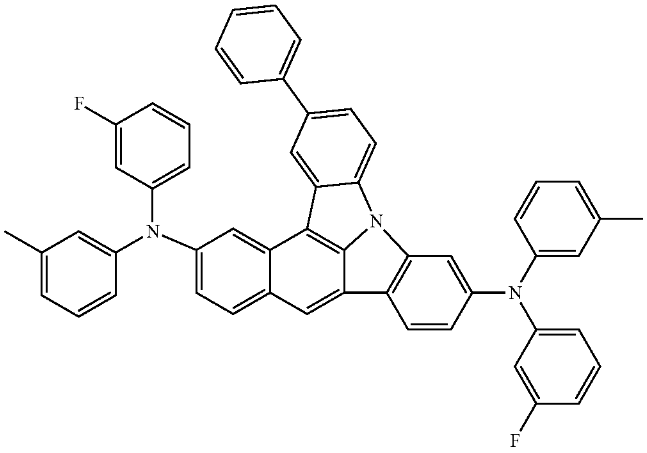

-continued
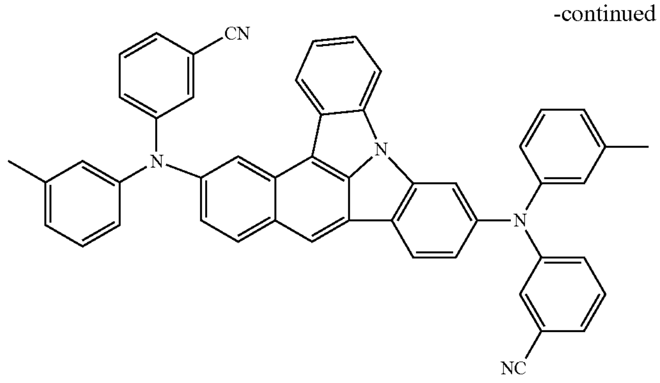
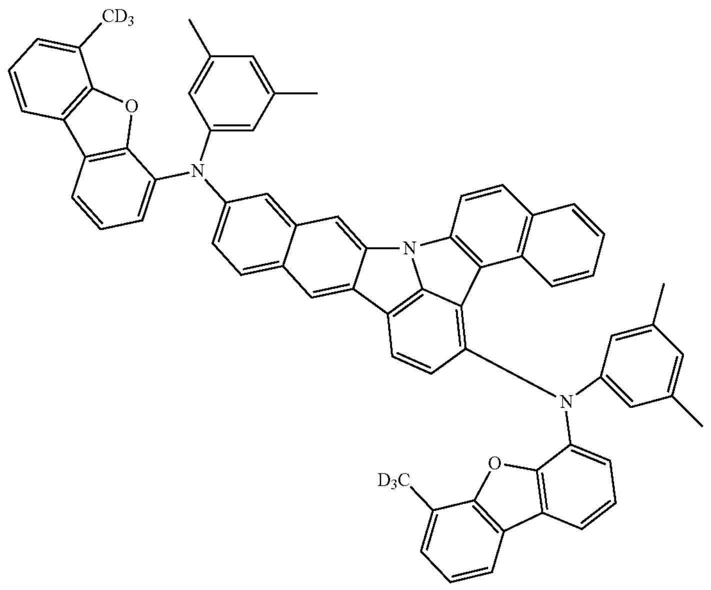
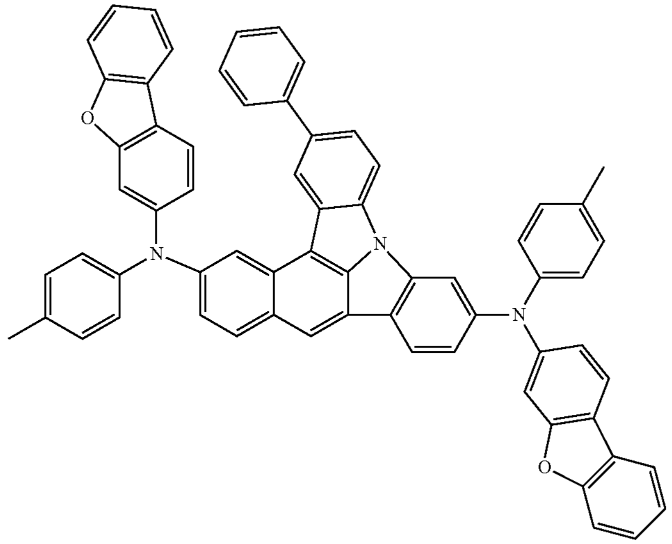

-continued
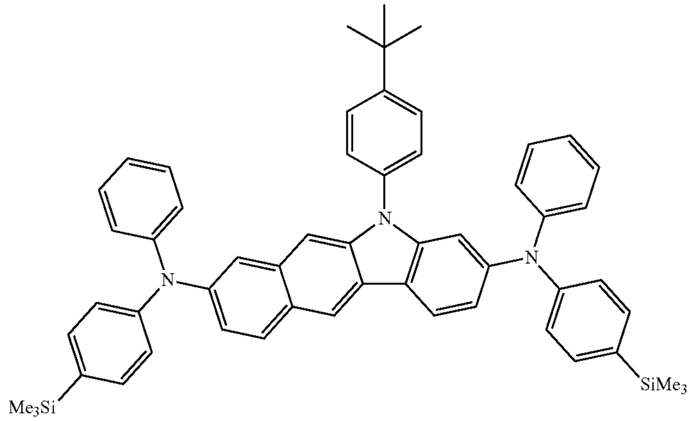
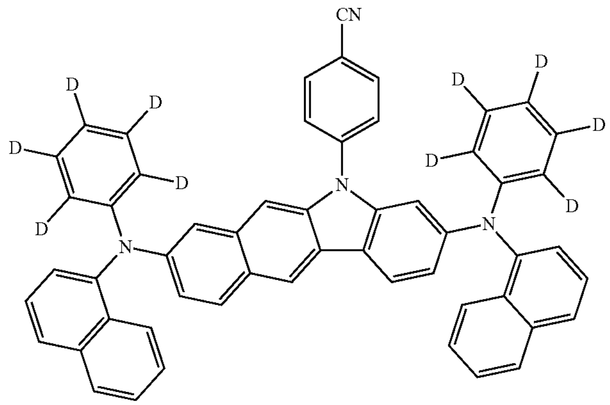
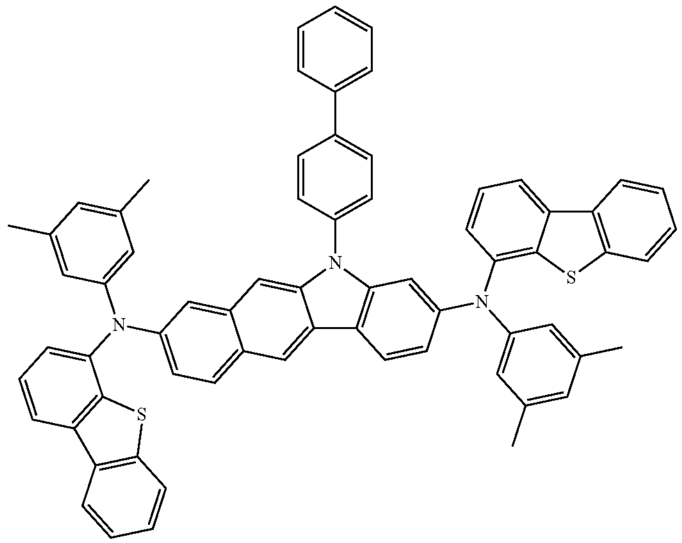

-continued
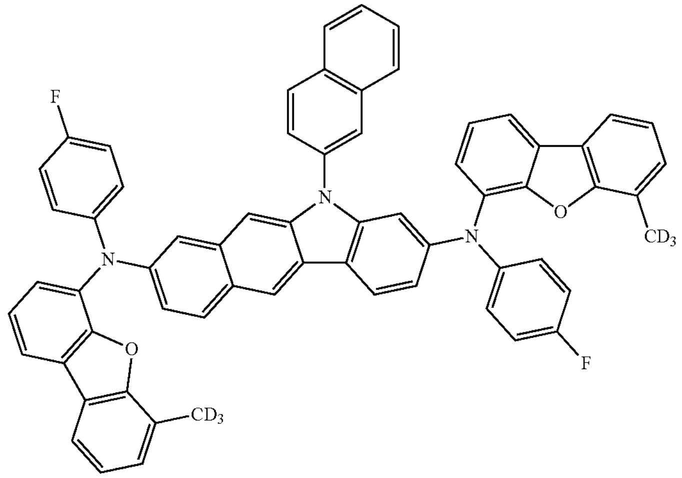
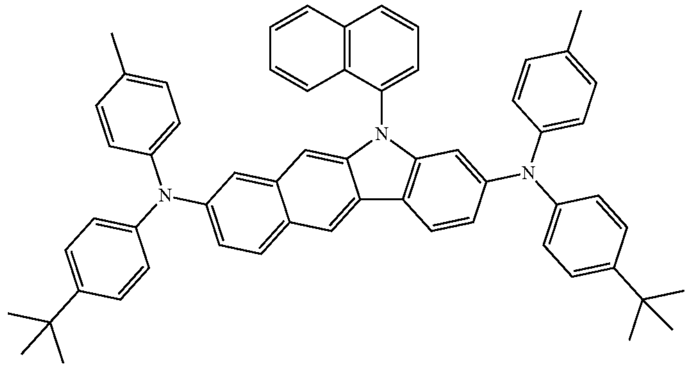
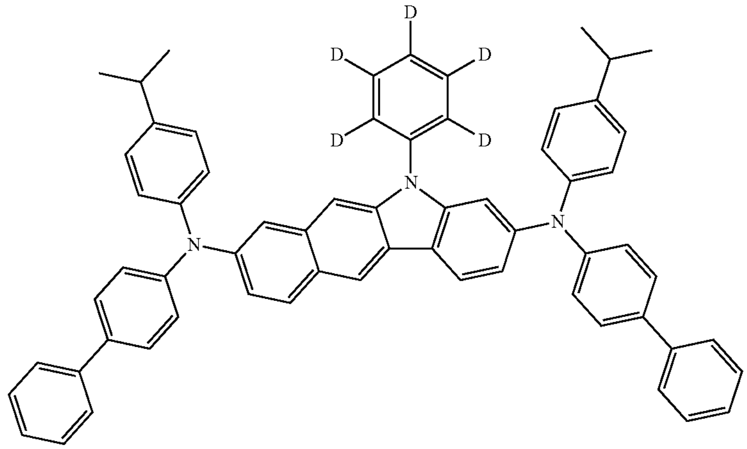
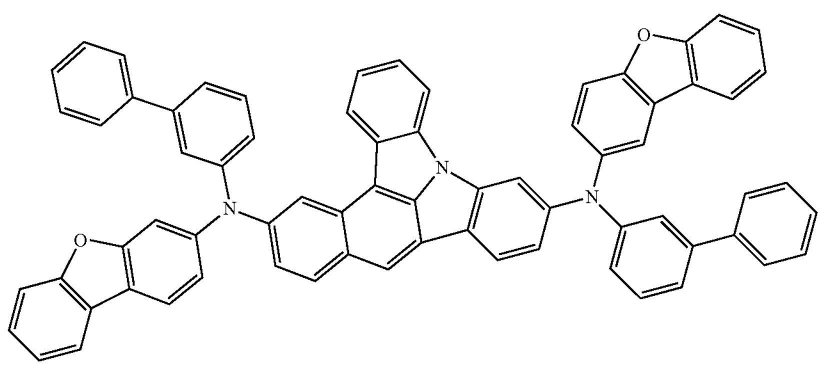

-continued
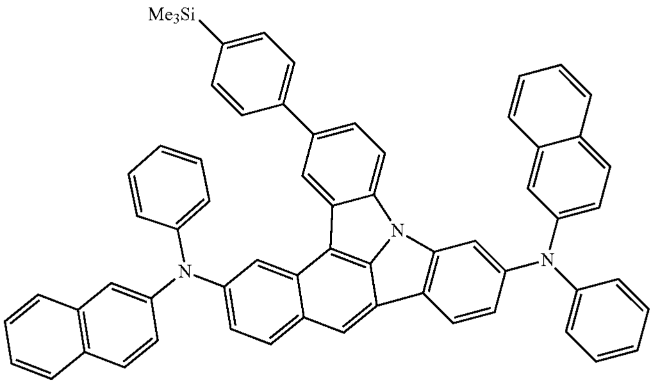
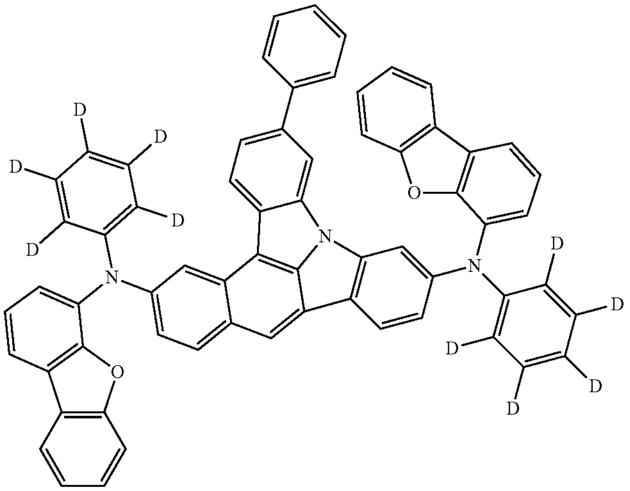
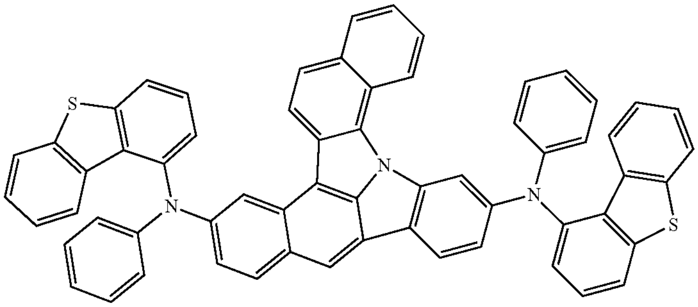
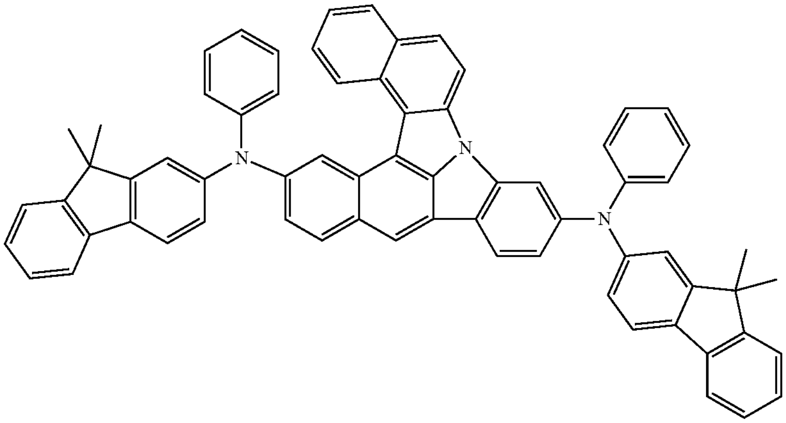

-continued
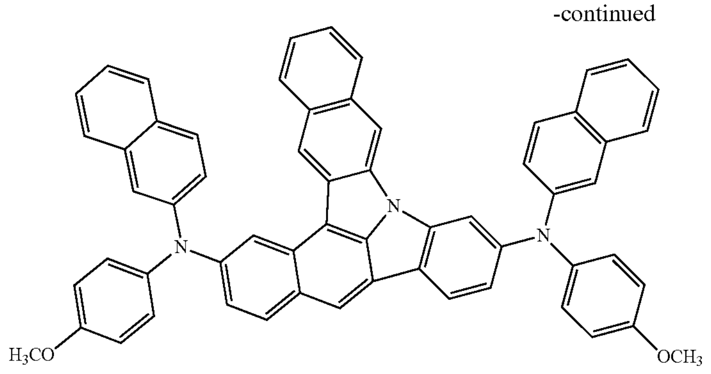
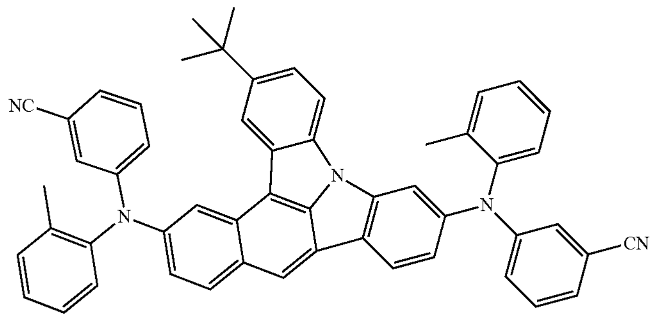
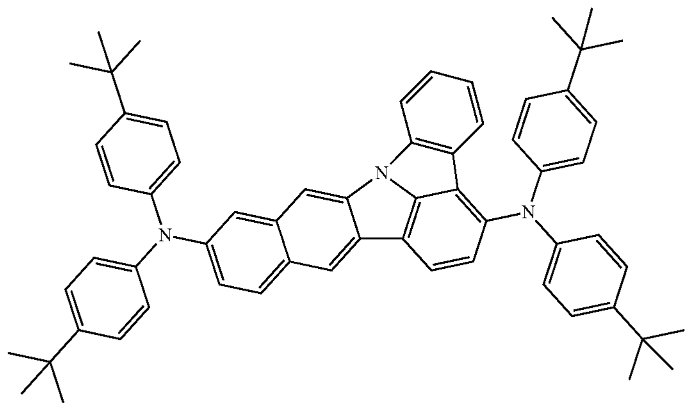
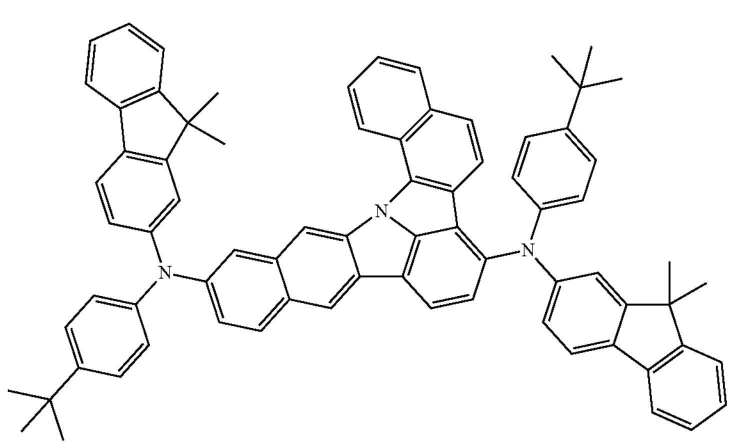

-continued
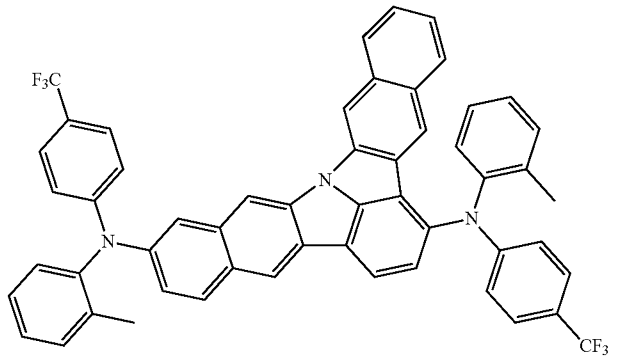
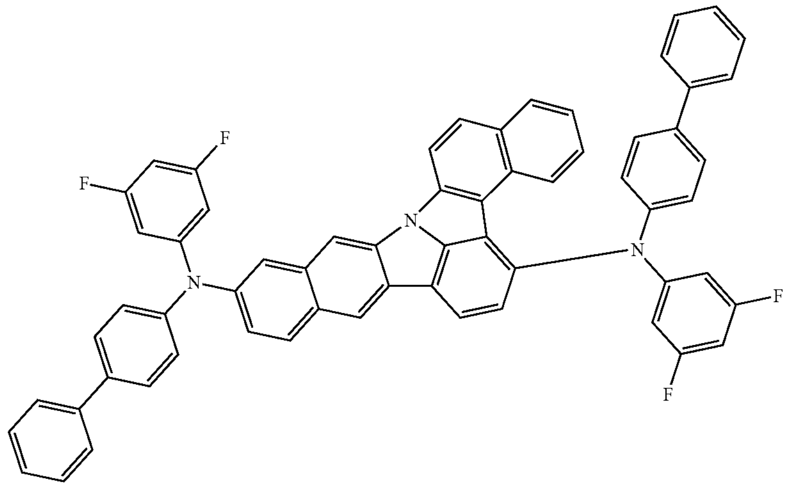
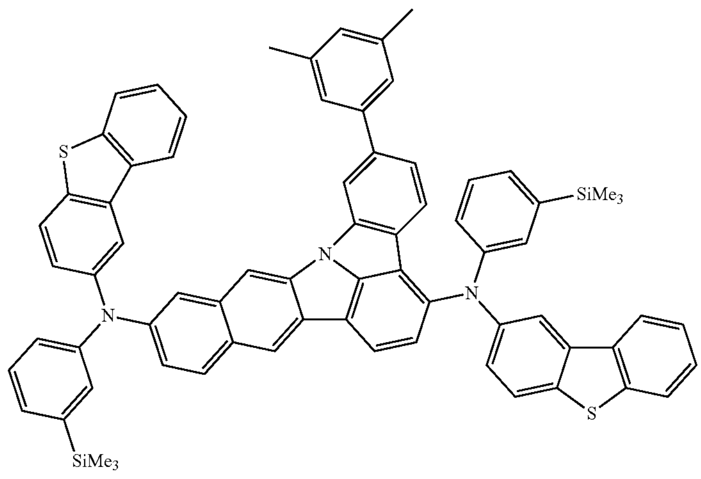

-continued

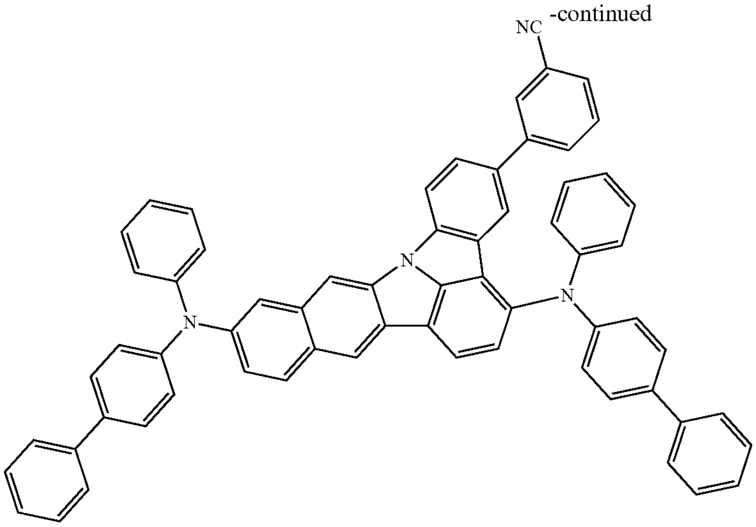

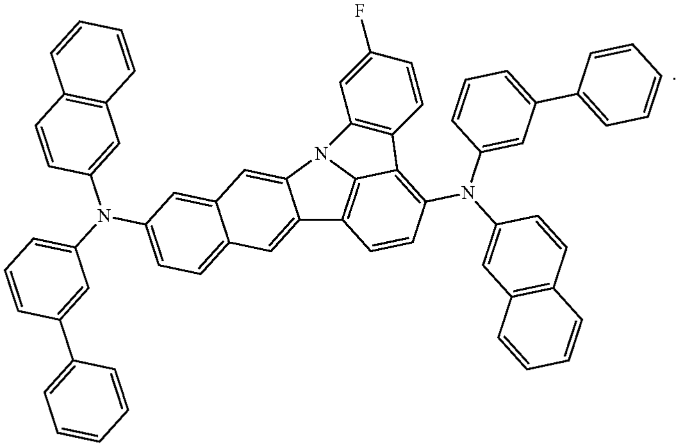

According to an exemplary embodiment of the present specification, a full width at half-maximum of the compound of Chemical Formula 1 is 40 nm or less. More preferably, the full width at half-maximum is 30 nm or less. When the full width at half-maximum is within the above range, the color purity of blue light emission is improved.

The fluorescence intensity and the maximum emission peak can be measured at room temperature (300 K) by dissolving a compound to be measured at a concentration of 1 μM in toluene as a solvent to prepare a sample for measuring fluorescence, putting the sample solution into a quartz cell, and then using a fluorescence measurement apparatus (JASCO FP-8600 fluorescence spectrophotometer). In this case, in the fluorescence spectrum, the x axis is the wavelength (λ, unit: nm), the y axis is the light emission degree, and a spread width of a peak at a height that is ½ of the height of the maximum emission peak refers to a full width at half-maximum.

The compound according to an exemplary embodiment of the present specification can be prepared by a preparation method described below. If necessary, a substituent can be added or excluded, and a position of the substituent can be changed. Further, a starting material, a reactant, reaction conditions, and the like can be changed based on the technology known in the art.

For example, a core structure of the compound of Chemical Formula 1 can be prepared as in the following General Reaction Schemes 1 to 3. The substituent can be bonded by a method known in the art, and the kind or position of the substituent or the number of substituents can be changed according to the technology known in the art. The substituent can be bonded as in the following General Reaction Schemes 1 to 3, but the bonding method is not limited thereto.

<General Reaction Scheme 1>

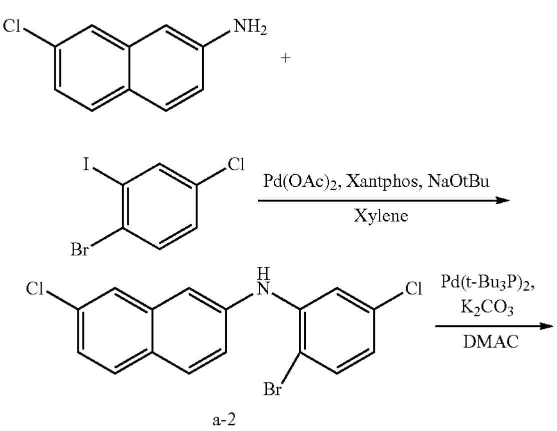

-continued
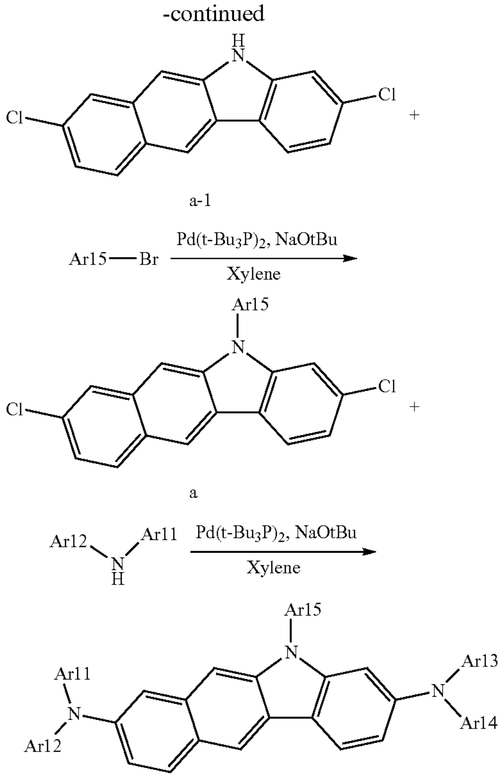
<General Reaction Scheme 2>
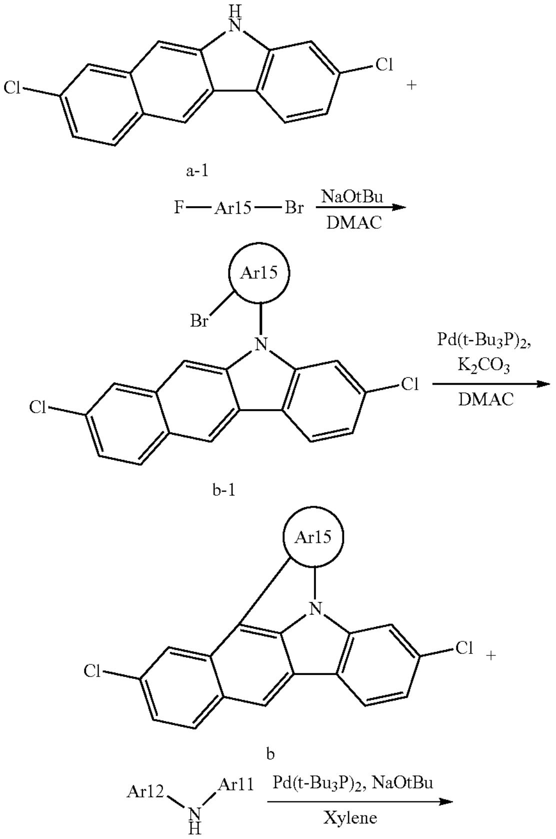
-continued
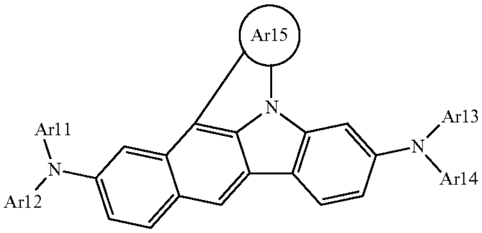
<General Reaction Scheme 3>
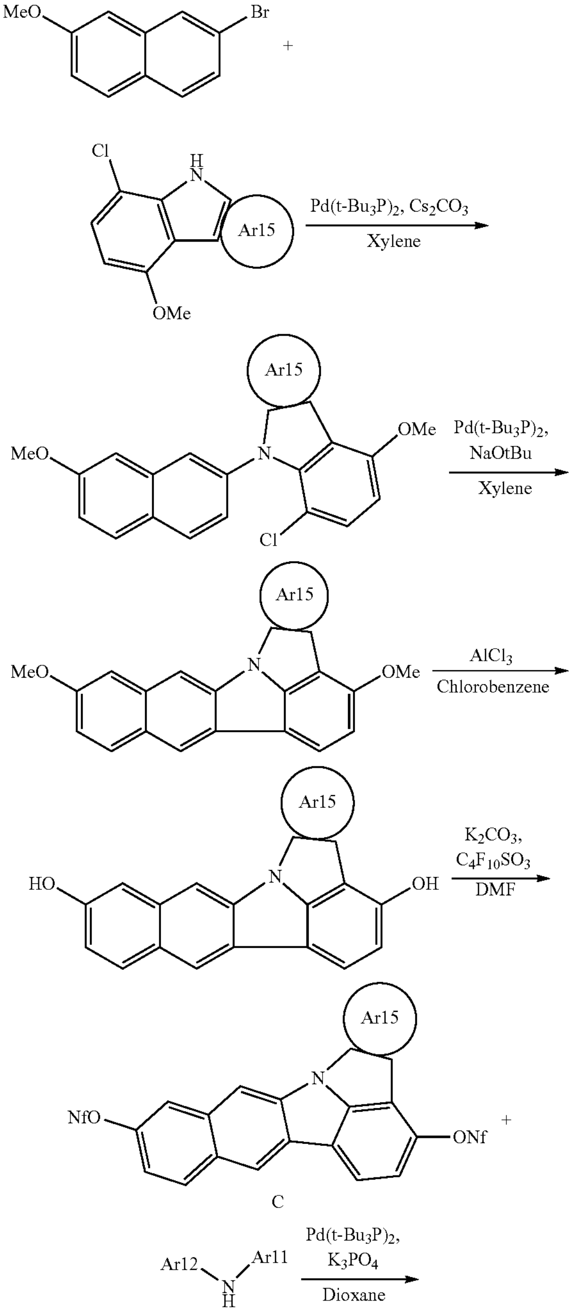

-continued

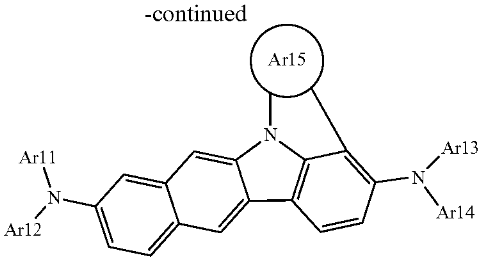

In General Reaction Schemes 1 to 3, the definitions of Ar11 to Ar15 are the same as those defined in Formula 1. In General Reaction Schemes 1 to 3, L and L2 to L5 are not represented, but when reactants in which L and L2 to L5 are substituted are used, a desired compound can be obtained.

An exemplary embodiment of the present specification provides an organic light emitting device including: a first electrode; a second electrode provided to face the first electrode; and an organic material layer having one or more layers provided between the first electrode and the second electrode, in which one or more layers of the organic material layer include the above-described compound.

According to an exemplary embodiment of the present specification, the organic material layer of the organic light emitting device of the present specification can be composed of a mono-layer structure, but can be composed of a multi-layer structure in which two or more organic material layers are stacked. For example, the organic light emitting device of the present invention can have a structure including a hole injection layer, a hole transport layer, an electron blocking layer, a light emitting layer, a hole blocking layer, an electron transport layer, an electron injection layer, and the like, as organic material layers. However, the structure of the organic light emitting device is not limited thereto, and can include fewer or more organic layers.

In the present specification, the 'layer' has a meaning compatible with a 'film' usually used in the art, and means a coating covering a target region. The size of the 'layer' is not limited, and the sizes of the respective 'layers' can be the same as or different from one another. In an exemplary embodiment, the size of the 'layer' can be the same as that of the entire device, can correspond to the size of a specific functional region, and can also be as small as a single sub-pixel.

In the present specification, the meaning that a specific A material is included in a B layer includes both i) the fact that one or more A materials are included in one B layer and ii) the fact that the B layer is composed of one or more layers, and the A material is included in one or more layers of the multi-layered B layers.

In the present specification, the meaning that a specific A material is included in a C layer or a D layer includes all of i) the fact that the A material is included in one or more layers of the C layer having one or more layers, ii) the fact that the A material is included in one or more layers of the D layer having one or more layers, and iii) the fact that the A material is included in each of the C layer having one or more layers and the D layer having one or more layers.

For example, the structure of the organic light emitting device of the present specification can have structures illustrated in FIGS. 1 to 4, but is not limited thereto.

FIG. 1 exemplifies the structure of an organic light emitting device in which a positive electrode 2, a light emitting layer 3, and a negative electrode 4 are sequentially stacked on a substrate 1. FIG. 1 is an exemplified structure of the organic light emitting device according to an exemplary embodiment of the present specification, and can further include other organic material layers. In the structure described above, the compound of Chemical Formula 1 can be included in the light emitting layer.

FIG. 2 exemplifies the structure of an organic light emitting device in which a positive electrode 2, a hole injection layer 5, a hole transport layer 6, a light emitting layer 3, an electron injection and transport layer 7, and a negative electrode 4 are sequentially stacked on a substrate 1. FIG. 2 is an exemplified structure according to exemplary embodiments of the present specification, and can further include other organic material layers. Here, the compound of Chemical Formula 1 can be included in the hole injection layer, the hole transport layer, the light emitting layer, or the electron injection and transport layer.

FIG. 3 exemplifies a structure of an organic light emitting device in which a positive electrode 2, a hole injection layer 5, a hole transport layer 6, an electron blocking layer 8, a light emitting layer 3, an electron injection and transport layer 7, and a negative electrode 4 are sequentially stacked on a substrate 1. FIG. 3 is an exemplified structure according to exemplary embodiments of the present specification, and can further include other organic material layers. Here, the compound of Chemical Formula 1 can be included in the hole injection layer, the hole transport layer, the electron blocking layer, the light emitting layer, or the electron injection and transport layer.

FIG. 4 exemplifies a structure of an organic light emitting device in which a positive electrode 2, a hole injection layer 5, a hole transport layer 6, an electron blocking layer 8, a light emitting layer 3, a hole blocking layer 9, an electron injection and transport layer 7, and a negative electrode 4 are sequentially stacked on a substrate 1. FIG. 4 is an exemplified structure according to exemplary embodiments of the present specification, and can further include other organic material layers. Here, the compound of Chemical Formula 1 can be included in the hole injection layer, the hole transport layer, the electron blocking layer, the light emitting layer, the hole blocking layer, or the electron injection and transport layer.

According to an exemplary embodiment of the present specification, the organic material layer includes a hole injection layer, a hole transport layer, or an electron blocking layer, and the hole injection layer, the hole transport layer, or the electron blocking layer includes the compound of Chemical Formula 1.

According to an exemplary embodiment of the present specification, the organic material layer includes a light emitting layer, and the light emitting layer includes the compound of Chemical Formula 1.

According to an exemplary embodiment of the present specification, the organic material layer includes a light emitting layer, and the light emitting layer includes the compound of Chemical Formula 1 as a dopant of the light emitting layer.

The organic light emitting device according to an exemplary embodiment of the present specification includes a light emitting layer, and the light emitting layer includes the compound of Chemical Formula 1 and a compound of Chemical Formula H:

Chemical Formula H

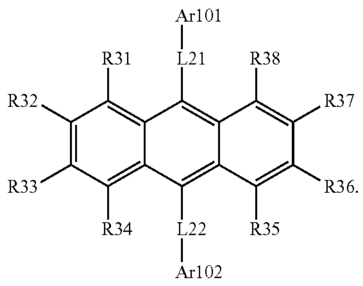

In Chemical Formula H:

L21 and L22 are the same as or different from each other, and are each independently a direct bond, a substituted or unsubstituted arylene group, or a substituted or unsubstituted heteroarylene group;

R31 to R38 are the same as or different from each other, and are each independently hydrogen, deuterium, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group; and Ar101 and Ar102 are the same as or different from each other, and are each independently a substituted or unsubstituted aryl group or a substituted or unsubstituted heteroaryl group.

In an exemplary embodiment of the present specification, L21 and L22 are the same as or different from each other, and are each independently a direct bond, a substituted or unsubstituted arylene group having 6 to 30 carbon atoms, or a substituted or unsubstituted heteroarylene group having 2 to 30 carbon atoms and including N, O, or S.

In an exemplary embodiment of the present specification, L21 and L22 are the same as or different from each other, and are each independently a direct bond, a substituted or unsubstituted phenylene group, a substituted or unsubstituted naphthylene group, or a substituted or unsubstituted thiophenylene group.

In an exemplary embodiment of the present specification, Ar101 and Ar102 are the same as or different from each other, and are each independently a substituted or unsubstituted aryl group having 6 to 50 carbon atoms or a substituted or unsubstituted heteroaryl group having 2 to 50 carbon atoms.

In an exemplary embodiment of the present specification, Ar101 and Ar102 are the same as or different from each other, and are each independently a substituted or unsubstituted monocyclic to tetracyclic aryl group or a substituted or unsubstituted monocyclic to tetracyclic heteroaryl group.

In an exemplary embodiment of the present specification, Ar101 and Ar102 are the same as or different from each other, and are each independently a substituted or unsubstituted phenyl group, a substituted or unsubstituted biphenyl group, a substituted or unsubstituted terphenyl group, a substituted or unsubstituted naphthyl group, a substituted or unsubstituted anthracene group, a substituted or unsubstituted phenanthryl group, a substituted or unsubstituted phenalene group, a substituted or unsubstituted fluorenyl group, a substituted or unsubstituted benzofluorenyl group, a substituted or unsubstituted furan group, a substituted or unsubstituted thiophene group, a substituted or unsubstituted dibenzofuran group, a substituted or unsubstituted naphthobenzofuran group, a substituted or unsubstituted dibenzothiophene group, or a substituted or unsubstituted naphthobenzothiophene group.

In an exemplary embodiment of the present specification, R31 to R38 are hydrogen.

In an exemplary embodiment of the present specification, the compound of Chemical Formula H is any one compound selected from the following compounds:

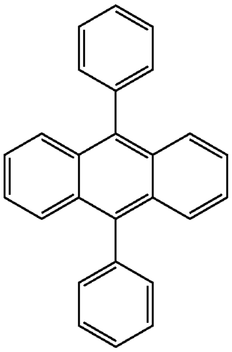
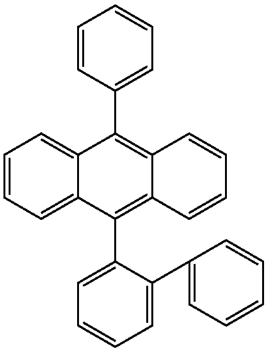

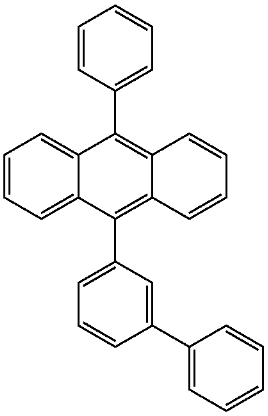
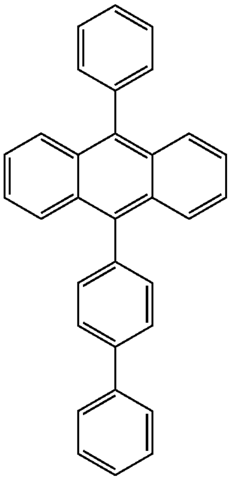

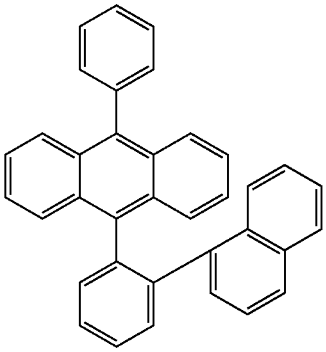
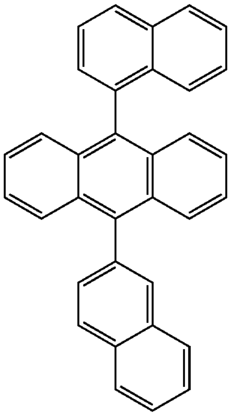

-continued
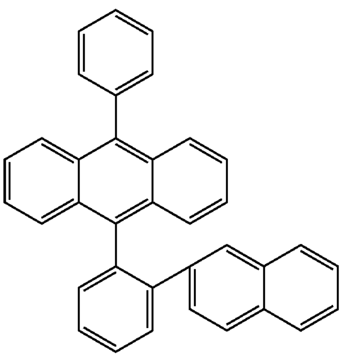
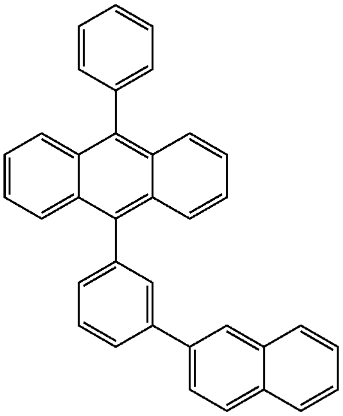
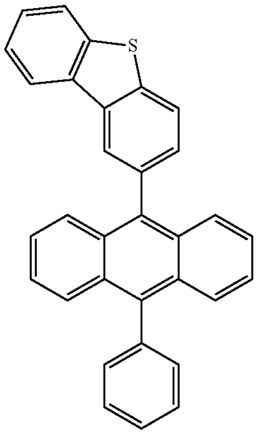
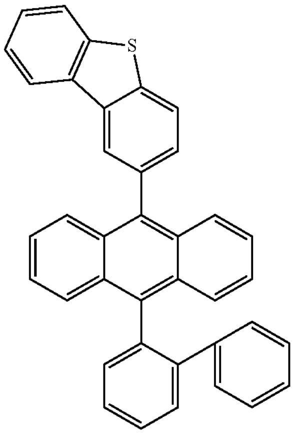
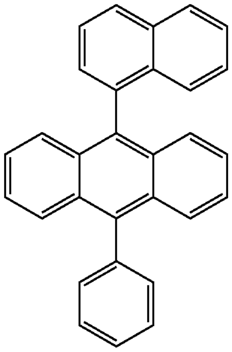
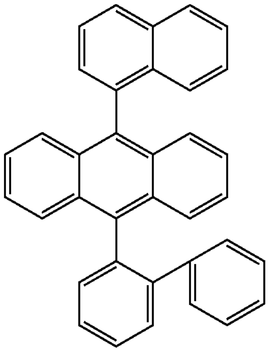
-continued
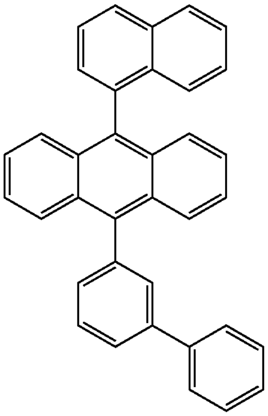
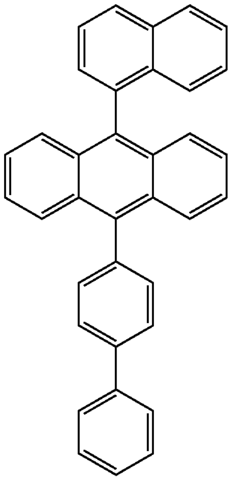
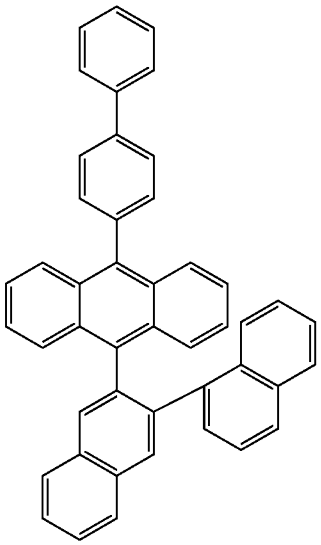
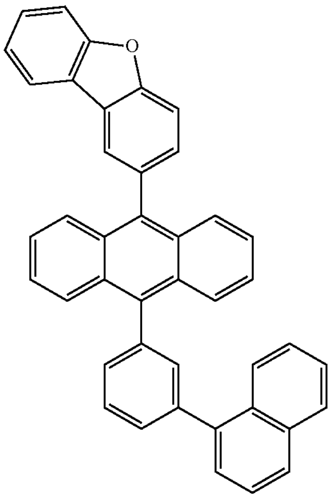

-continued
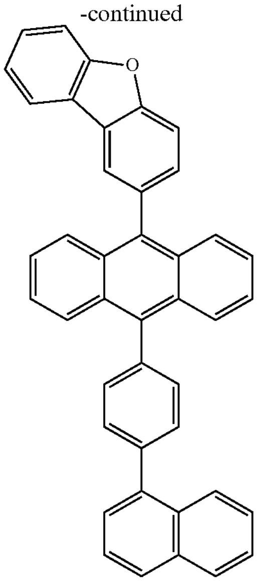
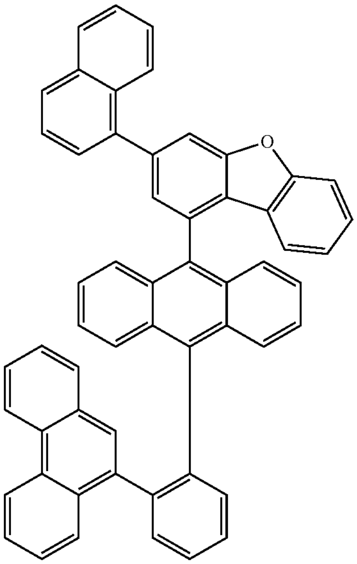
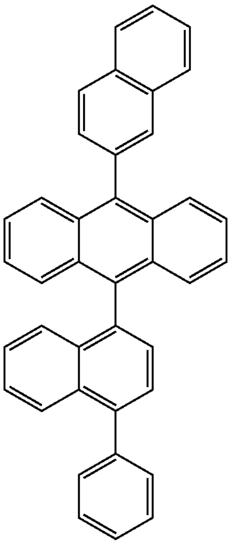
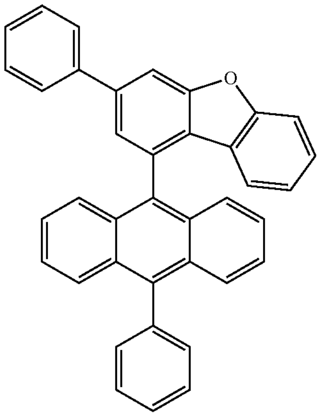
-continued
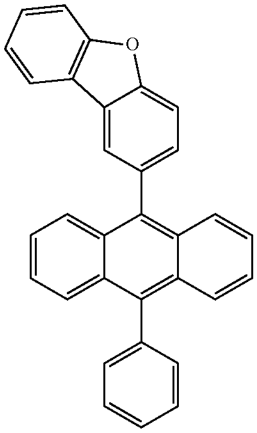
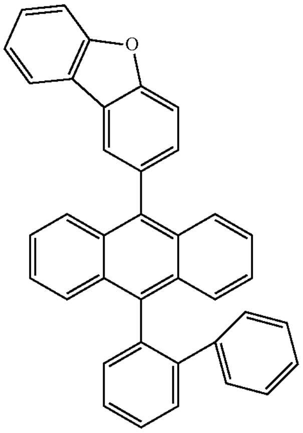
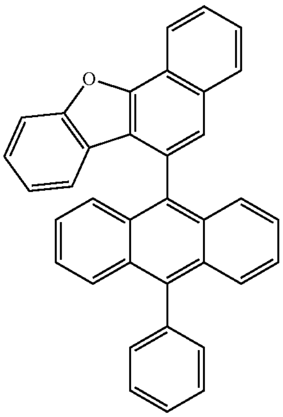
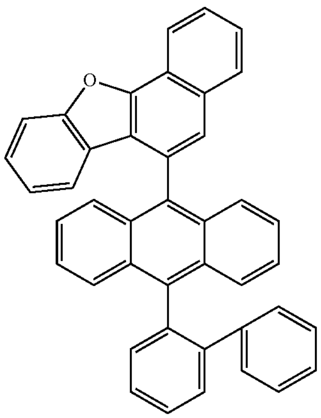

-continued

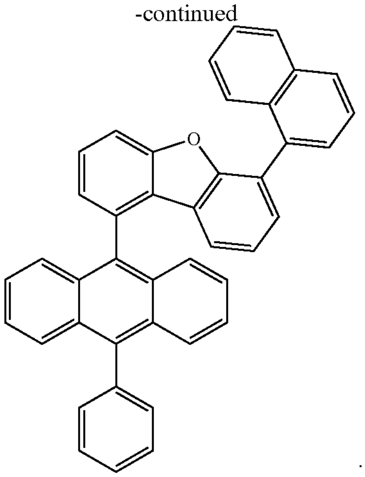

The organic light emitting device according to an exemplary embodiment of the present specification includes a light emitting layer, and the light emitting layer includes the compound of Chemical Formula 1 as a dopant of the light emitting layer, and includes the compound of Chemical Formula H as a host of the light emitting layer.

In an exemplary embodiment of the present specification, the content of the compound of Chemical Formula 1 is 0.01 part by weight to 30 parts by weight; 0.1 part by weight to 20 parts by weight; or 0.5 part by weight to 10 parts by weight, based on 100 parts by weight of the compound of Chemical Formula H.

In an exemplary embodiment of the present specification, the light emitting layer can further include one host material in addition to the compound of Chemical Formula H. In this case, examples of the further included host material (mixed host compound) include a fused aromatic ring derivative, a hetero ring-containing compound, or the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a dibenzofuran derivative, a ladder-type furan compound, a pyrimidine derivative, and the like, but the examples are not limited thereto.

A weight ratio of the compound of Chemical Formula H to the mixed host compound is 95:5 to 5:95, and more preferably 30:70 to 70:30.

In an exemplary embodiment of the present specification, the light emitting layer includes one or two or more compounds of Chemical Formula H.

In an exemplary embodiment of the present specification, the light emitting layer including the compound of Chemical Formula 1 and the compound of Chemical Formula H takes on a blue color.

The organic light emitting device according to an exemplary embodiment of the present specification includes a light emitting layer having two or more layers, and at least one of the light emitting layer having two or more layers includes the compound of Chemical Formula 1 and the compound of Chemical Formula H. The light emitting layer including the compound of Chemical Formula 1 and the compound of Chemical Formula H takes on a blue color, and a light emitting layer which does not include the compound of Chemical Formula 1 and the compound of Chemical Formula H can include a blue, red, or green light emitting compound known in the art.

According to an exemplary embodiment of the present specification, the organic material layer includes a hole blocking layer, an electron transport layer, an electron injection layer, or an electron injection and transport layer, and the hole blocking layer, the electron transport layer, the electron injection layer, or the electron injection and transport layer includes the compound of Chemical Formula 1.

According to an exemplary embodiment of the present specification, the organic material layer can further include one or more layers selected from the group consisting of a hole injection layer, a hole transport layer, an electron blocking layer, a hole blocking layer, an electron transport layer, and an electron injection layer.

The organic light emitting device of the present specification can be manufactured by the materials and methods known in the art, except that one or more layers of the organic material layer include the compound of the present specification, that is, the compound of Chemical Formula 1.

When the organic light emitting device includes a plurality of organic material layers, the organic material layers can be formed of the same material or different materials.

For example, the organic light emitting device of the present specification can be manufactured by sequentially stacking a first electrode, an organic material layer, and a second electrode on a substrate. In this case, the organic light emitting device can be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which can be used as a second electrode, thereon, by using a physical vapor deposition (PVD) method such as sputtering or e-beam evaporation. In addition to the method described above, an organic light emitting device can be made by sequentially depositing a second electrode material, an organic material layer, and a first electrode material on a substrate.

Further, the compound of Chemical Formula 1 can be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

It is preferred that as the positive electrode material, materials having a high work function are usually used so as to facilitate the injection of holes into an organic material layer. Specific examples of the positive electrode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

It is preferred that as the negative electrode material, materials having a low work function are usually used so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al and Mg/Ag; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

In an exemplary embodiment of the present specification, in a hole injection layer, an arylamine-based organic material is doped with a hexanitrilehexaaza-triphenylene-based organic material.

The hole transport layer is a layer which accepts holes from a hole injection layer and transports the holes to a light emitting layer, and a hole transport material is suitably a material having high hole mobility which can accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

A light emitting material for the light emitting layer is a material which can emit light in a visible light region by accepting and combining holes and electrons from a hole transport layer and an electron transport layer, respectively, and is preferably a material having high quantum efficiency for fluorescence or phosphorescence. Specific examples thereof include: 8-hydroxy-quinoline aluminum complexes ($Alq_3$); carbazole-based compounds; dimerized styryl compounds; BAlq; 10-hydroxybenzoquinoline-metal compounds; benzoxazole-based, benzothiazole-based and benzoimidazole-based compounds; poly(p-phenylenevinylene) (PPV)-based polymers; spiro compounds; polyfluorene, rubrene, and the like, but are not limited thereto.

The light emitting layer can include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which accepts electrons from an electron injection layer and transports the electrons to a light emitting layer, and an electron transporting material is suitably a material having high electron mobility which can proficiently accept electrons from a negative electrode and transfer the electrons to a light emitting layer. Specific examples thereof include: Al complexes of 8-hydroxyquinoline; complexes including $Alq_3$; organic radical compounds; hydroxyflavone-metal complexes; and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, an effect of injecting electrons from a negative electrode, and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

In an exemplary embodiment of the present specification, an electron injection and transport layer includes an alkali metal complex compound.

The electron blocking layer is a layer which can improve the service life and efficiency of a device by preventing electrons injected from an electron injection layer from passing through a light emitting layer and entering a hole injection layer. The publicly-known material can be used without limitation, and can be formed between a light emitting layer and a hole injection layer, or between a light emitting layer and a layer which simultaneously injects and transports holes.

The hole blocking layer is a layer which blocks holes from reaching a negative electrode, and can be generally formed under the same conditions as those of the electron injection layer. Specific examples thereof include an oxadiazole derivative or a triazole derivative, a phenanthroline derivative, an aluminum complex, and the like, but are not limited thereto.

The organic light emitting device according to the present specification can be a top emission type, a bottom emission type, or a dual emission type according to the materials to be used.

EXAMPLES

Hereinafter, the present invention will be described in detail with reference to Examples, Comparative Examples, and the like for specifically describing the present specification. However, the Examples and the Comparative Examples according to the present specification can be modified in various forms, and it is not interpreted that the scope of the present specification is limited to the Examples and the Comparative Examples described below in detail. The Examples and the Comparative Examples of the present specification are provided to more completely explain the present specification to a person with ordinary skill in the art.

SYNTHESIS EXAMPLES

Synthesis of Intermediate

1. Synthesis of Intermediate of General Reaction

Scheme 1

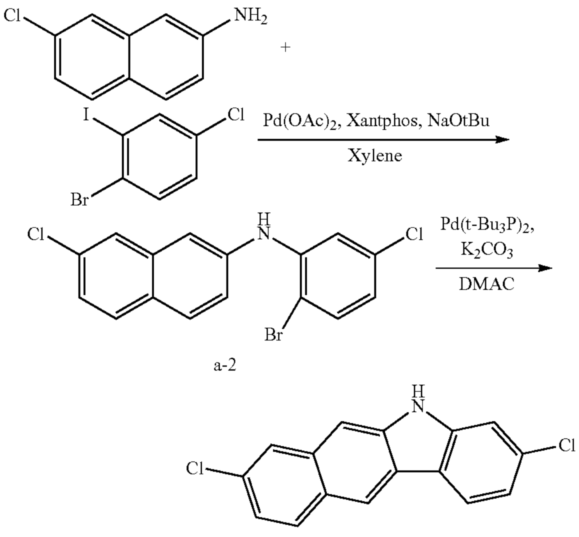

a-2 a-1

1) Preparation of Compound a-2

200.0 g (1.0 eq) of 7-chloronaphthalen-2-amine, 443.25 g (1.0 eq) of 1-bromo-4-chloro-2-iodobenzene, 201.3 g (1.5 eq) of NaOtBu, 3.13 g (0.01 eq) of $Pd(OAc)_2$, and 8.08 g (0.01 eq) of Xantphos were dissolved in 4 L of 1,4-dioxane, and the resulting solution was stirred under reflux. After 3 hours, when the reaction was terminated, the solvent was removed by reducing pressure. Thereafter, the resulting product was completely dissolved in ethyl acetate, the resulting solution was washed with water, and 70% of the solvent was removed again by reducing the pressure. Again, hexane was put thereinto in a reflux state, and crystals were precipitated, cooled, and then filtered. The resulting product was subjected to column chromatography to obtain 283.41 g (yield 61%) of Compound a-2. [M+H]=333

2) Preparation of Compound a-1

283.41 g (1.0 eq) of Compound a-2, 3.90 g (0.01 eq) of $Pd(t\text{-}Bu_3P)_2$, and 212.21 g (2.50 eq) of $K_2CO_3$ were added to 2 L of dimethylacetamide, and the resulting mixture was stirred under reflux. After 3 hours, crystals were precipitated by pouring the reactant into water, and filtered. After the filtered solid was completely dissolved in 1,2-dichlorobenzene, the resulting solution was washed with water, crystals were precipitated by concentrating the solution in which the product was dissolved, under reduced pressure, cooled, and then filtered. The product was purified by column chromatography to obtain 74.97 g (yield 39%) of Compound a-1 3,8-dichloro-5H-benzo[b]carbazole. [M+H]=252

2. Synthesis of Intermediate of General Reaction Scheme 3

1) Synthesis of Intermediate A-2

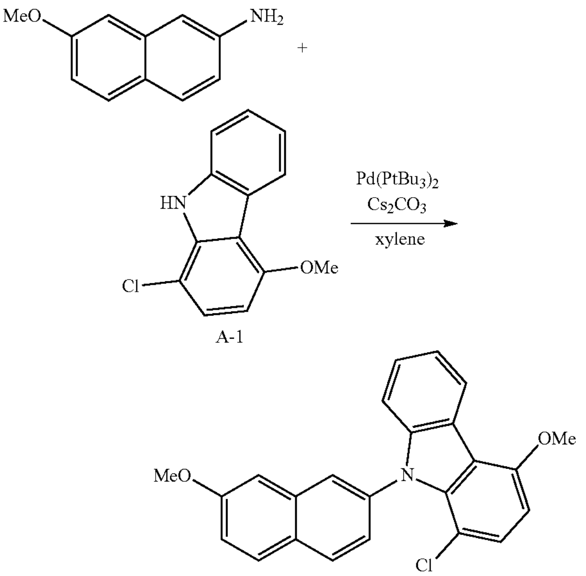

A-1

A-2

After 40 g of 2-bromo-7-methoxynaphthalene, 40 g of Intermediate A-1, 110 g of cesium carbonate, and 0.86 g of) [bis(tri(tert-butyl)phosphine)palladium(0)] $Pd(PtBu_3)_2$ were added to 1.2 L of xylene under a nitrogen atmosphere, the resulting mixture was heated at 150° C. and stirred for 5 hours. After the reaction was terminated, the reaction solution was cooled to room temperature, aliquoted by adding water and aq. $NH_4Cl$ thereto, and then filtered through a treatment with $MgSO_4$ (anhydrous). The filtered solution was distilled off under reduced pressure and purified with recrystallization (toluene/acetonitrile) to obtain 52 g of Intermediate A-2. [M+H]=388

2) Synthesis of Intermediate A-3

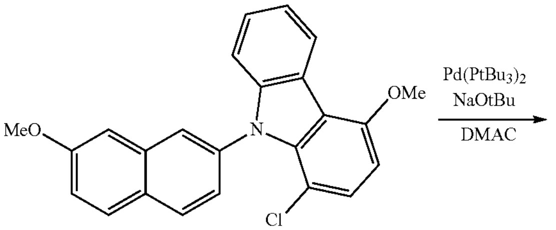

A-2

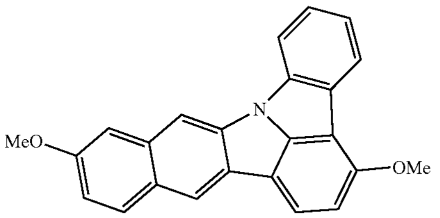

A-3

After 45 g of Intermediate A-2, 22 g of sodium tert-butoxide, and 1.2 g of [bis(tri(tert-) butyl)phosphine)palladium(0)] $Pd(PtBu_3)_2$ were added to 500 mL of dimethylacetamide under a nitrogen atmosphere, the resulting mixture was heated at 120° C. and stirred for 10 hours. After the reaction was terminated, the reaction solution was cooled to room temperature, aliquoted by adding water and aq. $NH_4Cl$ thereto, and then filtered through a treatment with $MgSO_4$ (anhydrous). The filtered solution was distilled off under reduced pressure and purified with recrystallization (toluene/hexane) to obtain 22 g of Intermediate A-3. [M+H]=352

3) Synthesis of Intermediate A-5

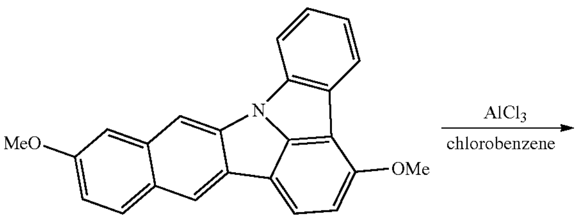

A-3

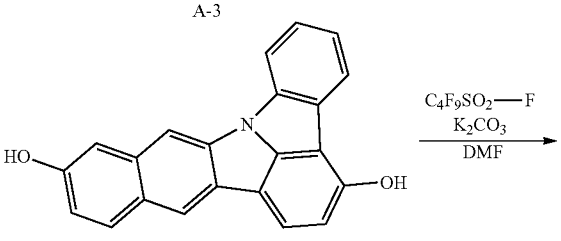

A-4

-continued

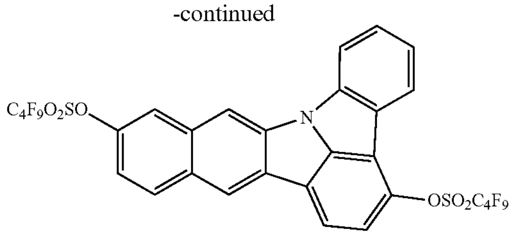

A-5

After 20 g of Intermediate A-3 and 23 g of aluminum chloride were added to 200 mL of chlorobenzene under a nitrogen atmosphere, the resulting mixture was heated at 130° C. and stirred for 8 hours. After the reaction was terminated, the reaction solution was cooled to room temperature, aliquoted by adding water and ethyl acetate thereto, and then filtered through a treatment with $MgSO_4$ (anhydrous). The filtered solution was distilled off under reduced pressure and purified with recrystallization (ethyl acetate/hexane) to obtain 15 g of Intermediate A-4.

After 300 mL of dimethylformamide was added to 15 g of Intermediate A-4 and 32 g of potassium carbonate, 17 mL of nonaflyl fluoride (nonafluorobutane-sulfonyl fluoride) was added dropwise thereto at room temperature. After the reaction was terminated by stirring the resulting mixture for 5 hours, the reaction solution was filtered. The filtered solution was aliquoted by adding water and ethyl acetate thereto, and then filtered with a treatment with $MgSO_4$ (anhydrous). The filtered solution was distilled off under reduced pressure and purified with recrystallization (toluene/hexane) to obtain 30 g of Intermediate A-5.

3. Synthesis of Compound

Synthesis Example 1

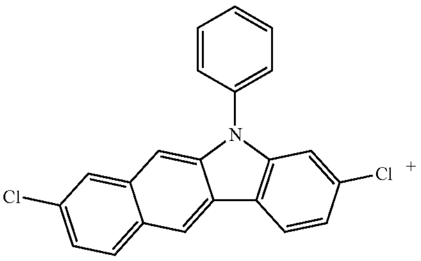

1-1

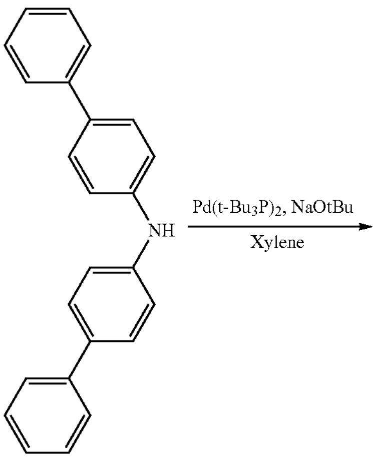

-continued

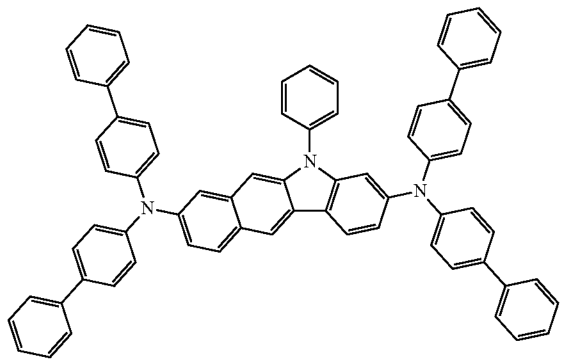

1

10.0 g (1.0 eq) of Compound 1-1, 19.52 g (2.2 eq) of di([1,1'-biphenyl]-4-yl)amine, 0.14 g (0.01 eq) of Pd(t-$Bu_3P)_2$, and 6.63 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 16.72 g (yield 65%) of Compound 1. [M+H]=933

Synthesis Example 2

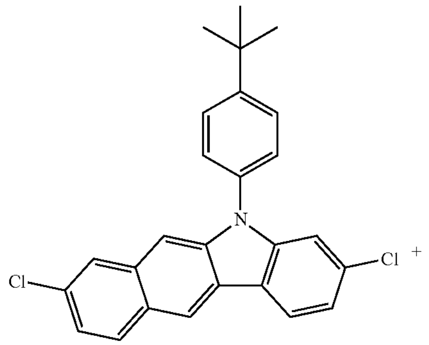

2-1

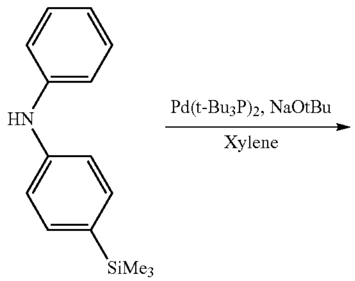

-continued

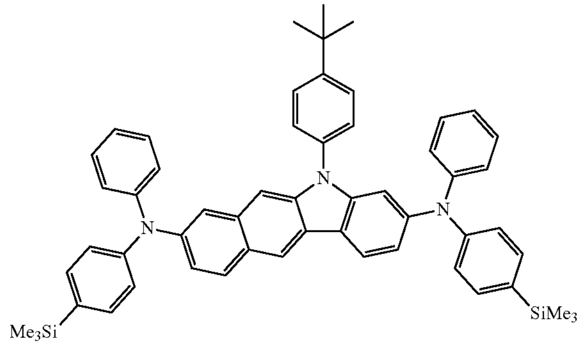

2

10.0 g (1.0 eq) of Compound 2-1, 12.69 g (2.2 eq) of N-phenyl-4-(trimethylsilyl)aniline, 0.12 g (0.01 eq) of Pd(t-$Bu_3P)_2$, and 5.74 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 12.57 g (yield 61%) of Compound 2. [M+H]=829

Synthesis Example 3

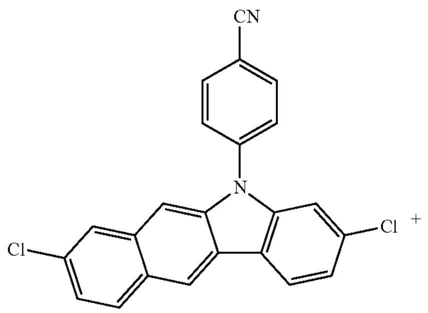

3-1

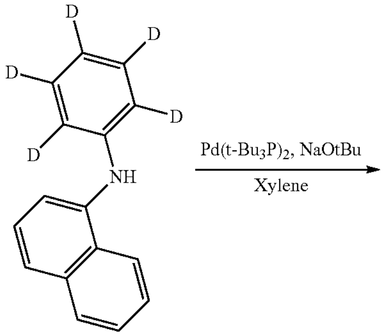

-continued

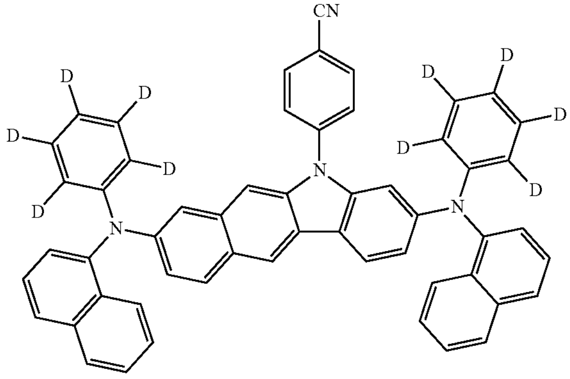

3

10.0 g (1.0 eq) of Compound 3-1, 12.74 g (2.2 eq) of N-(phenyl-d5)naphthalen-1-amine, 0.13 g (0.01 eq) of Pd(t-$Bu_3P)_2$, and 6.20 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 13.20 g (yield 67%) of Compound 3. [M+H]=763

Synthesis Example 4

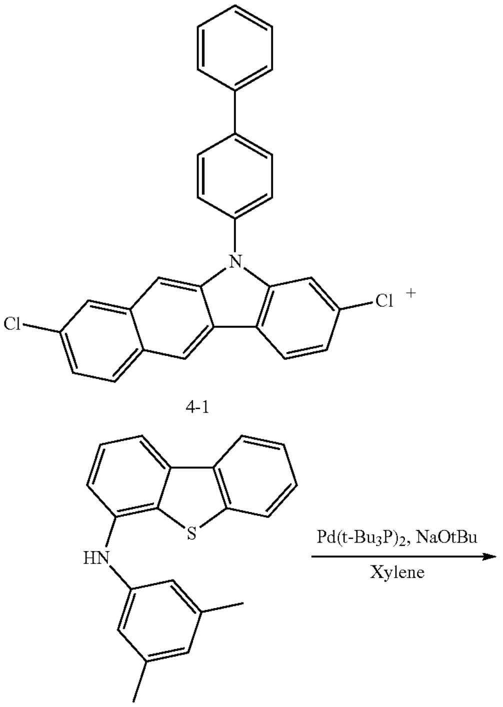

4-1

-continued

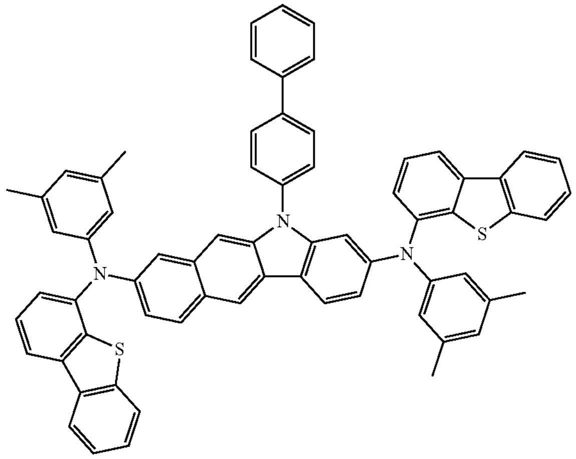

4

10.0 g (1.0 eq) of Compound 4-1, 15.22 g (2.2 eq) of N-(3,5-dimethylphenyl)dibenzo[b,d]thiophen-4-amine, 0.11 g (0.01 eq) of Pd(t-$Bu_3P)_2$, and 5.48 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 14.19 g (yield 64%) of Compound 4. [M+H]=973

Synthesis Example 5

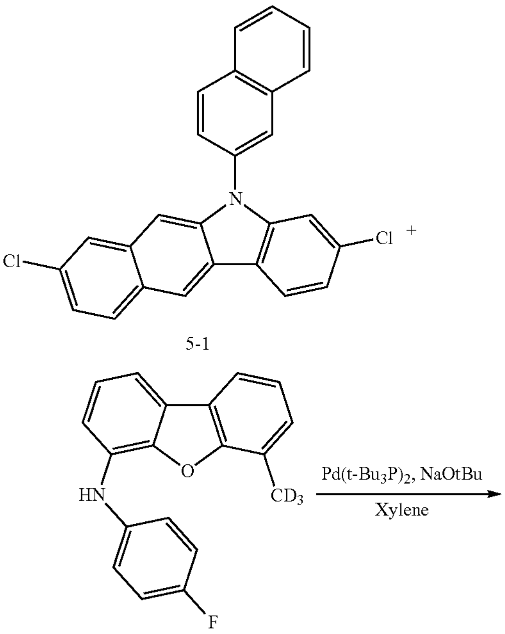

5-1

-continued

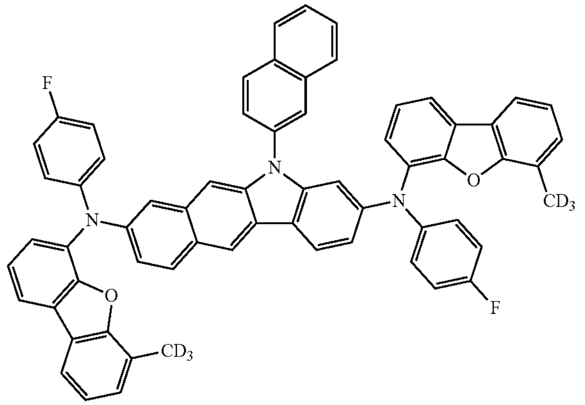

5

10.0 g (1.0 eq) of Compound 5-1, 15.70 g (2.2 eq) of N-(4-fluorophenyl)-6-(methyl-d3)dibenzo[b,d]furan-4-amine, 0.12 g (0.01 eq) of $Pd(t\text{-}Bu_3P)_2$, and 5.82 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 13.50 g (yield 60%) of Compound 5. [M+H]=929

Synthesis Example 6

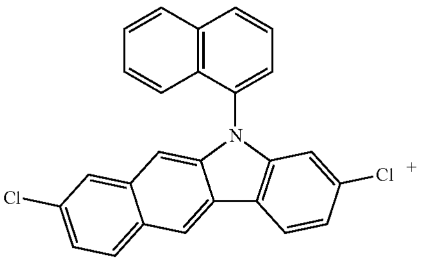

6-1

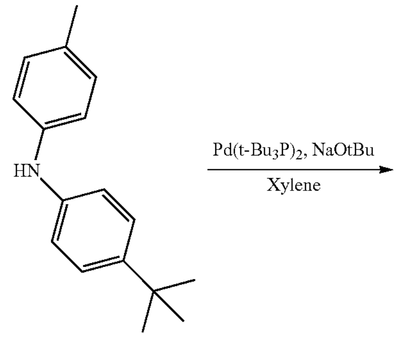

-continued

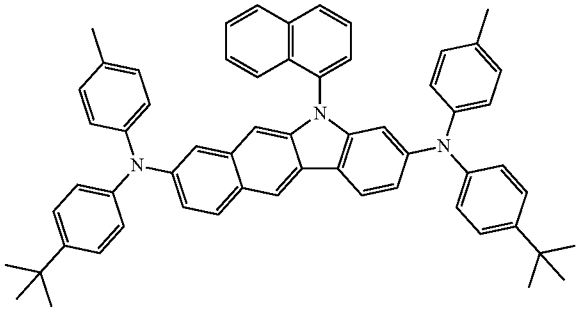

6

10 g (1.0 eq) of Compound 6-1, 12.77 g (2.2 eq) of 4-(tert-butyl)-N-(p-tolyl)aniline, 0.12 g (0.01 eq) of $Pd(t\text{-}Bu_3P)_2$, and 5.82 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 12.89 g (yield 65%) of Compound 6. [M+H]=819

Synthesis Example 7

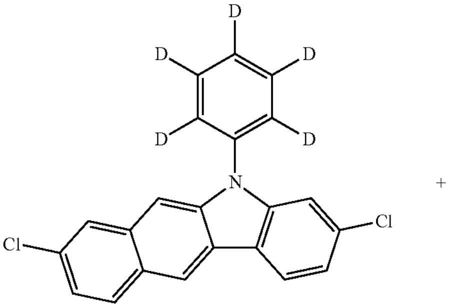

7-1

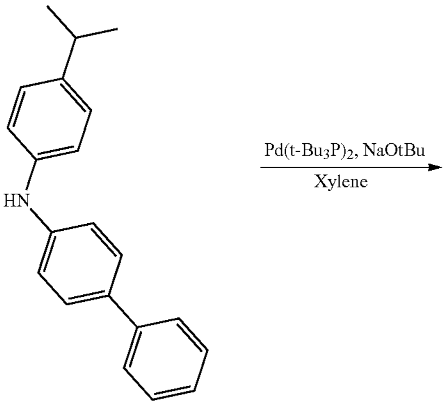

-continued

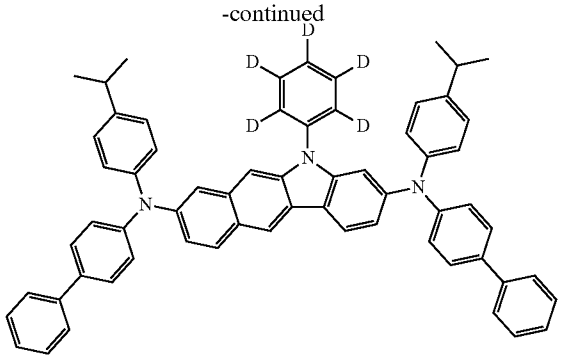

7

10.0 g (1.0 eq) of Compound 7-1, 17.21 g (2.2 eq) of N-(4-isopropylphenyl)-[1,1'-biphenyl]-4-amine, 0.14 g (0.01 eq) of $Pd(t\text{-}Bu_3P)_2$, and 6.54 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 15.38 g (yield 65%) of Compound 7. [M+H]=870

Synthesis Example 8

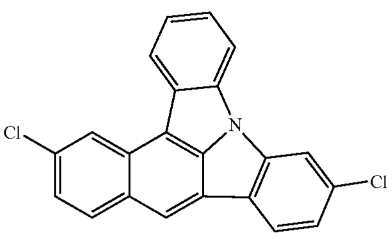

8-1

+

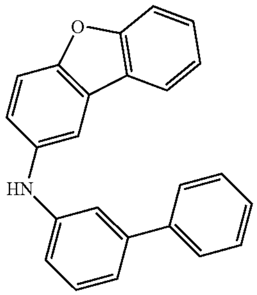

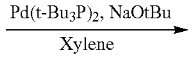

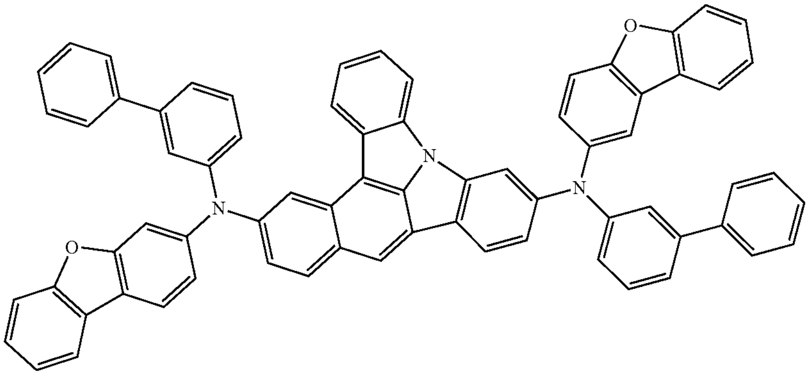

8

10.0 g (1.0 eq) of Compound 8-1, 20.48 g (2.2 eq) of N-([1,1'-biphenyl]-3-yl)dibenzo[b,d]furan-2-amine, 0.14 g (0.01 eq) of $Pd(t\text{-}Bu_3P)_2$, and 6.67 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 17.28 g (yield 65%) of Compound 8. [M+H]=959

Synthesis Example 9

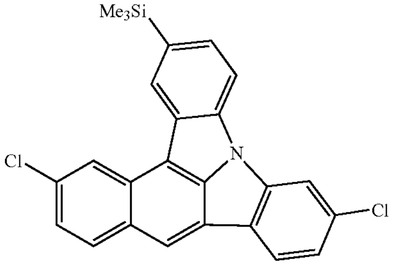

9-1

+

-continued

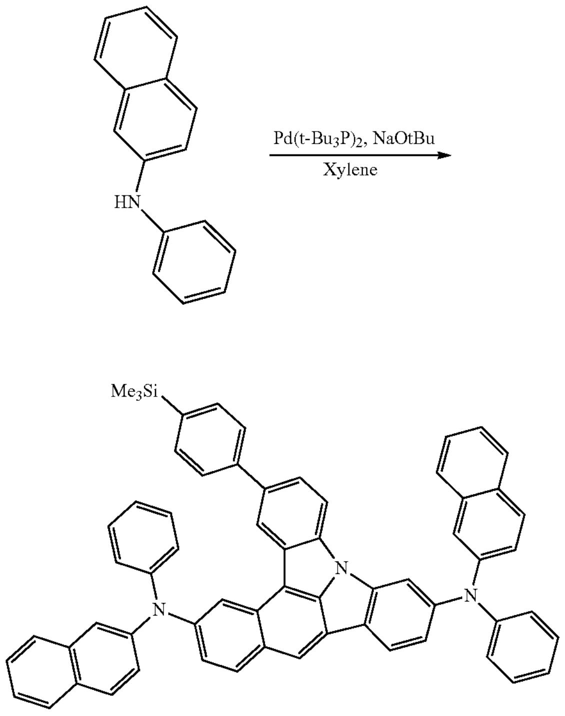

9

1.0 g (1.0 eq) of Compound 9-1, 11.15 g (2.2 eq) of N-phenylnaphthalen-2-amine, 0.12 g (0.01 eq) of Pd(t-$Bu_3P)_2$, and 5.56 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 12.33 g (yield 61%) of Compound 9. [M+H]=875

Synthesis Example 10

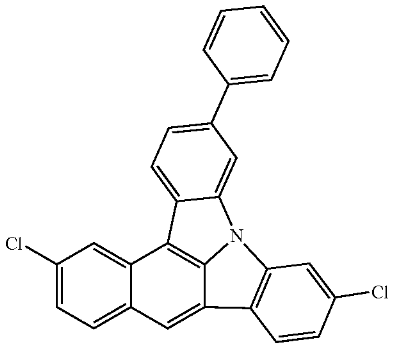

+

10-1

-continued

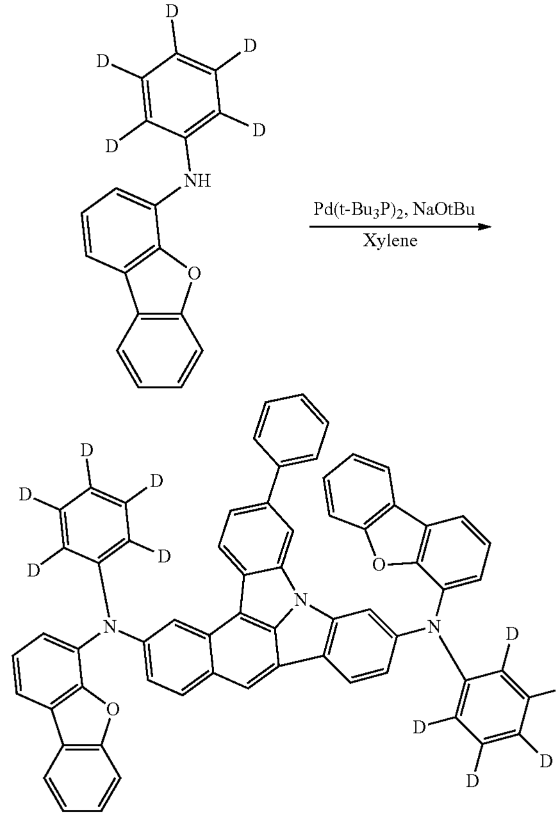

10

10.0 g (1.0 eq) of Compound 10-1, 13.32 g (2.2 eq) of N-(phenyl-d5)dibenzo[b,d]furan-4-amine, 0.14 g (0.01 eq) of Pd(t-$Bu_3P)_2$, and 5.50 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 12.88 g (yield 63%) of Compound 10. [M+H]=893

Synthesis Example 11

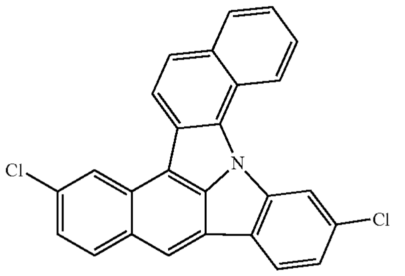

+

11-1

-continued

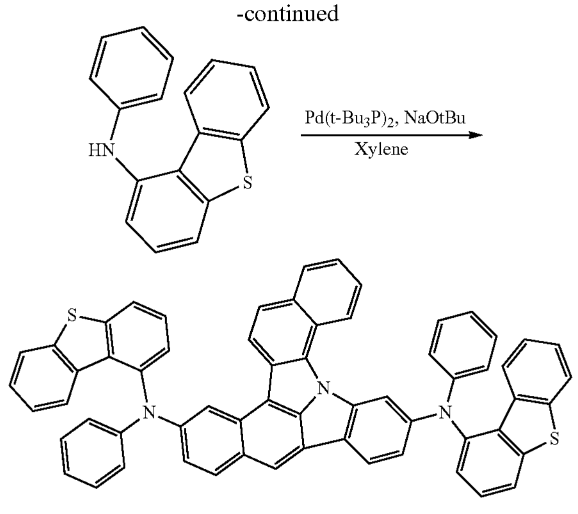

11

10.0 g (1.0 eq) of Compound 11-1, 14.76 g (2.2 eq) of N-phenyldibenzo[b,d]thiophen-1-amine, 0.12 g (0.01 eq) of Pd(t-$Bu_3P)_2$, and 5.85 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 14.07 g (yield 65%) of Compound 11. [M+H]=889

Synthesis Example 12

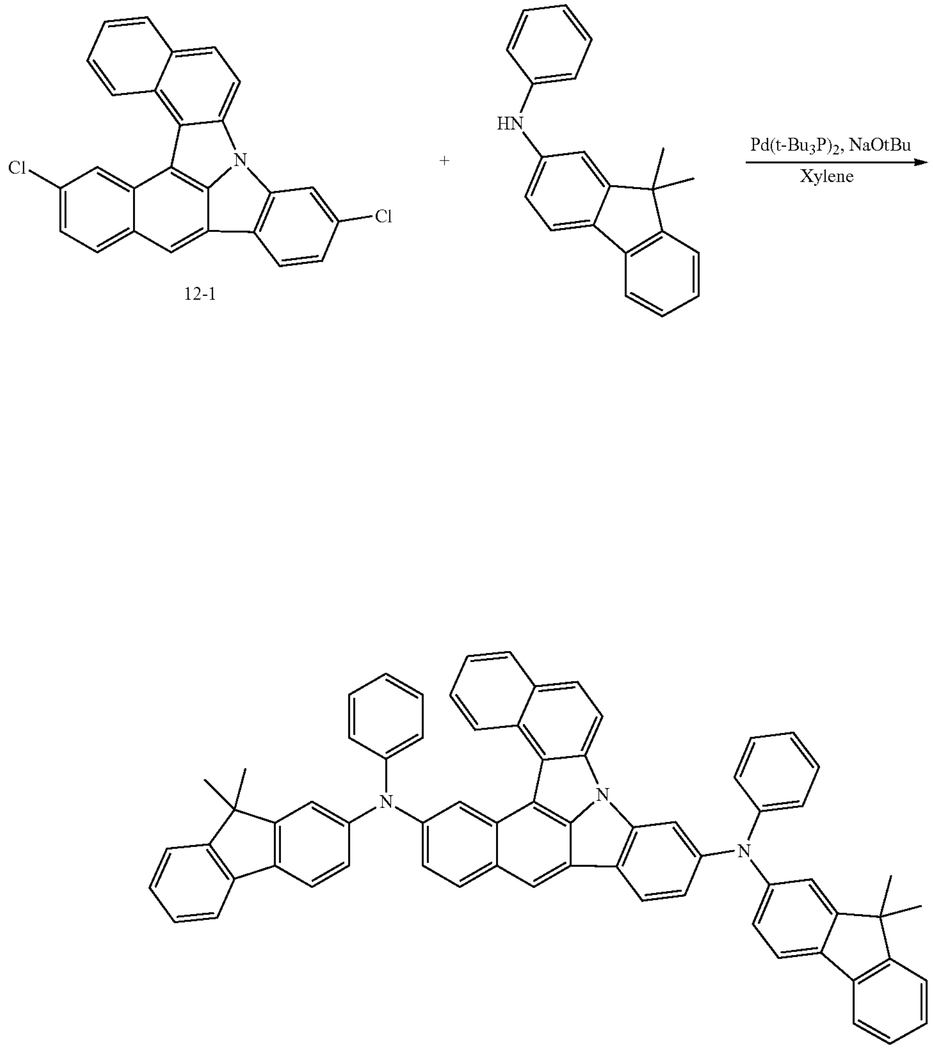

12-1

12

10.0 g (1.0 eq) of Compound 12-1, 15.30 g (2.2 eq) of 9,9-dimethyl-N-phenyl-9H-fluoren-2-amine, 0.12 g (0.01 eq) of Pd(t-$Bu_3P)_2$, and 5.86 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 13.50 g (yield 61%) of Compound 12. [M+H]=909

Synthesis Example 13

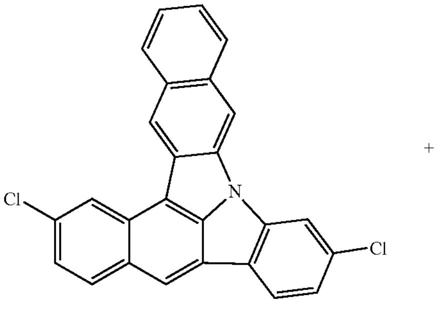

13-1

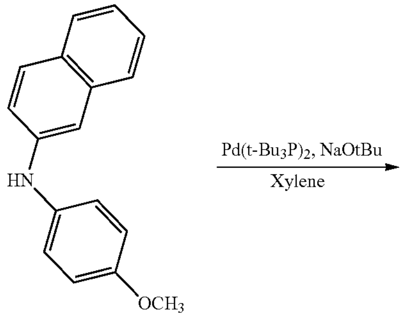

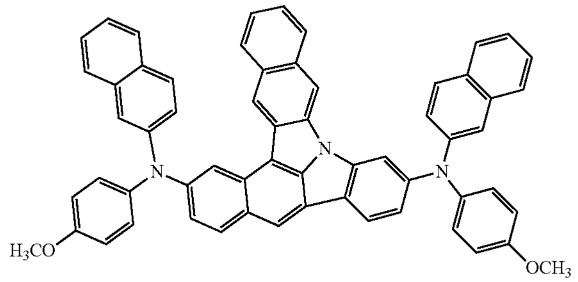

13

10.0 g (1.0 eq) of Compound 13-1, 13.36 g (2.2 eq) of N-(4-methoxyphenyl)naphthalen-2-amine, 0.12 g (0.01 eq) of Pd(t-$Bu_3P)_2$, and 5.86 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 13.04 g (yield 64%) of Compound 13. [M+H]=837

Synthesis Example 14

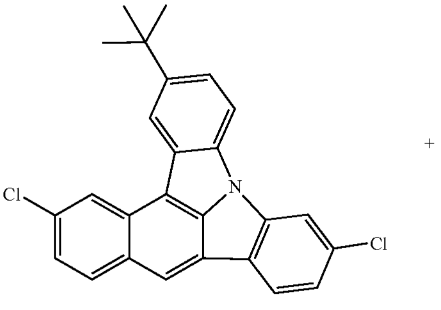

14-1

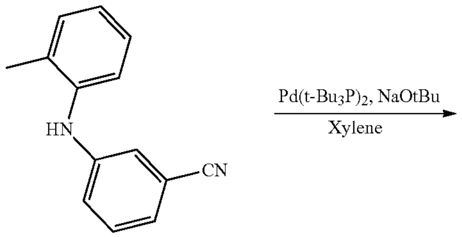

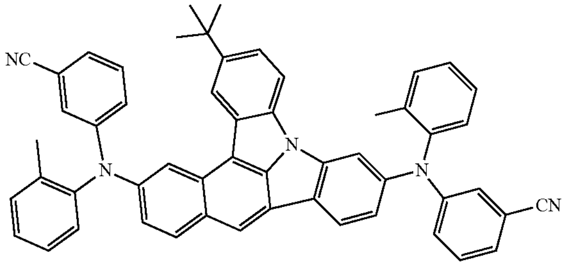

14

10.0 g (1.0 eq) of Compound 14-1, 11.00 g (2.2 eq) of 3-(o-tolylamino)benzonitrile, 0.12 g (0.01 eq) of Pd(t-$Bu_3$ $P)_2$, and 5.77 g (2.5 eq) of NaOtBu were added to 250 ml of xylene, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 11.13 g (yield 61%) of Compound 14. [M+H]=760

Synthesis Example 15

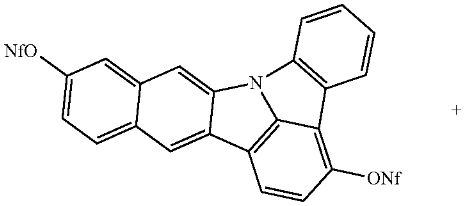

15-1

-continued

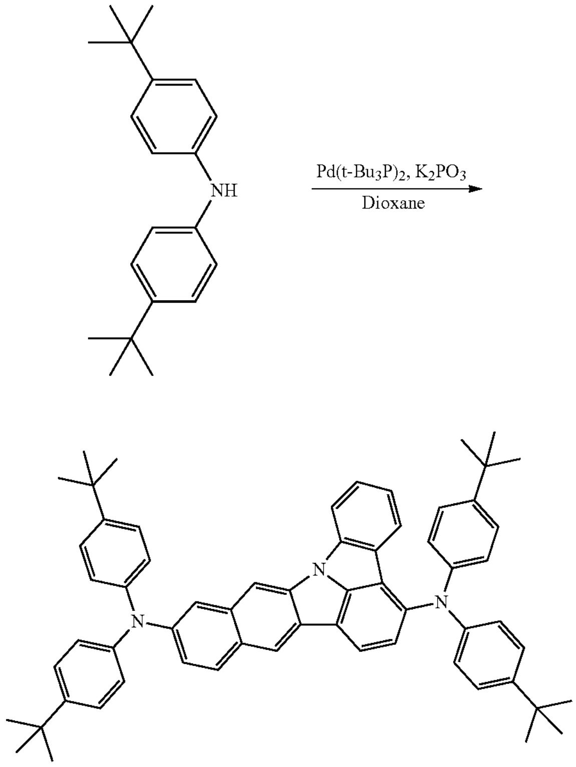

15

17.18 g (1.0 eq) of Compound 15-1, 5.79 g (2.2 eq) of bis(4-(tert-butyl)phenyl)amine, 0.14 g (0.01 eq) of $Pd(t-Bu_3P)_2$, and 18.34 g (2.5 eq) of $K_3PO_4$ were added to 250 ml of dioxane, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 14.45 g (yield 67%) of Compound 15. [M+H]=891

Synthesis Example 16

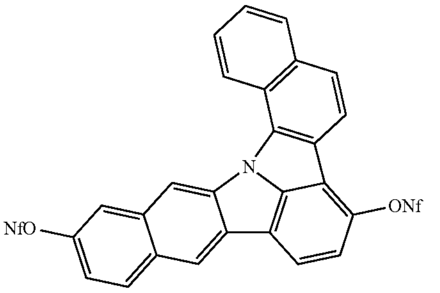

+

16-1

-continued

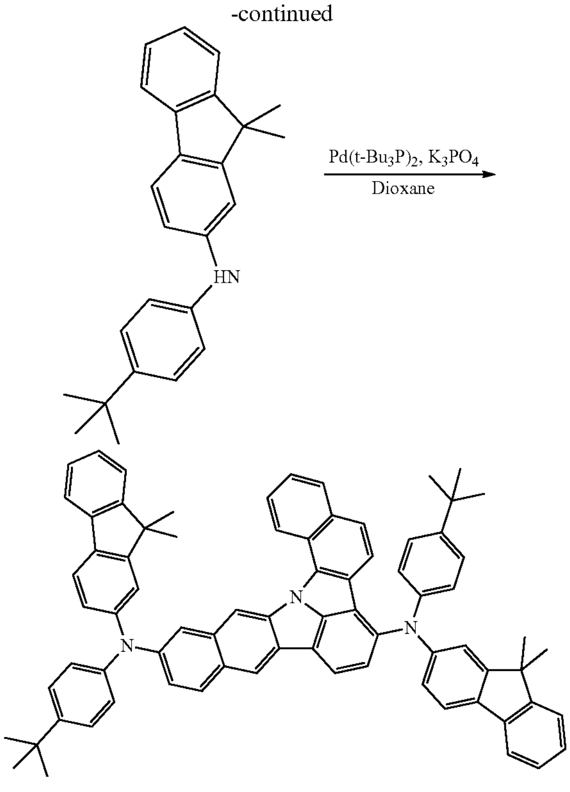

16

10.0 g (1.0 eq) of Compound 16-1, 22.13 g (2.2 eq) of N-(4-(tert-butyl)phenyl)-9,9-dimethyl-9H-fluoren-2-amine, 0.17 g (0.01 eq) of $Pd(t-Bu_3P)_2$, and 15.63 g (2.5 eq) of $K_3PO_4$ were added to 250 ml of dioxane, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 20.14 g (yield 67%) of Compound 16. [M+H]=1021

Synthesis Example 17

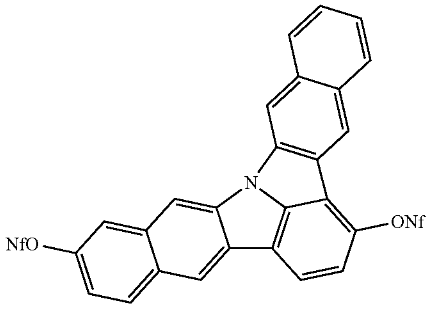

+

17-1

-continued

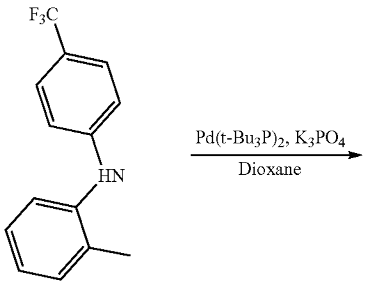

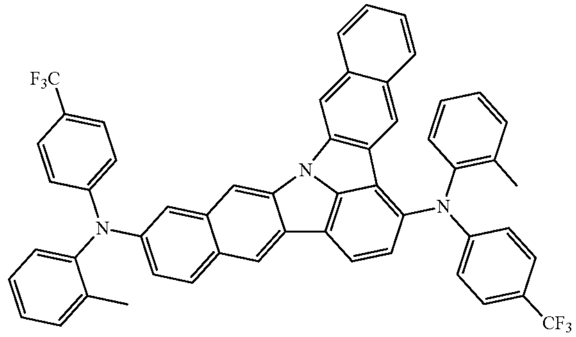

17

10.0 g (1.0 eq) of Compound 17-1, 16.28 g (2.2 eq) of 2-methyl-N-(4-(trifluoromethyl)phenyl)aniline, 0.15 g (0.01 eq) of $Pd(t\text{-}Bu_3P)_2$, and 15.63 g (2.5 eq) of $K_3PO_4$ were added to 250 ml of dioxane, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 15.84 g (yield 64%) of Compound 17. [M+H]=840

Synthesis Example 18

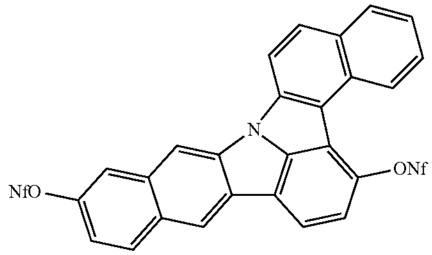

+

18-1

-continued

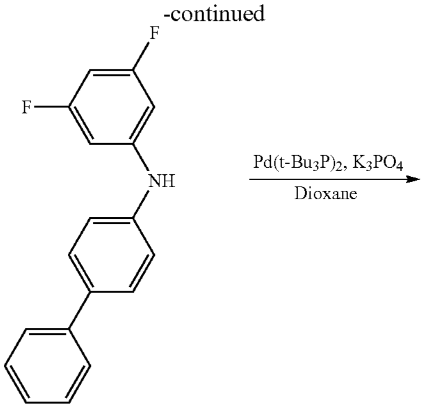

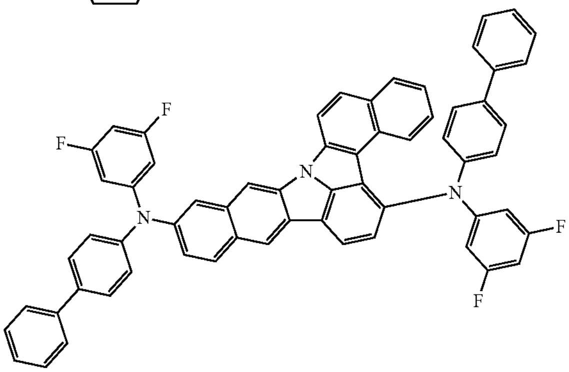

18

10.0 g (1.0 eq) of Compound 18-1, 18.23 g (2.2 eq) of N-(3,5-difluorophenyl)-[1,1'-biphenyl]-4-amine, 0.15 g (0.01 eq) of $Pd(t\text{-}Bu_3P)_2$, and 15.63 g (2.5 eq) of $K_3PO_4$ were added to 250 ml of dioxane, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 16.17 g (yield 61%) of Compound 18. [M+H]=900

Synthesis Example 19

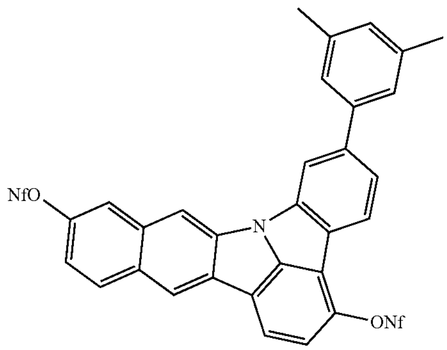

+

19-1

-continued

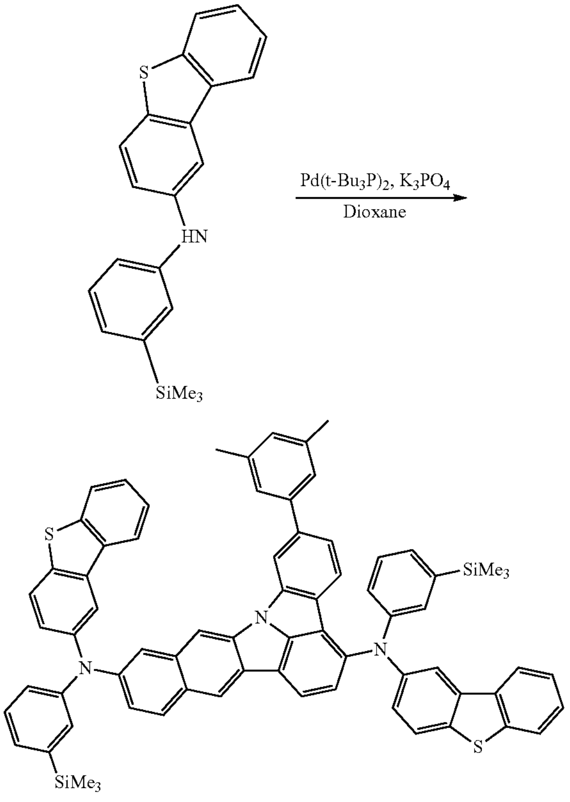

19

10.0 g (1.0 eq) of Compound 19-1, 19.43 g (2.2 eq) of N-(3-(trimethylsilyl)phenyl)dibenzo[b,d] thiophen-2-amine, 0.12 g (0.01 eq) of Pd(t-$Bu_3P)_2$, and 13.48 g (2.5 eq) of $K_3PO_4$ were added to 250 ml of dioxane, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 18.50 g (yield 67%) of Compound 19. [M+H]=1087

Synthesis Example 20

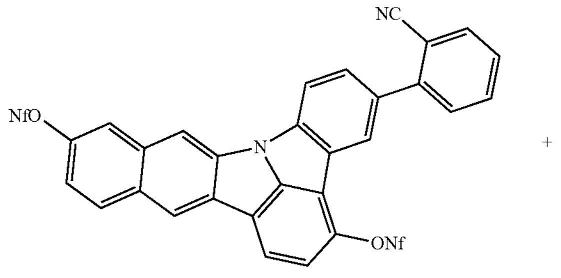

20-1

-continued

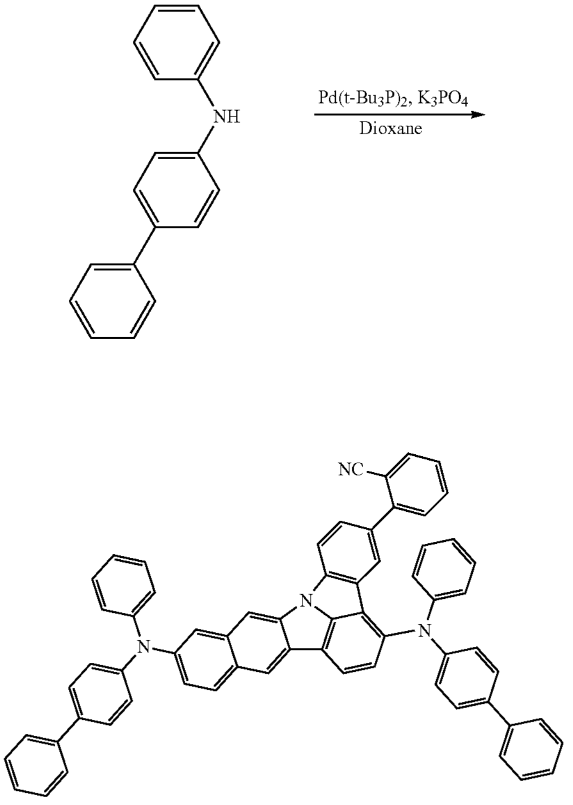

20

10.0 g (1.0 eq) of Compound 20-1, 13.82 g (2.2 eq) of N-phenyl-[1,1'-biphenyl]-4-amine, 0.13 g (0.01 eq) of Pd(t-$Bu_3P)_2$, and 13.59 g (2.5 eq) of $K_3PO_4$ were added to 250 ml of dioxane, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 13.73 g (yield 61%) of Compound 20. [M+H]=880

Synthesis Example 21

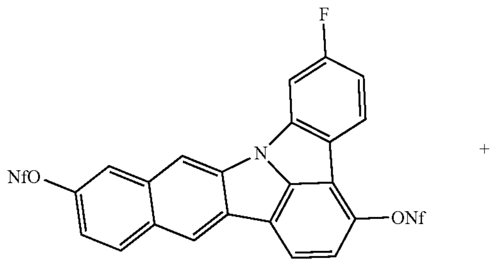

21-1

-continued

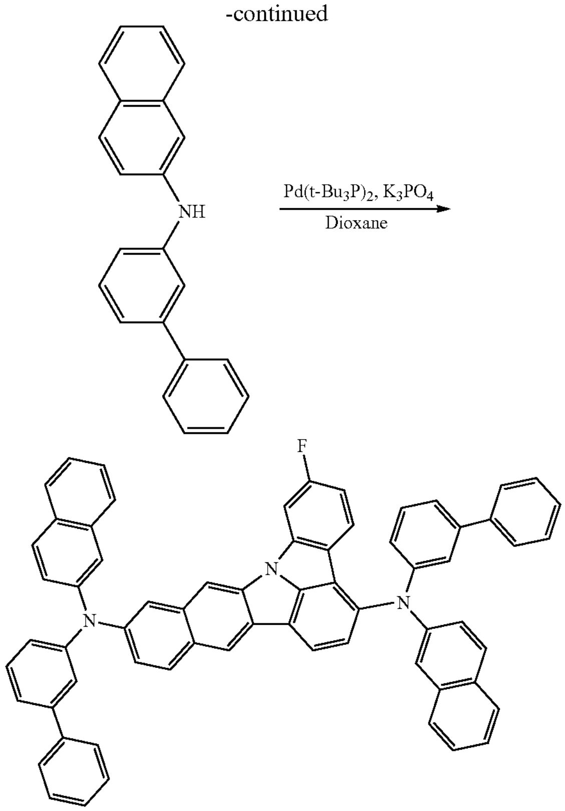

21

10.0 g (1.0 eq) of Compound 21-1, 21.14 g (2.2 eq) of N-([1,1'-biphenyl]-3-yl)naphthalen-2-amine, 0.16 g (0.01 eq) of $Pd(t-Bu_3P)_2$, and 17.26 g (2.5 eq) of $K_3PO_4$ were added to 250 ml of dioxane, and the resulting mixture was stirred under reflux. After 2 hours, when the reaction was terminated, the solvent was removed by reducing pressure. Thereafter, the resulting product was completely dissolved in $CHCl_3$, the resulting solution was washed with water, and approximately 50% of the solvent was removed again by reducing pressure. Again, ethyl acetate was put thereinto in a reflux state, and crystals were precipitated, cooled, and then filtered. The resulting product was subjected to column chromatography to obtain 18.95 g (yield 65%) of Compound 21. [M+H]=897

EXPERIMENTAL EXAMPLE

Example 1

A glass substrate thinly coated with indium tin oxide (ITO) to have a thickness of 1,000 Å was added to distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was repeated twice by using distilled water for 10 minutes. After the washing using distilled water was completed, ultrasonic washing was conducted by using isopropyl alcohol, acetone, and methanol solvents, and the resulting product was dried and then transported to a plasma washing machine. Furthermore, the substrate was cleaned by using an oxygen plasma for 5 minutes, and then was transported to a vacuum deposition machine.

The following HI-1 compound was formed to have a thickness of 1,150 Å as a hole injection layer on the thus prepared transparent ITO electrode, and was p-doped with the following A-1 compound at a concentration of 1.5%. The following HT-1 compound was vacuum deposited on the hole injection layer, thereby forming a hole transport layer having a film thickness of 800 Å. Next, the following EB-1 compound was vacuum deposited to have a film thickness of 150 Å on the hole transport layer, thereby forming an electron blocking layer. Next, the following BH-1 compound as a host and Compound 1 as a dopant were vacuum deposited at a weight ratio of 98:2 (host:dopant) on the electron blocking layer, thereby forming a blue light emitting layer having a thickness of 200 Å. The following HB-1 compound was vacuum deposited to have a film thickness of 30 Å on the light emitting layer, thereby forming a hole blocking layer. Next, the following ET-1 compound and the following LiQ compound were vacuum deposited at a weight ratio of 2:1 on the hole blocking layer, thereby forming an electron injection and transport layer having a thickness of 300 Å. Lithium fluoride (LiF) and aluminum were sequentially deposited on the electron injection and transport layer to have a thickness of 12 Å and 1,000 Å, respectively, thereby forming a negative electrode.

In the aforementioned procedure, the deposition rate of the organic material was maintained at 0.4 Å/sec to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ torr to $5\times10^{-6}$ torr, thereby manufacturing an organic light emitting device.

HI-1

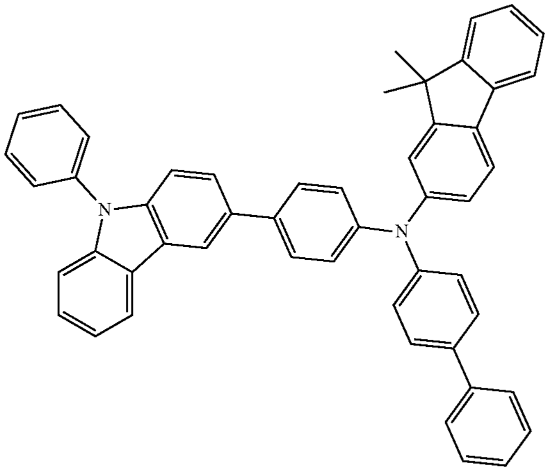

-continued
A-1
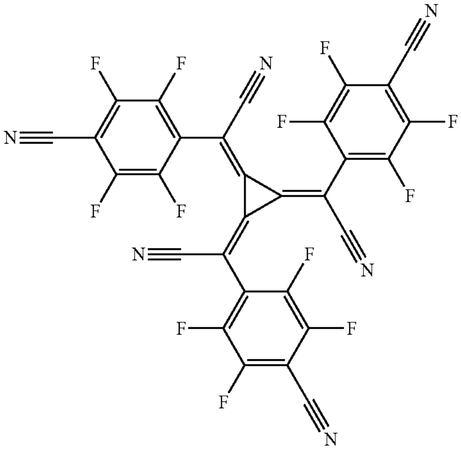
HT-1
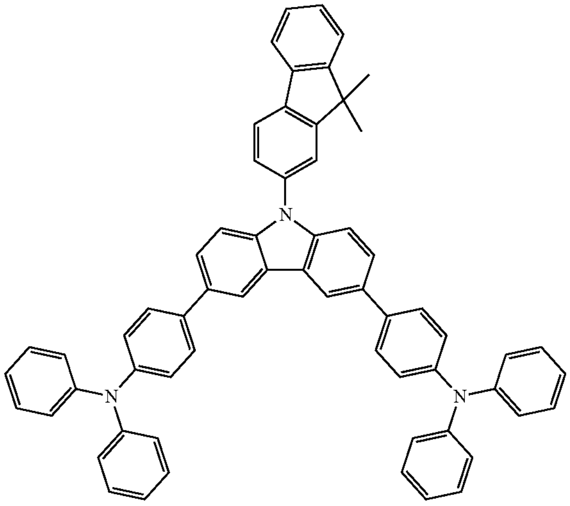
EB-1
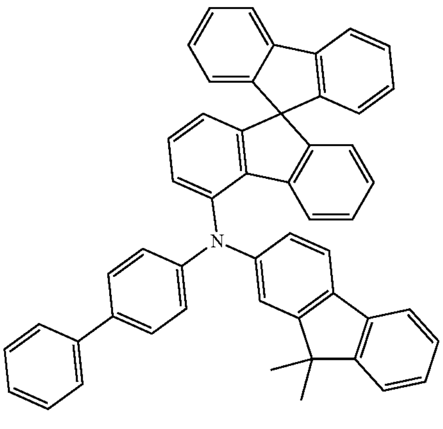
-continued
BH-1
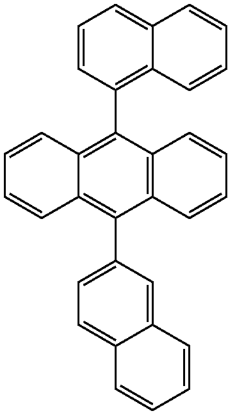
HB-1
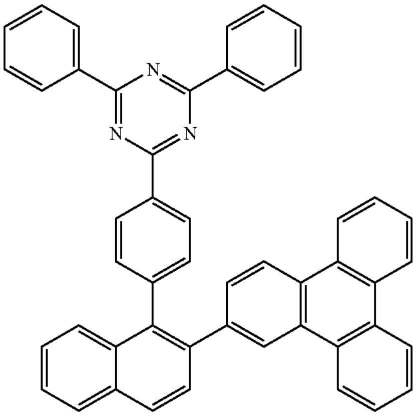
ET-1
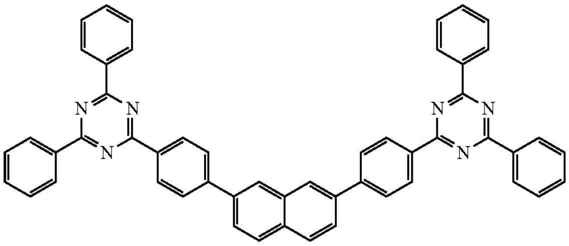
LiQ
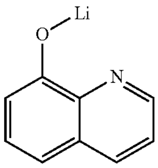
Examples 2 to 21
Organic light emitting devices were manufactured in the same manner as in Example 1, except that the compounds described in the following Table 1 were used instead of Compound 1 in the organic light emitting device in Example 1.

1
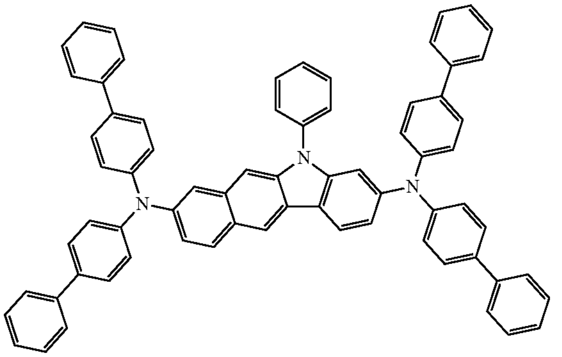
2
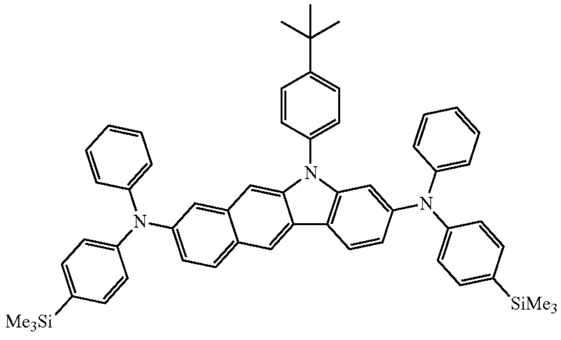
3
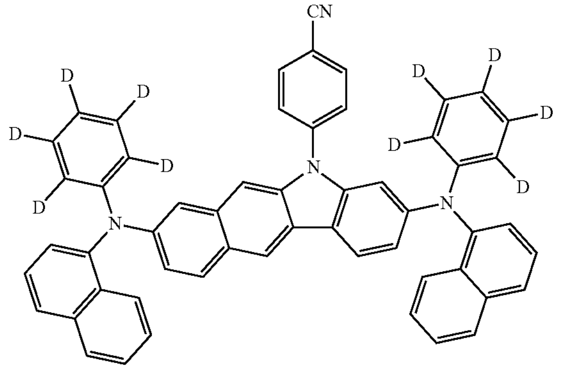
4
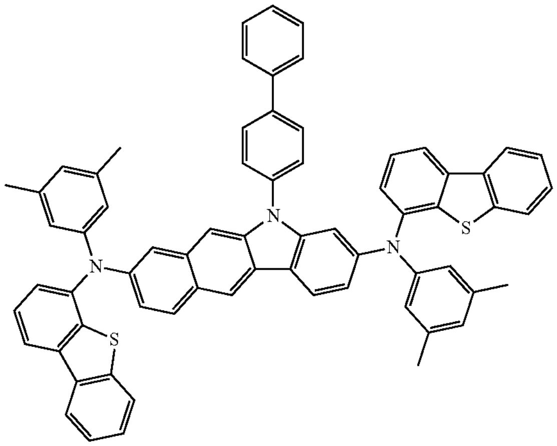
5
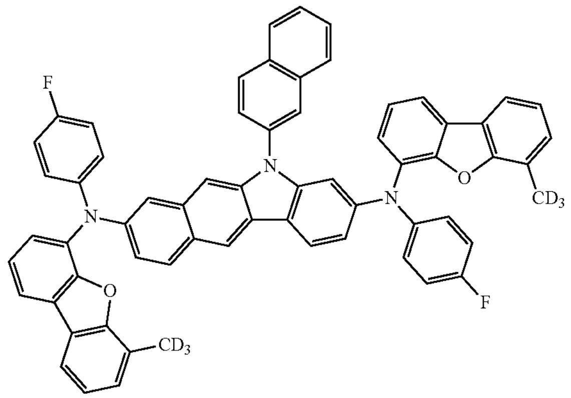
6
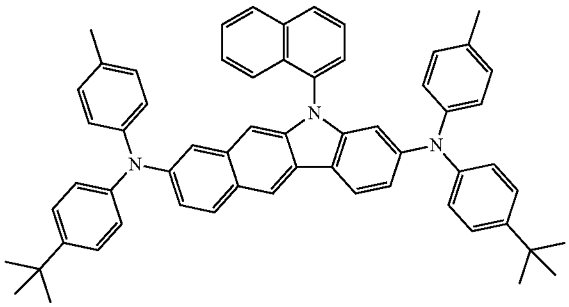
7
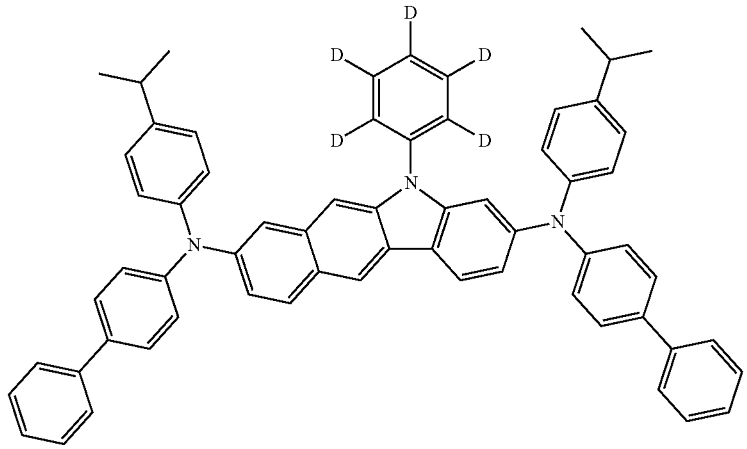

-continued
8
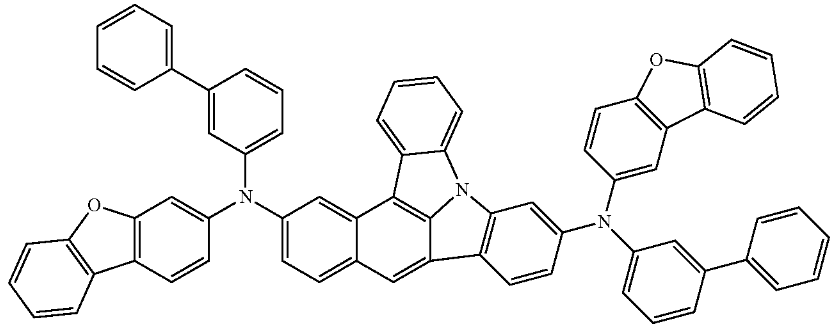
9
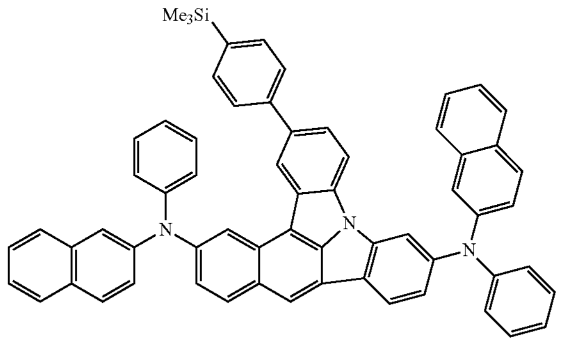
10
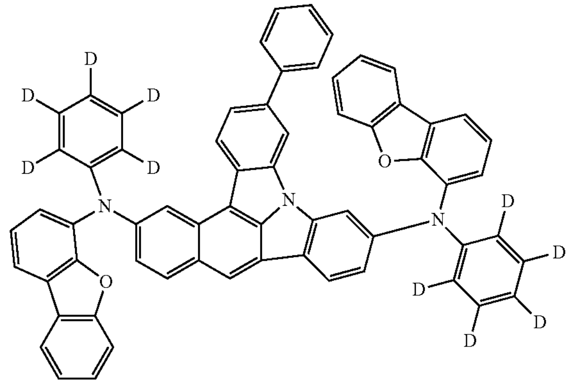
11
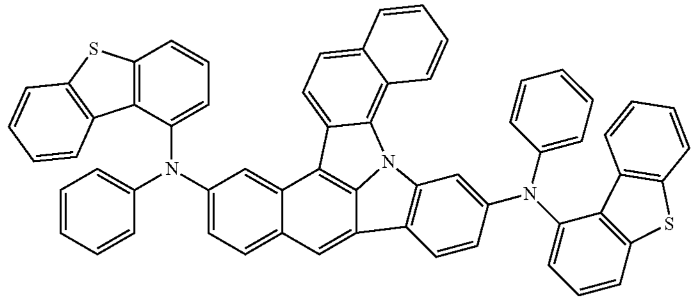
12
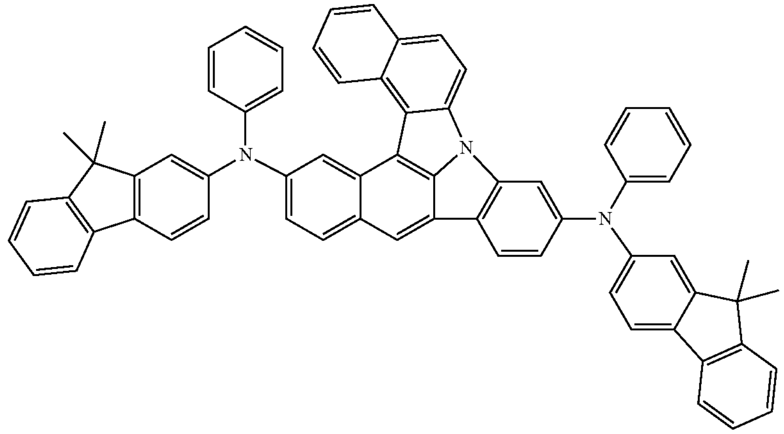

-continued
13
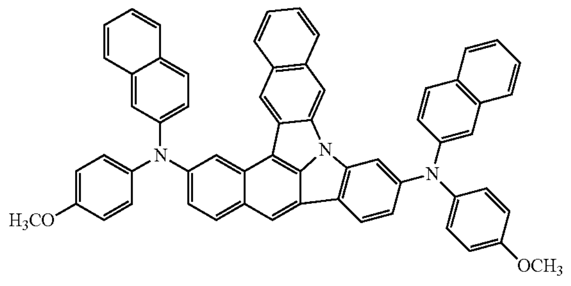
14
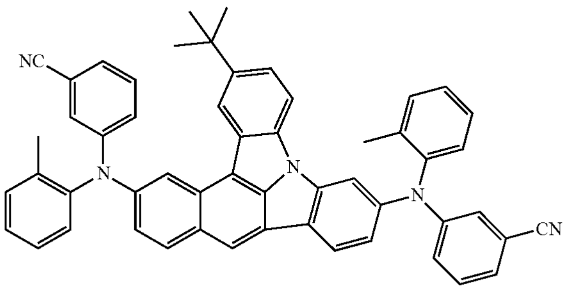
15
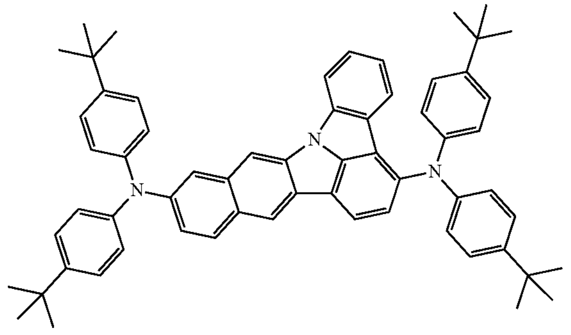
16
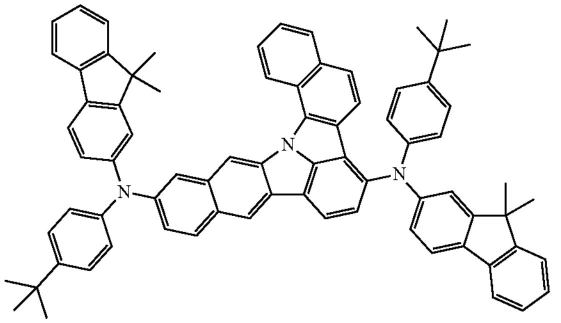
17
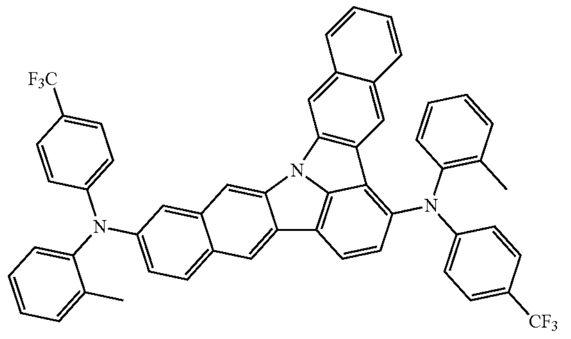
18
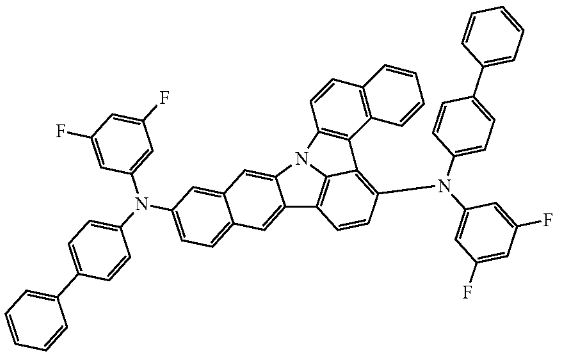
19
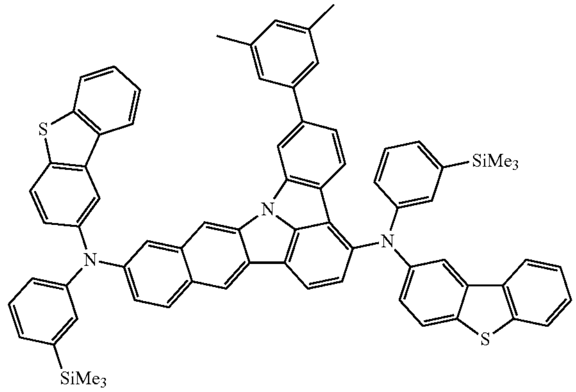
20
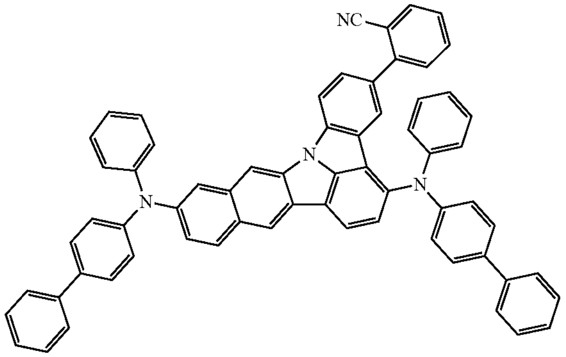

-continued
21
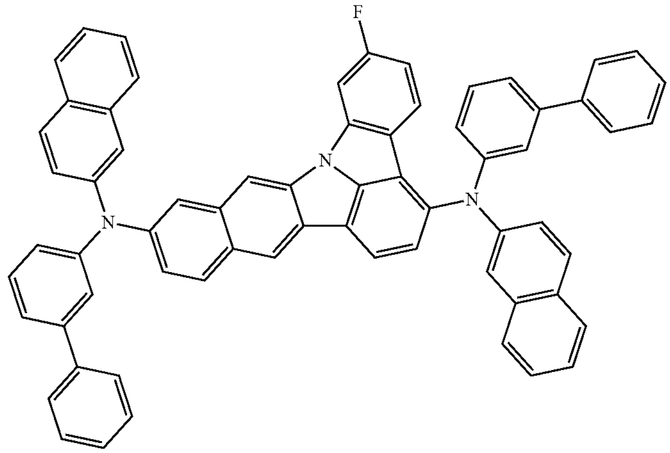
Comparative Examples 1 to 7
Organic light emitting devices were manufactured in the same manner as in Example 1, except that the compounds described in the following Table 1 were used instead of Compound 1 in the organic light emitting device in Example 1.
C-1
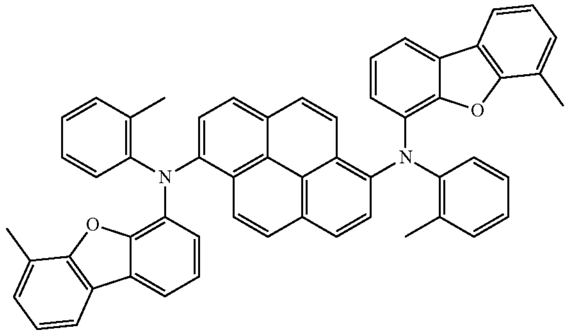
C-2
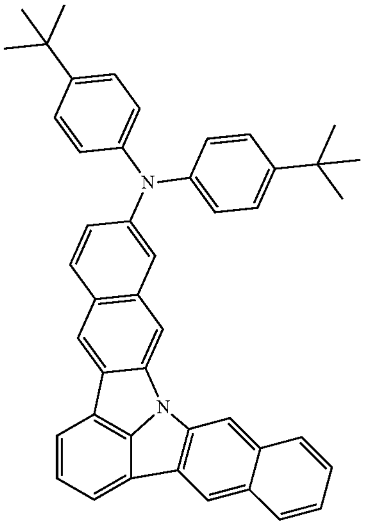
-continued
C-3
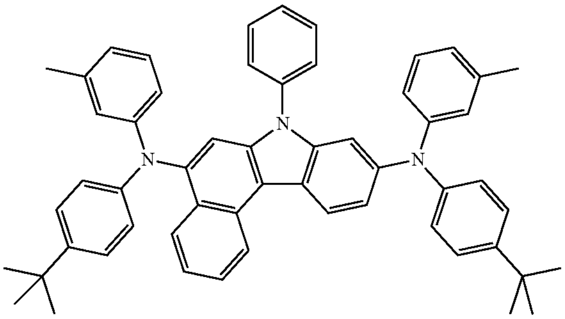
C-4
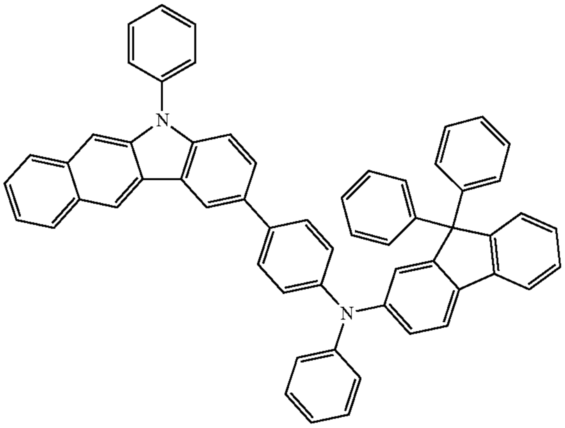

-continued

C-5

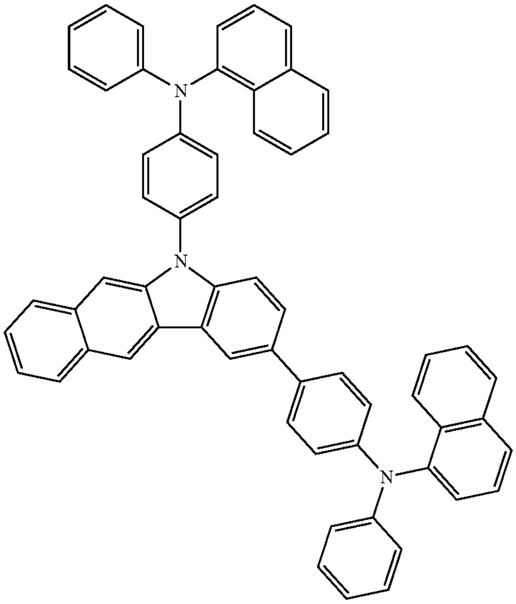

C-6

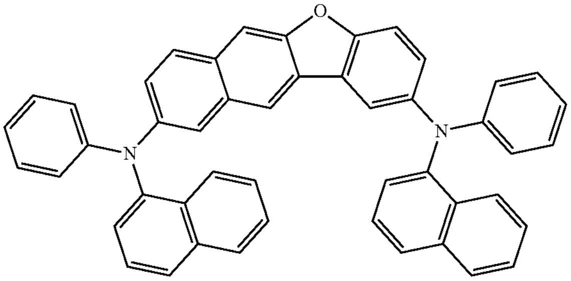

-continued

C-7

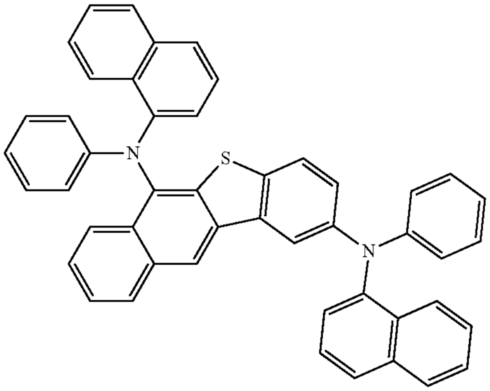

For the organic light emitting devices of Examples 1 to 21 and Comparative Examples 1 to 7, the driving voltage, the light emitting efficiency and color coordinate were measured at a current density of 10 mA/cm$^2$, and a time (LT95) for reaching a 95% value compared to the initial luminance was measured at a current density of 20 mA/cm$^2$. The results are shown in the following Table 1.

TABLE 1

| Example | Dopant | 10 mA/cm$^2$ Driving voltage (v) | Efficiency (cd/A) | CIEy | 20 mA/cm$^2$ Service life (hr), 95% |
|---|---|---|---|---|---|
| Example 1 | Compound 1 | 4.5 | 5.9 | 0.08 | 185 |
| Example 2 | Compound 2 | 4.6 | 6.1 | 0.12 | 189 |
| Example 3 | Compound 3 | 4.5 | 5.6 | 0.08 | 176 |
| Example 4 | Compound 4 | 4.6 | 5.7 | 0.08 | 177 |
| Example 5 | Compound 5 | 4.8 | 5.4 | 0.10 | 193 |
| Example 6 | Compound 6 | 4.4 | 5.5 | 0.09 | 205 |
| Example 7 | Compound 7 | 4.3 | 6.0 | 0.12 | 183 |
| Example 8 | Compound 8 | 4.5 | 6.1 | 0.10 | 194 |
| Example 9 | Compound 9 | 4.4 | 5.5 | 0.09 | 171 |
| Example 10 | Compound 10 | 4.6 | 5.7 | 0.11 | 176 |
| Example 11 | Compound 11 | 4.5 | 5.6 | 0.08 | 187 |
| Example 12 | Compound 12 | 4.7 | 5.7 | 0.09 | 177 |
| Example 13 | Compound 13 | 4.7 | 5.4 | 0.08 | 194 |
| Example 14 | Compound 14 | 4.5 | 6.1 | 0.12 | 203 |
| Example 15 | Compound 15 | 4.3 | 5.8 | 0.10 | 189 |
| Example 16 | Compound 16 | 4.5 | 5.7 | 0.09 | 164 |
| Example 17 | Compound 17 | 4.7 | 5.8 | 0.11 | 198 |
| Example 18 | Compound 18 | 4.6 | 6.0 | 0.12 | 183 |
| Example 19 | Compound 19 | 4.4 | 5.9 | 0.11 | 172 |
| Example 20 | Compound 20 | 4.8 | 5.5 | 0.09 | 180 |
| Example 21 | Compound 21 | 4.4 | 5.7 | 0.10 | 193 |
| Comparative Example 1 | C-1 | 4.8 | 4.9 | 0.12 | 157 |
| Comparative Example 2 | C-2 | 5.0 | 5.7 | 0.09 | 108 |

TABLE 1-continued

| Example | Dopant | 10 mA/cm² Driving voltage (v) | Efficiency (cd/A) | CIEy | 20 mA/cm² Service life (hr), 95% |
|---|---|---|---|---|---|
| Comparative Example 3 | C-3 | 5.0 | 4.1 | 0.17 | 121 |
| Comparative Example 4 | C-4 | 5.1 | 4.5 | 0.13 | 83 |
| Comparative Example 5 | C-5 | 4.8 | 4.9 | 0.15 | 137 |
| Comparative Example 6 | C-6 | 4.9 | 4.8 | 0.13 | 97 |
| Comparative Example 7 | C-7 | 4.6 | 5.0 | 0.16 | 145 |

When an electric current was applied to the organic light emitting devices manufactured in Examples 1 to 21 and Comparative Examples 1 to 7, the results of Table 1 were obtained. All of the Examples and the Comparative Examples exhibited blue light emission. From the results of Table 1, it could be seen that when the compound of the present invention was used as a dopant of a blue light emitting layer, the driving voltage was significantly lowered by 15% or more and the efficiency was increased by 48% or more, as compared to the materials in the Comparative Examples, and that the service life characteristics could be significantly improved while maintaining the high efficiency.

Example 22: Measurement of Maximum Emission Wavelength and Full Width at Half-Maximum The fluorescence intensity and the maximum emission peak were measured at room temperature (300 K) by dissolving Compound 12 at a concentration of 1 μM in toluene as a solvent to prepare a sample for measuring fluorescence, putting the sample solution into a quartz cell, and then using a fluorescence measurement apparatus (JASCO FP-8600 fluorescence spectrophotometer). In this case, in the fluorescence spectrum, the x axis is the wavelength (λ, unit: nm), the y axis is the light emission degree, and a spread width of a peak at a height that is ½ of the height of the maximum emission peak refers to a full width at half-maximum.

Example 23 and Comparative Examples 8 to 10

The maximum emission wavelengths and the full widths at half-maximum were measured by using the compounds shown in the following Table 2 instead of Compound 12 in Example 22, and are shown in Table 2.

TABLE 2

| Example | Dopant | Solution PL Maximum emission wavelength (nm) | Full width at half-maximum (nm) |
|---|---|---|---|
| Example 22 | Compound 12 | 447 | 24 |
| Example 23 | Compound 15 | 448 | 25 |
| Comparative Example 8 | C-1 | 451 | 44 |

TABLE 2-continued

| Example | Dopant | Solution PL Maximum emission wavelength (nm) | Full width at half-maximum (nm) |
|---|---|---|---|
| Comparative Example 9 | C-2 | 440 | 38 |
| Comparative Example 10 | C-3 | 448 | 52 |

From Table 2, it can be seen that the full widths at half-maximum in the Examples are 30 nm or less, whereas the full widths at half-maximum in the Comparative Examples were more than 30 nm. It can be seen that when the compound of Chemical Formula 1 is used as a blue emission dopant, the color purity is good due to the narrow full width at half-maximum.

The invention claimed is:

1. A compound of Chemical Formula 2:

Chemical Formula 2

Chemical Formula 2

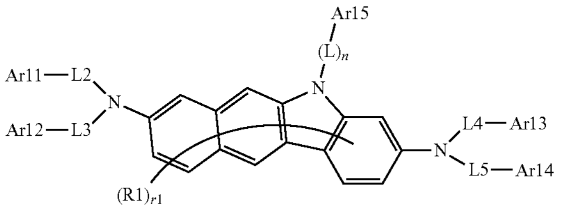

wherein in Chemical Formula 2:

-$(L)_n$-Ar15 is a phenyl group substituted with deuterium, a halogen group, a nitrile group, an alkoxy group, a silyl group, or an alkyl group which is unsubstituted or substituted with deuterium; or a biphenyl group which is unsubstituted or substituted with deuterium, a halogen group, a nitrile group, an alkoxy group, a silyl group, or an alkyl group which is unsubstituted or substituted with deuterium;

Ar11 to Ar14 are the same as or different from each other, and each independently is a phenyl group, a naphthyl group, a biphenyl group, a fluorenyl group, or a benzofluorenyl group, wherein the phenyl group, the naphthyl group, the biphenyl group, the fluorenyl group, or the benzofluorenyl group is unsubstituted or substituted with a substituent that is deuterium; a halogen group; a nitrile group; an alkyl group having 1 to 5 carbon atoms, which is unsubstituted or substituted with deuterium; a haloalkyl group having 1 to 5 carbon atoms; an alkoxy group having 1 to 5 carbon atoms; a haloalkoxy group having 1 to 5 carbon atoms; a silyl group having 3 to 20 carbon atoms; or a cycloalkyl group having 3 to 20 carbon atoms; or a substituted or unsubstituted heteroaryl group; or are bonded to an adjacent substituent to form a substituted or unsubstituted ring;

L2 to L5 are the same as or different from each other, and each independently is a direct bond or a substituted or unsubstituted arylene group;

R1 is hydrogen, deuterium, a halogen group, a nitrile group, or a substituted or unsubstituted aryl group; and r1 is an integer from 0 to 8, and when r1 is 2 or more, the R1s are the same as or different from each other.

2. The compound of claim 1, wherein the compound of Chemical Formula 2 is any one of the following compounds:

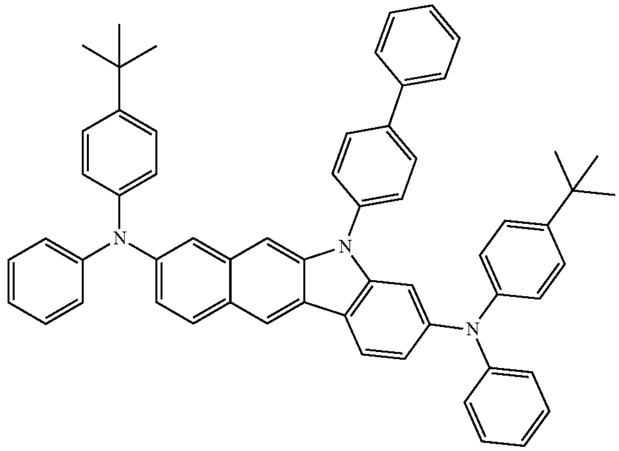

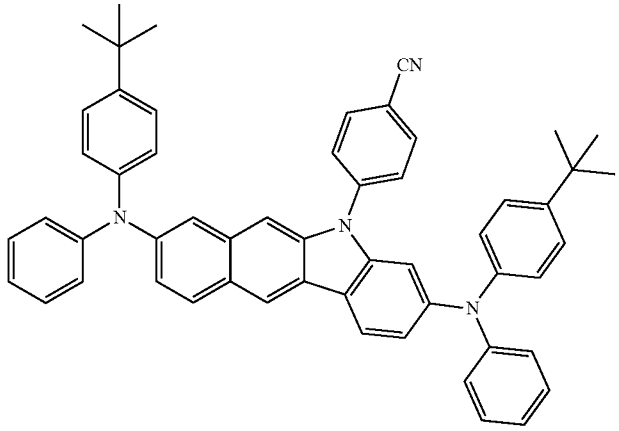

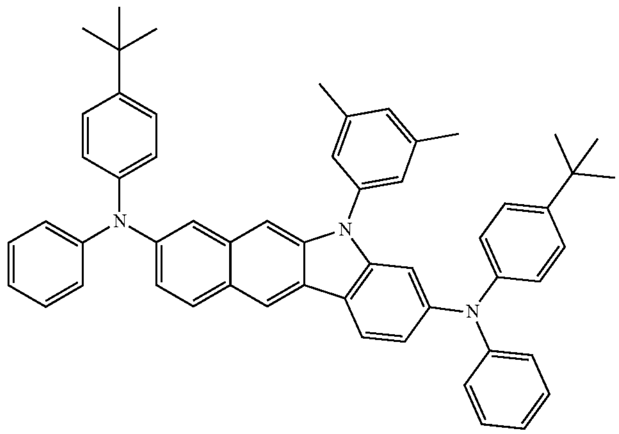

-continued
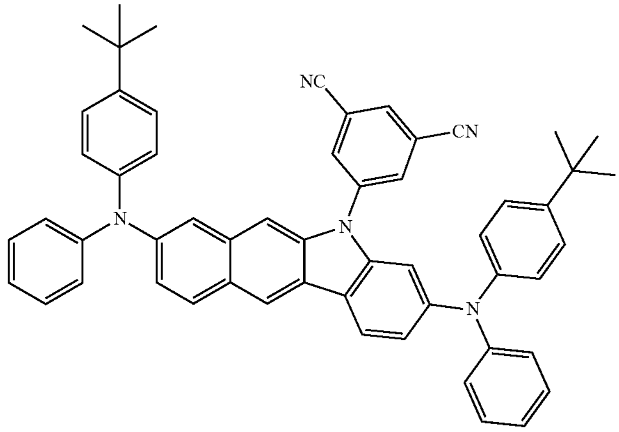
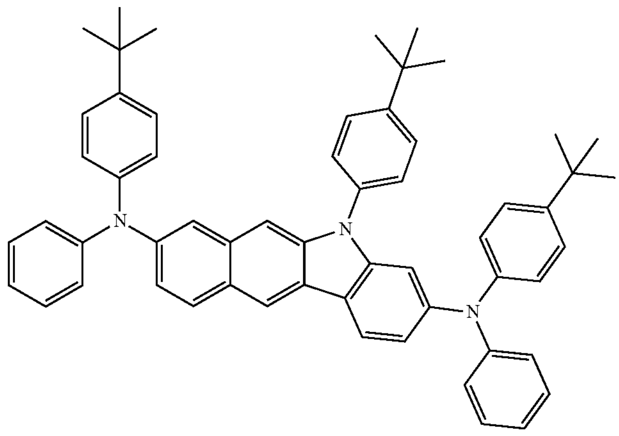
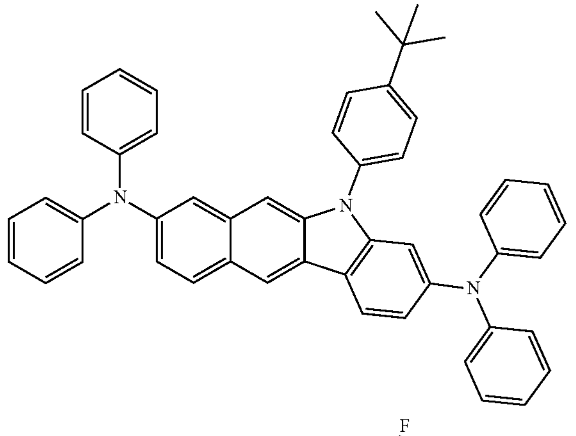
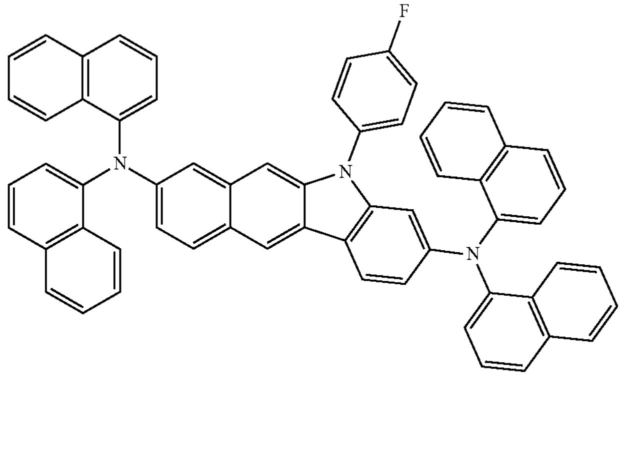

-continued
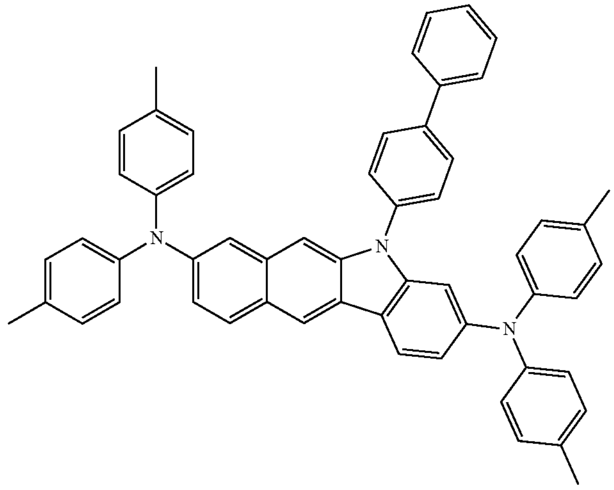
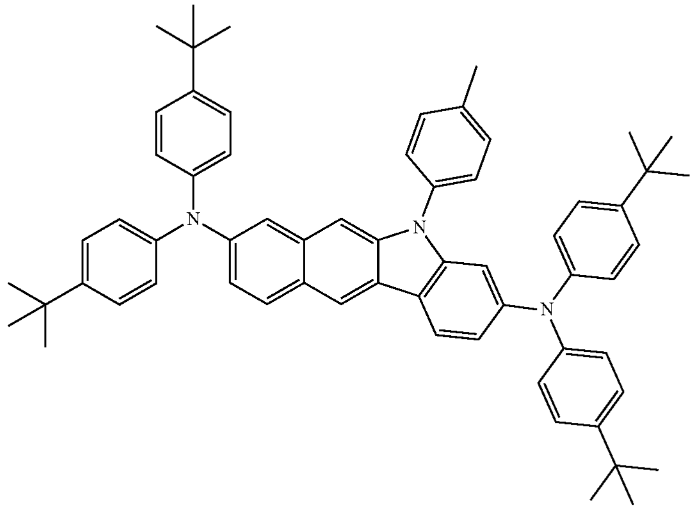
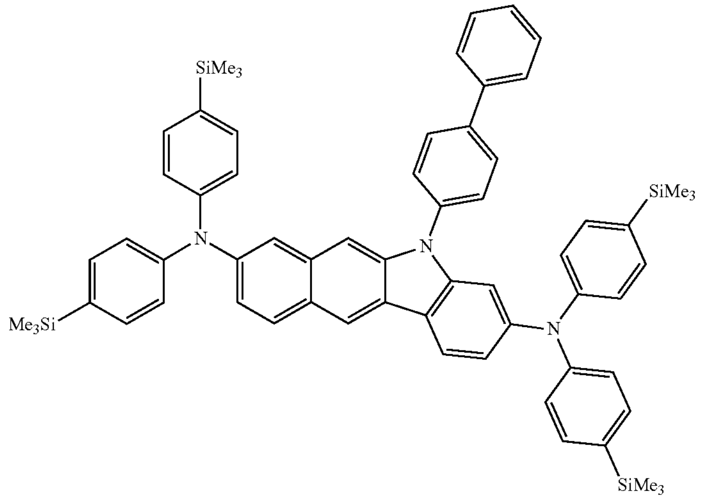

-continued
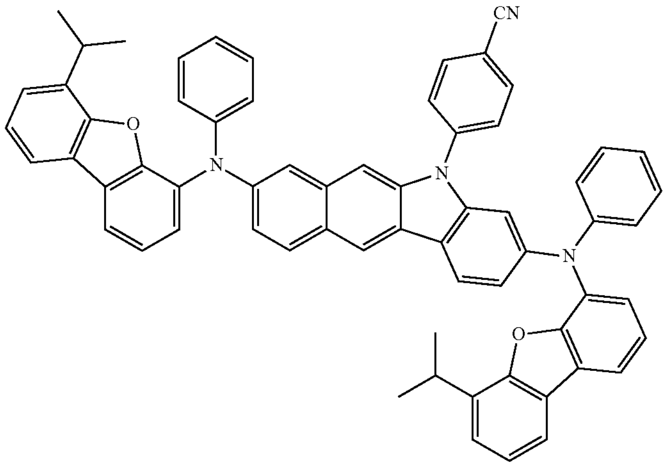
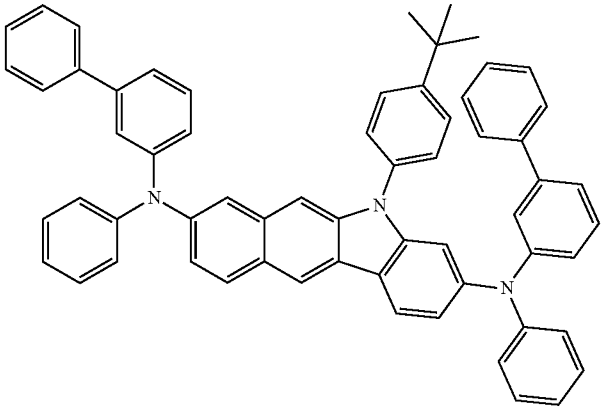
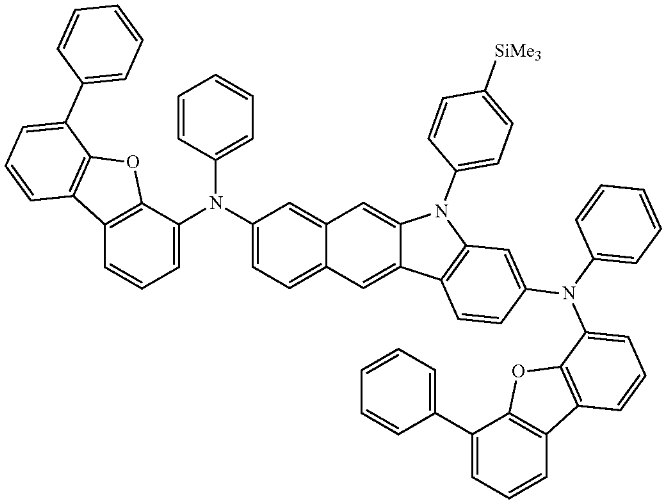

-continued
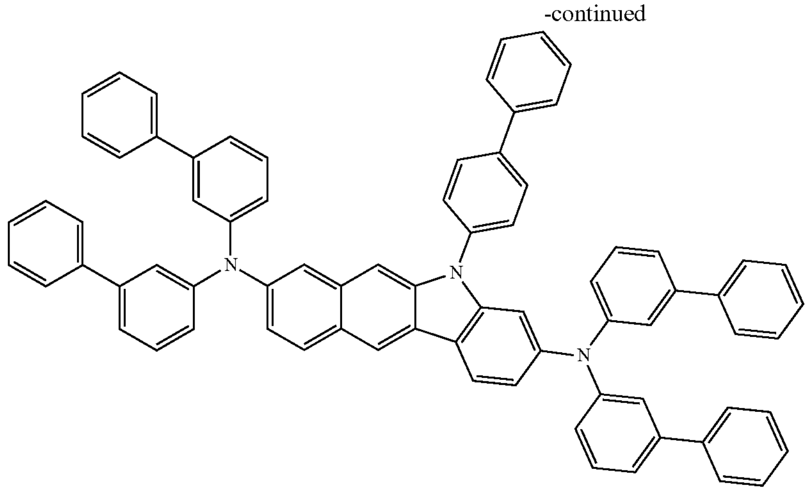
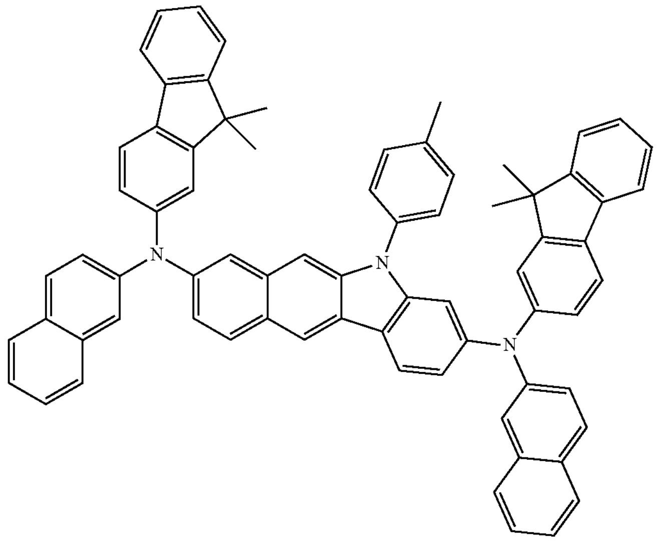
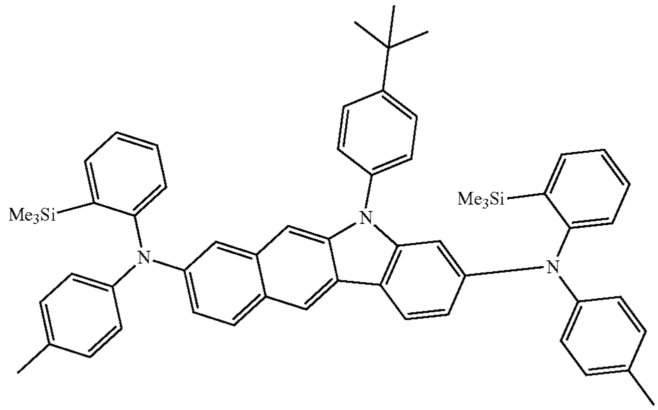

-continued
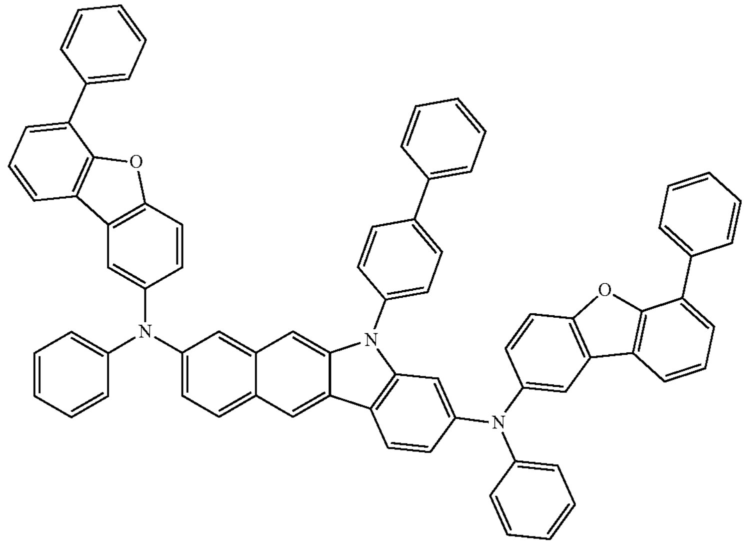
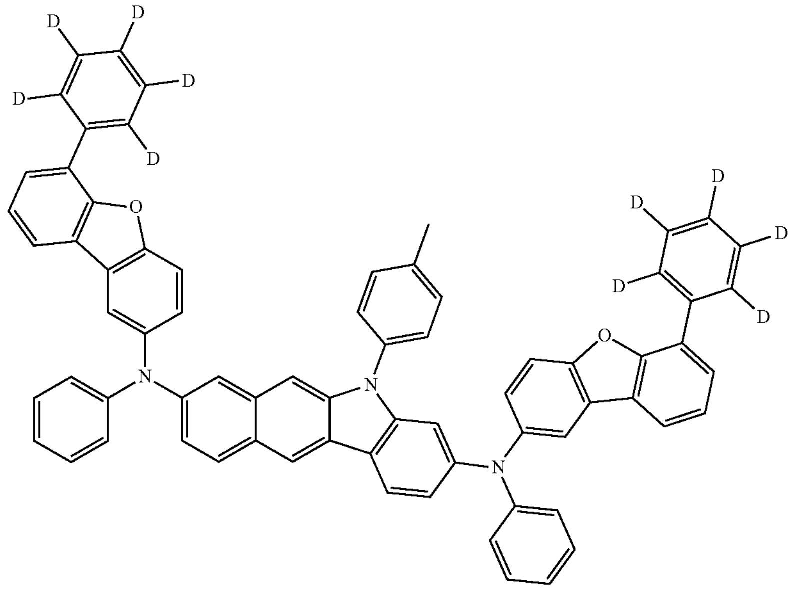
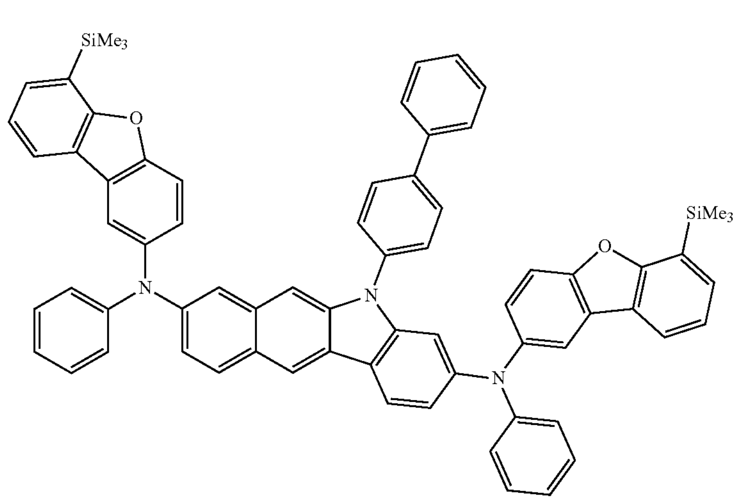

-continued
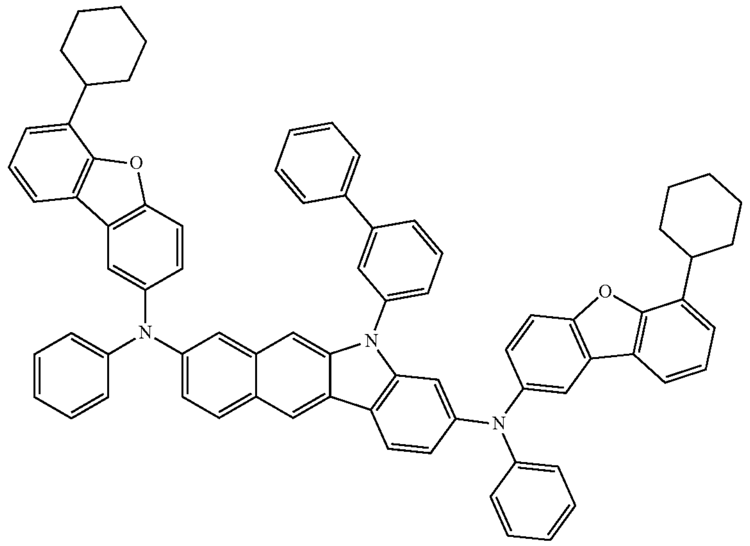
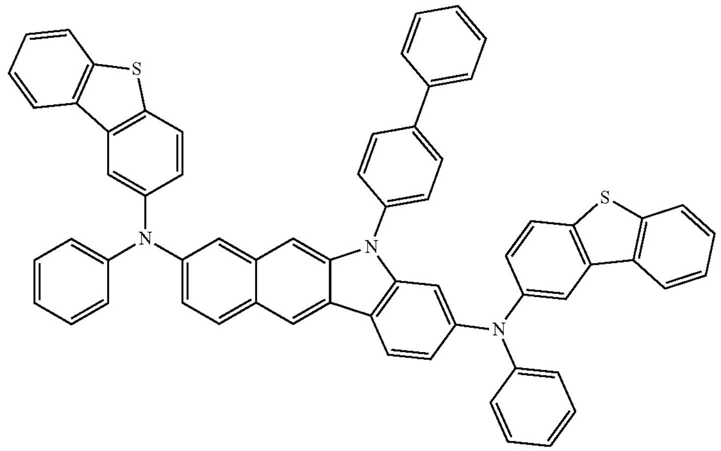
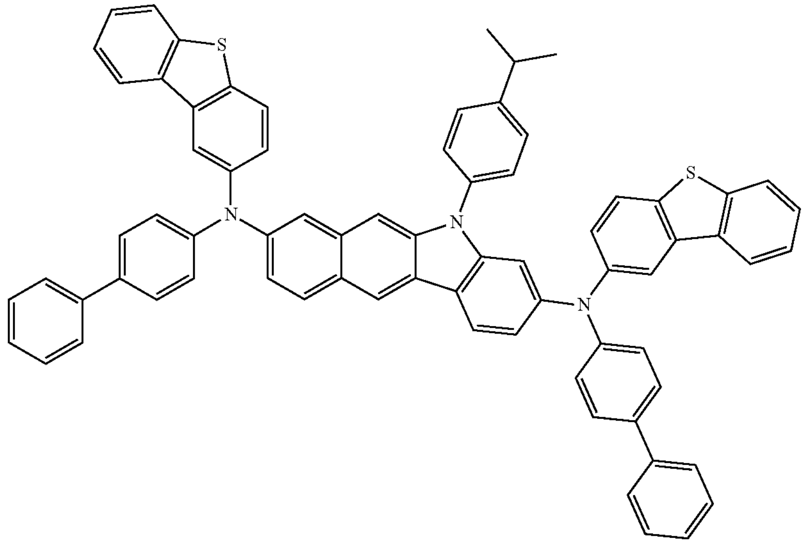

-continued
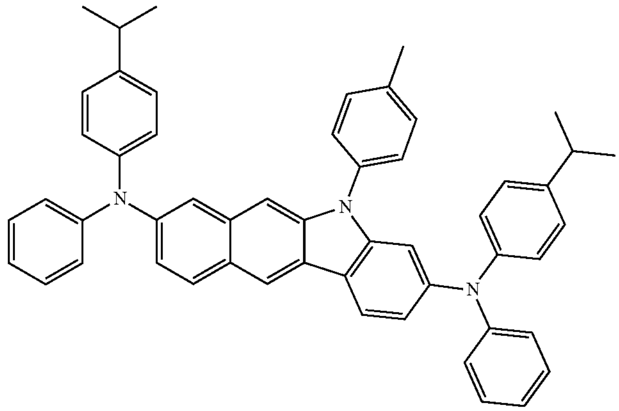
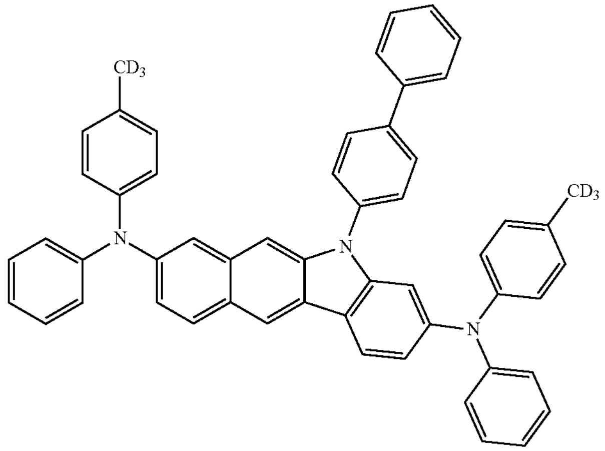
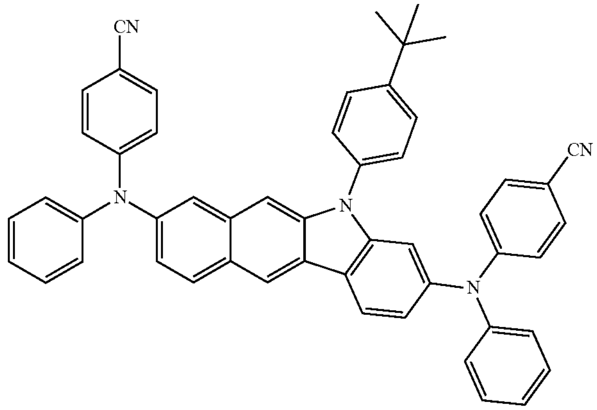
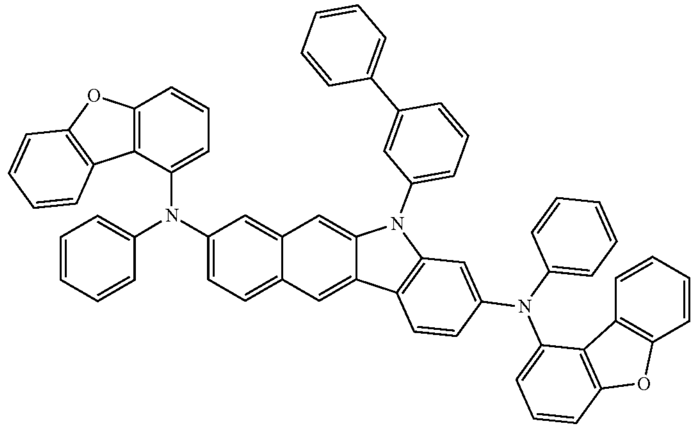

-continued
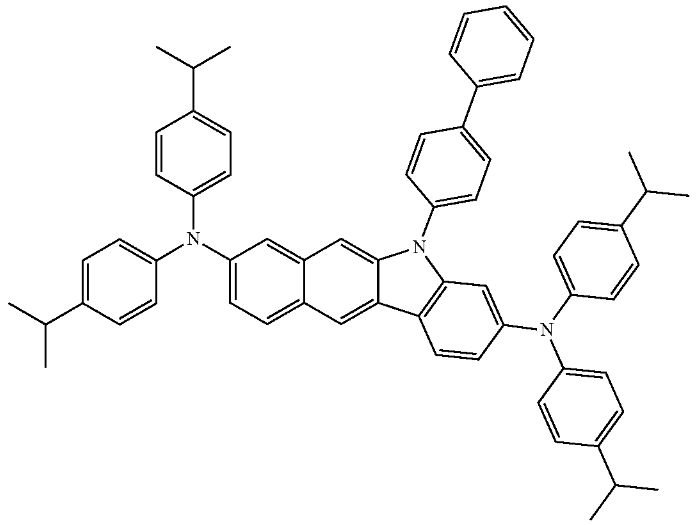
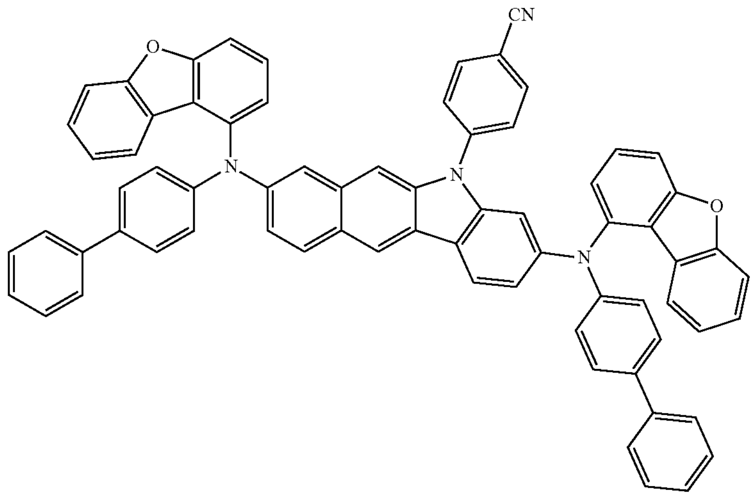
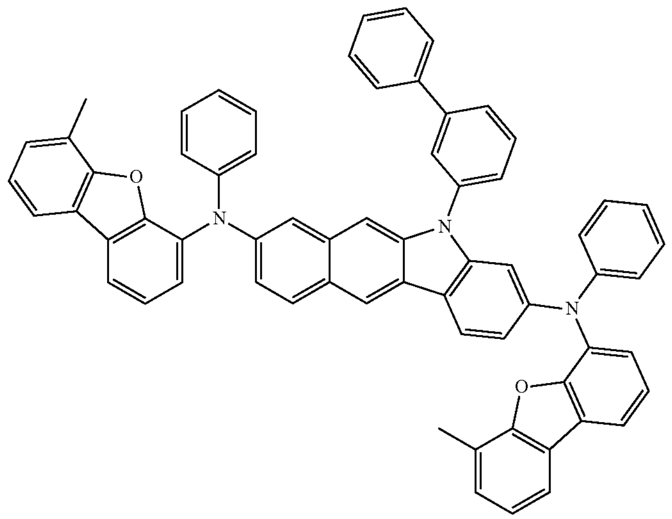

-continued
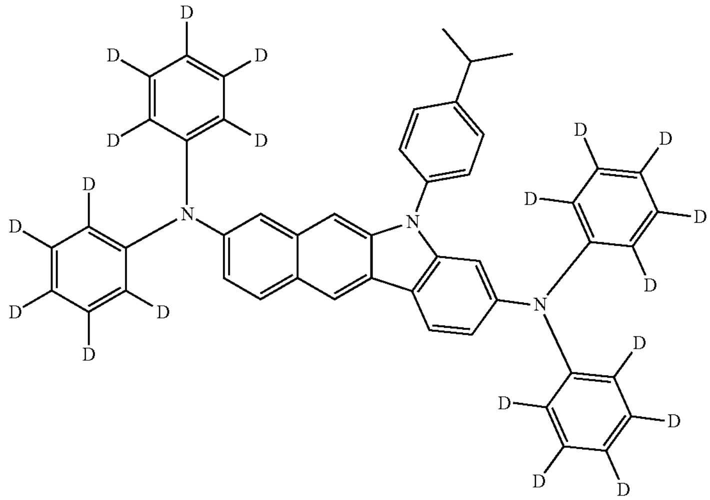
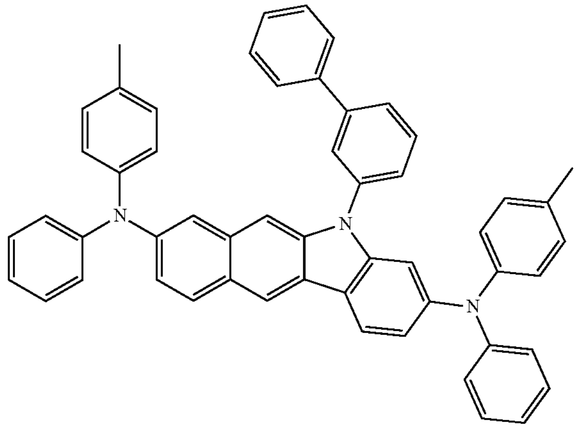
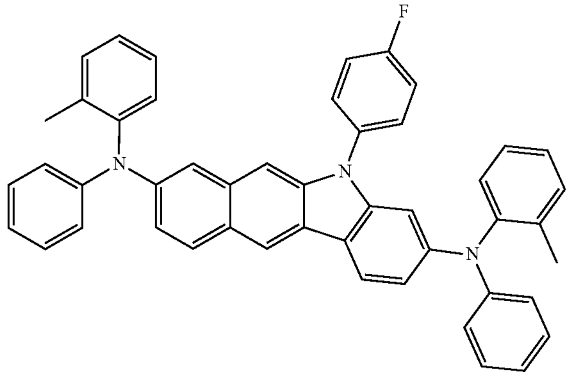
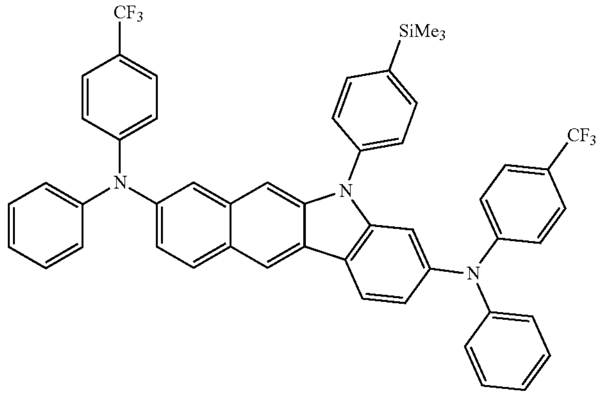

-continued
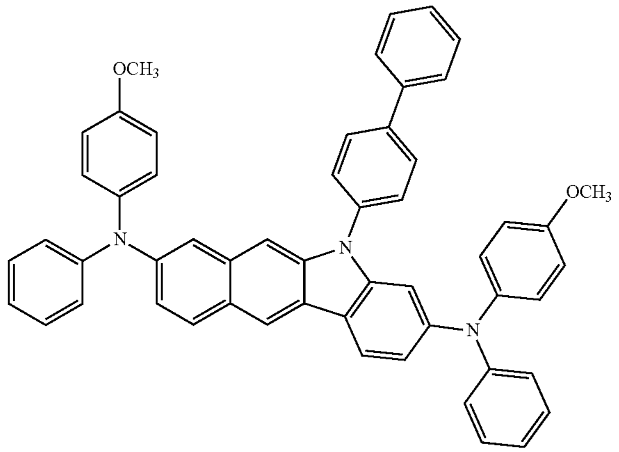
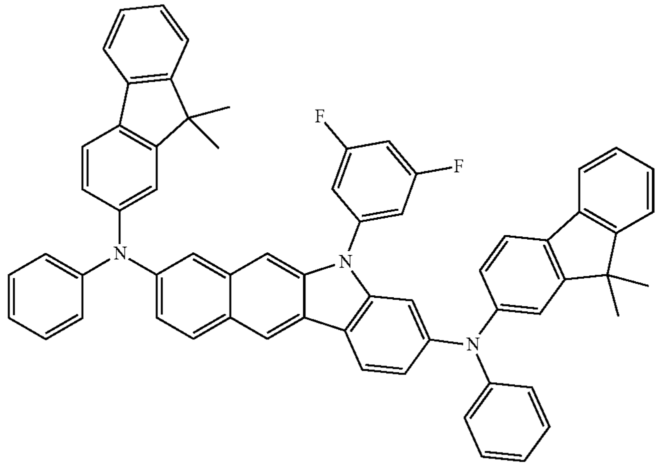
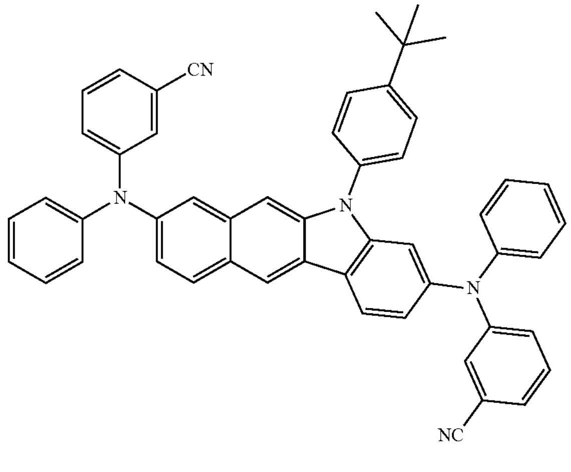
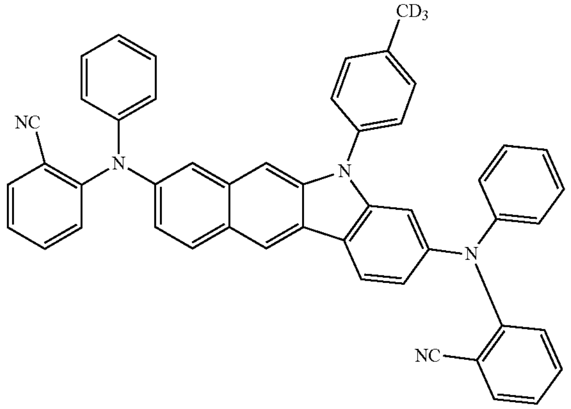

-continued
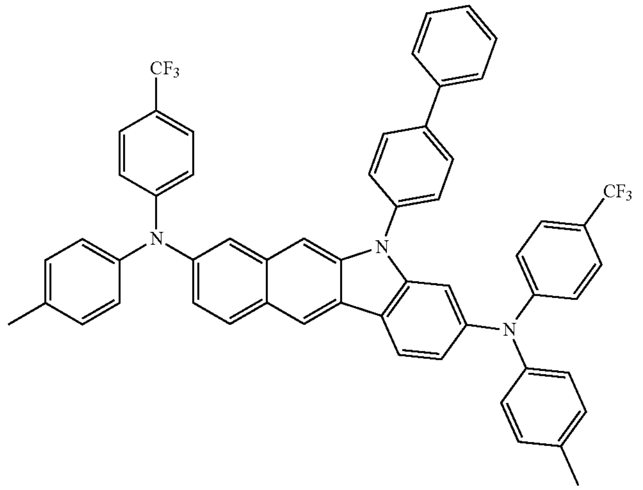
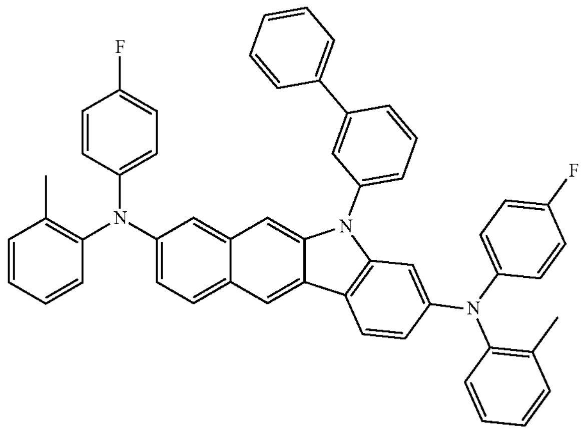
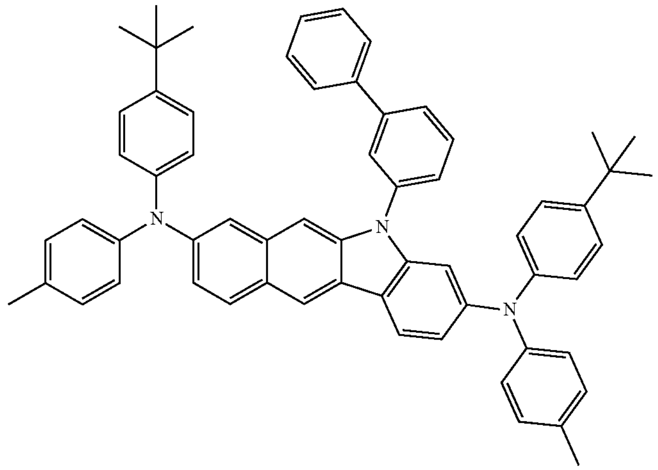

-continued
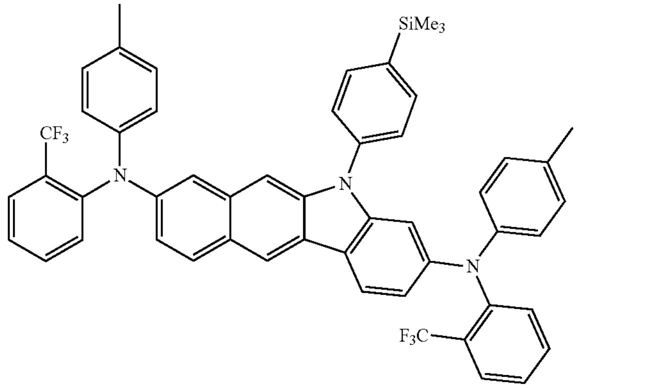
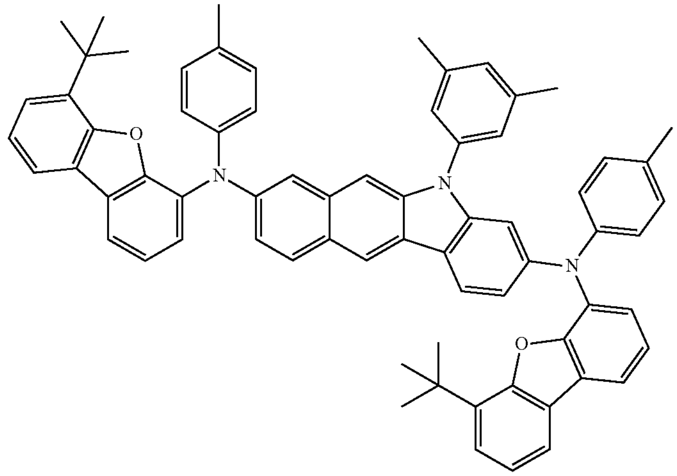
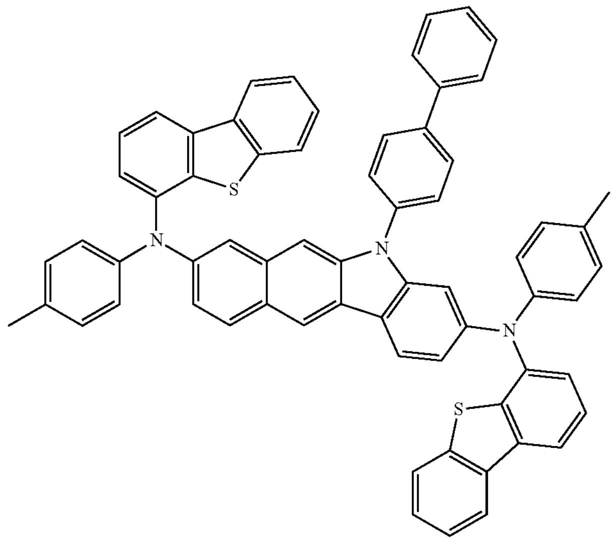

-continued
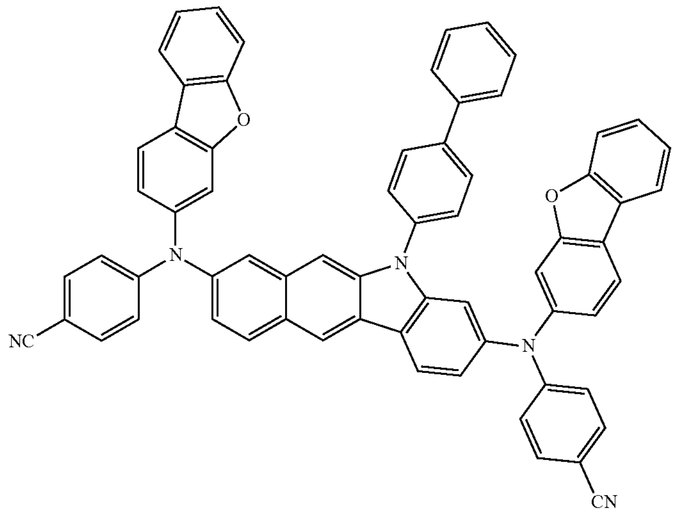
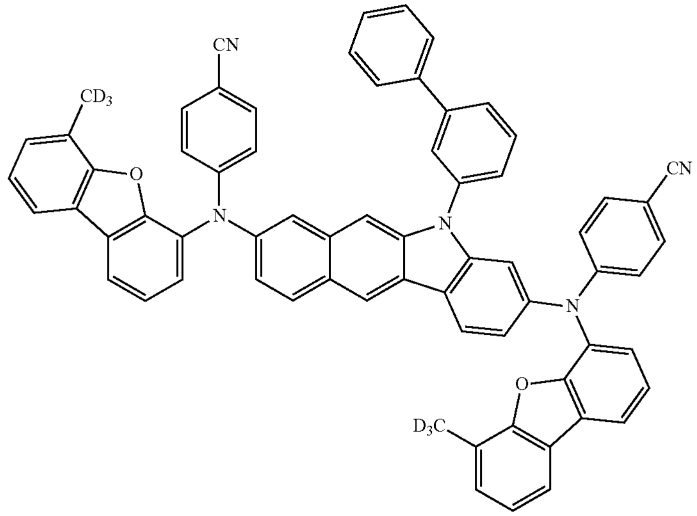
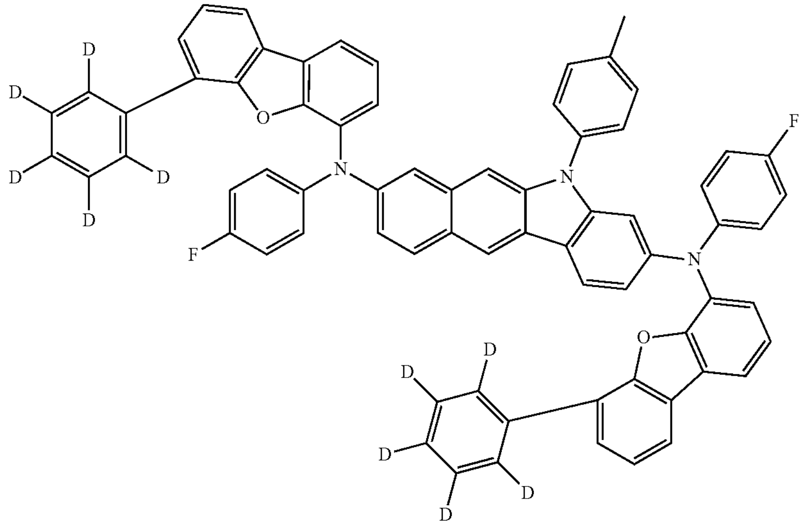

-continued
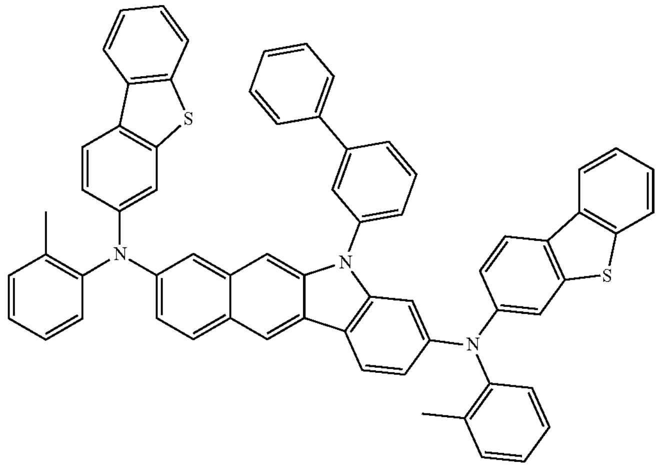
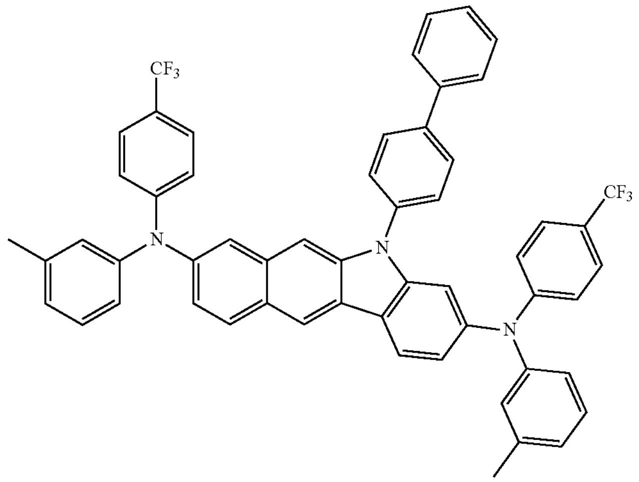
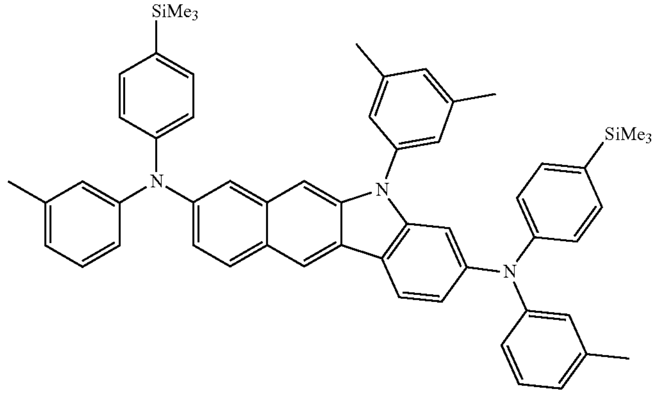

-continued
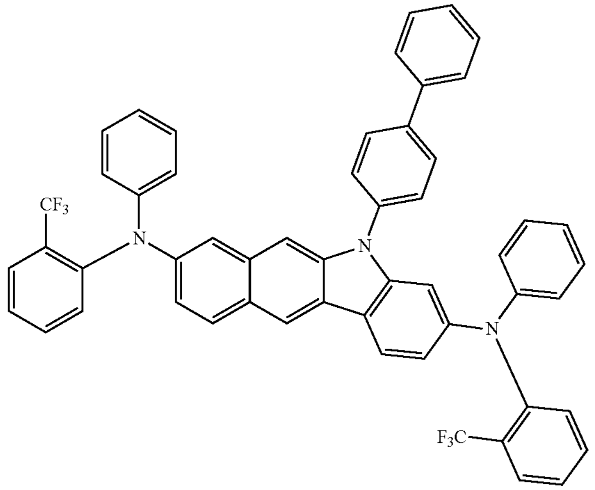
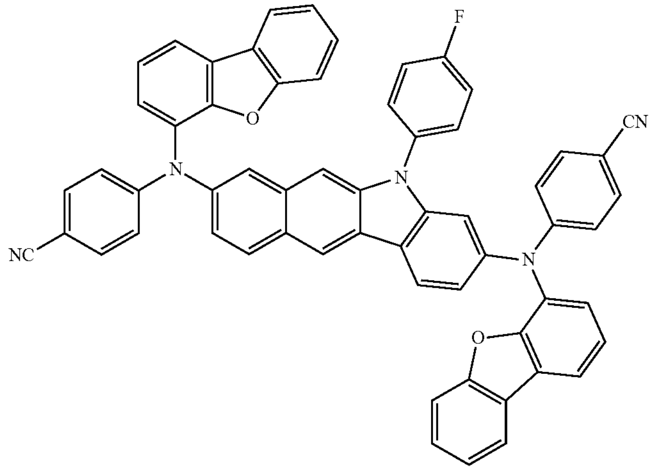
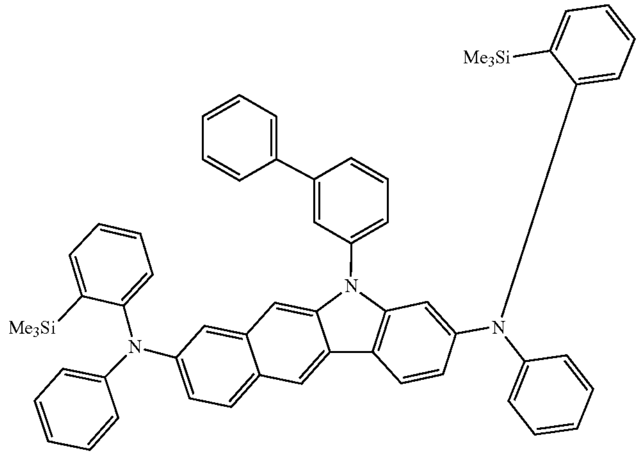

-continued
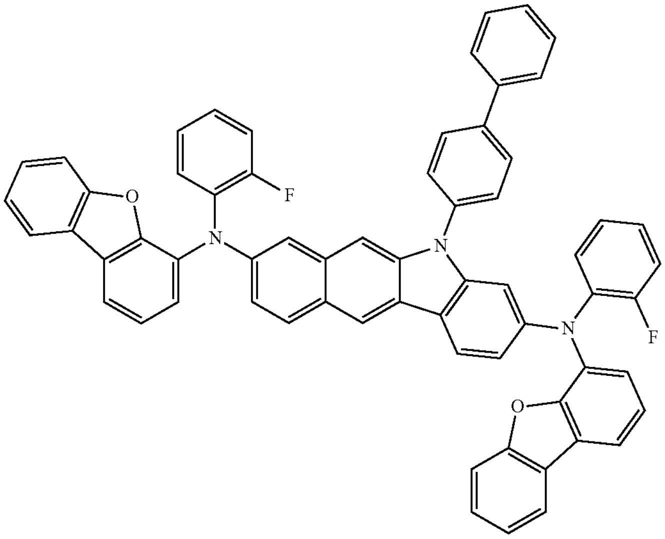
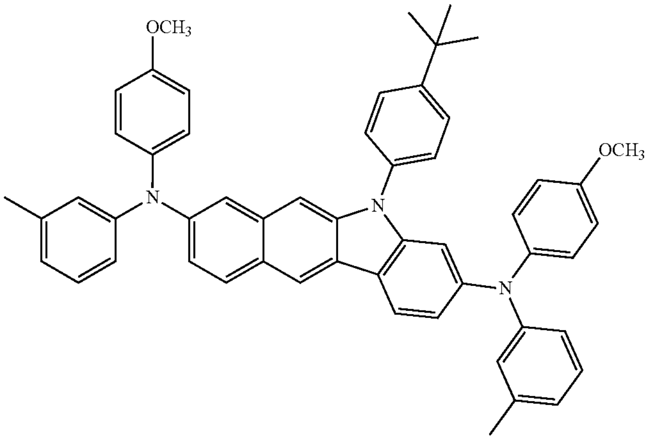
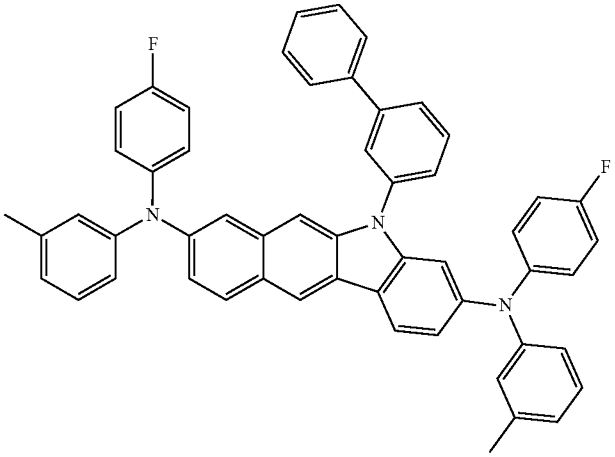

-continued
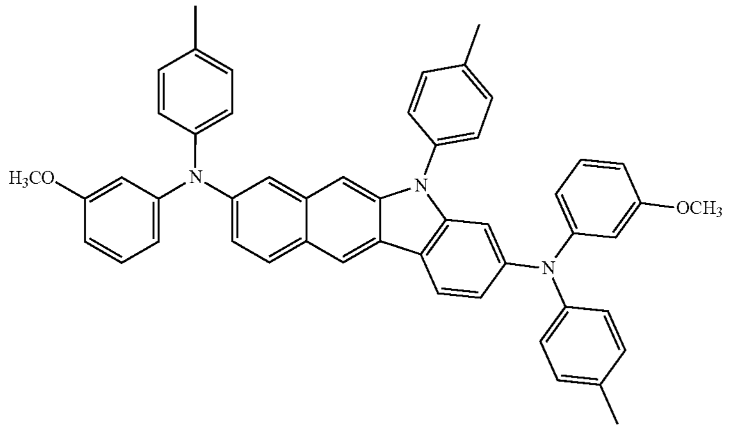
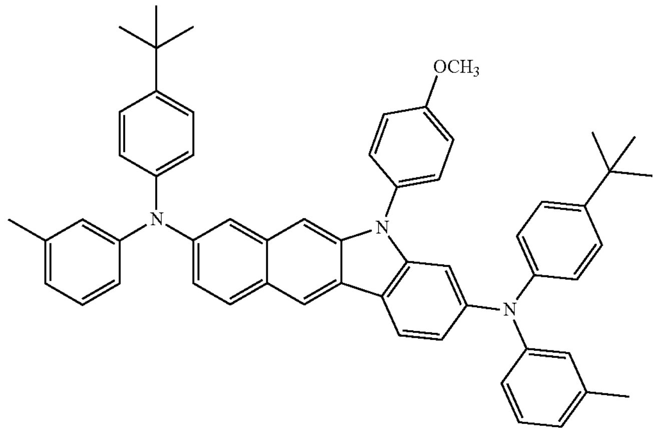
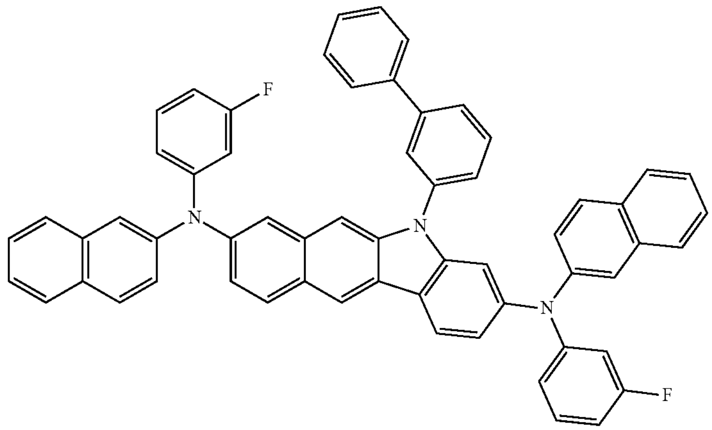

-continued
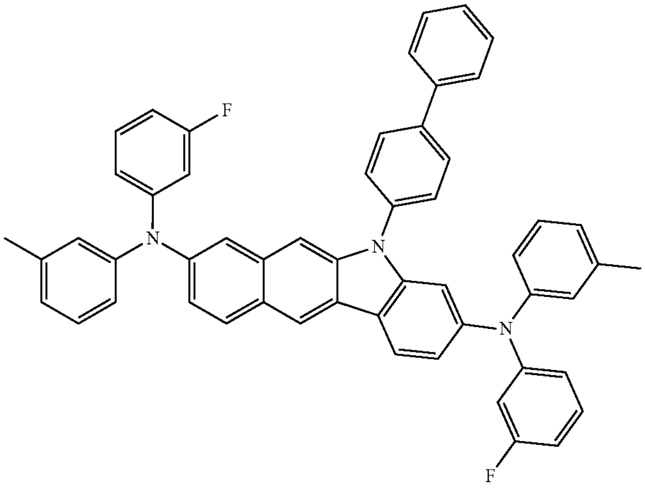
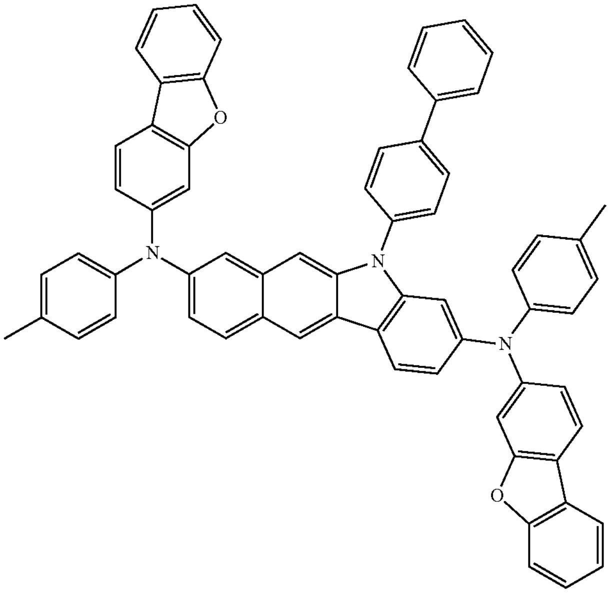
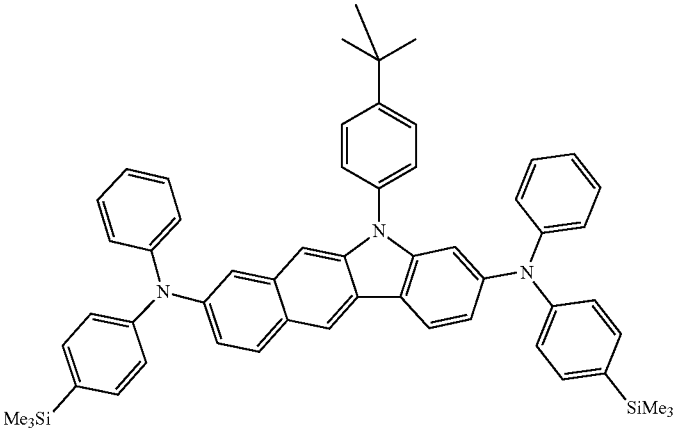

-continued

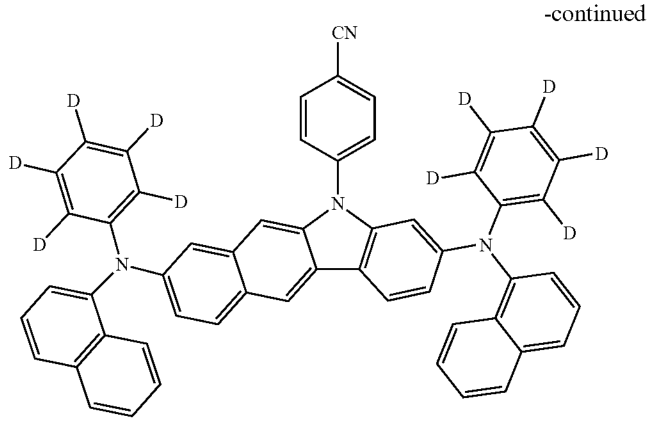

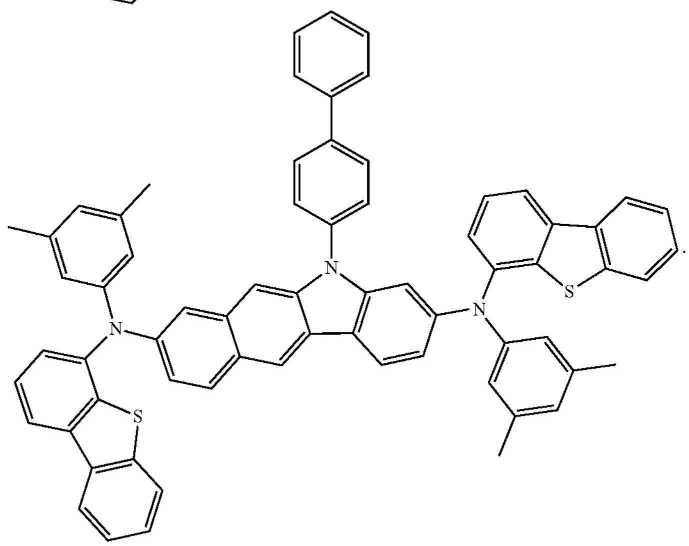

.

3. An organic light emitting device comprising:

a first electrode;

a second electrode provided to face the first electrode; and an organic material layer having one or two or more layers provided between the first electrode and the second electrode, wherein one or more layers of the organic material layer comprise the compound of claim 1.

4. The organic light emitting device of claim 3, wherein the organic material layer comprises a light emitting layer, and the light emitting layer comprises the compound.

5. The organic light emitting device of claim 3, wherein the organic material layer comprises a light emitting layer, and the light emitting layer comprises the compound as a dopant of the light emitting layer.

6. The organic light emitting device of claim 3, wherein the organic material layer comprises a light emitting layer, and the light emitting layer comprises the compound and a compound of Chemical Formula H:

Chemical Formula H

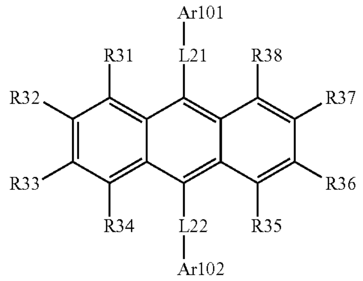

wherein in Chemical Formula H:

L21 and L22 are the same as or different from each other, and are each independently a direct bond, a substituted or unsubstituted arylene group, or a substituted or unsubstituted heteroarylene group;

R31 to R38 are the same as or different from each other, and are each independently hydrogen, deuterium, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group; and Ar101 and Ar102 are the same as or different from each other, and each independently is a substituted or unsubstituted aryl group or a substituted or unsubstituted heteroaryl group.

7. The compound of claim 1, wherein when any of Ar11 to Ar14 is a substituted heteroaryl group, the substituent of the heteroaryl group is deuterium; a halogen group; a nitrile group; an alkyl group having 1 to 5 carbon atoms, which is unsubstituted or substituted with deuterium; a haloalkyl group having 1 to 5 carbon atoms; an alkoxy group having 1 to 5 carbon atoms; a haloalkoxy group having 1 to 5 carbon atoms; a silyl group having 3 to 20 carbon atoms; a cycloalkyl group having 3 to 20 carbon atoms; or an aryl group having 6 to 20 carbon atoms, which is unsubstituted or substituted with deuterium.

8. A compound of the following Chemical Formula 402 or 403:

Chemical Formula 402

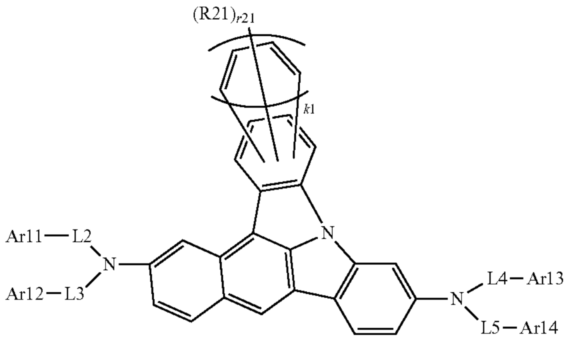

Chemical Formula 403

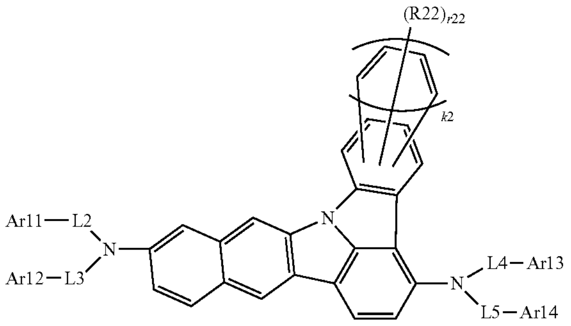

wherein in Chemical Formulae 402 and 403:

R21 and R22 are the same as or different from each other, and are each independently hydrogen, deuterium, a halogen group, a nitrile group, a substituted or unsubstituted alkyl group, a substituted or unsubstituted haloalkyl group, a substituted or unsubstituted silyl group, substituted or unsubstituted alkoxy group, a substituted or unsubstituted cycloalkyl group, a substituted or unsubstituted aryl group, or a substituted or unsubstituted heteroaryl group;

k1 and k2 are 1;

r21 and r22 are an integer from 0 to 6, wherein:

when r21 is 2 or more, the R21s are the same as or different from each other, and when r22 is 2 or more, the R22s are the same as or different from each other;

Ar11 to Ar14 are the same as or different from each other, and each independently is a substituted or unsubstituted aryl group or a substituted or unsubstituted heteroaryl group, or are bonded to an adjacent substituent to form a substituted or unsubstituted ring; and L2 to L5 are the same as or different from each other, and each independently is a direct bond or a substituted or unsubstituted arylene group.

9. The compound of claim 8, wherein Ar11 to Ar14 are the same as or different from each other, and each independently is an aryl group which is unsubstituted or substituted with one substituent selected from the group consisting of deuterium, a halogen group, a nitrile group, an alkyl group, a haloalkyl group, an alkoxy group, a haloalkoxy group, a silyl group, and a cycloalkyl group, or a substituent in which two or more of the recited substituents in the group of substituents of the aryl group are linked; or a heteroaryl group which is unsubstituted or substituted with one substituent selected from the group consisting of deuterium, a halogen group, a nitrile group, an alkyl group, a haloalkyl group, an alkoxy group, a haloalkoxy group, a silyl group, and a cycloalkyl group, or a substituent in which two or more of the recited substituents in the group of substituents of the heteroaryl group are linked.

10. The compound of claim 8, wherein the compound of Chemical Formula 402 or 403 is any one of the following compounds:

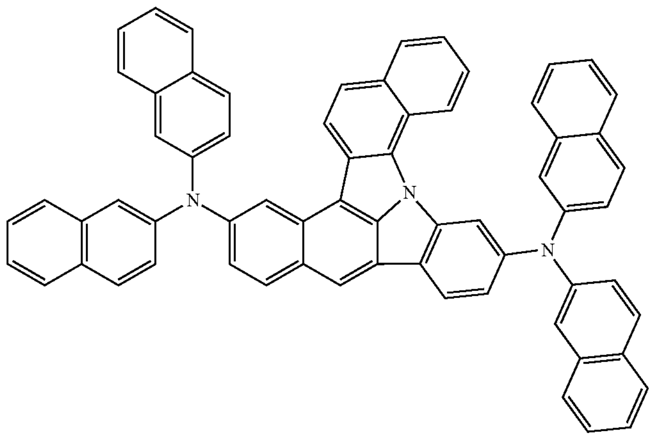

-continued
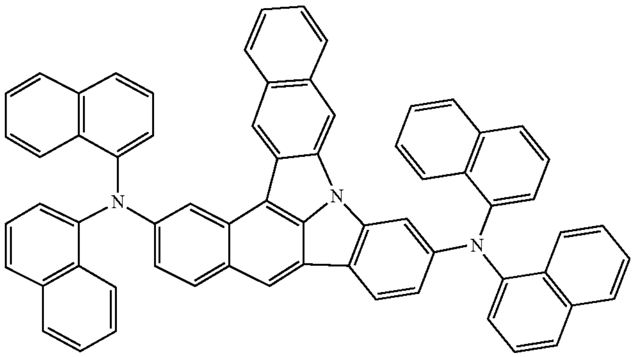
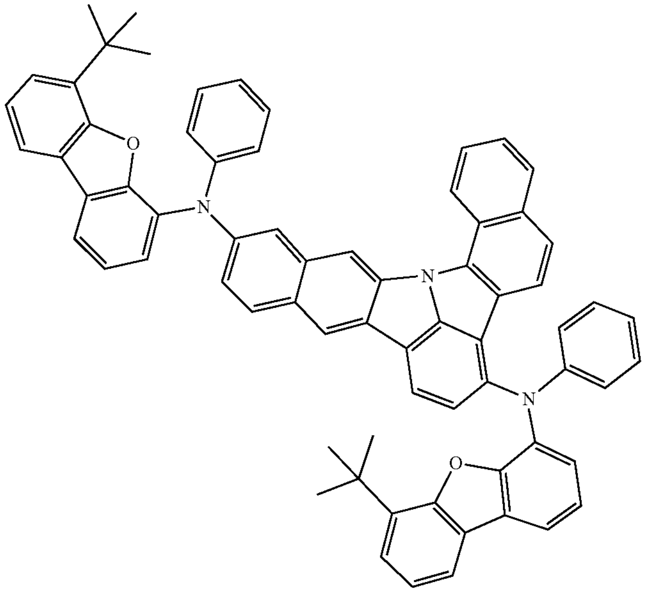
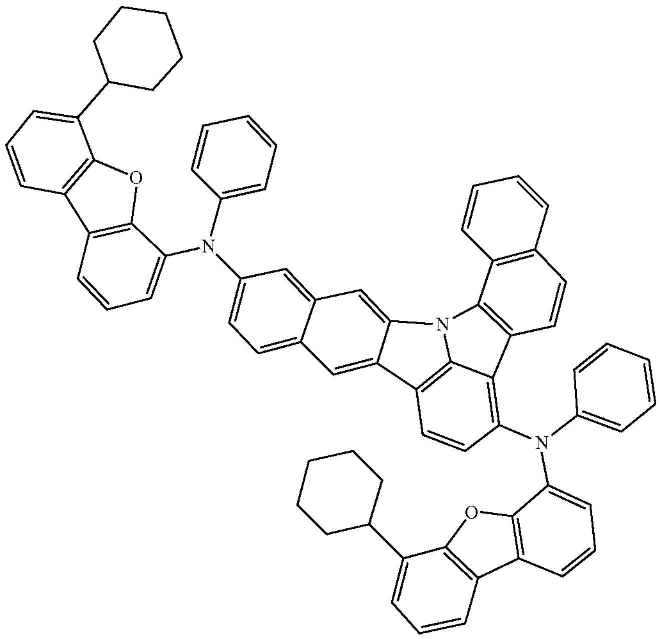

-continued
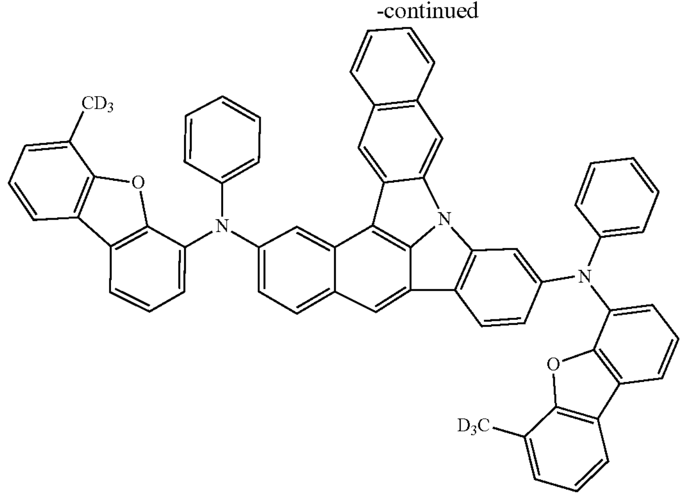
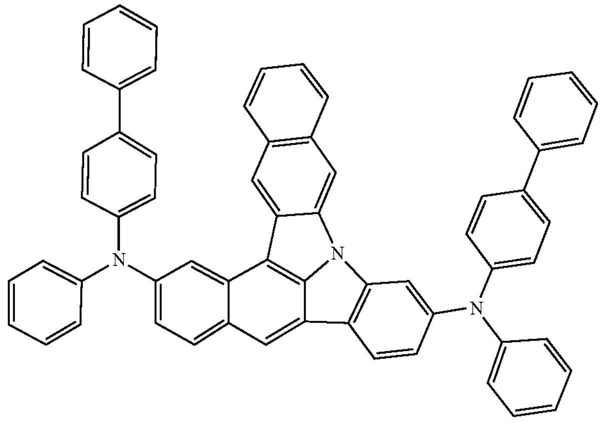
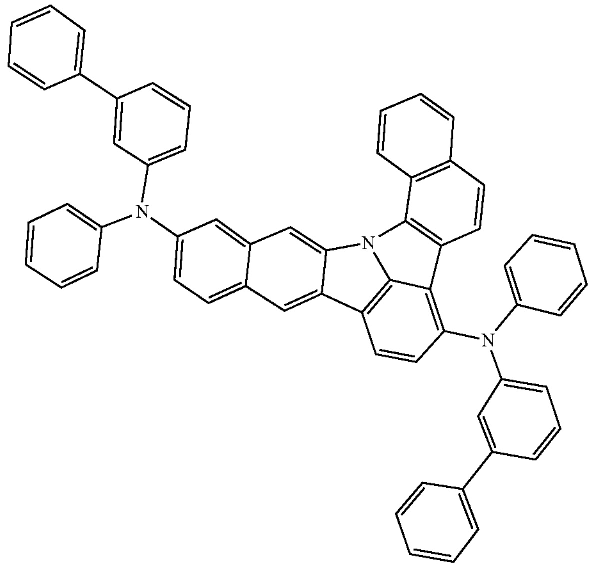

-continued
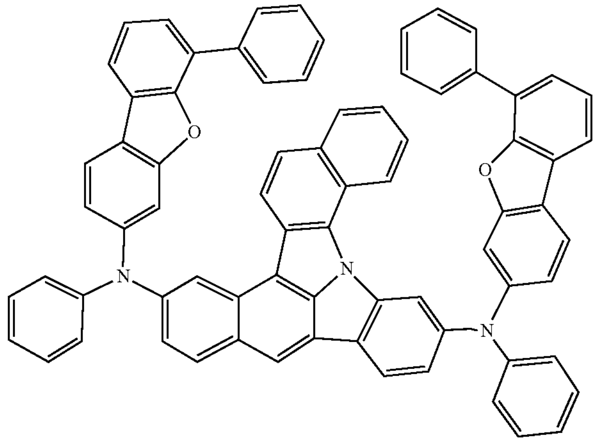
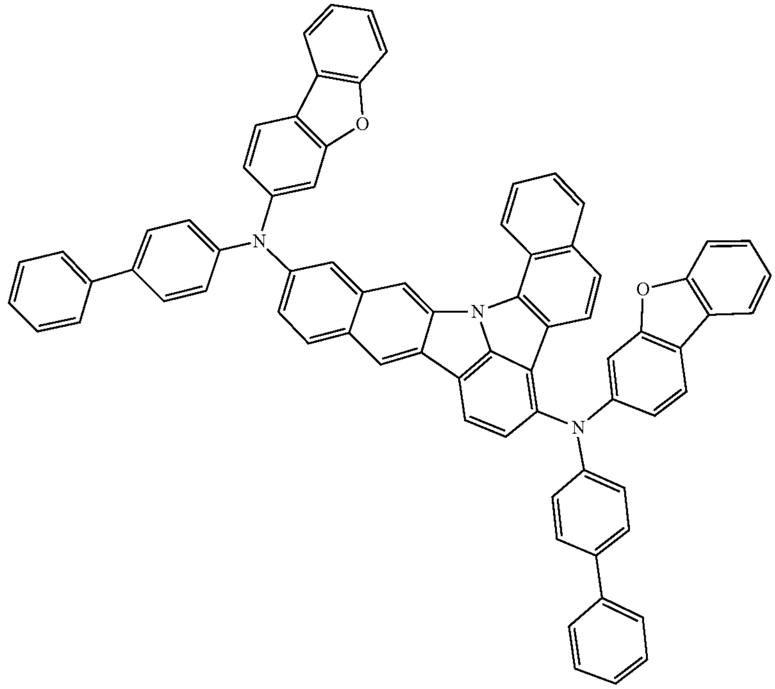

-continued
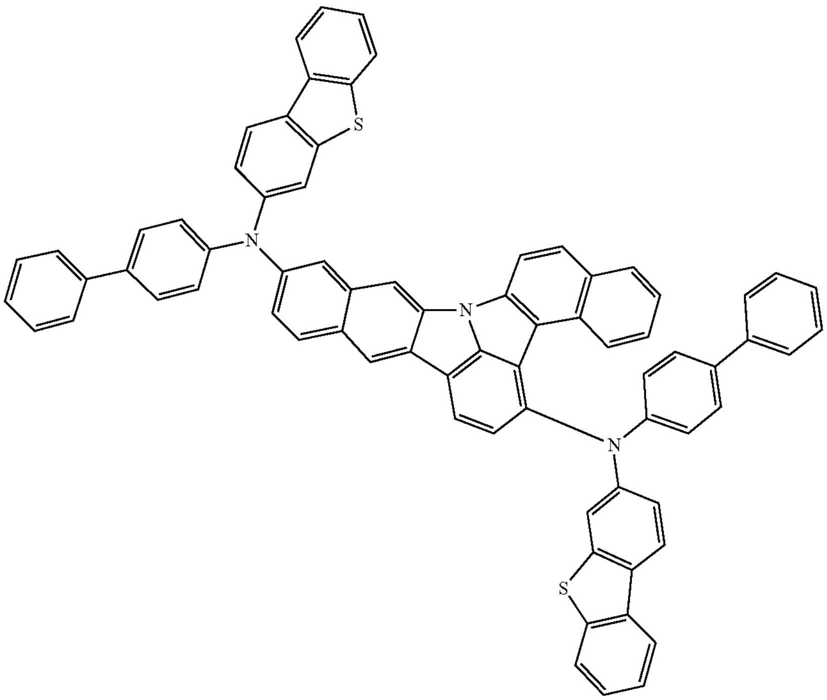
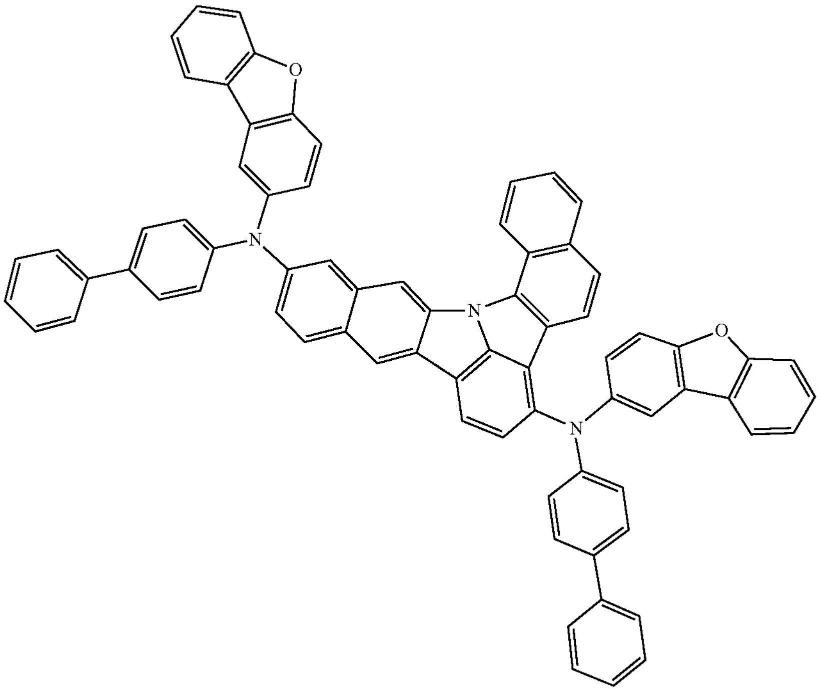

-continued
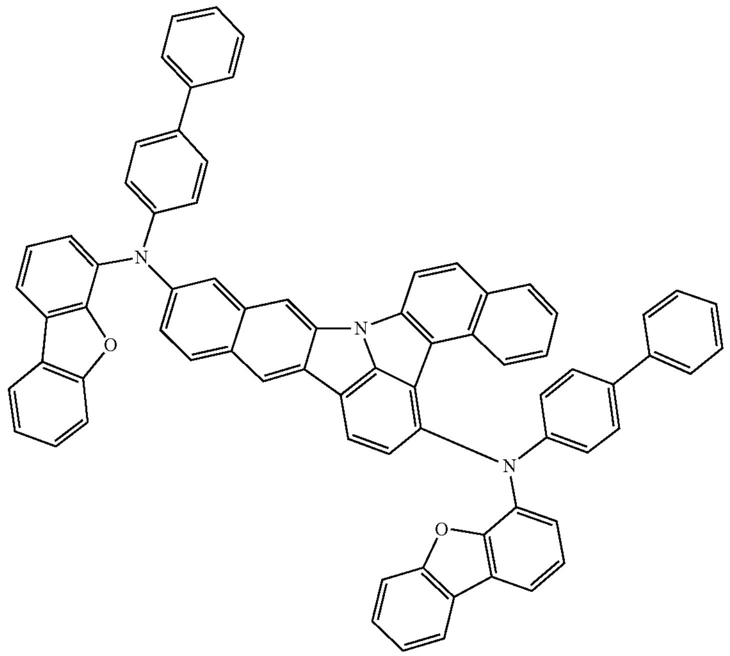
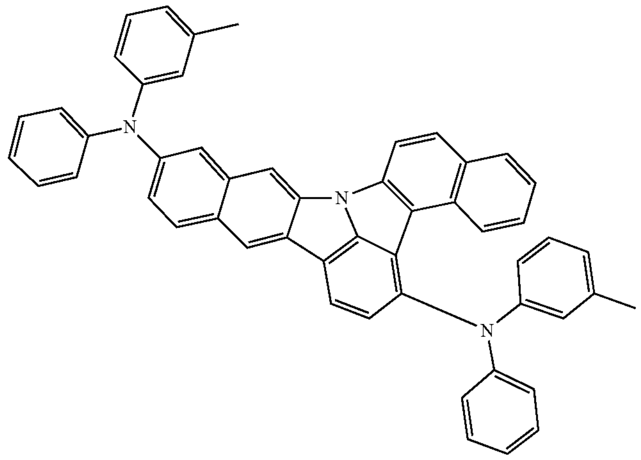
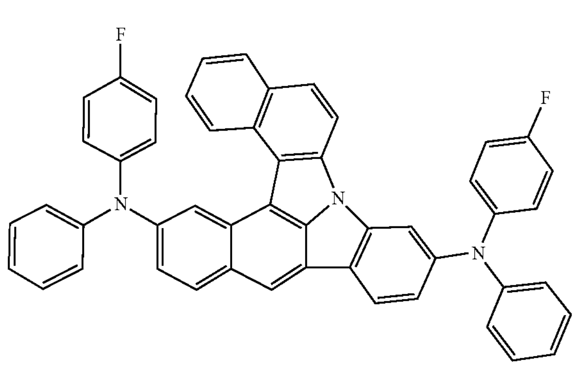

-continued
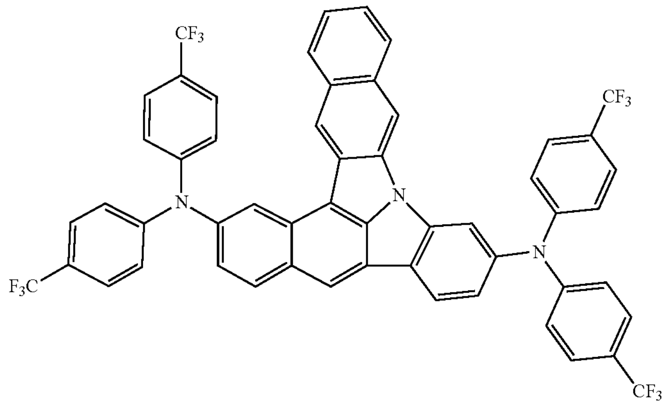
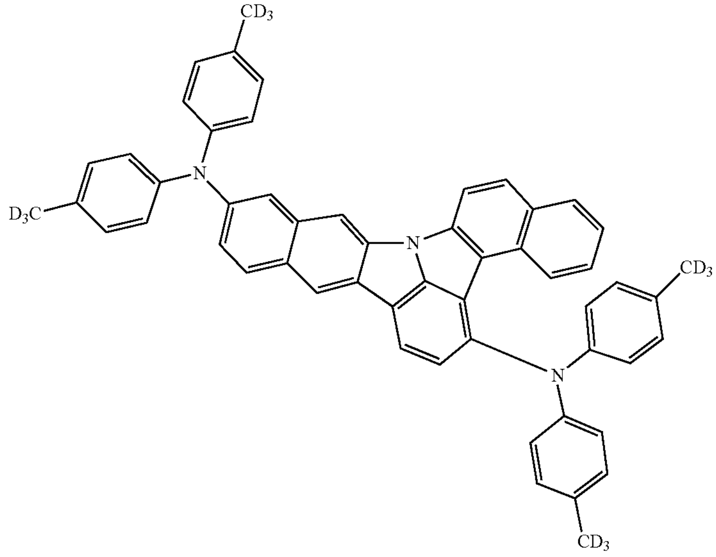
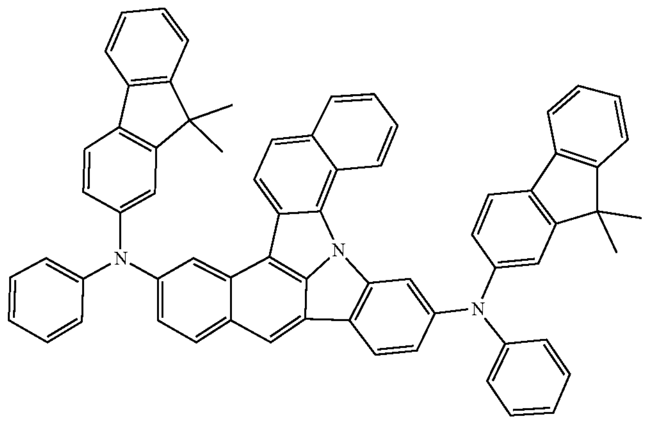

-continued
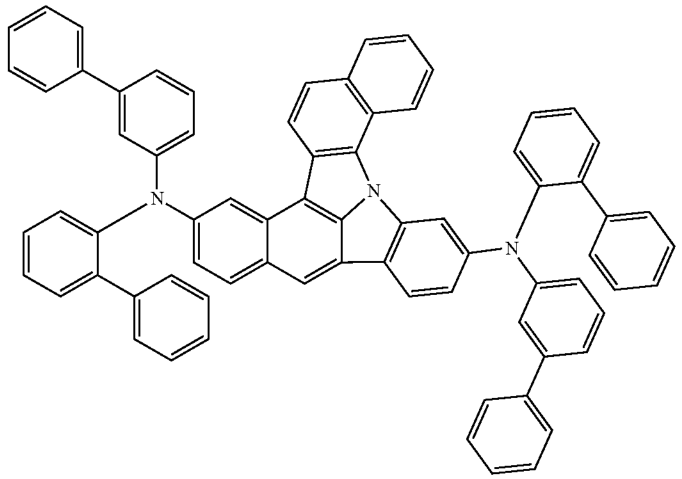
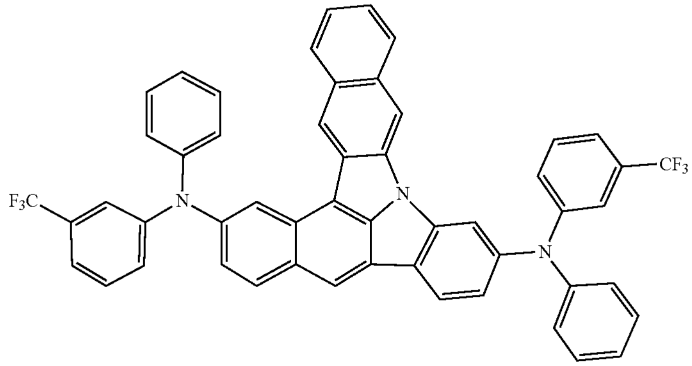
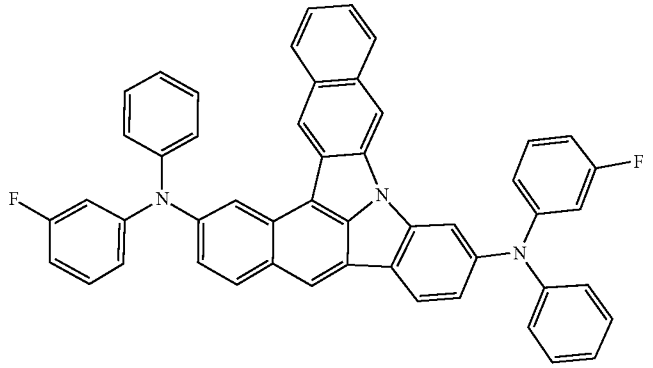
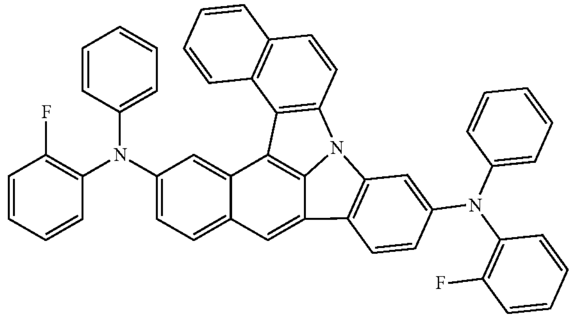

-continued
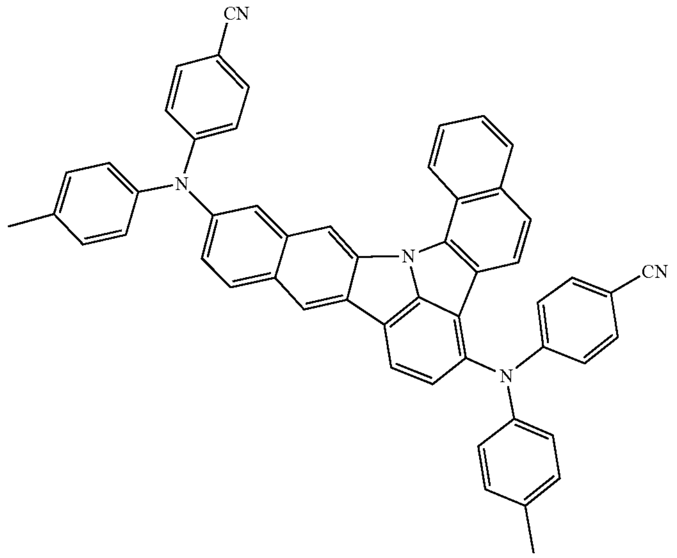
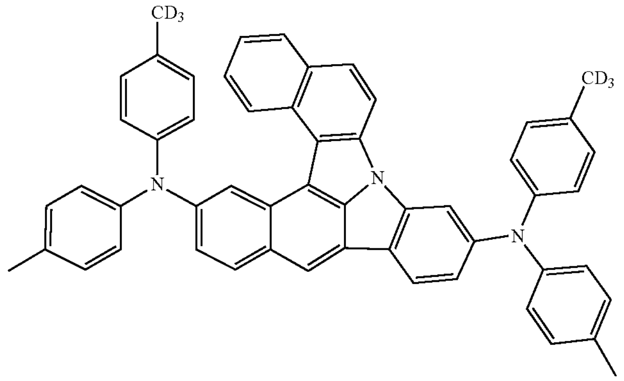
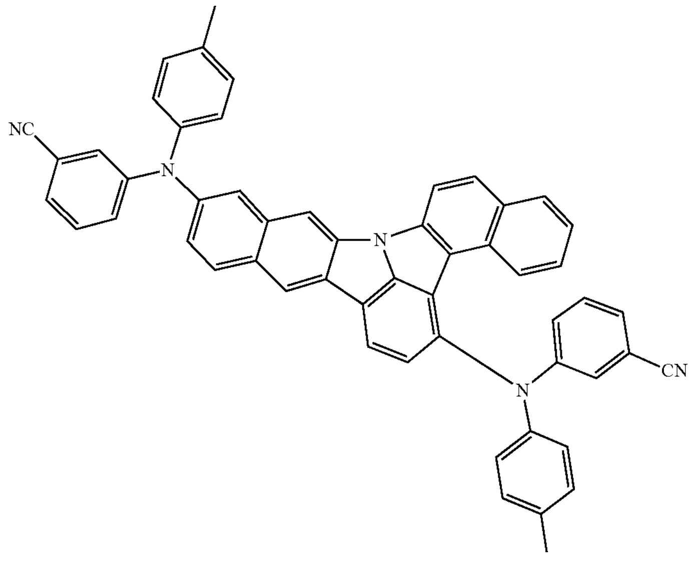

-continued
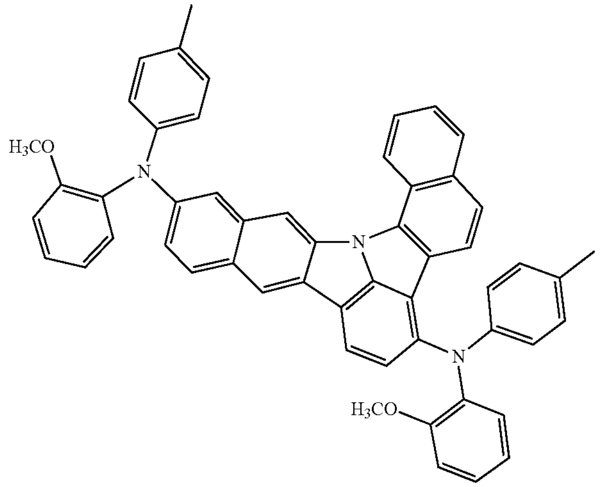
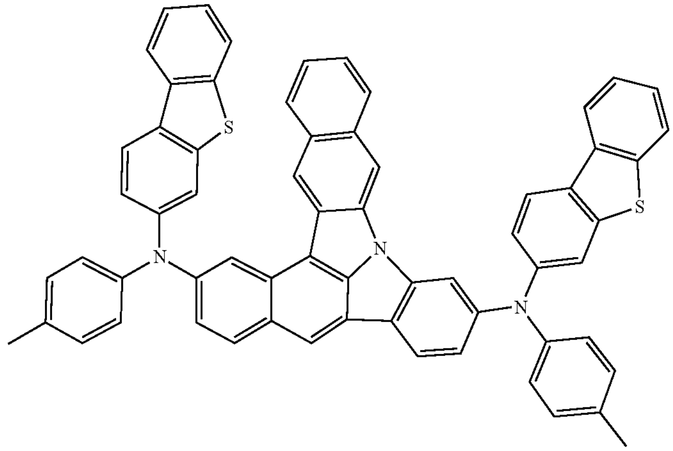
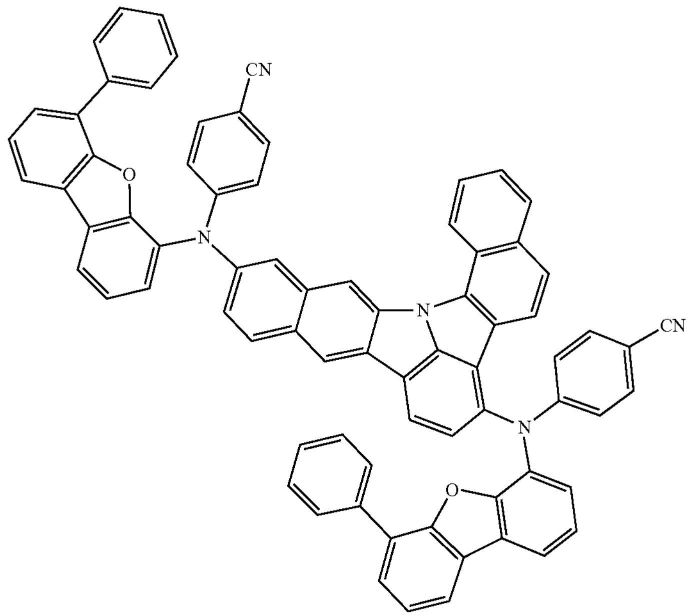

-continued
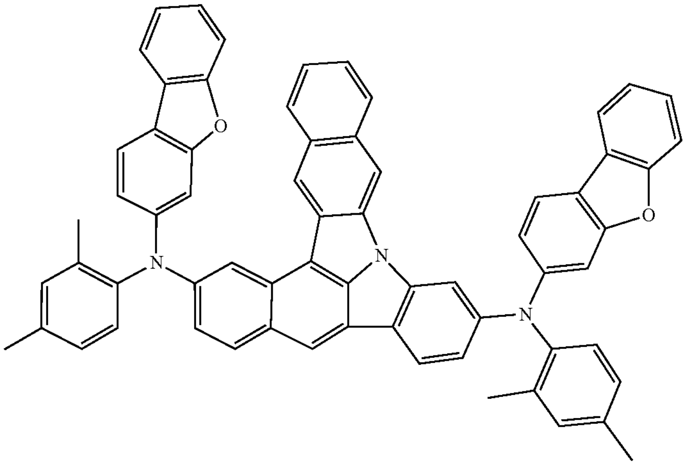
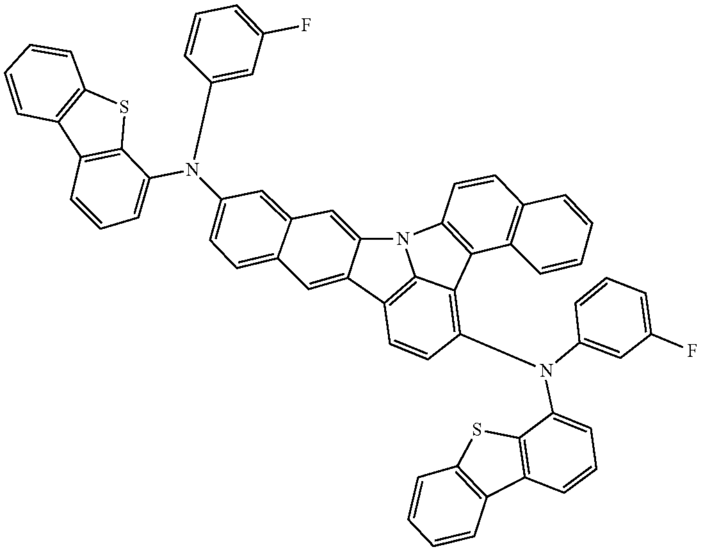
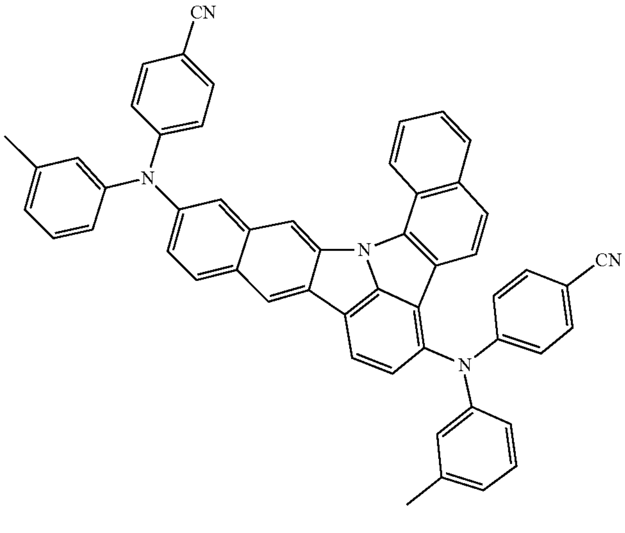

-continued
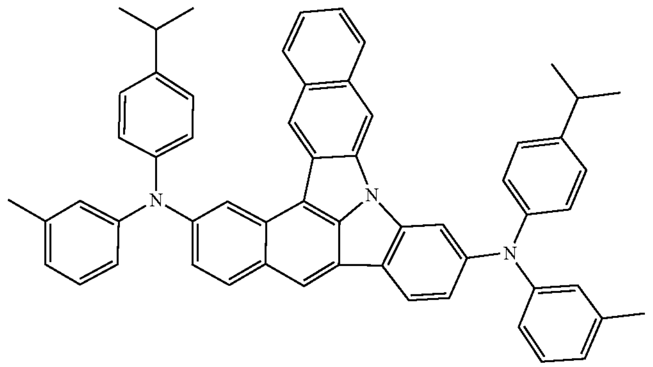
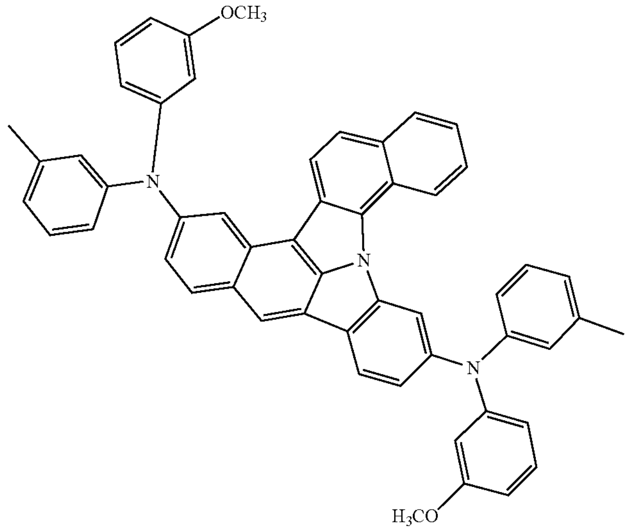
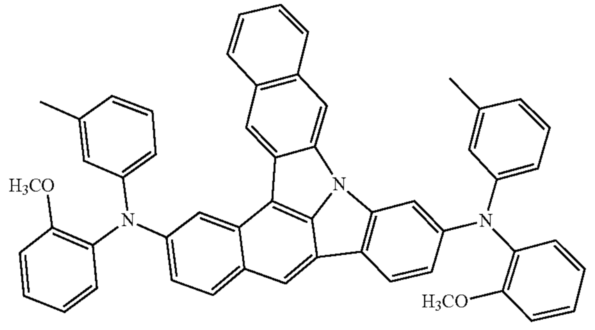
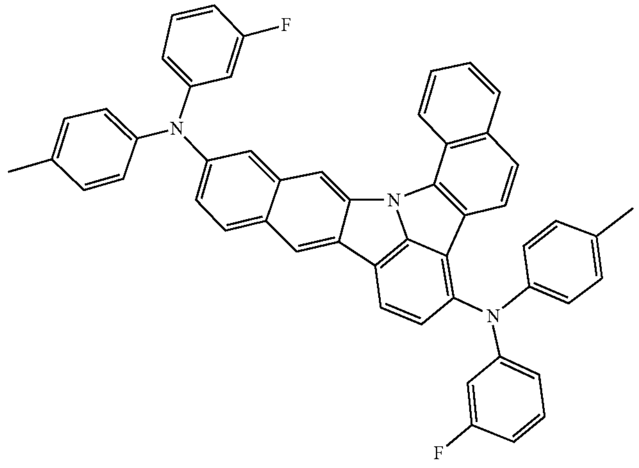

-continued
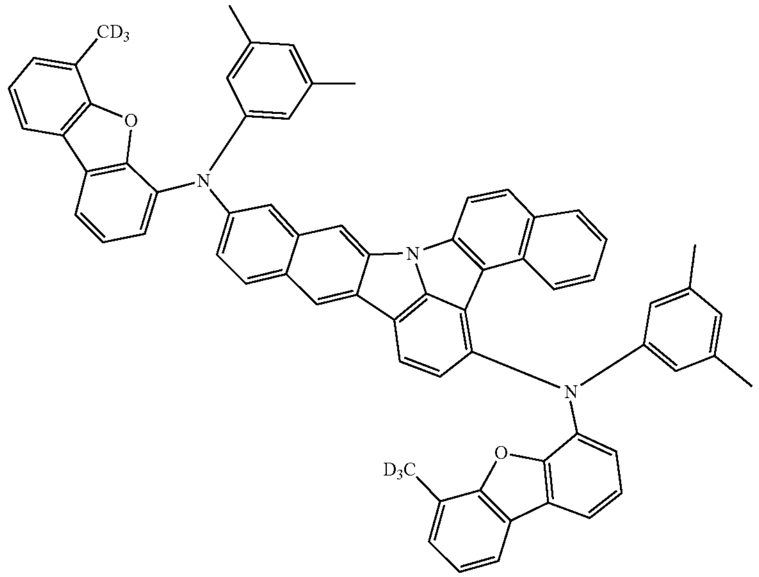
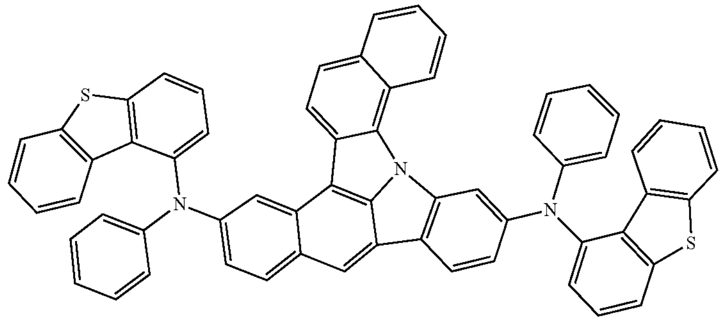
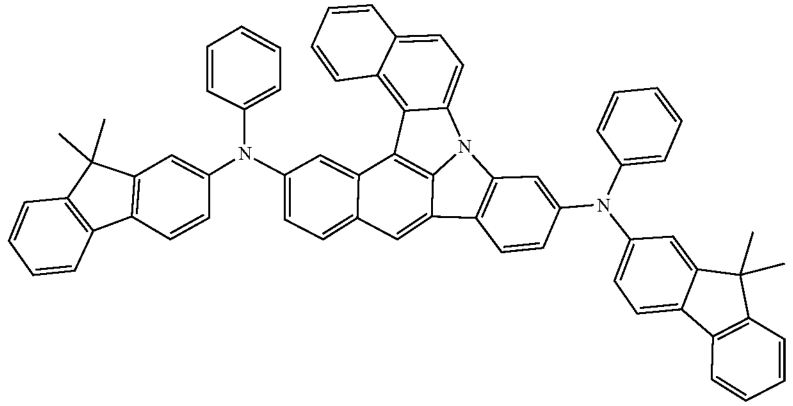
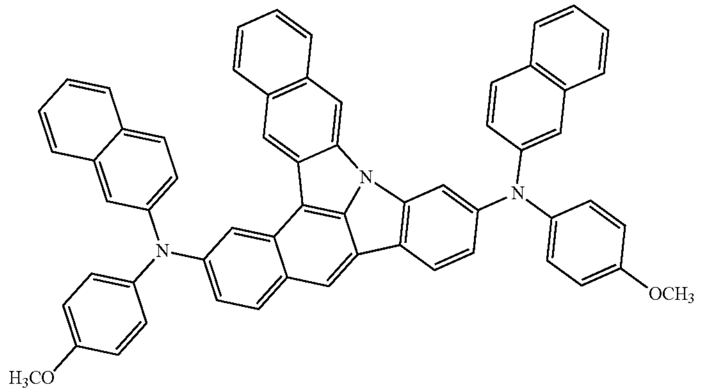

-continued

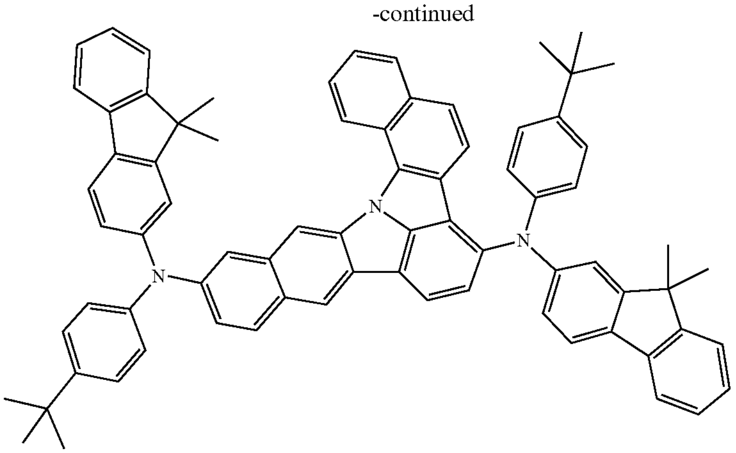

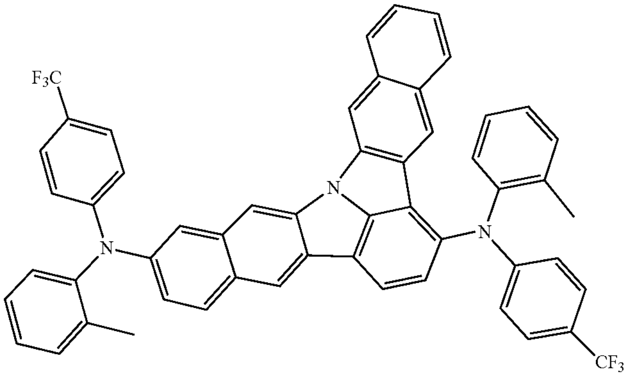

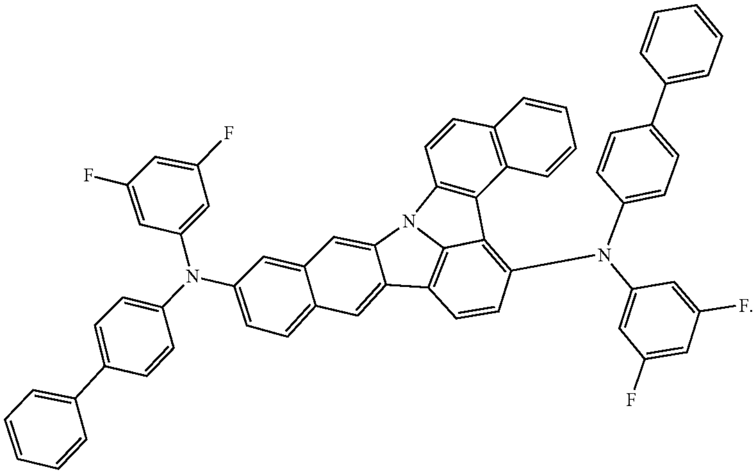

11. An organic light emitting device comprising:

a first electrode;

a second electrode provided to face the first electrode; and an organic material layer having one or two or more layers provided between the first electrode and the second electrode, wherein one or more layers of the organic material layer comprise the compound of claim 3.

12. The organic light emitting device of claim 11, wherein the organic material layer comprises a light emitting layer, and the light emitting layer comprises the compound.

13. The organic light emitting device of claim 11, wherein the organic material layer comprises a light emitting layer, and the light emitting layer comprises the compound as a dopant of the light emitting layer.

14. The organic light emitting device of claim 11, wherein the organic material layer comprises a light emitting layer, and the light emitting layer comprises the compound and a compound of Chemical Formula H:

Chemical Formula H

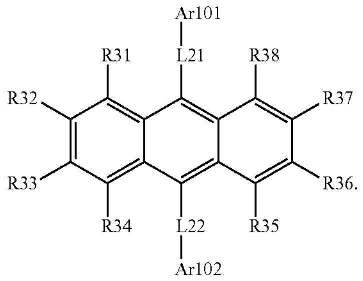

wherein in Chemical Formula H:

L21 and L22 are the same as or different from each other, and are each independently a direct bond, a substituted or unsubstituted arylene group, or a substituted or unsubstituted heteroarylene group;

R31 to R38 are the same as or different from each other, and are each independently hydrogen, deuterium, a substituted or unsubstituted alkyl group, a substituted or unsubstituted cycloalkyl group, a substituted or unsubstituted silyl group, a substituted or unsubstituted phosphine oxide group, a substituted or unsubstituted aryl group, or a substituted or unsubstituted heteroaryl group; and Ar101 and Ar102 are the same as or different from each other, and are each independently is a substituted or unsubstituted aryl group or a substituted or unsubstituted heteroaryl group.

* * * * *